United States Patent
Schneider et al.

(10) Patent No.: US 10,822,412 B2
(45) Date of Patent: Nov. 3, 2020

(54) COMPOSITIONS AND METHODS FOR TREATING CANCER WITH ANTI-CD19/CD22 IMMUNOTHERAPY

(71) Applicant: LentigenTechnology, Inc., Gaithersburg, MD (US)

(72) Inventors: Dina Schneider, Potomac, MD (US); Rimas J. Orentas, Seattle, WA (US); Boro Dropulic, Ellicott City, MD (US); Peirong Hu, Ijamsville, MD (US)

(73) Assignee: LENTIGEN TECHNOLOGY, INC., Gaithersburg, MD (US)

(*) Notice: Subject to any disclaimer, the term of this patent is extended or adjusted under 35 U.S.C. 154(b) by 0 days.

(21) Appl. No.: 16/584,308

(22) Filed: Sep. 26, 2019

(65) Prior Publication Data

US 2020/0087396 A1   Mar. 19, 2020

Related U.S. Application Data

(60) Provisional application No. 62/736,955, filed on Sep. 26, 2018.

(51) Int. Cl.
| | | |
|---|---|---|
| *C07K 16/28* | (2006.01) | |
| *A61P 35/02* | (2006.01) | |
| *A61K 35/17* | (2015.01) | |
| *C07K 14/725* | (2006.01) | |
| *C07K 14/705* | (2006.01) | |
| *A61K 38/00* | (2006.01) | |

(52) U.S. Cl.
CPC ........ *C07K 16/2803* (2013.01); *A61K 35/17* (2013.01); *A61P 35/02* (2018.01); *C07K 14/7051* (2013.01); *C07K 14/70517* (2013.01); *C07K 14/70521* (2013.01); *C07K 14/70578* (2013.01); *A61K 38/00* (2013.01); *C07K 2317/21* (2013.01); *C07K 2317/24* (2013.01); *C07K 2317/31* (2013.01); *C07K 2317/622* (2013.01); *C07K 2319/02* (2013.01); *C07K 2319/03* (2013.01); *C07K 2319/30* (2013.01); *C07K 2319/33* (2013.01)

(58) Field of Classification Search
CPC .......... C07K 16/2803; C07K 14/70521; C07K 14/7051; C07K 14/70578; C07K 14/70517; C07K 2319/03; C07K 2317/31; C07K 2319/30; C07K 2319/02; C07K 2317/21; C07K 2317/24; C07K 2319/33; C07K 2317/622; A61P 35/02; A61K 35/17; A61K 38/00
USPC ........................................................ 424/93.2
See application file for complete search history.

(56) References Cited

U.S. PATENT DOCUMENTS

2016/0362472 A1* 12/2016 Bitter ................. C07K 16/2803

FOREIGN PATENT DOCUMENTS

| WO | WO-2016149578 A1 * | 9/2016 | ......... C07K 14/7051 |
|---|---|---|---|
| WO | WO 2018045325 | 3/2018 | |

OTHER PUBLICATIONS

International Search Report and Written Opinion in PCT Application. No. PCT/US2019/053240, dated Mar. 23, 2020, 18 pages.
Fry, et al., "CD22-targeted CAR T cells induce remission in B-ALL that is naïve or resistant to CD19-targeted CAR immunotherapy," Nature Medicine, 2018, 24(1):20-28.

* cited by examiner

*Primary Examiner* — Janet L Epps-Smith
(74) *Attorney, Agent, or Firm* — Serge Sira, Esq.; Gregory J. Hwa, Esq.; Fish & Richardson P.C.

(57) ABSTRACT

Chimeric antigen receptors containing CD19/CD22 or CD22/CD19 antigen binding domains are disclosed. Nucleic acids, recombinant expression vectors, host cells, antigen binding fragments, and pharmaceutical compositions, relating to the chimeric antigen receptors are also disclosed. Methods of treating or preventing cancer in a subject, and methods of making chimeric antigen receptor T cells are also disclosed.

14 Claims, 9 Drawing Sheets

Specification includes a Sequence Listing.

LTG2681 (D0023, CAR22-19)

LTG2719 (D0024, CAR19-22)

(12) United States Patent
US 10,822,412 B2

COMPOSITIONS AND METHODS FOR TREATING CANCER WITH ANTI-CD19/CD22 IMMUNOTHERAPY

CROSS-REFERENCE TO RELATED APPLICATIONS

This application claims the benefit of priority under 35 U.S.C. Section 119(e) to U.S. Provisional Patent Application No. 62/736,955, filed on Sep. 26, 2018, the entire contents of which are incorporated herein by reference.

SEQUENCE LISTING

The instant application contains a Sequence Listing which has been submitted electronically in ASCII format and is hereby incorporated by reference in its entirety. Said ASCII copy, created on Sep. 25, 2019, is named Sequence Listing.txt and is 197 kilobytes in size.

FIELD OF THE DISCLOSURE

This application relates to the field of cancer, particularly to CARs targeting CD19 and CD22 B cell antigens simultaneously, via CD19/CD22 antigen-targeting domains and chimeric antigen receptors (CARs) containing such CD19/CD22 antigen targeting domains and methods of use thereof.

BACKGROUND

Cancer is one of the most deadly threats to human health. In the U.S. alone, cancer affects nearly 1.3 million new patients each year, and is the second leading cause of death after cardiovascular disease, accounting for approximately 1 in 4 deaths. Solid tumors are responsible for most of those deaths. Although there have been significant advances in the medical treatment of certain cancers, the overall 5-year survival rate for all cancers has improved only by about 10% in the past 20 years. Cancers, or malignant tumors, metastasize and grow rapidly in an uncontrolled manner, making treatment extremely difficult.

CD19 is a 85-95 kDa transmembrane cell surface glycoprotein receptor. CD19 is a member of immunoglobulin (Ig) superfamily of proteins, and contains two extracellular Ig-like domains, a transmembrane, and an intracellular signaling domain (Tedder T F, Isaacs, C M, 1989, J Immunol 143:712-171). CD19 modifies B cell receptor signaling, lowering the triggering threshold for the B cell receptor for antigen (Carter, R H, and Fearon, D T, 1992, Science, 256:105-107), and co-ordinates with CD81 and CD21 to regulate this essential B cell signaling complex (Bradbury, L E, Kansas G S, Levy S, Evans R L, Tedder T F, 1992, J Immunol, 149:2841-50). During B cell ontogeny CD19 is able to signal at the pro-B, pre-pre-B cell, pre-B, early B cell stages independent of antigen receptor, and is associated with Src family protein tyrosine kinases, is tyrosine phosphorylated, inducing both intracellular calcium mobilization and inositol phospholipid signaling (Uckun F M, Burkhardt A L, Jarvis L, Jun X, Stealy B, Dibirdik I, Myers D E, Tuel-Ahlgren L, Bolen J B, 1983, J Biol Chem 268:21172-84). The key point of relevance for treatment of B cell malignancies is that CD19 is expressed in a tightly regulated manner on normal B cells, being restricted to early B cell precursors at the stage of IgH gene rearrangement, mature B cells, but not expressed on hematopoietic stem cells, or mature plasma cells (Anderson, K C, Bates, M P, Slaughenhout B L, Pinkus G S, Schlossman S F, Nadler L M, 1984, Blood 63:1424-1433).

CD22, also known as SIGLEC-2 (sialic acid-binding immunoglobulin-likelectin-2), is 95 kDa transmembrane surface glycoprotein and contains 6 Ig-like C2-type domains and one Ig-like V-type domain (uniprot.org/uniprot/P20273# structure, accessed 07/12/2017). During B-cell ontogeny, CD22 is expressed on the B-cell surface starting at the pre-B cell stage, persists on mature B cells and is lost on plasma cells (Nitschke L, 2009, Immunological Reviews, 230:128-143). CD22 contains intracellular ITIM (immuoreceptor tyrosine-based inhibition motifs) domains which following the engagement of the B cell receptor for antigen serve to down-modulate cellular activation. Antibody binding of CD22 induces co-localization with SHP-1, and intracellular phosphatase that also serves to down-modulate phosorylation-based signal transduction (Lumb S, Fleishcer S J, Wiedemann A, Daridon C, Maloney A, Shock A, Domer T, 2016, Journal of Cell Communication and Signaling, 10:143-151). The key point of relevance for treatment of B cell malignancies is that CD22 is expressed in a tightly regulated manner on normal B cells, but not expressed on hematopoietic stem cells, or mature plasma cells, making it a suitable target antigen for B cell leukemias. The expression of CD22 on both adult and pediatric (pre-B-ALL) B cell malignancies has led to exploiting this target for both antibody and chimeric antigen receptor (CAR)-T cell-based therapy (Haso W, Lee D W, Shah N N, Stetler-Stevenson M, Yuan C M, Pastan I H, Dimitrov D S, Morgan R A, FitzGerlad D J, Barrett D M, Wayne A S, Mackall C L, Orentas R J, 2013, Blood, 121:1165-1174) (Wayne A S, Kreitman R J, Findley H W, Lew G, Delbrook C, Steinberg S M, Stetler-Stevenson M, FitzGerald D J, Pastan I, 2010, Clinical Cancer Research, 16:1894-1903.

A number of novel approaches to treat B cell leukemia and lymphoma have been developed, including anti-CD22 antibodies linked to bacterial toxins or chemotherapeutic agents (Wayne A S, FitzGerald D J, Kreitman R J, Pastan I, 2014, Immunotoxins for leukemia, Blood, 123:2470-2477). Inotuzumab Ozogamicin (CMC-544, a humanized version of the murine monoclonal antibody G5/44) is an antibody drug conjugate and is currently being evaluated in clinical trials, either as a single agent or given in combination with chemotherapy (NCT01664910, sponsor: M.D. Anderson Cancer Center) (DiJoseph J F, et al., 2004, Blood, 103:1807-1814). As a single agent, outcomes exceeded those seen with standard therapy, although significant liver toxicity was noted (Kantarjian H, et al., 2016, Inotuzumb ozogamicin versus standard therapy for acute lymphoblastic leukemia, New England Journal of Medicine, 375:740-753). Unmodified CD22 therapeutic antibody, Epratuzumab, is also being tested in combination with chemotherapy (NCT01219816, sponsor: Nantes University Hospital). Epratuzumab is a chimeric protein composed of murine CDRs grafted onto a human antibody framework. Although effective in some leukemias, Moxetumomab pasudotox in not in broad clinical development due to problems with both immunogenicity of the bacterial toxin to which the antibody is fused and modest or comparable levels of activity with other agents (see NCT01829711, sponsor: MedImmune, LLC). To date, many of the binding moieties for CD22 employed in CAR constructs utilize a domain derived from these murine antibodies and do not effectively activate T cells that target this CD22 domain (such as the HA22 anti-CD22 binder used as the basis for Moxetumomab pasudotox, see James S E, Greenberg P D, Jensen M C, Lin Y, Wang J, Till B G, Raubitschek A A, Forman S J, Press O W, 2008, Jounral of Immunology 180:7028-7038). One anti-CD22 binder that is effective as an anti-CD22 CAR is currently in clinical trial at the National Institutes of Health (NIH), although results have not been published (ClinicalTrials.gov Identifier: NCT02315612, Anti-CD22 Chimeric Receptor T Cells in Pediatric and Young Adults with Recurrent or Refractory CD22-expressing B Cell Malignancies, sponsor: NCI). This binder is based on the m971 fully human antibody developed in the laboratory of one of the inventors in this application, Dr. Dimiter Dimitrov (Xiao X, Ho M, Zhu Z, Pastan I, Dimitrov D, 2009, Identification and characterization of fully human anti-CD22 monoclonal antibodies, MABS, 1:297-303). The m971 domain was proven effective as a CAR in work supervised by another of the inventors in this application, Dr. Rimas Orentas (Haso W, et al., 2013, Anti-CD22-chimeric antigen receptors targeting B-cell precursor acute lymphoblastic leukemia, Blood, 121:1165-1174).

The traditional treatment approaches for B-lineage leukemias and lymphomas may involve chemotherapy, radiotherapy and stem cells transplant (see the world wide web at mayclinic.org). High toxicity associated with these treatments, as well as the risk of complications, such as relapse, secondary malignancy, or GVHD, motivate the search for better therapeutic alternatives. The expression of CD19 on both adult and pediatric (pre-B-ALL) B cell malignancies has led to exploiting this target for both antibody and chimeric antigen receptor (CAR)-T cell-based therapy (Kochenderfer J N, Wilson W H, Janik J E, Dudley M E, Stetler-Stevenson M, Feldman S A, Maric I, Raffeld M, Nathan D A, Lanier B J, Morgan R A, Rosenberg S A, 2010, Blood 116:4099-102; Lee D W, Kochenderfer J N, Stetler-Stevenson M, Cui Y K, Delbrook C, Feldman S A, Orentas R, Sabatino M, Shah N N, Steinberg S M, Stroncek D, Tschernia N, Yuan C, Zhang H, Zhang L, Rosenberg S A, Wayne A S, Mackall C L, 2015, Lancet 385:517-28). Moreover, the presence of CD22 antigen on lymphomas (DLBCL, F L), and leukemias (CLL) make it an attractive additional target for efficient tumor elimination and for the prevention of tumor antigen escape.

The present standard of care for B-lineage leukemias may consists of remission induction treatment by high dose of chemotherapy or radiation, followed by consolidation, and may feature stem cell transplantation and additional courses of chemotherapy as needed (see the world wide web at cancer.gov). High toxicity associated with these treatments, as well as the risk of complications, such as relapse, secondary malignancy, or GVHD, motivate the search for better therapeutic alternatives. The expression of CD19 on both adult and pediatric (pre-B-ALL) B cell malignancies has led to exploiting this target for both antibody and chimeric antigen receptor (CAR)-T cell-based therapy (Kochenderfer J N, Wilson W H, Janik J E, Dudley M E, Stetler-Stevenson M, Feldman S A, Maric I, Raffeld M, Nathan D A, Lanier B J, Morgan R A, Rosenberg S A, 2010, Blood 116:4099-102; Lee D W, Kochenderfer J N, Stetler-Stevenson M, Cui Y K, Delbrook C, Feldman S A, Orentas R, Sabatino M, Shah N N, Steinberg S M, Stroncek D, Tschernia N, Yuan C, Zhang H, Zhang L, Rosenberg S A, Wayne A S, Mackall C L, 2015, Lancet 385:517-28).

A number of novel approaches to treat B cell leukemia and lymphoma have been developed, including bi-specific antibodies that link an anti-CD19 or anti-CD22 binding motif to a T cell binding motif (i.e. Blinatumomab, Blincyto® indicated for the treatment of Philadelphia chromosome-negative relapsed or refractory B-cell precursor acute lymphoblastic leukemia (ALL). To date, many of the binding moieties for CD19 or CD22 employed in CAR constructs utilize a domain derived from murine antibodies. A number of these products are currently being considered for approval including those developed by Novartis and Kite Pharmaceuticals. In April of 2017 Novartis announced that CTL019 (tisagenlecleucel) received FDA breakthrough designation for treatment of adult patients with refractory or recurrent (r/r) DLBCL (diffuse large B cell lymphoma) who failed two or more prior therapies, adding this designation to that for r/r B-cell acute lymphoblastic leukemia (ALL). These indications were based on the Phase II JULIET study (NCT02445248) and the ELIANA study (NCT02435849), respectively. The JULIET trial showed and overall response rate (ORR) of 45%, with a 37% complete response (CR), and an 8% partial response (PR) at three months. In the ELIANA study, 82% of patients infused with the product achieved CR or CR with incomplete count recovery, and the relapse free survival rate at 6 months was 60%. The CAR-T product from Kite Pharmaceuticals (KTE-C19, axicabtagene ciloleucel) was granted breakthrough designation for diffuse large B-cell lymphoma (DLBLC), transformed follicular lymphoma (TFL), and primary mediastinal B-cell lymphoma (PMBCL). In the Kite ZUMA-3 phase II trial of KTE-C19 in r/r ALL, a 73% CR was reported (at 2 months or greater). Whether antibody of CAR-T therapies are utilized, there are still a significant number of patients who are not helped by these therapies, and there is considerable room for improved therapeutic approaches.

Chimeric Antigen Receptors (CARs) are hybrid molecules comprising three essential units: (1) an extracellular antigen-binding motif, (2) linking/transmembrane motifs, and (3) intracellular T-cell signaling motifs (Long A H, Haso W M, Orentas R J. Lessons learned from a highly-active CD22-specific chimeric antigen receptor. Oncoimmunology. 2013; 2 (4):e23621). The antigen-binding motif of a CAR is commonly fashioned after an single chain Fragment variable (ScFv), the minimal binding domain of an immunoglobulin (Ig) molecule. Alternate antigen-binding motifs, such as receptor ligands (i.e., IL-13 has been engineered to bind tumor expressed IL-13 receptor), intact immune receptors, library-derived peptides, and innate immune system effector molecules (such as NKG2D) also have been engineered. Alternate cell targets for CAR expression (such as NK or gamma-delta T cells) are also under development (Brown C E et al. Clin Cancer Res. 2012; 18(8):2199-209; Lehner M et al. PLoS One. 2012; 7 (2):e31210). There remains significant work to be done with regard to defining the most active T-cell population to transduce with CAR vectors, determining the optimal culture and expansion techniques, and defining the molecular details of the CAR protein structure itself.

The linking motifs of a CAR can be a relatively stable structural domain, such as the constant domain of IgG, or designed to be an extended flexible linker. Structural motifs, such as those derived from IgG constant domains, can be used to extend the ScFv binding domain away from the T-cell plasma membrane surface. This may be important for some tumor targets where the binding domain is particularly close to the tumor cell surface membrane (such as for the disialoganglioside GD2; Orentas et al., unpublished observations). To date, the signaling motifs used in CARs always include the CD3-ζ chain because this core motif is the key signal for T cell activation. The first reported second-generation CARs featured CD28 signaling domains and the CD28 transmembrane sequence. This motif was used in third-generation CARs containing CD137 (4-1BB) signaling motifs as well (Zhao Y et al. J Immunol. 2009; 183 (9): 5563-74). With the advent of new technology, the activation of T cells with beads linked to anti-CD3 and anti-CD28 antibody, and the presence of the canonical "signal 2" from CD28 was no longer required to be encoded by the CAR itself. Using bead activation, third-generation vectors were found to be not superior to second-generation vectors in in vitro assays, and they provided no clear benefit over second-generation vectors in mouse models of leukemia (Haso W, Lee D W, Shah N N, Stetler-Stevenson M, Yuan C M, Pastan I H, Dimitrov D S, Morgan R A, FitzGerald D J, Barrett D M, Wayne A S, Mackall C L, Orentas R J. Anti-CD22-chimeric antigen receptors targeting B cell precursor acute lymphoblastic leukemia, Blood. 2013; 121 (7):1165-74; Kochenderfer J N et al. Blood. 2012; 119 (12):2709-20). This is borne out by the clinical success of CD19-specific CARs that are in a second generation CD28/CD3-ζ (Lee D W et al. American Society of Hematology Annual Meeting. New Orleans, La.; Dec. 7-10, 2013) and a CD137/CD3-signaling format (Porter D L et al. N Engl J Med. 2011; 365 (8): 725-33). In addition to CD137, other tumor necrosis factor receptor superfamily members such as OX40 also are able to provide important persistence signals in CAR-transduced T cells (Yvon E et al. Clin Cancer Res. 2009; 15(18):5852-60). Equally important are the culture conditions under which the CAR T-cell populations were cultured, for example the inclusion of the cytokines IL-2, IL-7, and/or IL-15 (Kaiser A D et al. Cancer Gene Ther. 2015; 22(2):72-78).

Current challenges in the more widespread and effective adaptation of CAR therapy for cancer relate to a paucity of compelling targets. Creating binders to cell surface antigens is now readily achievable, but discovering a cell surface antigen that is specific for tumor while sparing normal tissues remains a formidable challenge. One potential way to imbue greater target cell specificity to CAR-expressing T cells is to use combinatorial CAR approaches. In one system, the CD3- and CD28 signal units are split between two different CAR constructs expressed in the same cell; in another, two CARs are expressed in the same T cell, but one has a lower affinity and thus requires the alternate CAR to be engaged first for full activity of the second (Lanitis E et al. Cancer Immunol Res. 2013; 1(1):43-53; Kloss C C et al. Nat Biotechnol. 2013; 31(1):71-5). A second challenge for the generation of a single ScFv-based CAR as an immunotherapeutic agent is tumor cell heterogeneity. At least one group has developed a CAR strategy for glioblastoma whereby the effector cell population targets multiple antigens (HER2, IL-13Ra, EphA2) at the same time in the hope of avoiding the outgrowth of target antigen-negative populations. (Hegde M et al. Mol Ther. 2013; 21(11):2087-101).

T-cell-based immunotherapy has become a new frontier in synthetic biology; multiple promoters and gene products are envisioned to steer these highly potent cells to the tumor microenvironment, where T cells can both evade negative regulatory signals and mediate effective tumor killing. The elimination of unwanted T cells through the drug-induced dimerization of inducible caspase 9 constructs with chemical-based dimerizers, such as AP1903, demonstrates one way in which a powerful switch that can control T-cell populations can be initiated pharmacologically (Di Stasi A et al. N Engl J Med. 2011; 365(18):1673-83). The creation of effector T-cell populations that are immune to the negative regulatory effects of transforming growth factor-β by the expression of a decoy receptor further demonstrates the degree to which effector T cells can be engineered for optimal antitumor activity (Foster A E et al. J Immunother. 2008; 31(5):500-5). Thus, while it appears that CARs can trigger T-cell activation in a manner similar to an endogenous T-cell receptor, a major impediment to the clinical application of this technology to date has been limited in vivo expansion of CAR+ T cells, rapid disappearance of the cells after infusion, and disappointing clinical activity. This may be due in part to the murine origin of some of the CAR sequences employed.

The use of Blinotumomab (bi-specific anti-CD19 and anti-CD3 antibody) has shown impressive results for the gravely ill patients who have received this therapy. Nevertheless the durable remission rate is less than 40%, and at best only 50% of responders can be salvaged to hematopoietic stem cell transplant (HSCT) (see Gore et al., 2014, NCT01471782 and Von Stackelberg, et al., 2014, NCT01471782, summarized in: Benjamin, J E, Stein A S, 2016, Therapeutic Advances in Hematology 7:142-156). The requirement of patients who have received either bi-specific antibody or CAR-T therapy to subsequently undergo HSCT in order to maintain durable responses remains an area of active debate. Although high responses are reported for CD19 CAR-T trials, some even greater than 90%, if the trials are re-cast as "intent to treat" trials the number may be closer to 70% (Davis K L, Mackall C L, 2016, Blood Advances 1:265-268). The best results at 12 months post-CAR19 treatment reported show a RFS of 55% and O S of 79% in patients who were able to receive the T cell product at the University of Pennsylvania (Maude S L, Teachey D T, Rheingold S R, Shaw P A, Aplenc R, Barrett D M, Barker C S, Callahan C, Frey N V, Farzana N, Lacey S F, Zheng A, Levine B, Melenhorst J J, Motley L, Prter D L, June C H, Grupp S A, 2016, J Clin Oncol 34, no15_suppl (May 2016) 3011-3011).

Accordingly, there is an urgent and long felt need in the art for discovering novel compositions and methods for treatment of B-ALL and other CD19 and/or CD22-expressing B cell malignancies using an approach that can exhibit specific and efficacious anti-tumor effect without the aforementioned short comings.

The present invention addresses these needs by providing CAR compositions and therapeutic methods that can be used to treat cancers and other diseases and/or conditions. In particular, the present invention as disclosed and described herein provides CARs that may be used for the treatment of diseases, disorders or conditions associated with dysregulated expression of CD19 and/or CD22 and which CARs contain tandem CD19/CD22 antigen binding domains that exhibit a high surface expression on transduced T cells, exhibit a high degree of cytolysis of CD19-expressing cells, and in which the transduced T cells demonstrate in vivo expansion and persistence.

SUMMARY

Novel tandem CD19 and CD22-targeting antibodies or antigen binding domains thereof in which the CD19 targeting moiety is positioned either before or after the CD22 targeting moiety in the amino acid sequence (hereinafter termed "CD19/CD22"), and chimeric antigen receptors (tandem CARs) that contain such CD19 and/or CD22 antigen binding domains are provided herein, as well as host cells (e.g., T cells) expressing the receptors, and nucleic acid molecules encoding the receptors. The CARs exhibit a high surface expression on transduced T cells, with a high degree of cytolysis, and with transduced T cell expansion and persistence in vivo. Methods of using the disclosed CARs, host cells, and nucleic acid molecules are also provided, for example, to treat a cancer in a subject.

In one aspect, an isolated nucleic acid molecule encoding a tandem CD19/CD22 chimeric antigen receptor (CAR) is provided comprising, from N-terminus to C-terminus, at least one CD19/CD22 antigen binding domain, at least one transmembrane domain, and at least one intracellular signaling domain, wherein the tandem CD19/CD22 CAR comprises a nucleic acid sequence selected from the group consisting of SEQ ID NOs: 1, 3, 60, 62, 64, 66, 68, 70, 72, 74, 76, 78, 80, and 82.

In one aspect, an isolated nucleic acid molecule encoding a tandem CD19/CD22 chimeric antigen receptor (CAR) is provided comprising, from N-terminus to C-terminus, at least one CD19/CD22 antigen binding domain, at least one transmembrane domain, and at least one intracellular signaling domain, wherein the tandem CD19/CD22 CAR encoded by the nucleic acid sequence selected from the group consisting of SEQ ID NOs: 1, 3, 60, 62, 64, 66, 68, 70, 72, 74, 76, 78, 80, and 82 encodes a tandem CD19/CD22 CAR comprising the amino acid sequence selected from the group consisting of SEQ ID NO. 2, 4, 61, 63, 65, 67, 69, 71, 73, 75, 77, 79, 81, and 83.

In one embodiment, an isolated nucleic acid molecule encoding the CAR is provided wherein the encoded extracellular CD19/CD22 antigen binding domain comprises at least one single chain variable fragment of an antibody that binds to CD19/CD22.

In another embodiment, an isolated nucleic acid molecule encoding the CAR is provided wherein the encoded extracellular CD19/CD22 antigen binding domain comprises at least one heavy chain variable region of an antibody that binds to CD19/CD22.

In yet another embodiment, an isolated nucleic acid molecule encoding the CAR is provided wherein the encoded CAR extracellular CD19/CD22 antigen binding domain further comprises at least one lipocalin-based antigen binding antigen (anticalins) that binds to CD19/CD22.

In one embodiment, an isolated nucleic acid molecule is provided wherein the encoded extracellular CD19/CD22 antigen binding domain is connected to the transmembrane domain by a linker domain.

In another embodiment, an isolated nucleic acid molecule encoding the CAR is provided wherein the encoded CD19/CD22 extracellular antigen binding domain is preceded by a sequence encoding a leader or signal peptide.

In yet another embodiment, an isolated nucleic acid molecule encoding the CAR is provided comprising at least one CD19/CD22 antigen binding domain encoded by a nucleotide sequence comprising a CD19/CD22 nucleotide sequence contained within SEQ ID Nos: 1, 3, 60, 62, 64, 66, 68, 70, 72, 74, 76, 78, 80, and 82, respectively, and wherein the CAR additionally encodes an extracellular antigen binding domain targets an antigen that includes, but is not limited to, CD22, ROR1, mesothelin, CD33, CD38, CD123 (IL3RA), CD138, BCMA (CD269), GPC2, GPC3, FGFR4, c-Met, PSMA, Glycolipid F77, EGFrvIII, GD-2, TSLPR, NY-ESO-1 TCR, MAGE A3 TCR, or any combination thereof.

In one embodiment, the CAR construct is comprised of two CAR chains co-expressed in the same cell via a 2A ribosomal skip element, one CAR chain comprises a targeting domain directed toward CD19 antigen, and another CAR chain comprises a CAR targeting domain directed toward CD22 antigen. Fused in frame to the targeting domain, each chain comprises a hinge/linker/spacer domain, a transmembrane domain, and a CD3z activation domain. None, one or more co-stimulatory domains may be included in frame in each CAR chain.

In one embodiment, the CAR chain comprises two co-stimulatory domains linked sequentially (a third generation CAR).

In certain embodiments, an isolated nucleic acid molecule encoding the CAR is provided wherein the additionally encoded extracellular antigen binding domain comprises an anti-CD22 ScFv antigen binding domain, an anti-ROR1 ScFv antigen binding domain, an anti-mesothelin ScFv antigen binding domain, an anti-CD33 ScFv antigen binding domain, an anti-CD38 ScFv antigen binding domain, an anti-CD123 (IL3RA) ScFv antigen binding domain, an anti-CD138 ScFv antigen binding domain, an anti-BCMA (CD269) ScFv antigen binding domain, an anti-GPC2 ScFv antigen binding domain, an anti-GPC3 ScFv antigen binding domain, an anti-FGFR4 ScFv antigen binding domain, an anti-TSLPR ScFv antigen binding domain an anti-c-Met ScFv antigen binding domain, an anti-PMSA ScFv antigen binding domain, an anti-glycolipid F77 ScFv antigen binding domain, an anti-EGFRvIII ScFv antigen binding domain, an anti-GD-2 ScFv antigen binding domain, an anti-NY-ESO-1 TCR ScFv antigen binding domain, an anti-MAGE A3 TCR ScFv antigen binding domain, or an amino acid sequence with 85%, 90%, 95%, 96%, 97%, 98% or 99% identity thereof, or any combination thereof.

In one aspect, the CARs provided herein further comprise a linker or spacer domain.

In one embodiment, an isolated nucleic acid molecule encoding the CAR is provided wherein the extracellular CD19/CD22 antigen binding domain, the intracellular signaling domain, or both are connected to the transmembrane domain by a linker or spacer domain.

In one embodiment, an isolated nucleic acid molecule encoding the CAR is provided wherein the encoded linker domain is derived from the extracellular domain of CD8 or CD28, and is linked to a transmembrane domain.

In another embodiment, an isolated nucleic acid molecule encoding the CAR is provided wherein the encoded CAR further comprises a transmembrane domain that comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD83, CD86, CD134, CD137 and CD154, or a combination thereof.

In yet another embodiment, an isolated nucleic acid molecule encoding the CAR is provided wherein the encoded intracellular signaling domain further comprises a CD3 zeta intracellular domain.

In one embodiment, an isolated nucleic acid molecule encoding the CAR is provided wherein the encoded intracellular signaling domain is arranged on a C-terminal side relative to the CD3 zeta intracellular domain.

In another embodiment, an isolated nucleic acid molecule encoding the CAR is provided wherein the encoded at least one intracellular signaling domain comprises a costimulatory domain, a primary signaling domain, or a combination thereof.

In further embodiments, an isolated nucleic acid molecule encoding the CAR is provided wherein the encoded at least one costimulatory domain comprises a functional signaling domain of OX40, CD70, CD27, CD28, CD5, ICAM-1, LFA-1 (CD11a/CD18), ICOS (CD278), DAP10, DAP12, and 4-1BB (CD137), or a combination thereof.

In one embodiment, an isolated nucleic acid molecule encoding the CAR is provided that further contains a leader sequence or signal peptide wherein the leader or signal peptide nucleotide sequence comprises the nucleotide sequence of SEQ ID NO: 11.

In yet another embodiment, an isolated nucleic acid molecule encoding the CAR is provided wherein the encoded leader sequence comprises the amino acid sequence of SEQ ID NO: 12.

In one aspect, a chimeric antigen receptor (CAR) is provided herein comprising, from N-terminus to C-terminus, at least one CD19/CD22 antigen binding domain, at least one transmembrane domain, and at least one intracellular signaling domain.

In one embodiment, a CAR is provided wherein the extracellular CD19/CD22 antigen binding domain comprises at least one single chain variable fragment of an antibody that binds to the antigen, or at least one heavy chain variable region of an antibody that binds to the antigen, or a combination thereof.

In another embodiment, a CAR is provided wherein the at least one transmembrane domain comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, TNFRSF19, or a combination thereof.

In some embodiments, the CAR is provided wherein CAR additionally encodes an extracellular antigen binding domain comprising CD22, ROR1, mesothelin, CD33, CD38, CD123 (IL3RA), CD138, BCMA (CD269), GPC2, GPC3, FGFR4, TSLPR, c-Met, PSMA, Glycolipid F77, EGFRvIII, GD-2, TSLPR, NY-ESO-1 TCR, MAGE A3 TCR, or an amino acid sequence with 85%, 90%, 95%, 96%, 97%, 98% or 99% identity thereof, or any combination thereof.

In one embodiment, the CAR is provided wherein the extracellular antigen binding domain comprises an anti-CD22 ScFv antigen binding domain, an anti-ROR1 ScFv antigen binding domain, an anti-mesothelin ScFv antigen binding domain, an anti-CD33 ScFv antigen binding domain, an anti-CD38 ScFv antigen binding domain, an anti-CD123 (IL3RA) ScFv antigen binding domain, an anti-CD138 ScFv antigen binding domain, an anti-BCMA (CD269) ScFv antigen binding domain, an anti-GPC2 ScFv antigen binding domain, an anti-GPC3 ScFv antigen binding domain, an anti-FGFR4 ScFv antigen binding domain, anti-TSLPR ScFv antigen binding domain, an anti-c-Met ScFv antigen binding domain, an anti-PMSA ScFv antigen binding domain, an anti-glycolipid F77 ScFv antigen binding domain, an anti-EGFRvIII ScFv antigen binding domain, an anti-GD-2 ScFv antigen binding domain, an anti-NY-ESO-1 TCR ScFv antigen binding domain, an anti-MAGE A3 TCR ScFv antigen binding domain, or an amino acid sequence with 85%, 90%, 95%, 96%, 97%, 98% or 99% identity thereof, or any combination thereof.

In another embodiment, a CAR is provided wherein the at least one intracellular signaling domain comprises a costimulatory domain and a primary signaling domain.

In yet another embodiment, a CAR is provided wherein the at least one intracellular signaling domain comprises a costimulatory domain comprising a functional signaling domain of a protein selected from the group consisting of OX40, CD70, CD27, CD28, CD5, ICAM-1, LFA-1 (CD11a/CD18), ICOS (CD278), DAP10, DAP12, and 4-1BB (CD137), or a combination thereof.

In one embodiment, the nucleic acid sequence encoding a CAR comprises the nucleic acid sequence of SEQ ID NO: 1.

In one embodiment, the nucleic acid sequence encodes a CAR comprising the amino acid sequence of SEQ ID NO: 2.

In another embodiment, the nucleic acid sequence encoding a CAR comprises the nucleic acid sequence of SEQ ID NO: 3.

In one embodiment, the nucleic acid sequence encodes a CAR comprising the amino acid sequence of SEQ ID NO: 4.

In one embodiment, the nucleic acid sequence encoding a CAR comprises the nucleic acid sequence of SEQ ID NO: 60.

In one embodiment, the nucleic acid sequence encodes a CAR comprising the amino acid sequence of SEQ ID NO: 61.

In one embodiment, the nucleic acid sequence encoding a CAR comprises the nucleic acid sequence of SEQ ID NO: 62.

In one embodiment, the nucleic acid sequence encodes a CAR comprising the amino acid sequence of SEQ ID NO: 63.

In one embodiment, the nucleic acid sequence encoding a CAR comprises the nucleic acid sequence of SEQ ID NO: 64.

In one embodiment, the nucleic acid sequence encodes a CAR comprising the amino acid sequence of SEQ ID NO: 65.

In one embodiment, the nucleic acid sequence encoding a CAR comprises the nucleic acid sequence of SEQ ID NO: 66.

In one embodiment, the nucleic acid sequence encodes a CAR comprising the amino acid sequence of SEQ ID NO: 67.

In one embodiment, the nucleic acid sequence encoding a CAR comprises the nucleic acid sequence of SEQ ID NO: 68.

In one embodiment, the nucleic acid sequence encodes a CAR comprising the amino acid sequence of SEQ ID NO: 69.

In one embodiment, the nucleic acid sequence encoding a CAR comprises the nucleic acid sequence of SEQ ID NO: 70.

In one embodiment, the nucleic acid sequence encodes a CAR comprising the amino acid sequence of SEQ ID NO: 71.

In one embodiment, the nucleic acid sequence encoding a CAR comprises the nucleic acid sequence of SEQ ID NO: 72.

In one embodiment, the nucleic acid sequence encodes a CAR comprising the amino acid sequence of SEQ ID NO: 73.

In one embodiment, the nucleic acid sequence encoding a CAR comprises the nucleic acid sequence of SEQ ID NO: 74.

In one embodiment, the nucleic acid sequence encodes a CAR comprising the amino acid sequence of SEQ ID NO: 75.

In one embodiment, the nucleic acid sequence encoding a CAR comprises the nucleic acid sequence of SEQ ID NO: 76.

In one embodiment, the nucleic acid sequence encodes a CAR comprising the amino acid sequence of SEQ ID NO: 77.

In one embodiment, the nucleic acid sequence encoding a CAR comprises the nucleic acid sequence of SEQ ID NO: 78.

In one embodiment, the nucleic acid sequence encodes a CAR comprising the amino acid sequence of SEQ ID NO: 79.

In one embodiment, the nucleic acid sequence encoding a CAR comprises the nucleic acid sequence of SEQ ID NO: 80.

In one embodiment, the nucleic acid sequence encodes a CAR comprising the amino acid sequence of SEQ ID NO: 81.

In one embodiment, the nucleic acid sequence encoding a CAR comprises the nucleic acid sequence of SEQ ID NO: 82.

In one embodiment, the nucleic acid sequence encodes a CAR comprising the amino acid sequence of SEQ ID NO: 83.

In one aspect, the CARs disclosed herein are modified to express or contain a detectable marker for use in diagnosis, monitoring, and/or predicting the treatment outcome such as progression free survival of cancer patients or for monitoring the progress of such treatment.

In one embodiment, the nucleic acid molecule encoding the disclosed CARs can be contained in a vector, such as a viral vector. The vector is a DNA vector, an RNA vector, a plasmid vector, a cosmid vector, a herpes virus vector, a measles virus vector, a lentivirus vector, adenoviral vector, or a retrovirus vector, or a combination thereof.

In certain embodiments, the vector further comprises a promoter wherein the promoter is an inducible promoter, a tissue specific promoter, a constitutive promoter, a suicide promoter or any combination thereof.

In yet another embodiment, the vector expressing the CAR can be further modified to include one or more operative elements to control the expression of CAR T cells, or to eliminate CAR-T cells by virtue of a suicide switch. The suicide switch can include, for example, an apoptosis inducing signaling cascade or a drug that induces cell death. In a preferred embodiment, the vector expressing the CAR can be further modified to express an enzyme such thymidine kinase (TK) or cytosine deaminase (CD).

In another aspect, host cells including the nucleic acid molecule encoding the CAR are also provided. In some embodiments, the host cell is a T cell, such as a primary T cell obtained from a subject. In one embodiment, the host cell is a CD8$^+$ T cell.

In yet another aspect, a pharmaceutical composition is provided comprising an anti-tumor effective amount of a population of human T cells, wherein the T cells comprise a nucleic acid sequence that encodes a chimeric antigen receptor (CAR) comprising the amino acid sequence of SEQ ID NO. 2, 4, 61, 63, 65, 67, 69, 71, 73, 75, 77, 79, 81, and 83, wherein the CAR comprises at least one extracellular antigen binding domain comprising a CD19/CD22 antigen binding domain, at least one linker domain, at least one transmembrane domain, and at least one intracellular signaling domain, wherein the T cells are T cells of a human having a cancer. The cancer includes, inter alia, a hematological cancer such as leukemia (e.g., chronic lymphocytic leukemia (CLL), acute lymphocytic leukemia (ALL), or chronic myelogenous leukemia (CML), lymphoma (e.g., mantle cell lymphoma, non-Hodgkin's lymphoma or Hodgkin's lymphoma) or multiple myeloma, or a combination thereof.

In one embodiment, a pharmaceutical composition is provided wherein the at least one transmembrane domain of the CAR contains a transmembrane domain of a protein selected from the group consisting of the alpha, beta or zeta chain of the T-cell receptor, CD28, CD3 epsilon, CD45, CD4, CD5, CD8, CD9, CD16, CD22, Mesothelin, CD33, CD37, CD64, CD80, CD83, CD86, CD134, CD137, CD154, TNFRSF19, or a combination thereof.

In another embodiment, a pharmaceutical composition is provided wherein the human cancer includes an adult carcinoma comprising oral and pharynx cancer (tongue, mouth, pharynx, head and neck), digestive system cancers (esophagus, stomach, small intestine, colon, rectum, anus, liver, interhepatic bile duct, gallbladder, pancreas), respiratory system cancers (larynx, lung and bronchus), bones and joint cancers, soft tissue cancers, skin cancers (melanoma, basal and squamous cell carcinoma), pediatric tumors (neuroblastoma, rhabdomyosarcoma, osteosarcoma, Ewing's sarcoma), tumors of the central nervous system (brain, astrocytoma, glioblastoma, glioma), and cancers of the breast, the genital system (uterine cervix, uterine corpus, ovary, vulva, vagina, prostate, testis, penis, endometrium), the urinary system (urinary bladder, kidney and renal pelvis, ureter), the eye and orbit, the endocrine system (thyroid), and the brain and other nervous system, or any combination thereof.

In yet another embodiment, a pharmaceutical composition is provided comprising an anti-tumor effective amount of a population of human T cells of a human having a cancer wherein the cancer is a refractory cancer non-responsive to one or more chemotherapeutic agents. The cancer includes hematopoietic cancer, myelodysplastic syndrome pancreatic cancer, head and neck cancer, cutaneous tumors, minimal residual disease (MRD) in acute lymphoblastic leukemia (ALL), acute myeloid leukemia (AML), adult B cell malignancies including, CLL (Chronic lymphocytic leukemia), CML (chronic myelogenous leukemia), non-Hodgkin's lymphoma (NHL), pediatric B cell malignancies (including B lineage ALL (acute lymphocytic leukemia)), multiple myeloma lung cancer, breast cancer, ovarian cancer, prostate cancer, colon cancer, melanoma or other hematological cancer and solid tumors, or any combination thereof.

In another aspect, methods of making CAR-containing T cells (hereinafter "CAR-T cells") are provided. The methods include transducing a T cell with a vector or nucleic acid molecule encoding a disclosed CAR that specifically binds CD19 and/or CD22, thereby making the CAR-T cell.

In yet another aspect, a method of generating a population of RNA-engineered cells is provided that comprises introducing an in vitro transcribed RNA or synthetic RNA of a nucleic acid molecule encoding a disclosed CAR into a cell of a subject, thereby generating a CAR cell.

In one embodiment, the disease, disorder or condition associated with the expression of CD19 is cancer including hematopoietic cancer, myelodysplastic syndrome pancreatic cancer, head and neck cancer, cutaneous tumors, minimal residual disease (MRD) in acute lymphoblastic leukemia (ALL), acute myeloid leukemia (AML), adult B cell malignancies including, CLL (Chronic lymphocytic leukemia), CML (chronic myelogenous leukemia), non-Hodgkin's lymphoma (NHL), pediatric B cell malignancies (including B lineage ALL (acute lymphocytic leukemia)), multiple myeloma lung cancer, breast cancer, ovarian cancer, prostate cancer, colon cancer, melanoma or other hematological cancer and solid tumors, or any combination thereof.

In another embodiment, a method of blocking T-cell inhibition mediated by a CD19- and/or CD22 expressing cell and altering the tumor microenvironment to inhibit tumor growth in a mammal, is provided comprising administering to the mammal an effective amount of a composition comprising a CAR comprising the amino acid sequence selected from the group consisting of SEQ ID NOs: 2, 4, 61, 63, 65, 67, 69, 71, 73, 75, 77, 79, 81, and 83. In one embodiment, the cell is selected from the group consisting of a CD19 and/or CD22-expressing tumor cell, a tumor-associated macrophage, and any combination thereof.

In another embodiment, a method of inhibiting, suppressing or preventing immunosuppression of an anti-tumor or anti-cancer immune response in a mammal, is provided comprising administering to the mammal an effective amount of a composition comprising a CAR selected from the group consisting of SEQ ID NOs: 2, 4, 61, 63, 65, 67, 69, 71, 73, 75, 77, 79, 81, and 83. In one embodiment, the CAR inhibits the interaction between a first cell with a T cell, wherein the first cell is selected from the group consisting of a CD19 and/or CD22-expressing tumor cell, a tumor-associated macrophage, and any combination thereof.

In another aspect, a method is provided for inducing an anti-tumor immunity in a mammal comprising administering to the mammal a therapeutically effective amount of a T cell transduced with vector or nucleic acid molecule encoding a disclosed CAR.

In another embodiment, a method of treating or preventing cancer in a mammal is provided comprising administering to the mammal one or more of the disclosed CARs, in an amount effective to treat or prevent cancer in the mammal. The method includes administering to the subject a therapeutically effective amount of host cells expressing a disclosed CAR that specifically binds CD19 and/or CD22 and/or one or more of the aforementioned antigens, under conditions sufficient to form an immune complex of the antigen binding domain on the CAR and the extracellular domain of CD19 and/or CD22 and/or one or more of the aforementioned antigens in the subject.

In yet another embodiment, a method is provided for treating a mammal having a disease, disorder or condition associated with an elevated expression of a tumor antigen, the method comprising administering to the subject a pharmaceutical composition comprising an anti-tumor effective amount of a population of T cells, wherein the T cells comprise a nucleic acid sequence that encodes a chimeric antigen receptor (CAR), wherein the CAR includes at least one extracellular CD19 and/or CD22 antigen binding domain, or any combination thereof, at least one linker or spacer domain, at least one transmembrane domain, at least one intracellular signaling domain, and wherein the T cells are T cells of the subject having cancer.

In yet another embodiment, a method is provided for treating cancer in a subject in need thereof comprising administering to the subject a pharmaceutical composition comprising an anti-tumor effective amount of a population of T cells, wherein the T cells comprise a nucleic acid sequence that encodes a chimeric antigen receptor (CAR), wherein the CAR comprises the amino acid sequence of SEQ ID NOs. 2, 4, 61, 63, 65, 67, 69, 71, 73, 75, 77, 79, 81, and 83, or any combination thereof, wherein the T cells are T cells of the subject having cancer. In some embodiments of the aforementioned methods, the at least one transmembrane domain comprises a transmembrane the alpha, beta or zeta chain of the T-cell receptor, CD28, CD3 epsilon, CD45, CD4, CD5, CD8, CD9, CD16, CD19, CD22, Mesothelin, CD33, CD37, CD64, CD80, CD83, CD86, CD134, CD137, CD154, TNFRSF16, TNFRSF19, or a combination thereof.

In yet another embodiment, a method is provided for generating a persisting population of genetically engineered T cells in a human diagnosed with cancer. In one embodiment, the method comprises administering to a human a T cell genetically engineered to express a CAR wherein the CAR comprises the amino acid sequence of SEQ ID NOs. 2, 4, 61, 63, 65, 67, 69, 71, 73, 75, 77, 79, 81, and 83, or any combination thereof, at least one transmembrane domain, and at least one intracellular signaling domain wherein the persisting population of genetically engineered T cells, or the population of progeny of the T cells, persists in the human for at least one month, two months, three months, four months, five months, six months, seven months, eight months, nine months, ten months, eleven months, twelve months, two years, or three years after administration.

In one embodiment, the progeny T cells in the human comprise a memory T cell. In another embodiment, the T cell is an autologous T cell.

In all of the aspects and embodiments of methods described herein, any of the aforementioned cancers, diseases, disorders or conditions associated with an elevated expression of a tumor antigen that may be treated or prevented or ameliorated using one or more of the CARs disclosed herein.

In yet another aspect, a kit is provided for making a chimeric antigen receptor T-cell as described supra or for preventing, treating, or ameliorating any of the cancers, diseases, disorders or conditions associated with an elevated expression of a tumor antigen in a subject as described supra, comprising a container comprising any one of the nucleic acid molecules, vectors, host cells, or compositions disclosed supra or any combination thereof, and instructions for using the kit.

It will be understood that the CARs, host cells, nucleic acids, and methods are useful beyond the specific aspects and embodiments that are described in detail herein. The foregoing features and advantages of the disclosure will become more apparent from the following detailed description, which proceeds with reference to the accompanying figures.

BRIEF DESCRIPTION OF THE FIGURES

FIG. 1A: The anti-CD22 and anti-CD19 dual targeting CAR construct (CAR22-19) was generated by linking single chain fragment variable sequence targeting the CD22 antigen membrane distal domain to a single chain fragment variable sequence targeting the CD19 antigen (membrane proximal) via a flexible glycine-serine linker. The resulting CD22-CD19 dual targeting domain was then connected in frame to CD8 hinge and transmembrane domain, the 4-1BB (CD137) signaling domain and the CD3 zeta signaling domain. FIG. 1B: Tandem targeting constructs CAR19-22 was generated in a similar manner, except that the single chain fragment variable regions of CD19 (distal to cell membrane) was linked via glycine serine flexible linker to a single chain variable region of CD22 targeting sequence (membrane proximal), followed by CD8, 4-1BB and CD3 zeta domains. Each CAR T construct is capable of activation via binding to either CD19 or CD22 tumor antigens, or both.

Percentage of CAR T-positive populations in relation to non-transduced T cell control (UTD) is noted above each histogram. Representative data of three separate donors is shown.

Figure 3:
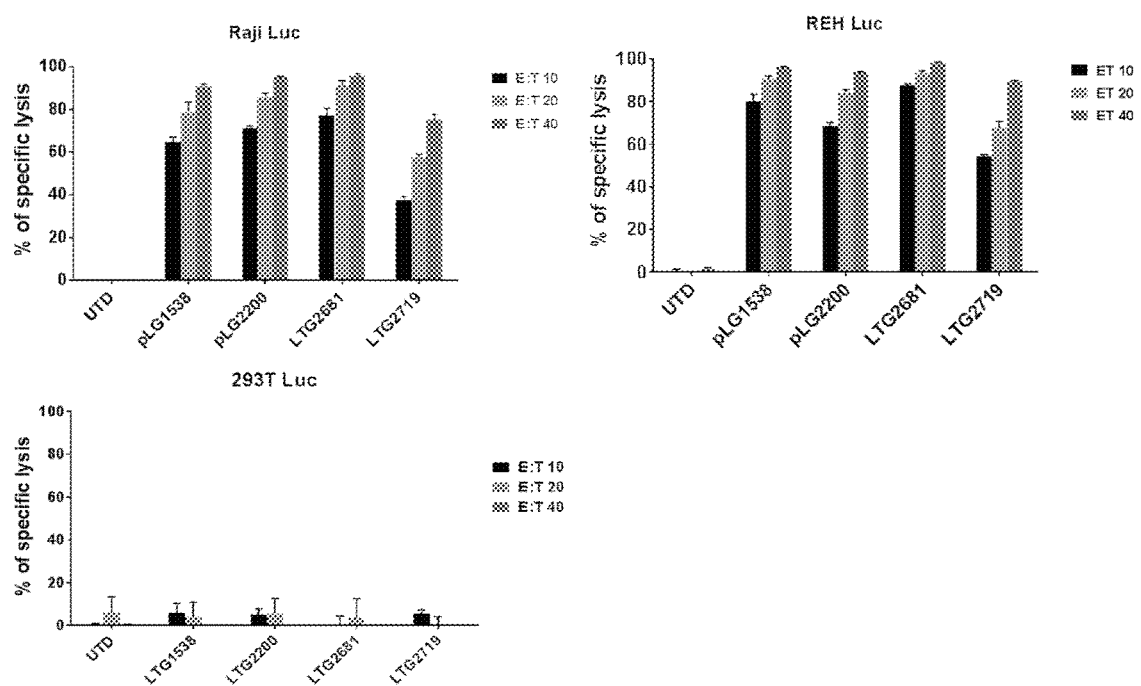

FIG. 3 depicts CAR T cytotoxicity in vitro. Luciferase-based cytotoxicity assays were performed using, Raji CD19+CD22+, REH CD19+CD22+, or CD19− CD22− cell line 293T, stably transduced with luciferase. A comparison between CAR 22-19 (LTG2681) and CAR 19-22 (LTG2719), which differ only in the order of antigen targeting domains. Comparator single-targeting CAR19 (pLTG1538) and CAR22 (pLTG2200), and negative control untransduced T cells were included. CAR T cells and target tumor cells were co-incubated overnight at the listed effector to target (E:T) ratios, x-axis. Error bars represent mean values from three technical replicates. One experiment representing three separate experiments in T cells from three donors, is shown.

Figure 4A:
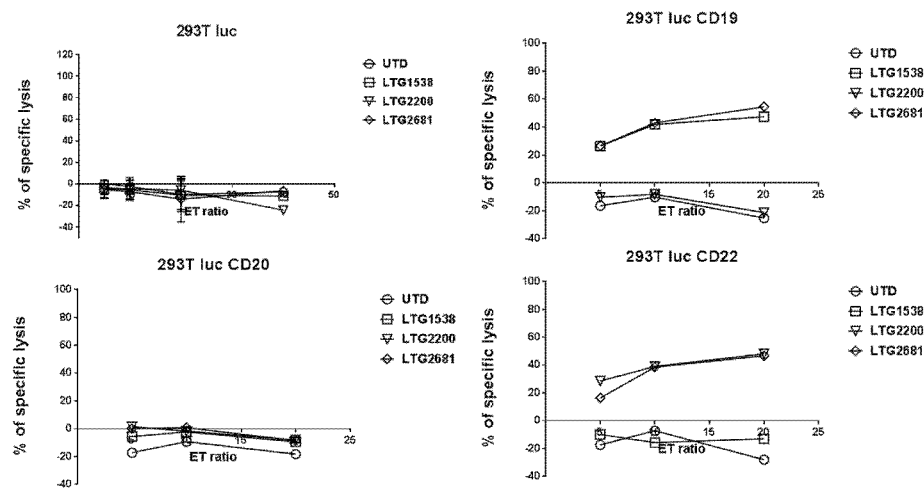
Figure 4B:
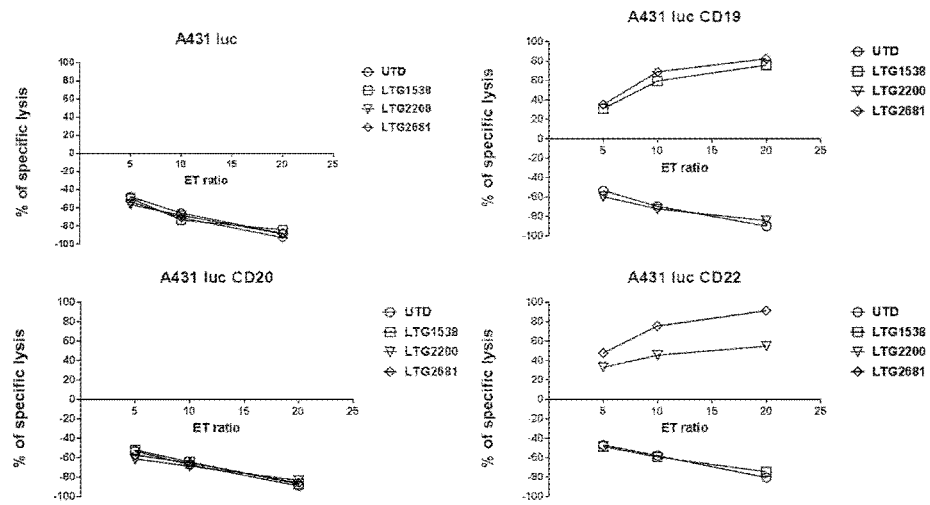

FIGS. 4A and 4B depict CAR T cytotoxicity in vitro against tumor lines A431 or 293T transduced to over express one target antigen only, in order to confirm the specificity of each binder domain of the CD22 CD19-targeting CAR T cells. Luciferase-based cytotoxicity assays were performed using, 293T cells, 293T CD19+, 293T CD20+, or 293T CD22+ cell lines (FIG. 4A), or A431, A431 CD19+, A431 CD22+, A431 CD20+ cell lines stably transduced with luciferase (FIG. 4B). Data points represent mean values from triplicate determination from one experiment, representing three independent experiments performed with CAR T cells from three separate donors.

Figure 5:
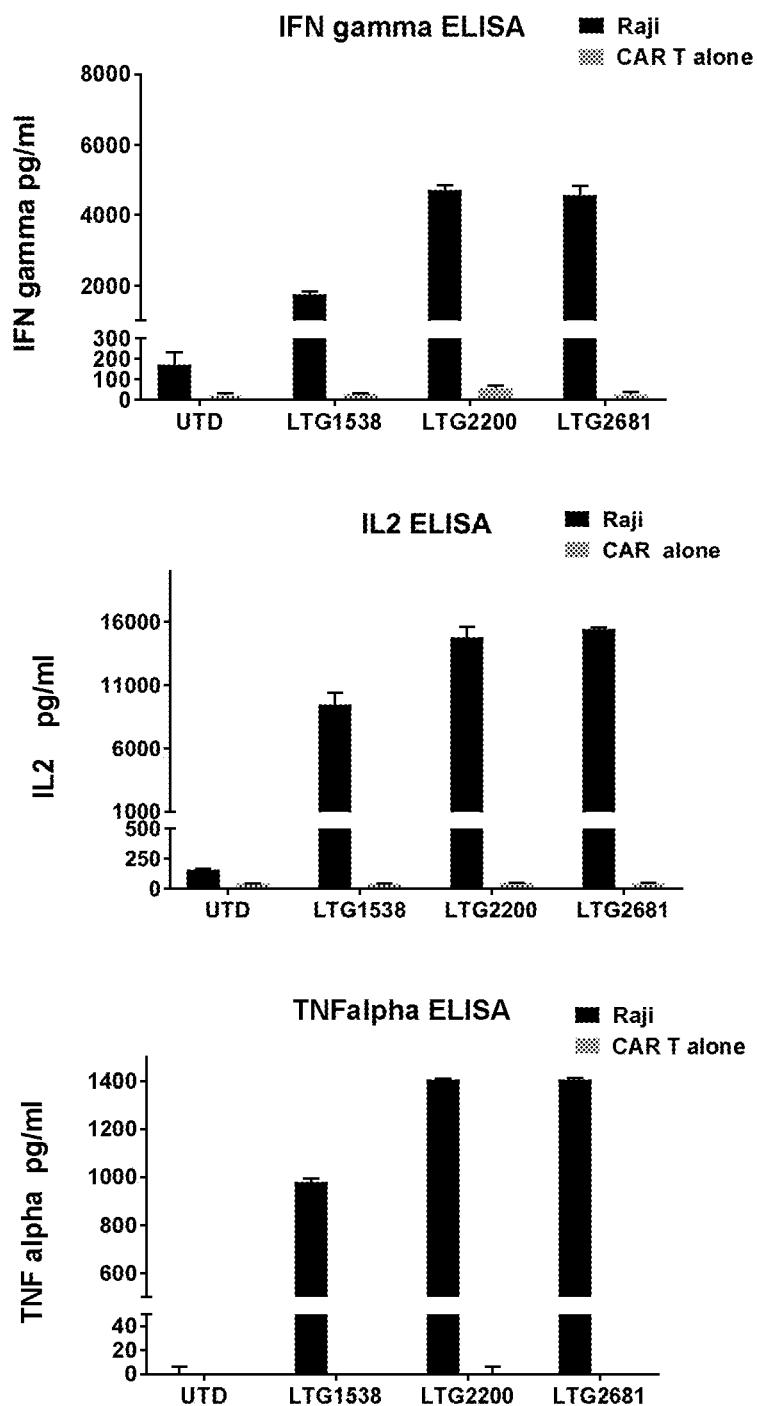

FIG. 5. CAR T cytokine release in response to leukemia cell lines. Cytokine production by CAR-T, listed on the x-axis, upon overnight co-culture with the Raji leukemia line at an E:T ratio of 10:1, was measured using ELISA. Bars represent mean+SD of three replicate samples. Data are representative of three independent experiments performed with CAR T cells from three separate donors.

FIGS. 6A-6D depict schematic representations of the various anti-CD22-19 CAR designs with different co-stimulatory domains. A second-generation CAR (FIG. 6A), third generation CAR (FIG. 6B), or bicistronic CARs combining one second generation CAR chain targeting the CD19 antigen and another first generation CAR chain targeting the CD22 antigen (FIG. 6C), or two second generation CAR chains (FIG. 6D) co-expressed in the same cell are shown. Abbreviations: scFv CAR targeting domain recognizing the CD19 antigen, a-CD22-scFv CAR targeting domain recognizing the CD22 antigen, H-hinge/linker domain, TM-transmembrane domain, Co-stim—costimulatory domain, CD3z—CD3 zeta-derived CAR activation domain, 2A—ribosomal skip element for bicistronic CAR expression.

Figure 7:
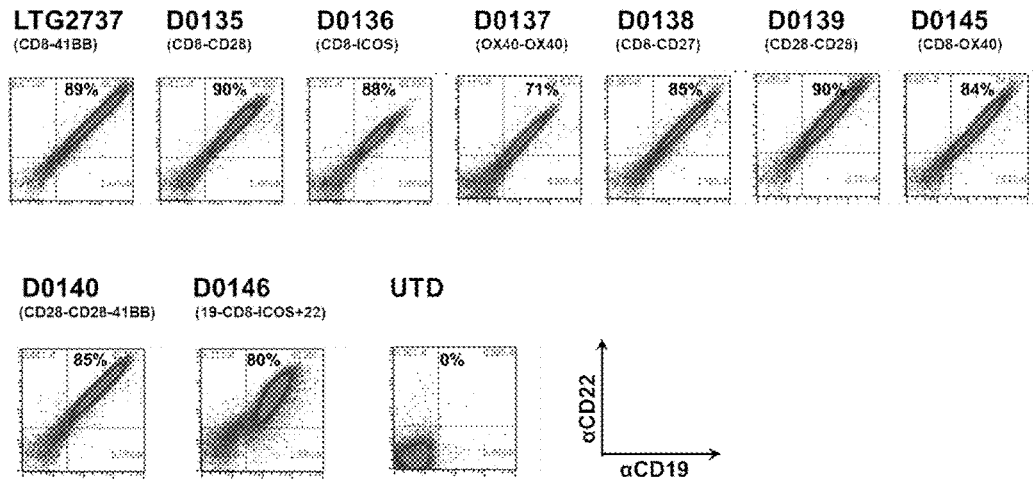

FIG. 7 depicts the expression of anti-CD22-19 CAR with different transmembrane and co-stimulatory domains as detected by flow cytometry. CAR T cells are stained for the expression of CD19 scFv and CD22 scFv simultaneously. Construct number and transmembrane and co-stimulatory domain configuration are noted above each flow diagram. Data are representative of three transduction experiments in T cells form different healthy donors.

Figure 8:
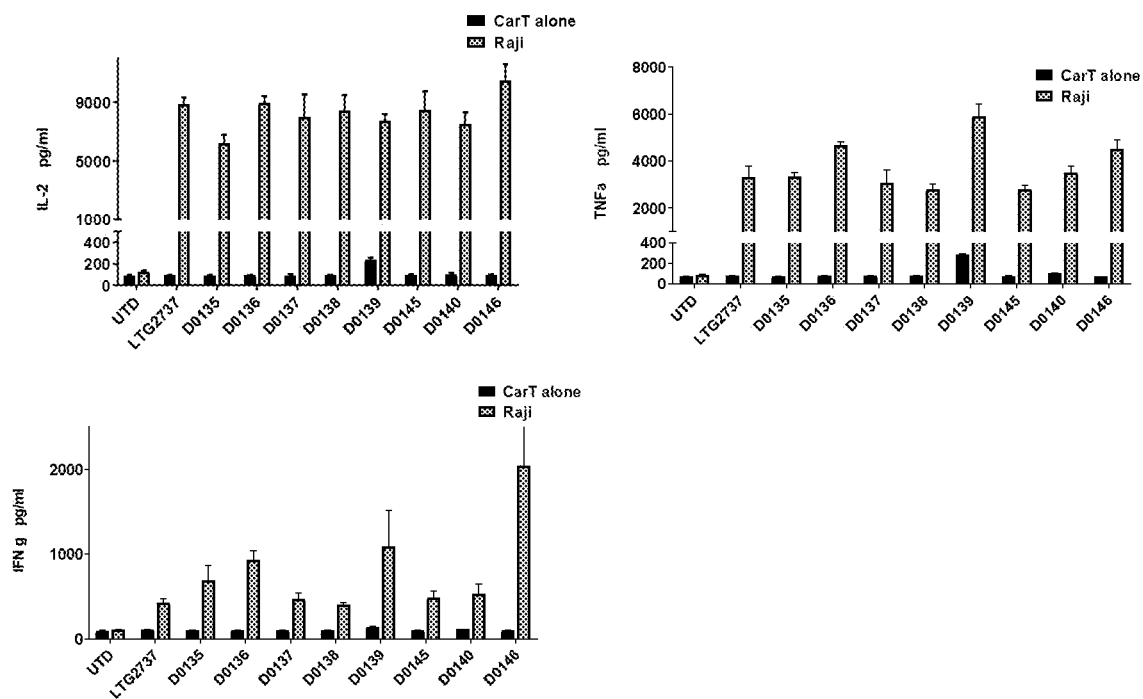

FIG. 8 depicts the cytolytic function of the anti-CD22-19 CAR incorporating different co-stimulatory domains at effector to target (ET) ratios of 10, 5 and 2.5, following 18 hr co-incubation of Raji target cells with CAR T cells. Percentage of specific target lysis is shown on the y-axis, and CAR construct designations are provided on the x-axis. N=3 technical replicates ±SEM. Data are from one experiment representative of three experiments in T cells form separate healthy donors.

FIGS. 9A-9D depict the cytokine responses to Raji targets for each of the anti-CD22-19 CAR with different co-stimulatory domain configurations. Effector ant target cells were co-cultured for 18 h at E:T ratio of 10, and supernatants were analyzed by ELISA for IL-2, TNFα and IFNγ. N=3 technical replicates ±SEM. Data are from one experiment representative of three experiments in T cells form separate healthy donors.

DETAILED DESCRIPTION

Definitions

As used herein, the singular forms "a," "an," and "the," refer to both the singular as well as plural, unless the context clearly indicates otherwise. For example, the term "an antigen" includes single or plural antigens and can be considered equivalent to the phrase "at least one antigen." As used herein, the term "comprises" means "includes." Thus, "comprising an antigen" means "including an antigen" without excluding other elements. The phrase "and/or" means "and" or "or." It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting. To facilitate review of the various embodiments, the following explanations of terms are provided:

The term "about" when referring to a measurable value such as an amount, a temporal duration, and the like, is meant to encompass variations of .+−.20% or in some instances .+−.10%, or in some instances .+−.5%, or in some instances .+−.1%, or in some instances .+−.0.1% from the specified value, as such variations are appropriate to perform the disclosed methods.

Unless otherwise noted, the technical terms herein are used according to conventional usage. Definitions of common terms in molecular biology can be found in Benjamin Lewin, Genes VII, published by Oxford University Press, 1999; Kendrew et al. (eds.), *The Encyclopedia of Molecular Biology*, published by Blackwell Science Ltd., 1994; and Robert A. Meyers (ed.), *Molecular Biology and Biotechnology: a Comprehensive Desk Reference*, published by VCH Publishers, Inc., 1995; and other similar references.

The present disclosure provides for CD19/CD22 antibodies or fragments thereof as well as chimeric antigen receptors (CARs) having such CD19/CD22 antigen binding domains. The enhancement of the functional activity of the CAR directly relates to the enhancement of functional activity of the CAR-expressing T cell. As a result of one or more of these modifications, the CARs exhibit both a high degree of cytokine-induced cytolysis and cell surface expression on transduced T cells, along with an increased level of in vivo T cell expansion and persistence of the transduced CAR-expressing T cell. The CARs of the present disclosure are advantageous in that one CART lentiviral product may be utilized to treat multiple patient populations (i.e. CD19+, CD22+ or double CD19+CD22+ cancer patients), which allows flexibility in circumstances where resources are limited.

The unique ability to combine functional moieties derived from different protein domains has been a key innovative feature of Chimeric Antigen Receptors (CARs). The choice of each of these protein domains is a key design feature, as is the way in which they are specifically combined. Each design domain is an essential component that can be used across different CAR platforms to engineer the function of lymphocytes. For example, the choice of the extracellular binding domain can make an otherwise ineffective CAR be effective.

The invariable framework components of the immunoglobulin-derived protein sequences used to create the extracellular antigen binding domain of a CAR can either be entirely neutral, or they can self-associate and drive the T cell to a state of metabolic exhaustion, thus making the therapeutic T cell expressing that CAR far less effective. This occurs independently of the antigen binding function of this CAR domain. Furthermore, the choice of the intracellular signaling domain(s) also can govern the activity and the durability of the therapeutic lymphocyte population used for immunotherapy. While the ability to bind target antigen and the ability to transmit an activation signal to the T cell through these extracellular and intracellular domains, respectively, are important CAR design aspects, what has also become apparent is that the choice of the source of the extracellular antigen binding fragments can have a significant effect on the efficacy of the CAR and thereby have a defining role for the function and clinical utility of the CAR.

The CARs disclosed herein are expressed at a high level in a cell. A cell expressing the CAR has a high in vivo proliferation rate, produces large amounts of cytokines, and has a high cytotoxic activity against a cell having, on its surface, a CD19/CD22 antigen to which a CAR binds. The use of an extracellular CD19/CD22 antigen binding domain results in generation of a CAR that functions better in vivo, while avoiding the induction of anti-CAR immunity in the host immune response and the killing of the CAR T cell population. The CARs expressing the extracellular CD19/CD22 ScFv antigen binding domain exhibit superior activities/properties including i) prevention of poor CAR T persistence and function as seen with mouse-derived binding sequences; ii) lack of regional (i.e. intrapleural) delivery of the CAR to be efficacious; and iii) ability to generate CAR T cell designs based both on binders with high and low affinity to CD19/CD22. This latter property allows investigators to better tune efficacy vs toxicity, and/or tissue specificity of the CAR T product, since lower-affinity binders may have higher specificity to tumors vs normal tissues due to higher expression of CD19/CD22 on tumors than normal tissue, which may prevent on-target off tumor toxicity and bystander cell killing.

What follows is a detailed description of the inventive CARs including a description of their extracellular CD19/CD22 antigen binding domain, the transmembrane domain and the intracellular domain, along with additional description of the CARs, antibodies and antigen binding fragments thereof, conjugates, nucleotides, expression, vectors, and host cells, methods of treatment, compositions, and kits employing the disclosed CARs.

A. Chimeric Antigen Receptors (CARs)

The CARs disclosed herein comprise at least one CD19/CD22 antigen binding domain capable of binding to CD19/CD22, at least one transmembrane domain, and at least one intracellular domain.

A chimeric antigen receptor (CAR) is an artificially constructed hybrid protein or polypeptide containing the antigen binding domains of an antibody (e.g., single chain variable fragment (ScFv)) linked to T-cell signaling domains via the transmembrane domain. Characteristics of CARs include their ability to redirect T-cell specificity and reactivity toward a selected target in a non-MHC-restricted manner, and exploiting the antigen-binding properties of monoclonal antibodies. The non-MHC-restricted antigen recognition gives T cells expressing CARs the ability to recognize antigen independent of antigen processing, thus bypassing a major mechanism of tumor escape. Moreover, when expressed in T-cells, CARs advantageously do not dimerize with endogenous T cell receptor (TCR) alpha and beta chains.

As disclosed herein, the intracellular T cell signaling domains of the CARs can include, for example, a T cell receptor signaling domain, a T cell costimulatory signaling domain, or both. The T cell receptor signaling domain refers to a portion of the CAR comprising the intracellular domain of a T cell receptor, such as, for example, and not by way of limitation, the intracellular portion of the CD3 zeta protein. The costimulatory signaling domain refers to a portion of the CAR comprising the intracellular domain of a costimulatory molecule, which is a cell surface molecule other than an antigen receptor or their ligands that are required for an efficient response of lymphocytes to antigen.

1. Extracellular Domain

In one embodiment, the CAR comprises a target-specific binding element otherwise referred to as an antigen binding domain or moiety. The choice of domain depends upon the type and number of ligands that define the surface of a target cell. For example, the antigen binding domain may be chosen to recognize a ligand that acts as a cell surface marker on target cells associated with a particular disease state. Thus examples of cell surface markers that may act as ligands for the antigen binding domain in the CAR include those associated with viral, bacterial and parasitic infections, autoimmune disease and cancer cells.

In one embodiment, the CAR can be engineered to target a tumor antigen of interest by way of engineering a desired antigen binding domain that specifically binds to an antigen on a tumor cell. Tumor antigens are proteins that are produced by tumor cells that elicit an immune response, particularly T-cell mediated immune responses. The selection of the antigen binding domain will depend on the particular type of cancer to be treated. Tumor antigens include, for example, a glioma-associated antigen, carcinoembryonic antigen (CEA), .beta.-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-1a, p53, prostein, PSMA, Her2/neu, survivin and telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor and CD19/CD22. The tumor antigens disclosed herein are merely included by way of example. The list is not intended to be exclusive and further examples will be readily apparent to those of skill in the art.

In one embodiment, the tumor antigen comprises one or more antigenic cancer epitopes associated with a malignant tumor. Malignant tumors express a number of proteins that can serve as target antigens for an immune attack. These molecules include, but are not limited to, tissue-specific antigens such as MART-1, tyrosinase and GP 100 in melanoma and prostatic acid phosphatase (PAP) and prostate-specific antigen (PSA) in prostate cancer. Other target molecules belong to the group of transformation-related molecules such as the oncogene HER-2/Neu/ErbB-2. Yet another group of target antigens are onco-fetal antigens such as carcinoembryonic antigen (CEA). In B-cell lymphoma the tumor-specific idiotype immunoglobulin constitutes a truly tumor-specific immunoglobulin antigen that is unique to the individual tumor. B-cell differentiation antigens such as CD19, CD22, CD22, BCMA, ROR1, and CD37 are other candidates for target antigens in B-cell lymphoma. Some of these antigens (CEA, HER-2, CD19, CD22, idiotype) have been used as targets for passive immunotherapy with monoclonal antibodies with limited success.

In one preferred embodiment, the tumor antigens are CD19/CD22 and the tumors associated with expression of CD19/CD22 comprise lung mesothelioma, ovarian, and pancreatic cancers that express high levels of the extracellular proteins CD19/CD22, or any combination thereof.

The type of tumor antigen may also be a tumor-specific antigen (TSA) or a tumor-associated antigen (TAA). A TSA is unique to tumor cells and does not occur on other cells in the body. A TAA is not unique to a tumor cell and instead is also expressed on a normal cell under conditions that fail to induce a state of immunologic tolerance to the antigen. The expression of the antigen on the tumor may occur under conditions that enable the immune system to respond to the antigen. TAAs may be antigens that are expressed on normal cells during fetal development when the immune system is immature and unable to respond or they may be antigens that are normally present at extremely low levels on normal cells but which are expressed at much higher levels on tumor cells.

Non-limiting examples of TSAs or TAAs include the following: Differentiation antigens such as MART-1/MelanA (MART-I), gp100 (Pmel 17), tyrosinase, TRP-1, TRP-2 and tumor-specific multi-lineage antigens such as MAGE-1, MAGE-3, BAGE, GAGE-1, GAGE-2, p15; overexpressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, p185erbB2, p180erbB-3, c-met, nm-23H1, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27.29\BCAA, CA 195, CA 242, CA-50, CAM43, CD68P1, CO-029, FGF-5, G250, Ga733\EpCAM, HTgp-175, M344, MA-50, MG7-Ag, MOV18, NB/70K, NY-CO-1, RCAS1, SDCCAG16, TA-90\Mac-2 binding protein\cyclophilin C-associated protein, TAAL6, TAG72, TLP, and TPS.

In one embodiment, the antigen binding domain portion of the CAR targets an antigen that includes but is not limited to CD19, CD20, CD22, ROR1, CD33, CD38, CD123, CD138, BCMA, c-Met, PSMA, Glycolipid F77, EGFRvIII, GD-2, FGFR4, TSLPR, NY-ESO-1 TCR, MAGE A3 TCR, and the like.

In a preferred embodiment, the antigen binding domain portion of the CAR targets the extracellular CD19/CD22 antigen.

Figure 1A:
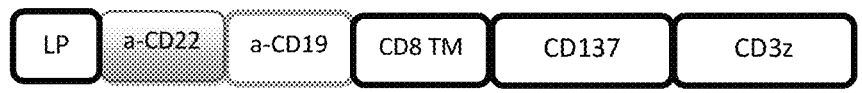
FIGS. 1A and 1B depict the construction of a tandem CARs targeting CD22 and CD19.
Figure 1B:
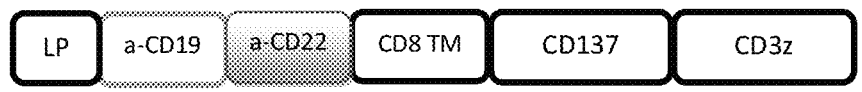

In the various embodiments of the CD19/CD22-specific CARs disclosed herein, the general scheme is set forth in FIGS. 1A and 1B and includes, from the N-terminus to the C-terminus, a signal or leader peptide, anti-CD19/CD22 ScFv (where the CD19 binder is distal to the T cell membrane and the CD22 binder is proximal to the T cell membrane, or where the CD22 binder is distal to the T cell membrane and the CD19 binder is proximal to the T cell membrane), CD8 extracellular linker, CD8 transmembrane domain, 4-1BB costimulatory domain, CD3 zeta activation domain.

In one embodiment, the nucleic acid sequence encoding a CAR comprises the nucleic acid sequence of SEQ ID NO: 1 (Leader-CD22 VH-(GGGGS)-3 CD22 VL (GGGGS)-5 CD19 VH (GGGGS)-3 CD19 VL CD8 hinge+TM-4-1BB-CD3z (Construct 2219)), and encodes the CAR comprising the amino acid sequence as set forth in SEQ ID NO: 2 (Leader-CD22 VH-(GGGGS)-3 CD22 VL (GGGGS)-5 CD19 VH (GGGGS)-3 CD19 VL CD8 hinge+TM-4-1BB-CD3z (Construct 2219).

In one embodiment, the nucleic acid sequence encoding a CAR comprises the nucleic acid sequence of SEQ ID NO: 1, or a sequence with 85%, 90%, 95%, 96%, 97%, 98% or 99% identity thereof, and encodes the CAR comprising the amino acid sequence as set forth in SEQ ID NO: 2 or a sequence with 85%, 90%, 95%, 96%, 97%, 98% or 99% identity thereof Leader-CD22 VH-(GGGGS)-3 CD22 VL (GGGGS)-5 CD19 VH (GGGGS)-3 CD19 VL CD8 hinge+TM-4-1BB-CD3z (Construct 2219).

In another embodiment, the nucleic acid sequence encoding a CAR comprises the nucleic acid sequence of SEQ ID NO: 3 (Leader-CD19 VH (GGGGS)3-CD19 VL-(GGGGS)5-CD22 VL-(GGGGS)3-CD22 VH CD8 hinge+TM-4-1BB-CD3z (Construct 1922) (FIG. 2)), and encodes the CAR comprising the amino acid sequence as set forth in SEQ ID NO: 4 [Leader-CD19 VH (GGGGS)3-CD19 VL-(GGGGS)5-CD22 VL-(GGGGS)3-CD22 VH CD8 hinge+TM-4-1BB-CD3z (Construct 1922)].

In another embodiment, the nucleic acid sequence encoding a CAR comprises the nucleic acid sequence of SEQ ID NO: 3 or a sequence with 85%, 90%, 95%, 96%, 97%, 98% or 99% identity thereof, and encodes the CAR comprising the amino acid sequence as set forth in SEQ ID NO: 4 or a sequence with 85%, 90%, 95%, 96%, 97%, 98% or 99% identity thereof (Leader-CD19 VH (GGGGS)3-CD19 VL-(GGGGS)5-CD22 VL-(GGGGS)3-CD22 VH CD8 hinge+TM-4-1BB-CD3z (Construct 1922)).

The surface expression of anti-CD19/CD22 CARs incorporating single chain fragment variable (ScFv) sequences reactive with CD19/CD22 antigen, is shown in Example 2 infra. The expression level for each ScFv-containing CAR was determined by flow cytometric analysis of LV-transduced T cells from healthy donors using one of two detection methods: i) CD22 his, followed anti-his-FL; ii) CD19 Fc recombinant protein, followed by anti Fc-FL. The ScFv-based anti-CD19/CD22 CAR constructs CAR22-19 and CAR19-22 were highly expressed in human primary T cells as compared to non-transduced T cell controls.

As shown in EXAMPLE 2 and FIG. 3, high cytolytic activity of the CD19/CD22 CARs was demonstrated. FIG. 3: Human primary T cells were transduced with LV encoding CAR constructs (CAR 22-19 (LTG2681, D0023), CAR 19-22 (D0024), CAR19 (LTG1538), or CAR22 (LTG2200); see Methods), then incubated for 18 hours with the Raji, REH, K562 or 293T cell lines, stably transduced with firefly luciferase, for luminescence based in vitro killing assays. Raji and Reh leukemia lines express CD19 and CD22 on their surface, while the negative controls, 293T do not. Raji and REH cells were lysed effectively by the tandem CAR 22-19, (LTG2681), tandem CAR 19-22 (LTG2719) and the single-targeting CAR19 (LTG1538) and CAR22 (LTG2200). These results demonstrate target antigen-restricted killing of the single CAR controls and the tandem CD19-targeting CD22-targeting CARs.

As an additional specificity controls, 293T-luc lines and A431-luc lines were created that express CD19, or CD20, or CD22 (FIGS. 4A and 4B). 293T-19+ were lysed by the CAR 19 (LTG1538) and tandem CAR 22-19 (LTG 2681), but not by CAR22 LTG 2200 or untransduced T cells control (FIG. 3). 293T-CD22+ were lysed by the tandem CAR 22-19 (LTG 2681) and the single CAR20 LTG2200, but not by the single CAR19 (LTG 1538), or untransduced control, demonstrating antigen specificity of the tandem CAR. Finally, no CAR construct lysed the 293T luc CD20 cells, since this antigen was not targeted (FIG. 4A). Similarly, A431-luc 19 lines were lysed by tandem CAR LTG2681, or single CAR19 LTG1538, but not CAR22 LTG2200 or UTD control. Vice versa, A431 luc CD22 cells were lysed by tandem CAR 1TG2681 or single CAR22 LTG2200, but not by CD19 CAR LTG1538 or UTD control. Notably, no CAR construct lysed the irrelevant antigen expressing A431-luc CD20 line, because the CD20 antigen was not targeted (FIG. 4B). This results underscores the independent functionality and specificity of each targeting domain of the tandemCAR22-19 (FIG. 4). Moreover, this experiment demonstrates that the tandem CAR 22-19 will be effective against tumor cells even if one of the two antigens (CD19 CD22) was downregulated and is no longer expressed. Therefore tandem CARs, in contract to single CARs, can mitigate tumor antigen escape.

The capacity of anti-CD19/CD22 CAR T cells for cytokine secretion was then evaluated (FIG. 5). The CD19+ CD22+ Raji tumor cells were co-incubated with the tandem 22-19 CAR T cells (LTG2681) or positive control CAR19 (LTG1538), positive control CAR22 (LTG2200), or negative control untransduced T cells (UTD) at effector to target ratio of 10:1 overnight, and culture supernatants were analyzed by ELISA for IFN gamma, TNF alpha, and IL-2. The tandem CAR 22-19 (LTG2681) strongly induced cytokines in response to tumor cells, whereas the negative control (untransduced, UTD.) yielded no appreciable cytokine induction. Notably, tandem CAR T-expressing cells LTG2681 showed similar levels of IFN gamma, TNF alpha, IL-2, to CAR22 control (LTG2200), and somewhat higher cytokine response than the single CAR19 (LTG1538) control, demonstrating the high potency of the tandem CAR. Importantly, CAR 22-19 produced no cytokine secretion in the absence of tumor cells (CART alone group), which further confirms CAR specificity, and indicates a lack of tonic signaling by the tandem car.

In another embodiment, the nucleic acid sequence encoding a CAR comprises the nucleic acid sequence of SEQ ID NO: 60 [CD22-19 CD8 BBz (Construct LTG 2737) (FIGS. 6, 7, 8, and 9, respectively)], and encodes the CAR comprising the amino acid sequence as set forth in SEQ ID NO: 61 [CD22-19 CD8 BBz (Construct LTG2737)].

In another embodiment, the nucleic acid sequence encoding a CAR comprises the nucleic acid sequence of SEQ ID NO: 60 or a sequence with 85%, 90%, 95%, 96%, 97%, 98% or 99% identity thereof, and encodes the CAR comprising the amino acid sequence as set forth in SEQ ID NO: 61 or a sequence with 85%, 90%, 95%, 96%, 97%, 98% or 99% identity thereof (CD22-19 CD8 BBz (Construct LTG2737)).

In another embodiment, the nucleic acid sequence encoding a CAR comprises the nucleic acid sequence of SEQ ID NO: 64 [CD22-19 CD8 ICOSz DNA (Construct D0136) (FIGS. 6, 7, 8, and 9, respectively))], and encodes the CAR comprising the amino acid sequence as set forth in SEQ ID NO: 65 [CD22-19 CD8 ICOSz DNA (Construct D0136)].

In another embodiment, the nucleic acid sequence encoding a CAR comprises the nucleic acid sequence of SEQ ID NO: 64 or a sequence with 85%, 90%, 95%, 96%, 97%, 98% or 99% identity thereof, and encodes the CAR comprising the amino acid sequence as set forth in SEQ ID NO: 65 or a sequence with 85%, 90%, 95%, 96%, 97%, 98% or 99% identity thereof (CD22-19 CD8 ICOSz DNA (Construct D0136)).

In another embodiment, the nucleic acid sequence encoding a CAR comprises the nucleic acid sequence of SEQ ID NO: 70 [CD22-19 CD28 CD28z (Construct D0139) (FIGS. 6, 7, 8, and 9, respectively)], and encodes the CAR comprising the amino acid sequence as set forth in SEQ ID NO: 71 [CD22-19 CD28 CD28z (Construct D0139)].

In another embodiment, the nucleic acid sequence encoding a CAR comprises the nucleic acid sequence of SEQ ID NO: 70 or a sequence with 85%, 90%, 95%, 96%, 97%, 98% or 99% identity thereof, and encodes the CAR comprising the amino acid sequence as set forth in SEQ ID NO: 71 or a sequence with 85%, 90%, 95%, 96%, 97%, 98% or 99% identity thereof (CD22-19 CD28 CD28z (Construct D0139)).

In another embodiment, the nucleic acid sequence encoding a CAR comprises the nucleic acid sequence of SEQ ID NO: 76 [CD19 CD8H&TM ICOS z_CD22 CD8H&TM 3z (Construct D0146) (FIGS. 6, 7, 8, and 9, respectively)], and encodes the CAR comprising the amino acid sequence as set forth in SEQ ID NO: 77 [CD19 CD8H&TM ICOS z_CD22 CD8H&TM 3z (Construct D0146)].

In another embodiment, the nucleic acid sequence encoding a CAR comprises the nucleic acid sequence of SEQ ID NO: 76 or a sequence with 85%, 90%, 95%, 96%, 97%, 98% or 99% identity thereof, and encodes the CAR comprising the amino acid sequence as set forth in SEQ ID NO: 77 or a sequence with 85%, 90%, 95%, 96%, 97%, 98% or 99% identity thereof (CD19 CD8H&TM ICOS z_CD22 CD8H&TM 3z (Construct D0146)).

In another embodiment, the nucleic acid sequence encoding a CAR comprises the nucleic acid sequence of SEQ ID NO: 62, 66, 68, 72, 74, 78, 80, and 82 or a sequence with 85%, 90%, 95%, 96%, 97%, 98% or 99% identity thereof, and encodes the CAR comprising the amino acid sequence as set forth in SEQ ID NO: 63, 67, 69, 73, 75, 79, 81, and 83 or a sequence with 85%, 90%, 95%, 96%, 97%, 98% or 99% identity thereof.

The surface expression of anti-CD22/CD19 CARs incorporating single chain fragment variable (ScFv) sequences reactive with CD22/CD19 antigen, is shown in Example 3 infra.

Figure 6A:
Figure 6B:
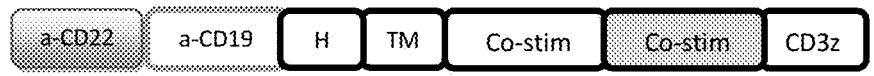

In one embodiment, dual-targeting CAR constructs comprised of different co-stimulatory domains were designed. CAR constructs are listed in Table 1 of Example 3, infra. Schematic representations of CAR design configurations are provided in FIGS. 6A-D. In some embodiments, the tandem CAR antigen-binding domain, comprised of anti-CD22 ScFv and anti-CD19 scFv sequences, were linked in tandem, in the following order: anti-CD22 scFv-anti CD19-scFv-hinge-transmembrane domain-endodomain (FIGS. 6A, 6B). The targeting tandem domain configuration was based on CAR 22-19 (LTG2681) in all cases. Anti-CD 22-19 CAR construct LTG2737 contained the CAR sequence identical to the Anti-CD 22-19 CAR construct LTG2681, but without use of the Woodchuck Hepatitis Virus (WHP) Posttranscriptional Regulatory Element (WPRE) during its construction.

In another embodiment, several CAR T constructs were generated by linking the CAR antigen-binding domain in frame to CD8a hinge and transmembrane domains (constructs LTG2737, D0135, D0136, D0137, D0145, D0146, D0147, D0148, and D0149) as described in Example 3, infra. In other constructs a transmembrane domain sequence matching the co-stimulatory domain was utilized: CD28 for D139, D140, OX40 for D0137, D0147, D0148. The transmembrane domain was linked in frame to a co-stimulatory domain derived from 4-1BB (LTG2737), CD28 (D0135, D0139, D0140), ICOS (D0136, D0146, D0148, D0149), OX40 (D0137, D0145, D0147, D0148) or CD27 (D0138, D0149). All CAR molecules contained the CD3 zeta signaling domain (CD247, aa 52-163, Ref sequence ID: NP_000725.1).

In yet another embodiment, the endodomain of the CAR was comprised of two co-stimulatory domains, CD28 and 4-1BB, connected in tandem (D0140, FIG. 6B). In some embodiments, two distinct CAR molecules were co-expressed in the same T cell using a 2A ribosomal skip element for bicistronic expression (D146, D147, D148, D149, FIG. 6C, 6D). In this configuration, each CAR chain contained only one scFv, targeting either the CD19 or CD22 antigen, and both chains were co-expressed in each transduced T cell via transduction with a single lentiviral vector encoding the bicistronic sequence.

Figure 6C:
Figure 6D:

In yet other embodiments, on at least one of the CAR chains, no co-stimulatory domain was used, so that the CD3 activation domain was linked in frame directly to the transmembrane domain of one of the CAR chains expressed concurrently in the same cell (D0146, D0147, FIG. 6C). CAR constructs sequences were cloned into a third generation lentiviral plasmid backbone under the control of the human EF-1α promoter (Lentigen Technology Inc., Gaithersburg, Md.).

The surface expression of anti-CD22-19 CAR incorporating various co-stimulatory domains, is shown in FIG. 7. The expression level for each ScFv-containing CAR was determined by flow cytometric analysis of LV-transduced T cells from healthy donors using simultaneous staining for the two scFv CAR targeting domains i) CD22-his, followed anti-his-PE; ii) CD19 Fc recombinant protein, followed by anti Fc-A647. All anti-CD22-19 CAR were highly expressed in human primary T cells as compared to non-transduced T cell controls. CAR expression levels ranged from 71%-90% (FIG. 7).

As shown in FIGS. 9A-9D, high cytolytic activity of the anti-CD22-19 CAR was demonstrated: Human primary T cells were transduced with LV encoding CAR constructs LTG2737, D0135, D0136, D0137, D0138, D0139, D0140, D0145, D0146), then incubated for 18 hours with the Raji, 293T, 293TCD19 or 293TCD22 cell lines, stably transduced with firefly luciferase, for luminescence based in vitro killing assays. Effector to target (ET) ratios of 2.5:1, 5:1 or 10:1 were used, as noted in the legend to the right of each plot. Raji cells express CD19 and CD22 on their surface, while the negative controls, 293T do not. The 293TCD19 and 293TCD22 target lines were generated to stably express either the CD19 or CD22 target antigen, respectively, and were used to evaluate the capability of the dual-targeting CAR constructs with different co-stimulatory domains to accomplish target lysis when triggered by each single target antigen, CD19 or CD22, independently of the other antigen.

Figure 9A:
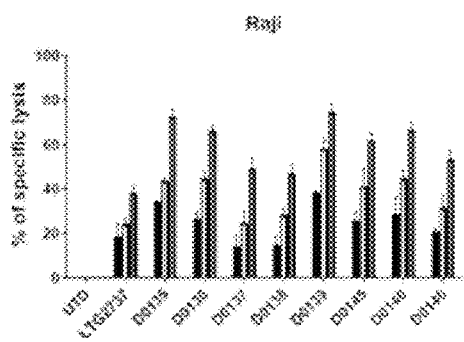
Figure 9C:
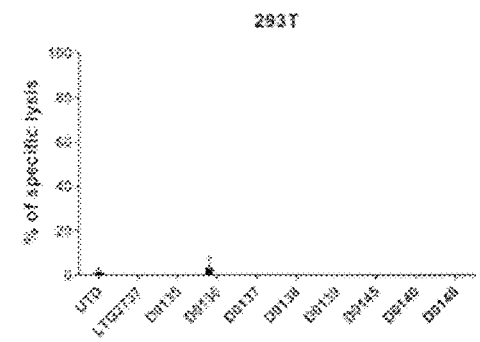
Figure 9B:
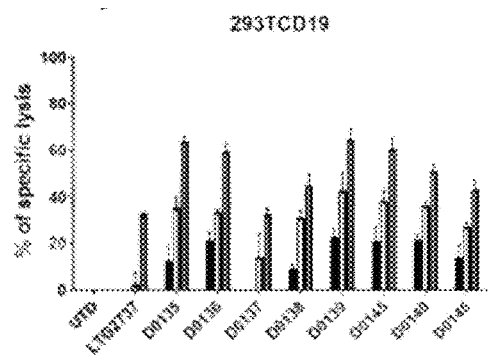
Figure 9D:
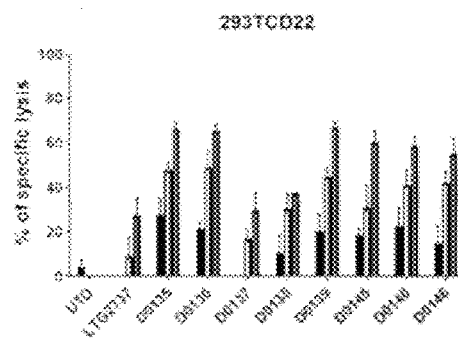

Raji cells were lysed effectively by all dual targeting CARs, but not by the untransduced T cells, UTD, a negative control (FIG. 9A). By comparison, all dual-targeting CAR constructs lysed the single-antigens lines 293TCD19 and 293TCD22, demonstrating the capability of these CAR constructs to trigger their anti-tumor lytic function when activated either by CD19 antigen alone, or by CD22 antigen alone (FIGS. 9B and 9D, respectively). By contrast, none of the dual-targeting anti-CD22-19 CAR lysed the antigen-negative cell line 293T (FIG. 9C). Therefore, all anti-CD22-19 CAR were functional in tumor Raji line co-expressing the CD19 and CD22 antigens, and also in 293TCD19 and 293T CD22 lines expressing either CD19 or CD22 single antigen, and had no spontaneous killing activity against CD19−CD22− cell line 293T, underscoring the target specificity of these constructs.

The capacity of anti-CD22-19 CAR with various co-stimulatory domains for cytokine secretion was then evaluated (FIG. 8). The CD19+CD22+ Raji tumor cells were co-incubated with the tandem anti-CD22-19 CAR T cells expressing constructs LTG2737, D0135, D0136, D0137, D0138, D0139, D0140, D0145, D0146, or negative control untransduced T cells (UTD) at effector to target ratio of 10:1 overnight, and culture supernatants were analyzed by ELISA for IFN gamma, TNF alpha, and IL-2 (FIG. 8). All dual-targeting CARs strongly induced IL-2 and TNFα in response to tumor cells, whereas the negative control (untransduced, UTD) yielded no appreciable cytokine induction (FIG. 8). Notably, the elaborated levels of IFN gamma, were strongly induced in all CAR 22-19, but were especially high for CAR constructs D0146, D0139, D0136, indicating that the strength of cytokine response of the anti-CD22-19 CAR may be modulated by the composition of co-stimulatory domains utilized in CAR design. Overall, the induced secretion profiles of IFN gamma, TNF alpha, and IL-2 demonstrated the high potency of all CAR 22-19 constructs. Importantly, anti-CD22-19 CAR produced little to no cytokine secretion in the absence of tumor cells (CAR T alone group), which further confirms CAR specificity, and indicates a lack of tonic signaling by the tandem anti-CD22-19 CAR with various co-stimulatory domains.

Without being intended to limit to any particular mechanism of action, it is believed that possible reasons for the enhanced therapeutic function associated with the exemplary tandem CD22 and CD19 targeting CARs of the invention include, for example, and not by way of limitation, a) improved lateral movement within the plasma membrane allowing for more efficient signal transduction, b) superior location within plasma membrane microdomains, such as lipid rafts, and greater ability to interact with transmembrane signaling cascades associated with T cell activation, c) superior location within the plasma membrane by preferential movement away from dampening or down-modulatory interactions, such as less proximity to or interaction with phosphatases such as CD45, and d) superior assembly into T cell receptor signaling complexes (i.e. the immune synapse), or e) superior ability to engage with tumor antigen due to two distinct targeting domains present in each CAR molecule, or any combination thereof.

While the disclosure has been illustrated with an exemplary extracellular CD19/CD22 variable heavy chain only and ScFv antigen binding domains, other nucleotide and/or amino acid variants within the CD19/CD22 variable heavy chain only and ScFv antigen binding domains may be used to derive the CD19/CD22 antigen binding domains for use in the CARs described herein.

Depending on the desired antigen to be targeted, the CAR can be additionally engineered to include the appropriate antigen binding domain that is specific to the desired antigen target. For example, if CD19/CD22 is the desired antigen that is to be targeted, an antibody for CD19/CD22 can be used as the antigen bind domain incorporation into the CAR.

In one exemplary embodiment, the antigen binding domain portion of the CAR additionally targets CD33. Preferably, the antigen binding domain in the CAR is anti-CD33 ScFv, wherein the nucleic acid sequence of the anti-CD33 ScFv comprises the sequence set forth in SEQ ID NO: 46. In one embodiment, the anti-CD33 ScFv comprises the nucleic acid sequence that encodes the amino acid sequence of SEQ ID NO: 46. In another embodiment, the anti-CD19/CD22 ScFv portion of the CAR comprises the amino acid sequence set forth in SEQ ID NO: 47.

In one exemplary embodiment, the antigen binding domain portion of the CAR additionally targets mesothelin. Preferably, the antigen binding domain in the CAR is anti-mesothelin ScFv, wherein the nucleic acid sequence of the anti-mesothelin ScFv comprises the sequence set forth in SEQ ID NO: 48. In one embodiment, the anti-mesothelin ScFv comprises the nucleic acid sequence that encodes the amino acid sequence of SEQ ID NO: 48. In another embodiment, the anti-mesothelin ScFv portion of the CAR comprises the amino acid sequence set forth in SEQ ID NO: 49.

In one aspect of the present invention, there is provided a CAR capable of binding to a non-TSA or non-TAA including, for example and not by way of limitation, an antigen derived from Retroviridae (e.g. human immunodeficiency viruses such as HIV-1 and HIV-LP), Picomaviridae (e.g. poliovirus, hepatitis A virus, enterovirus, human coxsackievirus, rhinovirus, and echovirus), rubella virus, coronavirus, vesicular stomatitis virus, rabies virus, ebola virus, parainfluenza virus, mumps virus, measles virus, respiratory syncytial virus, influenza virus, hepatitis B virus, parvovirus, Adenoviridae, Herpesviridae [e.g. type 1 and type 2 herpes simplex virus (HSV), varicella-zoster virus, cytomegalovirus (CMV), and herpes virus], Poxviridae (e.g. smallpox virus, vaccinia virus, and pox virus), or hepatitis C virus, or any combination thereof.

In another aspect of the present invention, there is provided a CAR capable of binding to an antigen derived from a bacterial strain of Staphylococci, *Streptococcus*, *Escherichia coli*, *Pseudomonas*, or *Salmonella*. Particularly, there is provided a CAR capable of binding to an antigen derived from an infectious bacterium, for example, *Helicobacter pyloris*, *Legionella pneumophilia*, a bacterial strain of Mycobacteria sps. (e.g. *M. tuberculosis, M. avium, M. intracellulare, M. kansaii*, or *M. gordonea*), *Staphylococcus aureus, Neisseria gonorrhoeae, Neisseria meningitides, Listeria monocytogenes, Streptococcus pyogenes*, Group A *Streptococcus*, Group B *Streptococcus* (*Streptococcus agalactiae*), *Streptococcus pneumoniae*, or *Clostridium tetani*, or a combination thereof.

2. Transmembrane Domain

With respect to the transmembrane domain, the CAR comprises one or more transmembrane domains fused to the extracellular CD19/CD22 antigen binding domain of the CAR.

The transmembrane domain may be derived either from a natural or from a synthetic source. Where the source is natural, the domain may be derived from any membrane-bound or transmembrane protein.

Transmembrane regions of particular use in the CARs described herein may be derived from (i.e. comprise at least the transmembrane region(s) of) the alpha, beta or zeta chain of the T-cell receptor, CD28, CD3 epsilon, CD45, CD4, CD5, CD8, CD9, CD16, CD22, mesothelin, CD33, CD37, CD64, CD80, CD83, CD86, CD134, CD137, CD154, TNFRSF16, or TNFRSF19.

Alternatively the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

In one embodiment, the transmembrane domain that naturally is associated with one of the domains in the CAR is used in addition to the transmembrane domains described supra.

In some instances, the transmembrane domain can be selected or by amino acid substitution to avoid binding of such domains to the transmembrane domains of the same or different surface membrane proteins to minimize interactions with other members of the receptor complex.

In one embodiment, the transmembrane domain in the CAR of the invention is the CD8 transmembrane domain. In one embodiment, the CD8 transmembrane domain comprises the nucleic acid sequence of SEQ ID NO: 35. In one embodiment, the CD8 transmembrane domain comprises the nucleic acid sequence that encodes the amino acid sequence of SEQ ID NO: 36. In another embodiment, the CD8 transmembrane domain comprises the amino acid sequence of SEQ ID NO: 36.

In one embodiment, the encoded transmembrane domain comprises an amino acid sequence having at least one, two or three modifications (e.g., substitutions) but not more than 20, 10 or 5 modifications (e.g., substitutions) of an amino acid sequence of SEQ ID NO: 28, or a sequence with 95-99% identity to an amino acid sequence of SEQ ID NO: 28.

In some instances, the transmembrane domain of the CAR comprises the CD8.alpha.hinge domain. In one embodiment, the CD8 hinge domain comprises the nucleic acid sequence of SEQ ID NO: 37. In one embodiment, the CD8 hinge domain comprises the nucleic acid sequence that encodes the amino acid sequence of SEQ ID NO: 38. In another embodiment, the CD8 hinge domain comprises the amino acid sequence of SEQ ID NO: 38, or a sequence with 95-99% identify thereof.

In one embodiment, an isolated nucleic acid molecule is provided wherein the encoded linker domain is derived from the extracellular domain of CD8, and is linked to the transmembrane CD8 domain, the transmembrane CD28 domain, or a combination thereof.

3. Spacer Domain

In the CAR, a spacer domain can be arranged between the extracellular domain and the transmembrane domain, or between the intracellular domain and the transmembrane domain. The spacer domain means any oligopeptide or polypeptide that serves to link the transmembrane domain with the extracellular domain and/or the transmembrane domain with the intracellular domain. The spacer domain comprises up to 300 amino acids, preferably 10 to 100 amino acids, and most preferably 25 to 50 amino acids.

In several embodiments, the linker can include a spacer element, which, when present, increases the size of the linker such that the distance between the effector molecule or the detectable marker and the antibody or antigen binding fragment is increased. Exemplary spacers are known to the person of ordinary skill, and include those listed in U.S. Pat. Nos. 7,964,566, 7,498,298, 6,884,869, 6,323,315, 6,239,104, 6,034,065, 5,780,588, 5,665,860, 5,663,149, 5,635,483, 5,599,902, 5,554,725, 5,530,097, 5,521,284, 5,504,191, 5,410,024, 5,138,036, 5,076,973, 4,986,988, 4,978,744, 4,879,278, 4,816,444, and 4,486,414, as well as U.S. Pat. Pub. Nos. 20110212088 and 20110070248, each of which is incorporated by reference herein in its entirety.

The spacer domain preferably has a sequence that promotes binding of a CAR with an antigen and enhances signaling into a cell. Examples of an amino acid that is expected to promote the binding include cysteine, a charged amino acid, and serine and threonine in a potential glycosylation site, and these amino acids can be used as an amino acid constituting the spacer domain.

As the spacer domain, the entire or a part of amino acid numbers 137-206 (SEQ ID NO: 39) which is a hinge region of CD8.alpha. (NCBI RefSeq: NP.sub.--001759.3), amino acid numbers 135 to 195 of CD8.beta. (GenBank: AAA35664.1), amino acid numbers 315 to 396 of CD4 (NCBI RefSeq: NP.sub.--000607.1), or amino acid numbers 137 to 152 of CD28 (NCBI RefSeq: NP.sub.--006130.1) can be used. Also, as the spacer domain, a part of a constant region of an antibody H chain or L chain can be used. Further, the spacer domain may be an artificially synthesized sequence.

Further, in the CAR, a signal peptide sequence can be linked to the N-terminus. The signal peptide sequence exists at the N-terminus of many secretory proteins and membrane proteins, and has a length of 15 to 30 amino acids. Since many of the protein molecules mentioned above as the intracellular domain have signal peptide sequences, the signal peptides can be used as a signal peptide for the CAR. In one embodiment, the signal peptide comprises the amino acid sequence shown in SEQ ID NO: 18.

4. Intracellular Domain

The cytoplasmic domain or otherwise the intracellular signaling domain of the CAR is responsible for activation of at least one of the normal effector functions of the immune cell in which the CAR has been placed in. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Preferred examples of intracellular signaling domains for use in the CAR include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

It is known that signals generated through the TCR alone are insufficient for full activation of the T cell and that a secondary or co-stimulatory signal is also required. Thus, T cell activation can be said to be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs.

Examples of ITAM containing primary cytoplasmic signaling sequences that are of particular use in the CARs disclosed herein include those derived from TCR zeta (CD3 Zeta), FcR gamma, FcR beta, CD3 gamma, CD3 delta, CD3 epsilon, CD5, CD22, CD79a, CD79b, and CD66d. Specific, non-limiting examples, of the ITAM include peptides having sequences of amino acid numbers 51 to 164 of CD3 zeta. (NCBI RefSeq: NP.sub.--932170.1), amino acid numbers 45 to 86 of Fc epsilon RI gamma. (NCBI RefSeq: NP.sub.--004097.1), amino acid numbers 201 to 244 of Fc epsilon RI beta. (NCBI RefSeq: NP.sub.--000130.1), amino acid numbers 139 to 182 of CD3 gamma. (NCBI RefSeq: NP.sub.--000064.1), amino acid numbers 128 to 171 of CD3 delta. (NCBI RefSeq: NP.sub.--000723.1), amino acid numbers 153 to 207 of CD3.epsilon. (NCBI RefSeq: NP.sub.--000724.1), amino acid numbers 402 to 495 of CD5 (NCBI RefSeq: NP.sub.--055022.2), amino acid numbers 707 to 847 of 0022 (NCBI RefSeq: NP.sub.--001762.2), amino acid numbers 166 to 226 of CD79a (NCBI RefSeq: NP.sub.--001774.1), amino acid numbers 182 to 229 of CD79b (NCBI RefSeq: NP.sub.--000617.1), and amino acid numbers 177 to 252 of CD66d (NCBI RefSeq: NP.sub.--001806.2), and their variants having the same function as these peptides have. The amino acid number based on amino acid sequence information of NCBI RefSeq ID or GenBank described herein is numbered based on the full length of the precursor (comprising a signal peptide sequence etc.) of each protein. In one embodiment, the cytoplasmic signaling molecule in the CAR comprises a cytoplasmic signaling sequence derived from CD3 zeta.

In a preferred embodiment, the intracellular domain of the CAR can be designed to comprise the CD3-zeta signaling domain by itself or combined with any other desired cytoplasmic domain(s) useful in the context of the CAR. For example, the intracellular domain of the CAR can comprise a CD3 zeta chain portion and a costimulatory signaling region. The costimulatory signaling region refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such costimulatory molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like. Specific, non-limiting examples, of such costimulatory molecules include peptides having sequences of amino acid numbers 236 to 351 of CD2 (NCBI RefSeq: NP.sub.--001758.2), amino acid numbers 421 to 458 of CD4 (NCBI RefSeq: NP.sub.--000607.1), amino acid numbers 402 to 495 of CD5 (NCBI RefSeq: NP.sub.--055022.2), amino acid numbers 207 to 235 of CD8 alpha. (NCBI RefSeq: NP.sub.--001759.3), amino acid numbers 196 to 210 of CD83 (GenBank: AAA35664.1), amino acid numbers 181 to 220 of CD28 (NCBI RefSeq: NP.sub.--006130.1), amino acid numbers 214 to 255 of CD137 (4-1BB, NCBI RefSeq: NP.sub.--001552.2), amino acid numbers 241 to 277 of CD134

(OX40, NCBI RefSeq: NP.sub.--003318.1), and amino acid numbers 166 to 199 of ICOS (NCBI RefSeq: NP.sub.--036224.1), and their variants having the same function as these peptides have. Thus, while the disclosure herein is exemplified primarily with 4-1BB as the co-stimulatory signaling element, other costimulatory elements are within the scope of the disclosure.

The cytoplasmic signaling sequences within the cytoplasmic signaling portion of the CAR may be linked to each other in a random or specified order. Optionally, a short oligo- or polypeptide linker, preferably between 2 and 10 amino acids in length may form the linkage. A glycine-serine doublet provides a particularly suitable linker.

In one embodiment, the intracellular domain is designed to comprise the signaling domain of CD3-zeta and the signaling domain of CD28. In another embodiment, the intracellular domain is designed to comprise the signaling domain of CD3-zeta and the signaling domain of 4-1BB. In yet another embodiment, the intracellular domain is designed to comprise the signaling domain of CD3-zeta and the signaling domain of CD28 and 4-1BB.

In one embodiment, the intracellular domain in the CAR is designed to comprise the signaling domain of 4-1BB and the signaling domain of CD3-zeta, wherein the signaling domain of 4-1BB comprises the nucleic acid sequence set forth in SEQ ID NO: 40 and the signaling domain of CD3-zeta comprises the nucleic acid sequence set forth in SEQ ID NO: 42.

In one embodiment, the intracellular domain in the CAR is designed to comprise the signaling domain of 4-1BB and the signaling domain of CD3-zeta, wherein the signaling domain of 4-1BB comprises the nucleic acid sequence that encodes the amino acid sequence of SEQ ID NO: 41 and the signaling domain of CD3-zeta comprises the nucleic acid sequence that encodes the amino acid sequence of SEQ ID NO: 43.

In one embodiment, the intracellular domain in the CAR is designed to comprise the signaling domain of 4-1BB and the signaling domain of CD3-zeta, wherein the signaling domain of 4-1BB comprises the amino acid sequence set forth in SEQ ID NO: 41 and the signaling domain of CD3-zeta comprises the amino acid sequence set forth in SEQ ID NO: 43.

5. Additional Description of CARs

Also expressly included within the scope of the invention are functional portions of the CARs disclosed herein. The term "functional portion" when used in reference to a CAR refers to any part or fragment of one or more of the CARs disclosed herein, which part or fragment retains the biological activity of the CAR of which it is a part (the parent CAR). Functional portions encompass, for example, those parts of a CAR that retain the ability to recognize target cells, or detect, treat, or prevent a disease, to a similar extent, the same extent, or to a higher extent, as the parent CAR. In reference to the parent CAR, the functional portion can comprise, for instance, about 10%, 25%, 30%, 50%, 68%, 80%, 90%, 95%, or more, of the parent CAR.

The functional portion can comprise additional amino acids at the amino or carboxy terminus of the portion, or at both termini, which additional amino acids are not found in the amino acid sequence of the parent CAR. Desirably, the additional amino acids do not interfere with the biological function of the functional portion, e.g., recognize target cells, detect cancer, treat or prevent cancer, etc. More desirably, the additional amino acids enhance the biological activity, as compared to the biological activity of the parent CAR.

Included in the scope of the disclosure are functional variants of the CARs disclosed herein. The term "functional variant" as used herein refers to a CAR, polypeptide, or protein having substantial or significant sequence identity or similarity to a parent CAR, which functional variant retains the biological activity of the CAR of which it is a variant. Functional variants encompass, for example, those variants of the CAR described herein (the parent CAR) that retain the ability to recognize target cells to a similar extent, the same extent, or to a higher extent, as the parent CAR. In reference to the parent CAR, the functional variant can, for instance, be at least about 30%, 50%, 75%, 80%, 90%, 98% or more identical in amino acid sequence to the parent CAR.

A functional variant can, for example, comprise the amino acid sequence of the parent CAR with at least one conservative amino acid substitution. Alternatively or additionally, the functional variants can comprise the amino acid sequence of the parent CAR with at least one non-conservative amino acid substitution. In this case, it is preferable for the non-conservative amino acid substitution to not interfere with or inhibit the biological activity of the functional variant. The non-conservative amino acid substitution may enhance the biological activity of the functional variant, such that the biological activity of the functional variant is increased as compared to the parent CAR.

Amino acid substitutions of the CARs are preferably conservative amino acid substitutions. Conservative amino acid substitutions are known in the art, and include amino acid substitutions in which one amino acid having certain physical and/or chemical properties is exchanged for another amino acid that has the same or similar chemical or physical properties. For instance, the conservative amino acid substitution can be an acidic/negatively charged polar amino acid substituted for another acidic/negatively charged polar amino acid (e.g., Asp or Glu), an amino acid with a nonpolar side chain substituted for another amino acid with a nonpolar side chain (e.g., Ala, Gly, Val, He, Leu, Met, Phe, Pro, Trp, Cys, Val, etc.), a basic/positively charged polar amino acid substituted for another basic/positively charged polar amino acid (e.g. Lys, His, Arg, etc.), an uncharged amino acid with a polar side chain substituted for another uncharged amino acid with a polar side chain (e.g., Asn, Gin, Ser, Thr, Tyr, etc.), an amino acid with a beta-branched side-chain substituted for another amino acid with a beta-branched side-chain (e.g., He, Thr, and Val), an amino acid with an aromatic side-chain substituted for another amino acid with an aromatic side chain (e.g., His, Phe, Trp, and Tyr), etc.

The CAR can consist essentially of the specified amino acid sequence or sequences described herein, such that other components, e.g., other amino acids, do not materially change the biological activity of the functional variant.

The CARs (including functional portions and functional variants) can be of any length, i.e., can comprise any number of amino acids, provided that the CARs (or functional portions or functional variants thereof) retain their biological activity, e.g., the ability to specifically bind to antigen, detect diseased cells in a mammal, or treat or prevent disease in a mammal, etc. For example, the CAR can be about 50 to about 5000 amino acids long, such as 50, 70, 75, 100, 125, 150, 175, 200, 300, 400, 500, 600, 700, 800, 900, 1000 or more amino acids in length.

The CARs (including functional portions and functional variants of the invention) can comprise synthetic amino acids in place of one or more naturally-occurring amino acids. Such synthetic amino acids are known in the art, and include, for example, aminocyclohexane carboxylic acid, norleucine, -amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, a-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, omithine, -aminocyclopentane carboxylic acid, a-aminocyclohexane carboxylic acid, a-aminocycloheptane carboxylic acid, a-(2-amino-2-norbomane)-carboxylic acid, γ-diaminobutyric acid, β-diaminopropionic acid, homophenylalanine, and a-tert-butylglycine.

The CARs (including functional portions and functional variants) can be glycosylated, amidated, carboxylated, phosphorylated, esterified, N-acylated, cyclized via, e.g., a disulfide bridge, or converted into an acid addition salt and/or optionally dimerized or polymerized, or conjugated.

The CARs (including functional portions and functional variants thereof) can be obtained by methods known in the art. The CARs may be made by any suitable method of making polypeptides or proteins. Suitable methods of de novo synthesizing polypeptides and proteins are described in references, such as Chan et al., Fmoc Solid Phase Peptide Synthesis, Oxford University Press, Oxford, United Kingdom, 2000; Peptide and Protein Drug Analysis, ed. Reid, R., Marcel Dekker, Inc., 2000; Epitope Mapping, ed. Westwood et al., Oxford University Press, Oxford, United Kingdom, 2001; and U.S. Pat. No. 5,449,752. Also, polypeptides and proteins can be recombinantly produced using the nucleic acids described herein using standard recombinant methods. See, for instance, Sambrook et al., Molecular Cloning: A Laboratory Manual, 3rd ed., Cold Spring Harbor Press, Cold Spring Harbor, N.Y. 2001; and Ausubel et al., Current Protocols in Molecular Biology, Greene Publishing Associates and John Wiley & Sons, N Y, 1994. Further, some of the CARs (including functional portions and functional variants thereof) can be isolated and/or purified from a source, such as a plant, a bacterium, an insect, a mammal, e.g., a rat, a human, etc. Methods of isolation and purification are well-known in the art. Alternatively, the CARs described herein (including functional portions and functional variants thereof) can be commercially synthesized by companies. In this respect, the CARs can be synthetic, recombinant, isolated, and/or purified.

B. Antibodies and Antigen Binding Fragments

One embodiment further provides a CAR, a T cell expressing a CAR, an antibody, or antigen binding domain or portion thereof, which specifically binds to one or more of the antigens disclosed herein. As used herein, a "T cell expressing a CAR," or a "CAR T cell" means a T cell expressing a CAR, and has antigen specificity determined by, for example, the antibody-derived targeting domain of the CAR.

As used herein, and "antigen binding domain" can include an antibody and antigen binding fragments thereof. The term "antibody" is used herein in the broadest sense and encompasses various antibody structures, including but not limited to monoclonal antibodies, polyclonal antibodies, multi-specific antibodies (e.g., bispecific antibodies), and antigen binding fragments thereof, so long as they exhibit the desired antigen-binding activity. Non-limiting examples of antibodies include, for example, intact immunoglobulins and variants and fragments thereof known in the art that retain binding affinity for the antigen.

A "monoclonal antibody" is an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic epitope. The modifier "monoclonal" indicates the character of the antibody as being obtained from a substantially homogeneous population of antibodies, and is not to be construed as requiring production of the antibody by any particular method. In some examples, a monoclonal antibody is an antibody produced by a single clone of B lymphocytes or by a cell into which nucleic acid encoding the light and heavy variable regions of the antibody of a single antibody (or an antigen binding fragment thereof) have been transfected, or a progeny thereof. In some examples monoclonal antibodies are isolated from a subject. Monoclonal antibodies can have conservative amino acid substitutions which have substantially no effect on antigen binding or other immunoglobulin functions. Exemplary methods of production of monoclonal antibodies are known, for example, see Harlow & Lane, Antibodies, A Laboratory Manual, 2nd ed. Cold Spring Harbor Publications, New York (2013).

Typically, an immunoglobulin has heavy (H) chains and light (L) chains interconnected by disulfide bonds. Immunoglobulin genes include the kappa, lambda, alpha, gamma, delta, epsilon and mu constant region genes, as well as the myriad immunoglobulin variable domain genes. There are two types of light chain, lambda (λ) and kappa (κ). There are five main heavy chain classes (or isotypes) which determine the functional activity of an antibody molecule: IgM, IgD, IgG, IgA and IgE.

Each heavy and light chain contains a constant region (or constant domain) and a variable region (or variable domain; see, e.g., Kindt et al. Kuby Immunology, $6^{th}$ ed., W.H. Freeman and Co., page 91 (2007).) In several embodiments, the heavy and the light chain variable regions combine to specifically bind the antigen. In additional embodiments, only the heavy chain variable region is required. For example, naturally occurring camelid antibodies consisting of a heavy chain only are functional and stable in the absence of light chain (see, e.g., Hamers-Casterman et al., Nature, 363:446-448, 1993; Sheriff et al., Nat. Struct. Biol., 3:733-736, 1996). References to "VH" or "VH" refer to the variable region of an antibody heavy chain, including that of an antigen binding fragment, such as Fv, ScFv, dsFv or Fab. References to "VL" or "VL" refer to the variable domain of an antibody light chain, including that of an Fv, ScFv, dsFv or Fab.

Light and heavy chain variable regions contain a "framework" region interrupted by three hypervariable regions, also called "complementarity-determining regions" or "CDRs" (see, e.g., Kabat et al., Sequences of Proteins of Immunological Interest, U.S. Department of Health and Human Services, 1991). The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The amino acid sequence boundaries of a given CDR can be readily determined using any of a number of well-known schemes, including those described by Kabat et al. ("Sequences of Proteins of Immunological Interest," $5^{th}$ Ed. Public Health Service, National Institutes of Health, Bethesda, Md., 1991; "Kabat" numbering scheme), Al-Lazikani et al., (JMB 273, 927-948, 1997; "Chothia" numbering scheme), and Lefranc et al. ("IMGT unique numbering for immunoglobulin and T cell receptor variable domains and Ig superfamily V-like domains," Dev. Comp. Immunol., 27:55-77, 2003; "IMGT" numbering scheme). The CDRs of each chain are typically referred to as CDR1, CDR2, and CDR3 (from the N-terminus to C-terminus), and are also typically identified by the chain in which the particular CDR is located. Thus, a VH CDR3 is the CDR3 from the variable domain of the heavy chain of the antibody in which it is found, whereas a VL CDR1 is the CDR1 from the variable domain of the light chain of the antibody in which it is found. Light chain CDRs are sometimes referred to as LCDR1, LCDR2, and LCDR3. Heavy chain CDRs are sometimes referred to as LCDR1, LCDR2, and LCDR3.

An "antigen binding fragment" is a portion of a full length antibody that retains the ability to specifically recognize the cognate antigen, as well as various combinations of such portions. Non-limiting examples of antigen binding fragments include Fv, Fab, Fab', Fab'-SH, F(ab')2; diabodies; linear antibodies; single-chain antibody molecules (e.g. ScFv); and multi-specific antibodies formed from antibody fragments. Antibody fragments include antigen binding fragments either produced by the modification of whole antibodies or those synthesized de novo using recombinant DNA methodologies (see, e.g., Kontermann and Dubel (Ed), Antibody Engineering, Vols. 1-2, 2nd Ed., Springer Press, 2010).

A single-chain antibody (ScFv) is a genetically engineered molecule containing the VH and VL domains of one or more antibody(ies) linked by a suitable polypeptide linker as a genetically fused single chain molecule (see, for example, Bird et al., Science, 242:423 426, 1988; Huston et al., Proc. Natl. Acad. Sci., 85:5879 5883, 1988; Ahmad et al., Clin. Dev. Immunol., 2012, doi:10.1155/2012/980250; Marbry, IDrugs, 13:543-549, 2010). The intramolecular orientation of the VH-domain and the VL-domain in a ScFv, is typically not decisive for ScFvs. Thus, ScFvs with both possible arrangements (VH-domain-linker domain-VL-domain; VL-domain-linker domain-VH-domain) may be used.

In a dsFv, the heavy and light chain variable chains have been mutated to introduce a disulfide bond to stabilize the association of the chains. Diabodies also are included, which are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see, for example, Holliger et al., Proc. Natl. Acad. Sci., 90:6444 6448, 1993; Poljak et al., Structure, 2:1121 1123, 1994).

Antibodies also include genetically engineered forms such as chimeric antibodies (such as humanized murine antibodies) and heteroconjugate antibodies (such as bispecific antibodies). See also, Pierce Catalog and Handbook, 1994-1995 (Pierce Chemical Co., Rockford, Ill.); Kuby, J., Immunology, 3rd Ed., W.H. Freeman & Co., New York, 1997.

Non-naturally occurring antibodies can be constructed using solid phase peptide synthesis, can be produced recombinantly, or can be obtained, for example, by screening combinatorial libraries consisting of variable heavy chains and variable light chains as described by Huse et al., Science 246:1275-1281 (1989), which is incorporated herein by reference. These and other methods of making, for example, chimeric, humanized, CDR-grafted, single chain, and bifunctional antibodies, are well known to those skilled in the art (Winter and Harris, Immunol. Today 14:243-246 (1993); Ward et al., Nature 341:544-546 (1989); Harlow and Lane, supra, 1988; Hilyard et al., Protein Engineering: A practical approach (IRL Press 1992); Borrabeck, Antibody Engineering, 2d ed. (Oxford University Press 1995); each of which is incorporated herein by reference).

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. Antibody competition assays are known, and an exemplary competition assay is provided herein.

A "humanized" antibody or antigen binding fragment includes a human framework region and one or more CDRs from a non-human (such as a mouse, rat, or synthetic) antibody or antigen binding fragment. The non-human antibody or antigen binding fragment providing the CDRs is termed a "donor," and the human antibody or antigen binding fragment providing the framework is termed an "acceptor." In one embodiment, all the CDRs are from the donor immunoglobulin in a humanized immunoglobulin. Constant regions need not be present, but if they are, they can be substantially identical to human immunoglobulin constant regions, such as at least about 85-90%, such as about 95% or more identical. Hence, all parts of a humanized antibody or antigen binding fragment, except possibly the CDRs, are substantially identical to corresponding parts of natural human antibody sequences.

A "chimeric antibody" is an antibody which includes sequences derived from two different antibodies, which typically are of different species. In some examples, a chimeric antibody includes one or more CDRs and/or framework regions from one human antibody and CDRs and/or framework regions from another human antibody.

A "fully human antibody" or "human antibody" is an antibody which includes sequences from (or derived from) the human genome, and does not include sequence from another species. In some embodiments, a human antibody includes CDRs, framework regions, and (if present) an Fc region from (or derived from) the human genome. Human antibodies can be identified and isolated using technologies for creating antibodies based on sequences derived from the human genome, for example by phage display or using transgenic animals (see, e.g., Barbas et al. Phage display: A Laboratory Manuel. 1st Ed. New York: Cold Spring Harbor Laboratory Press, 2004. Print.; Lonberg, Nat. Biotech., 23: 1117-1125, 2005; Lonenberg, Curr. Opin. Immunol., 20:450-459, 2008).

An antibody may have one or more binding sites. If there is more than one binding site, the binding sites may be identical to one another or may be different. For instance, a naturally-occurring immunoglobulin has two identical binding sites, a single-chain antibody or Fab fragment has one binding site, while a bispecific or bifunctional antibody has two different binding sites.

Methods of testing antibodies for the ability to bind to any functional portion of the CAR are known in the art and include any antibody-antigen binding assay, such as, for example, radioimmunoassay (RIA), ELISA, Western blot, immunoprecipitation, and competitive inhibition assays (see, e.g., Janeway et al., infra, U.S. Patent Application Publication No. 2002/0197266 A1, and U.S. Pat. No. 7,338, 929).

Also, a CAR, a T cell expressing a CAR, an antibody, or antigen binding portion thereof, can be modified to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

C. Conjugates

A CAR, a T cell expressing a CAR, or monoclonal antibodies, or antigen binding fragments thereof, specific for one or more of the antigens disclosed herein, can be conjugated to an agent, such as an effector molecule or detectable marker, using any number of means known to those of skill in the art. Both covalent and noncovalent attachment means may be used. Conjugates include, but are not limited to, molecules in which there is a covalent linkage of an effector molecule or a detectable marker to an antibody or antigen binding fragment that specifically binds one or more of the antigens disclosed herein. One of skill in the art will appreciate that various effector molecules and detectable markers can be used, including (but not limited to) chemotherapeutic agents, anti-angiogenic agents, toxins, radioactive agents such as $^{125}$I, $^{32}$P, $^{14}$C, $^{3}$H and $^{35}$S and other labels, target moieties and ligands, etc.

The choice of a particular effector molecule or detectable marker depends on the particular target molecule or cell, and the desired biological effect. Thus, for example, the effector molecule can be a cytotoxin that is used to bring about the death of a particular target cell (such as a tumor cell).

The procedure for attaching an effector molecule or detectable marker to an antibody or antigen binding fragment varies according to the chemical structure of the effector. Polypeptides typically contain a variety of functional groups; such as carboxylic acid (COOH), free amine (—NH$_2$) or sulfhydryl (—SH) groups, which are available for reaction with a suitable functional group on an antibody to result in the binding of the effector molecule or detectable marker. Alternatively, the antibody or antigen binding fragment is derivatized to expose or attach additional reactive functional groups. The derivatization may involve attachment of any of a number of known linker molecules such as those available from Pierce Chemical Company, Rockford, Ill. The linker can be any molecule used to join the antibody or antigen binding fragment to the effector molecule or detectable marker. The linker is capable of forming covalent bonds to both the antibody or antigen binding fragment and to the effector molecule or detectable marker. Suitable linkers are well known to those of skill in the art and include, but are not limited to, straight or branched-chain carbon linkers, heterocyclic carbon linkers, or peptide linkers. Where the antibody or antigen binding fragment and the effector molecule or detectable marker are polypeptides, the linkers may be joined to the constituent amino acids through their side groups (such as through a disulfide linkage to cysteine) or to the alpha carbon amino and carboxyl groups of the terminal amino acids.

In several embodiments, the linker can include a spacer element, which, when present, increases the size of the linker such that the distance between the effector molecule or the detectable marker and the antibody or antigen binding fragment is increased. Exemplary spacers are known to the person of ordinary skill, and include those listed in U.S. Pat. Nos. 7,964,566, 7,498,298, 6,884,869, 6,323,315, 6,239, 104, 6,034,065, 5,780,588, 5,665,860, 5,663,149, 5,635,483, 5,599,902, 5,554,725, 5,530,097, 5,521,284, 5,504,191, 5,410,024, 5,138,036, 5,076,973, 4,986,988, 4,978,744, 4,879,278, 4,816,444, and 4,486,414, as well as U.S. Pat. Pub. Nos. 20110212088 and 20110070248, each of which is incorporated by reference herein in its entirety.

In some embodiments, the linker is cleavable under intracellular conditions, such that cleavage of the linker releases the effector molecule or detectable marker from the antibody or antigen binding fragment in the intracellular environment. In yet other embodiments, the linker is not cleavable and the effector molecule or detectable marker is released, for example, by antibody degradation. In some embodiments, the linker is cleavable by a cleaving agent that is present in the intracellular environment (for example, within a lysosome or endosome or caveolea). The linker can be, for example, a peptide linker that is cleaved by an intracellular peptidase or protease enzyme, including, but not limited to, a lysosomal or endosomal protease. In some embodiments, the peptide linker is at least two amino acids long or at least three amino acids long. However, the linker can be 4, 5, 6, 7, 8, 9, 10, 11, 12, 13, 14 or 15 amino acids long, such as 1-2, 1-3, 2-5, 3-10, 3-15, 1-5, 1-10, 1-15 amino acids long. Proteases can include cathepsins B and D and plasmin, all of which are known to hydrolyze dipeptide drug derivatives resulting in the release of active drug inside target cells (see, for example, Dubowchik and Walker, 1999, Pharm. Therapeutics 83:67-123). For example, a peptide linker that is cleavable by the thiol-dependent protease cathepsin-B, can be used (for example, a Phenylalanine-Leucine or a Glycine-Phenylalanine-Leucine-Glycine linker). Other examples of such linkers are described, for example, in U.S. Pat. No. 6,214,345, incorporated herein by reference. In a specific embodiment, the peptide linker cleavable by an intracellular protease is a Valine-Citruline linker or a Phenylalanine-Lysine linker (see, for example, U.S. Pat. No. 6,214,345, which describes the synthesis of doxorubicin with the Valine-Citruline linker).

In other embodiments, the cleavable linker is pH-sensitive, i.e., sensitive to hydrolysis at certain pH values. Typically, the pH-sensitive linker is hydrolyzable under acidic conditions. For example, an acid-labile linker that is hydrolyzable in the lysosome (for example, a hydrazone, semicarbazone, thiosemicarbazone, cis-aconitic amide, orthoester, acetal, ketal, or the like) can be used. (See, for example, U.S. Pat. Nos. 5,122,368; 5,824,805; 5,622,929; Dubowchik and Walker, 1999, Pharm. Therapeutics 83:67-123; Neville et al., 1989, Biol. Chem. 264:14653-14661.) Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, for example, a thioether attached to the therapeutic agent via an acylhydrazone bond (see, for example, U.S. Pat. No. 5,622,929).

In other embodiments, the linker is cleavable under reducing conditions (for example, a disulfide linker). A variety of disulfide linkers are known in the art, including, for example, those that can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio) toluene)-, SPDB and SMPT. (See, for example, Thorpe et al., 1987, Cancer Res. 47:5924-5931; Wawrzynczak et al., In Immunoconjugates: Antibody Conjugates in Radioimagery and Therapy of Cancer (C. W. Vogel ed., Oxford U. Press, 1987); Phillips et al., Cancer Res. 68:92809290, 2008). See also U.S. Pat. No. 4,880,935.) In yet other specific embodiments, the linker is a malonate linker (Johnson et al., 1995, Anticancer Res. 15:1387-93), a maleimidobenzoyl linker (Lau et al., 1995, Bioorg-Med-Chem. 3(10): 1299-1304), or a 3'-N-amide analog (Lau et al., 1995, Bioorg-Med-Chem. 3(10): 1305-12).

In yet other embodiments, the linker is not cleavable and the effector molecule or detectable marker is released by antibody degradation. (See U.S. Publication No. 2005/0238649 incorporated by reference herein in its entirety).

In several embodiments, the linker is resistant to cleavage in an extracellular environment. For example, no more than about 20%, no more than about 15%, no more than about 10%, no more than about 5%, no more than about 3%, or no more than about 1% of the linkers, in a sample of conjugate, are cleaved when the conjugate is present in an extracellular environment (for example, in plasma). Whether or not a linker is resistant to cleavage in an extracellular environment can be determined, for example, by incubating the conjugate containing the linker of interest with plasma for a predetermined time period (for example, 2, 4, 8, 16, or 24 hours) and then quantitating the amount of free effector molecule or detectable marker present in the plasma. A variety of exemplary linkers that can be used in conjugates are described in WO 2004-010957, U.S. Publication No. 2006/0074008, U.S. Publication No. 20050238649, and U.S. Publication No. 2006/0024317, each of which is incorporated by reference herein in its entirety.

In several embodiments, conjugates of a CAR, a T cell expressing a CAR, an antibody, or antigen binding portion thereof, and one or more small molecule toxins, such as a calicheamicin, maytansinoids, dolastatins, auristatins, a trichothecene, and CC1065, and the derivatives of these toxins that have toxin activity, are provided.

Maytansine compounds suitable for use as maytansinoid toxin moieties are well known in the art, and can be isolated from natural sources according to known methods, produced using genetic engineering techniques (see Yu et al (2002) PNAS 99:7968-7973), or maytansinol and maytansinol analogues prepared synthetically according to known methods. Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248, 870; 4,256,746; 4,260,608; 4,265,814; 4,294,757; 4,307, 016; 4,308,268; 4,308,269; 4,309,428; 4,313,946; 4,315, 929; 4,317,821; 4,322,348; 4,331,598; 4,361,650; 4,364, 866; 4,424,219; 4,450,254; 4,362,663; and 4,371,533, each of which is incorporated herein by reference. Conjugates containing maytansinoids, methods of making same, and their therapeutic use are disclosed, for example, in U.S. Pat. Nos. 5,208,020; 5,416,064; 6,441,163 and European Patent EP 0 425 235 B1, the disclosures of which are hereby expressly incorporated by reference.

Additional toxins can be employed with a CAR, a T cell expressing a CAR, an antibody, or antigen binding portion thereof. Exemplary toxins include *Pseudomonas* exotoxin (PE), ricin, abrin, diphtheria toxin and subunits thereof, ribotoxin, ribonuclease, saporin, and calicheamicin, as well as botulinum toxins A through F. These toxins are well known in the art and many are readily available from commercial sources (for example, Sigma Chemical Company, St. Louis, Mo.). Contemplated toxins also include variants of the toxins (see, for example, see, U.S. Pat. Nos. 5,079,163 and 4,689,401).

Saporin is a toxin derived from *Saponaria officinalis* that disrupts protein synthesis by inactivating the 60S portion of the ribosomal complex (Stirpe et al., Bio/Technology, 10:405-412, 1992). However, the toxin has no mechanism for specific entry into cells, and therefore requires conjugation to an antibody or antigen binding fragment that recognizes a cell-surface protein that is internalized in order to be efficiently taken up by cells.

Diphtheria toxin is isolated from *Corynebacterium diphtheriae*. Typically, diphtheria toxin for use in immunotoxins is mutated to reduce or to eliminate non-specific toxicity. A mutant known as CRM107, which has full enzymatic activity but markedly reduced non-specific toxicity, has been known since the 1970's (Laird and Groman, J. Virol. 19:220, 1976), and has been used in human clinical trials. See, U.S. Pat. Nos. 5,792,458 and 5,208,021.

Ricin is the lectin RCA60 from *Ricinus communis* (Castor bean). For examples of ricin, see, U.S. Pat. Nos. 5,079,163 and 4,689,401. *Ricinus communis* agglutinin (RCA) occurs in two forms designated $RCA_{60}$ and $RCA_{120}$ according to their molecular weights of approximately 65 and 120 kD, respectively (Nicholson & Blaustein, J. Biochim. Biophys. Acta 266:543, 1972). The A chain is responsible for inactivating protein synthesis and killing cells. The B chain binds ricin to cell-surface galactose residues and facilitates transport of the A chain into the cytosol (Olsnes et al., Nature 249:627-631, 1974 and U.S. Pat. No. 3,060,165).

Ribonucleases have also been conjugated to targeting molecules for use as immunotoxins (see Suzuki et al., Nat. Biotech. 17:265-70, 1999). Exemplary ribotoxins such as α-sarcin and restrictocin are discussed in, for example Rathore et al., Gene 190:31-5, 1997; and Goyal and Batra, Biochem. 345 Pt 2:247-54, 2000. Calicheamicins were first isolated from *Micromonospora echinospora* and are members of the enediyne antitumor antibiotic family that cause double strand breaks in DNA that lead to apoptosis (see, for example Lee et al., J. Antibiot. 42:1070-87, 1989). The drug is the toxic moiety of an immunotoxin in clinical trials (see, for example, Gillespie et al., Ann. Oncol. 11:735-41, 2000).

Abrin includes toxic lectins from *Abrus precatorius*. The toxic principles, abrin a, b, c, and d, have a molecular weight of from about 63 and 67 kD and are composed of two disulfide-linked polypeptide chains A and B. The A chain inhibits protein synthesis; the B chain (abrin-b) binds to D-galactose residues (see, Funatsu et al., Agr. Biol. Chem. 52:1095, 1988; and Olsnes, Methods Enzymol. 50:330-335, 1978).

A CAR, a T cell expressing a CAR, monoclonal antibodies, antigen binding fragments thereof, specific for one or more of the antigens disclosed herein, can also be conjugated with a detectable marker; for example, a detectable marker capable of detection by ELISA, spectrophotometry, flow cytometry, microscopy or diagnostic imaging techniques (such as computed tomography (CT), computed axial tomography (CAT) scans, magnetic resonance imaging (MRI), nuclear magnetic resonance imaging NMRI), magnetic resonance tomography (MTR), ultrasound, fiberoptic examination, and laparoscopic examination). Specific, non-limiting examples of detectable markers include fluorophores, chemiluminescent agents, enzymatic linkages, radioactive isotopes and heavy metals or compounds (for example super paramagnetic iron oxide nanocrystals for detection by MRI). For example, useful detectable markers include fluorescent compounds, including fluorescein, fluorescein isothiocyanate, rhodamine, 5-dimethylamine-1-napthalenesulfonyl chloride, phycoerythrin, lanthanide phosphors and the like. Bioluminescent markers are also of use, such as luciferase, Green fluorescent protein (GFP), Yellow fluorescent protein (YFP). A CAR, a T cell expressing a CAR, an antibody, or antigen binding portion thereof, can also be conjugated with enzymes that are useful for detection, such as horseradish peroxidase, 0-galactosidase, luciferase, alkaline phosphatase, glucose oxidase and the like. When a CAR, a T cell expressing a CAR, an antibody, or antigen binding portion thereof, is conjugated with a detectable enzyme, it can be detected by adding additional reagents that the enzyme uses to produce a reaction product that can be discerned. For example, when the agent horseradish peroxidase is present the addition of hydrogen peroxide and diaminobenzidine leads to a colored reaction product, which is visually detectable. A CAR, a T cell expressing a CAR, an antibody, or antigen binding portion thereof, may also be conjugated with biotin, and detected through indirect measurement of avidin or streptavidin binding. It should be noted that the avidin itself can be conjugated with an enzyme or a fluorescent label.

A CAR, a T cell expressing a CAR, an antibody, or antigen binding portion thereof, may be conjugated with a paramagnetic agent, such as gadolinium. Paramagnetic agents such as superparamagnetic iron oxide are also of use as labels. Antibodies can also be conjugated with lanthanides (such as europium and dysprosium), and manganese. An antibody or antigen binding fragment may also be labeled with a predetermined polypeptide epitopes recognized by a secondary reporter (such as leucine zipper pair sequences, binding sites for secondary antibodies, metal binding domains, epitope tags).

A CAR, a T cell expressing a CAR, an antibody, or antigen binding portion thereof, can also be conjugated with a radiolabeled amino acid. The radiolabel may be used for both diagnostic and therapeutic purposes. For instance, the radiolabel may be used to detect one or more of the antigens disclosed herein and antigen expressing cells by x-ray, emission spectra, or other diagnostic techniques. Further, the radiolabel may be used therapeutically as a toxin for treatment of tumors in a subject, for example for treatment of a neuroblastoma. Examples of labels for polypeptides include, but are not limited to, the following radioisotopes or radionucleotides: $^{3}H$, $^{14}C$, $^{15}N$, $^{35}S$, $^{90}Y$, $^{99}Tc$, $^{111}In$, $^{125}I$, and $^{131}I$.

Means of detecting such detectable markers are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

D. Nucleotides, Expression, Vectors, and Host Cells

Further provided by an embodiment of the invention is a nucleic acid comprising a nucleotide sequence encoding any of the CARs, an antibody, or antigen binding portion thereof, described herein (including functional portions and functional variants thereof). The nucleic acids of the invention may comprise a nucleotide sequence encoding any of the leader sequences, antigen binding domains, transmembrane domains, and/or intracellular T cell signaling domains described herein.

In some embodiments, the nucleotide sequence may be codon-modified. Without being bound to a particular theory, it is believed that codon optimization of the nucleotide sequence increases the translation efficiency of the mRNA transcripts. Codon optimization of the nucleotide sequence may involve substituting a native codon for another codon that encodes the same amino acid, but can be translated by tRNA that is more readily available within a cell, thus increasing translation efficiency. Optimization of the nucleotide sequence may also reduce secondary mRNA structures that would interfere with translation, thus increasing translation efficiency.

In an embodiment of the invention, the nucleic acid may comprise a codon-modified nucleotide sequence that encodes the antigen binding domain of the inventive CAR. In another embodiment of the invention, the nucleic acid may comprise a codon-modified nucleotide sequence that encodes any of the CARs described herein (including functional portions and functional variants thereof).

"Nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. In some embodiments, the nucleic acid does not comprise any insertions, deletions, inversions, and/or substitutions. However, it may be suitable in some instances, as discussed herein, for the nucleic acid to comprise one or more insertions, deletions, inversions, and/or substitutions.

A recombinant nucleic acid may be one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques, such as those described in Sambrook et al., supra. The nucleic acids can be constructed based on chemical synthesis and/or enzymatic ligation reactions using procedures known in the art. See, for example, Sambrook et al., supra, and Ausubel et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Integrated DNA Technologies (Coralville, Iowa, USA).

The nucleic acid can comprise any isolated or purified nucleotide sequence which encodes any of the CARs or functional portions or functional variants thereof. Alternatively, the nucleotide sequence can comprise a nucleotide sequence which is degenerate to any of the sequences or a combination of degenerate sequences.

An embodiment also provides an isolated or purified nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions may hybridize under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive CARs. It is generally appreciated that conditions can be rendered more stringent by the addition of increasing amounts of formamide.

Also provided is a nucleic acid comprising a nucleotide sequence that is at least about 70% or more, e.g., about 80%, about 90%, about 91%, about 92%, about 93%, about 94%, about 95%, about 96%, about 97%, about 98%, or about 99% identical to any of the nucleic acids described herein.

In an embodiment, the nucleic acids can be incorporated into a recombinant expression vector. In this regard, an embodiment provides recombinant expression vectors comprising any of the nucleic acids. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors are not naturally-occurring as a whole.

However, parts of the vectors can be naturally-occurring. The recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring or non-naturally-occurring internucleotide linkages, or both types of linkages. Preferably, the non-naturally occurring or altered nucleotides or internucleotide linkages do not hinder the transcription or replication of the vector.

In an embodiment, the recombinant expression vector can be any suitable recombinant expression vector, and can be used to transform or transfect any suitable host cell. Suitable vectors include those designed for propagation and expansion or for expression or both, such as plasmids and viruses. The vector can be selected from the group consisting of the pUC series (Fermentas Life Sciences, Glen Burnie, Md.), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.).

Bacteriophage vectors, such as λ[$]$¨$$[$]$¨AÄ [|$]$¨gñTIO, λvTI 1, λZapII (Stratagene), EMBL4, and λNMI 149, also can be used. Examples of plant expression vectors include pBIO1, pBI101.2, pBHO1.3, pBI121 and pBIN19 (Clontech). Examples of animal expression vectors include pEUK-C1, pMAM, and pMAMneo (Clontech). The recombinant expression vector may be a viral vector, e.g., a retroviral vector or a lentiviral vector. A lentiviral vector is a vector derived from at least a portion of a lentivirus genome, including especially a self-inactivating lentiviral vector as provided in Milone et al., Mol. Ther. 17(8): 1453-1464 (2009). Other examples of lentivirus vectors that may be used in the clinic, include, for example, and not by way of limitation, the LENTIVECTOR® gene delivery technology from Oxford BioMedica plc, the LENTIMAX™ vector system from Lentigen and the like. Nonclinical types of lentiviral vectors are also available and would be known to one skilled in the art.

A number of transfection techniques are generally known in the art (see, e.g., Graham et al., Virology, 52: 456-467 (1973); Sambrook et al., supra; Davis et al., Basic Methods in Molecular Biology, Elsevier (1986); and Chu et al, Gene, 13: 97 (1981).

Transfection methods include calcium phosphate co-precipitation (see, e.g., Graham et al., supra), direct micro injection into cultured cells (see, e.g., Capecchi, Cell, 22: 479-488 (1980)), electroporation (see, e.g., Shigekawa et al., BioTechniques, 6: 742-751 (1988)), liposome mediated gene transfer (see, e.g., Mannino et al., BioTechniques, 6: 682-690 (1988)), lipid mediated transduction (see, e.g., Feigner et al., Proc. Natl. Acad. Sci. USA, 84: 7413-7417 (1987)), and nucleic acid delivery using high velocity microprojectiles (see, e.g., Klein et al, Nature, 327: 70-73 (1987)).

In an embodiment, the recombinant expression vectors can be prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColEl, 2μ plasmid, λ, SV40, bovine papilloma virus, and the like.

The recombinant expression vector may comprise regulatory sequences, such as transcription and translation initiation and termination codons, which are specific to the type of host cell (e.g., bacterium, fungus, plant, or animal) into which the vector is to be introduced, as appropriate, and taking into consideration whether the vector is DNA- or RNA-based. The recombinant expression vector may comprise restriction sites to facilitate cloning.

The recombinant expression vector can include one or more marker genes, which allow for selection of transformed or transfected host cells. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or nonnative promoter operably linked to the nucleotide sequence encoding the CAR (including functional portions and functional variants thereof), or to the nucleotide sequence which is complementary to or which hybridizes to the nucleotide sequence encoding the CAR. The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, or a promoter found in the long-terminal repeat of the murine stem cell virus.

The recombinant expression vectors can be designed for either transient expression, for stable expression, or for both. Also, the recombinant expression vectors can be made for constitutive expression or for inducible expression.

Further, the recombinant expression vectors can be made to include a suicide gene. As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art (see, for example, Suicide Gene Therapy: Methods and Reviews, Springer, Caroline J. (Cancer Research UK Centre for Cancer Therapeutics at the Institute of Cancer Research, Sutton, Surrey, UK), Humana Press, 2004) and include, for example, the Herpes Simplex Virus (HSV) thymidine kinase (TK) gene, cytosine diminase, purine nucleoside phosphorylase, and nitroreductase.

An embodiment further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5a $E.$ $coli$ cells, Chinese hamster ovarian cells, monkey VERO cells, COS cells, HEK293 cells, and the like. For purposes of amplifying or replicating the recombinant expression vector, the host cell may be a prokaryotic cell, e.g., a DH5a cell. For purposes of producing a recombinant CAR, the host cell may be a mammalian cell. The host cell may be a human cell. While the host cell can be of any cell type, can originate from any type of tissue, and can be of any developmental stage, the host cell may be a peripheral blood lymphocyte (PBL) or a peripheral blood mononuclear cell (PBMC). The host cell may be a T cell.

For purposes herein, the T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. The T cell may be a human T cell. The T cell may be a T cell isolated from a human. The T cell can be any type of T cell and can be of any developmental stage, including but not limited to, CD4+/CD8+ double positive T cells, CD4+ helper T cells, e.g., Th1 and Th2 cells, CD8+ T cells (e.g., cytotoxic T cells), tumor infiltrating cells, memory T cells, memory stem cells, i.e. Tscm, naive T cells, and the like. The T cell may be a CD8+ T cell or a CD4+ T cell.

In an embodiment, the CARs as described herein can be used in suitable non-T cells. Such cells are those with an immune-effector function, such as, for example, NK cells, and T-like cells generated from pluripotent stem cells.

Also provided by an embodiment is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cell, a muscle cell, a brain cell, etc. Alternatively, the population of cells can be a substantially homogeneous population, in which the population comprises mainly host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

CARs (including functional portions and variants thereof), nucleic acids, recombinant expression vectors, host cells (including populations thereof), and antibodies (including antigen binding portions thereof), can be isolated and/or purified. For example, a purified (or isolated) host cell preparation is one in which the host cell is more pure than cells in their natural environment within the body. Such host cells may be produced, for example, by standard purification techniques. In some embodiments, a preparation of a host cell is purified such that the host cell represents at least about 50%, for example at least about 70%, of the total cell content of the preparation. For example, the purity can be at least about 50%, can be greater than about 60%, about 70% or about 80%, or can be about 100%.

E. Methods of Treatment

It is contemplated that the CARs disclosed herein can be used in methods of treating or preventing a disease in a mammal. In this regard, an embodiment provides a method of treating or preventing cancer in a mammal, comprising administering to the mammal the CARs, the nucleic acids, the recombinant expression vectors, the host cells, the population of cells, the antibodies and/or the antigen binding portions thereof, and/or the pharmaceutical compositions in an amount effective to treat or prevent cancer in the mammal.

An embodiment further comprises lymphodepleting the mammal prior to administering the CARs disclosed herein. Examples of lymphodepletion include, but may not be limited to, nonmyeloablative lymphodepleting chemotherapy, myeloablative lymphodepleting chemotherapy, total body irradiation, etc.

For purposes of the methods, wherein host cells or populations of cells are administered, the cells can be cells that are allogeneic or autologous to the mammal. Preferably, the cells are autologous to the mammal. As used herein, allogeneic means any material derived from a different animal of the same species as the individual to whom the material is introduced. Two or more individuals are said to be allogeneic to one another when the genes at one or more loci are not identical. In some aspects, allogeneic material from individuals of the same species may be sufficiently unlike genetically to interact antigenically. As used herein, "autologous" means any material derived from the same individual to whom it is later to be re-introduced into the individual.

The mammal referred to herein can be any mammal. As used herein, the term "mammal" refers to any mammal, including, but not limited to, mammals of the order Rodentia, such as mice and hamsters, and mammals of the order Logomorpha, such as rabbits. The mammals may be from the order Carnivora, including Felines (cats) and Canines (dogs). The mammals may be from the order Artiodactyla, including Bovines (cows) and Swines (pigs) or of the order Perssodactyla, including Equines (horses). The mammals may be of the order Primates, Ceboids, or Simoids (monkeys) or of the order Anthropoids (humans and apes). Preferably, the mammal is a human.

With respect to the methods, the cancer can be any cancer, including any of acute lymphocytic cancer, acute myeloid leukemia, alveolar rhabdomyosarcoma, bladder cancer (e.g., bladder carcinoma), bone cancer, brain cancer (e.g., medulloblastoma), breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, fibrosarcoma, gastrointestinal carcinoid tumor, head and neck cancer (e.g., head and neck squamous cell carcinoma), Hodgkin lymphoma, hypopharynx cancer, kidney cancer, larynx cancer, leukemia, liquid tumors, liver cancer, lung cancer (e.g., non-small cell lung carcinoma and lung adenocarcinoma), lymphoma, mesothelioma, mastocytoma, melanoma, multiple myeloma, nasopharynx cancer, non-Hodgkin lymphoma, B-chronic lymphocytic leukemia, hairy cell leukemia, acute lymphocytic leukemia (ALL), and Burkitt's lymphoma, ovarian cancer, pancreatic cancer, peritoneum, omentum, and mesentery cancer, pharynx cancer, prostate cancer, rectal cancer, renal cancer, skin cancer, small intestine cancer, soft tissue cancer, solid tumors, synovial sarcoma, gastric cancer, testicular cancer, thyroid cancer, and ureter cancer.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the methods can provide any amount or any level of treatment or prevention of cancer in a mammal.

Furthermore, the treatment or prevention provided by the method can include treatment or prevention of one or more conditions or symptoms of the disease, e.g., cancer, being treated or prevented. Also, for purposes herein, "prevention" can encompass delaying the onset of the disease, or a symptom or condition thereof.

Another embodiment provides a method of detecting the presence of cancer in a mammal, comprising: (a) contacting a sample comprising one or more cells from the mammal with the CARs, the nucleic acids, the recombinant expression vectors, the host cells, the population of cells, the antibodies, and/or the antigen binding portions thereof, or the pharmaceutical compositions, thereby forming a complex, (b) and detecting the complex, wherein detection of the complex is indicative of the presence of cancer in the mammal.

The sample may be obtained by any suitable method, e.g., biopsy or necropsy. A biopsy is the removal of tissue and/or cells from an individual. Such removal may be to collect tissue and/or cells from the individual in order to perform experimentation on the removed tissue and/or cells. This experimentation may include experiments to determine if the individual has and/or is suffering from a certain condition or disease-state. The condition or disease may be, e.g., cancer.

With respect to an embodiment of the method of detecting the presence of a proliferative disorder, e.g., cancer, in a mammal, the sample comprising cells of the mammal can be a sample comprising whole cells, lysates thereof, or a fraction of the whole cell lysates, e.g., a nuclear or cytoplasmic fraction, a whole protein fraction, or a nucleic acid fraction. If the sample comprises whole cells, the cells can be any cells of the mammal, e.g., the cells of any organ or tissue, including blood cells or endothelial cells.

The contacting can take place in vitro or in vivo with respect to the mammal. Preferably, the contacting is in vitro.

Also, detection of the complex can occur through any number of ways known in the art. For instance, the CARs disclosed herein, polypeptides, proteins, nucleic acids, recombinant expression vectors, host cells, populations of cells, or antibodies, or antigen binding portions thereof, described herein, can be labeled with a detectable label such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles) as disclosed supra.

Methods of testing a CAR for the ability to recognize target cells and for antigen specificity are known in the art. For instance, Clay et al., J. Immunol, 163: 507-513 (1999), teaches methods of measuring the release of cytokines (e.g., interferon-γ, granulocyte/monocyte colony stimulating factor (GM-CSF), tumor necrosis factor a (TNF-a) or interleukin 2 (IL-2)). In addition, CAR function can be evaluated by measurement of cellular cytotoxicity, as described in Zhao et al, J. Immunol, 174: 4415-4423 (2005).

Another embodiment provides for the use of the CARs, nucleic acids, recombinant expression vectors, host cells, populations of cells, antibodies, or antigen binding portions thereof, and/or pharmaceutical compositions of the invention, for the treatment or prevention of a proliferative disorder, e.g., cancer, in a mammal. The cancer may be any of the cancers described herein.

Any method of administration can be used for the disclosed therapeutic agents, including local and systemic administration. For example topical, oral, intravascular such as intravenous, intramuscular, intraperitoneal, intranasal, intradermal, intrathecal and subcutaneous administration can be used. The particular mode of administration and the dosage regimen will be selected by the attending clinician, taking into account the particulars of the case (for example the subject, the disease, the disease state involved, and whether the treatment is prophylactic). In cases in which more than one agent or composition is being administered, one or more routes of administration may be used; for example, a chemotherapeutic agent may be administered orally and an antibody or antigen binding fragment or conjugate or composition may be administered intravenously. Methods of administration include injection for which the CAR, CAR T Cell, conjugates, antibodies, antigen binding fragments, or compositions are provided in a nontoxic pharmaceutically acceptable carrier such as water, saline, Ringer's solution, dextrose solution, 5% human serum albumin, fixed oils, ethyl oleate, or liposomes. In some embodiments, local administration of the disclosed compounds can be used, for instance by applying the antibody or antigen binding fragment to a region of tissue from which a tumor has been removed, or a region suspected of being prone to tumor development. In some embodiments, sustained intra-tumoral (or near-tumoral) release of the pharmaceutical preparation that includes a therapeutically effective amount of the antibody or antigen binding fragment may be beneficial. In other examples, the conjugate is applied as an eye drop topically to the cornea, or intravitreally into the eye.

The disclosed therapeutic agents can be formulated in unit dosage form suitable for individual administration of precise dosages. In addition, the disclosed therapeutic agents may be administered in a single dose or in a multiple dose schedule. A multiple dose schedule is one in which a primary course of treatment may be with more than one separate dose, for instance 1-10 doses, followed by other doses given at subsequent time intervals as needed to maintain or reinforce the action of the compositions. Treatment can involve daily or multi-daily doses of compound(s) over a period of a few days to months, or even years. Thus, the dosage regime will also, at least in part, be determined based on the particular needs of the subject to be treated and will be dependent upon the judgment of the administering practitioner.

Typical dosages of the antibodies or conjugates can range from about 0.01 to about 30 mg/kg, such as from about 0.1 to about 10 mg/kg.

In particular examples, the subject is administered a therapeutic composition that includes one or more of the conjugates, antibodies, compositions, CARs, CAR T cells or additional agents, on a multiple daily dosing schedule, such as at least two consecutive days, 10 consecutive days, and so forth, for example for a period of weeks, months, or years. In one example, the subject is administered the conjugates, antibodies, compositions or additional agents for a period of at least 30 days, such as at least 2 months, at least 4 months, at least 6 months, at least 12 months, at least 24 months, or at least 36 months.

In some embodiments, the disclosed methods include providing surgery, radiation therapy, and/or chemotherapeutics to the subject in combination with a disclosed antibody, antigen binding fragment, conjugate, CAR or T cell expressing a CAR (for example, sequentially, substantially simultaneously, or simultaneously). Methods and therapeutic dosages of such agents and treatments are known to those skilled in the art, and can be determined by a skilled clinician. Preparation and dosing schedules for the additional agent may be used according to manufacturer's instructions or as determined empirically by the skilled practitioner. Preparation and dosing schedules for such chemotherapy are also described in Chemotherapy Service, (1992) Ed., M. C. Perry, Williams & Wilkins, Baltimore, Md.

In some embodiments, the combination therapy can include administration of a therapeutically effective amount of an additional cancer inhibitor to a subject. Non-limiting examples of additional therapeutic agents that can be used with the combination therapy include microtubule binding agents, DNA intercalators or cross-linkers, DNA synthesis inhibitors, DNA and RNA transcription inhibitors, antibodies, enzymes, enzyme inhibitors, gene regulators, and angiogenesis inhibitors. These agents (which are administered at a therapeutically effective amount) and treatments can be used alone or in combination. For example, any suitable anti-cancer or anti-angiogenic agent can be administered in combination with the CARS, CAR-T cells, antibodies, antigen binding fragment, or conjugates disclosed herein. Methods and therapeutic dosages of such agents are known to those skilled in the art, and can be determined by a skilled clinician.

Additional chemotherapeutic agents include, but are not limited to alkylating agents, such as nitrogen mustards (for example, chlorambucil, chlormethine, cyclophosphamide, ifosfamide, and melphalan), nitrosoureas (for example, carmustine, fotemustine, lomustine, and streptozocin), platinum compounds (for example, carboplatin, cisplatin, oxaliplatin, and BBR3464), busulfan, dacarbazine, mechlorethamine, procarbazine, temozolomide, thiotepa, and uramustine; antimetabolites, such as folic acid (for example, methotrexate, pemetrexed, and raltitrexed), purine (for example, cladribine, clofarabine, fludarabine, mercaptopurine, and tioguanine), pyrimidine (for example, capecitabine), cytarabine, fluorouracil, and gemcitabine; plant alkaloids, such as podophyllum (for example, etoposide, and teniposide), taxane (for example, docetaxel and paclitaxel), vinca (for example, vinblastine, vincristine, vindesine, and vinorelbine); cytotoxic/antitumor antibiotics, such as anthracycline family members (for example, daunorubicin, doxorubicin, epirubicin, idarubicin, mitoxantrone, and valrubicin), bleomycin, rifampicin, hydroxyurea, and mitomycin; topoisomerase inhibitors, such as topotecan and irinotecan; monoclonal antibodies, such as alemtuzumab, bevacizumab, cetuximab, gemtuzumab, rituximab, panitumumab, pertuzumab, and trastuzumab; photosensitizers, such as aminolevulinic acid, methyl aminolevulinate, porfimer sodium, and verteporfin; and other agents, such as alitretinoin, altretamine, amsacrine, anagrelide, arsenic trioxide, asparaginase, axitinib, bexarotene, bevacizumab, bortezomib, celecoxib, denileukin diftitox, erlotinib, estramustine, gefitinib, hydroxycarbamide, imatinib, lapatinib, pazopanib, pentostatin, masoprocol, mitotane, pegaspargase, tamoxifen, sorafenib, sunitinib, vemurafinib, vandetanib, and tretinoin. Selection and therapeutic dosages of such agents are known to those skilled in the art, and can be determined by a skilled clinician.

The combination therapy may provide synergy and prove synergistic, that is, the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation, a synergistic effect may be attained when the compounds are administered or delivered sequentially, for example by different injections in separate syringes. In general, during alternation, an effective dosage of each active ingredient is administered sequentially, i.e. serially, whereas in combination therapy, effective dosages of two or more active ingredients are administered together.

In one embodiment, an effective amount of an antibody or antigen binding fragment that specifically binds to one or more of the antigens disclosed herein or a conjugate thereof is administered to a subject having a tumor following anti-cancer treatment. After a sufficient amount of time has elapsed to allow for the administered antibody or antigen binding fragment or conjugate to form an immune complex with the antigen expressed on the respective cancer cell, the immune complex is detected. The presence (or absence) of the immune complex indicates the effectiveness of the treatment. For example, an increase in the immune complex compared to a control taken prior to the treatment indicates that the treatment is not effective, whereas a decrease in the immune complex compared to a control taken prior to the treatment indicates that the treatment is effective.

F. Biopharmaceutical Compositions

Biopharmaceutical or biologics compositions (hereinafter, "compositions") are provided herein for use in gene therapy, immunotherapy and/or cell therapy that include one or more of the disclosed CARs, or T cells expressing a CAR, antibodies, antigen binding fragments, conjugates, CARs, or T cells expressing a CAR that specifically bind to one or more antigens disclosed herein, in a carrier (such as a pharmaceutically acceptable carrier). The compositions can be prepared in unit dosage forms for administration to a subject. The amount and timing of administration are at the discretion of the treating clinician to achieve the desired outcome. The compositions can be formulated for systemic (such as intravenus) or local (such as intra-tumor) administration. In one example, a disclosed CARs, or T cells expressing a CAR, antibody, antigen binding fragment, conjugate, is formulated for parenteral administration, such as intravenous administration. Compositions including a CAR, or T cell expressing a CAR, a conjugate, antibody or antigen binding fragment as disclosed herein are of use, for example, for the treatment and detection of a tumor, for example, and not by way of limitation, a neuroblastoma. In some examples, the compositions are useful for the treatment or detection of a carcinoma. The compositions including a CAR, or T cell expressing a CAR, a conjugate, antibody or antigen binding fragment as disclosed herein are also of use, for example, for the detection of pathological angiogenesis.

The compositions for administration can include a solution of the CAR, or T cell expressing a CAR, conjugate, antibody or antigen binding fragment dissolved in a pharmaceutically acceptable carrier, such as an aqueous carrier. A variety of aqueous carriers can be used, for example, buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents, adjuvant agents, and the like, for example, sodium acetate, sodium chloride, potassium chloride, calcium chloride, sodium lactate and the like. The concentration of a CAR, or T cell expressing a CAR, antibody or antigen binding fragment or conjugate in these formulations can vary widely, and will be selected primarily based on fluid volumes, viscosities, body weight and the like in accordance with the particular mode of administration selected and the subject's needs. Actual methods of preparing such dosage forms for use in in gene therapy, immunotherapy and/or cell therapy are known, or will be apparent, to those skilled in the art.

A typical composition for intravenous administration includes about 0.01 to about 30 mg/kg of antibody or antigen binding fragment or conjugate per subject per day (or the corresponding dose of a CAR, or T cell expressing a CAR, conjugate including the antibody or antigen binding fragment). Actual methods for preparing administrable compositions will be known or apparent to those skilled in the art and are described in more detail in such publications as *Remington's Pharmaceutical Science*, 19th ed., Mack Publishing Company, Easton, Pa. (1995).

A CAR, or T cell expressing a CAR, antibodies, antigen binding fragments, or conjugates may be provided in lyophilized form and rehydrated with sterile water before administration, although they are also provided in sterile solutions of known concentration. The CARs, or T cells expressing a CAR, antibody or antigen binding fragment or conjugate solution is then added to an infusion bag containing 0.9% sodium chloride, USP, and in some cases administered at a dosage of from 0.5 to 15 mg/kg of body weight. Considerable experience is available in the art in the administration of antibody or antigen binding fragment and conjugate drugs; for example, antibody drugs have been marketed in the U.S. since the approval of RITUXAN® in 1997. A CAR, or T cell expressing a CAR, antibodies, antigen binding fragments and conjugates thereof can be administered by slow infusion, rather than in an intravenous push or bolus. In one example, a higher loading dose is administered, with subsequent, maintenance doses being administered at a lower level. For example, an initial loading dose of 4 mg/kg antibody or antigen binding fragment (or the corresponding dose of a conjugate including the antibody or antigen binding fragment) may be infused over a period of some 90 minutes, followed by weekly maintenance doses for 4-8 weeks of 2 mg/kg infused over a 30 minute period if the previous dose was well tolerated.

Controlled release parenteral formulations can be made as implants, oily injections, or as particulate systems. For a broad overview of protein delivery systems see, Banga, A. J., *Therapeutic Peptides and Proteins: Formulation, Processing, and Delivery Systems*, Technomic Publishing Company, Inc., Lancaster, Pa., (1995). Particulate systems include microspheres, microparticles, microcapsules, nanocapsules, nanospheres, and nanoparticles. Microcapsules contain the therapeutic protein, such as a cytotoxin or a drug, as a central core. In microspheres, the therapeutic is dispersed throughout the particle. Particles, microspheres, and microcapsules smaller than about 1 μm are generally referred to as nanoparticles, nanospheres, and nanocapsules, respectively. Capillaries have a diameter of approximately 5 μm so that only nanoparticles are administered intravenously. Microparticles are typically around 100 μm in diameter and are administered subcutaneously or intramuscularly. See, for example, Kreuter, J., *Colloidal Drug Delivery Systems*, J. Kreuter, ed., Marcel Dekker, Inc., New York, N.Y., pp. 219-342 (1994); and Tice & Tabibi, *Treatise on Controlled Drug Delivery*, A. Kydonieus, ed., Marcel Dekker, Inc. New York, N.Y., pp. 315-339, (1992).

Polymers can be used for ion-controlled release of the CARs, or T cells expressing a CAR, antibody or antigen binding fragment or conjugate compositions disclosed herein. Various degradable and nondegradable polymeric matrices for use in controlled drug delivery are known in the art (Langer, *Accounts Chem. Res.* 26:537-542, 1993). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., *Pharm. Res.* 9:425-434, 1992; and Pec et al., *J Parent. Sci. Tech.* 44(2):58-65, 1990). Alternatively, hydroxyapatite has been used as a microcarrier for controlled release of proteins (Ijntema et al., *Int. J Pharm.* 112:215-224, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa. (1993)). Numerous additional systems for controlled delivery of therapeutic proteins are known (see U.S. Pat. Nos. 5,055,303; 5,188,837; 4,235,871; 4,501,728; 4,837,028; 4,957,735; 5,019,369; 5,055,303; 5,514,670; 5,413,797; 5,268,164; 5,004,697; 4,902,505; 5,506,206; 5,271,961; 5,254,342 and 5,534,496).

G. Kits

In one aspect, kits employing the CARs disclosed herein are also provided. For example, kits for treating a tumor in a subject, or making a CAR T cell that expresses one or more of the CARs disclosed herein. The kits will typically include a disclosed antibody, antigen binding fragment, conjugate, nucleic acid molecule, CAR or T cell expressing a CAR as disclosed herein. More than one of the disclosed antibodies, antigen binding fragments, conjugates, nucleic acid molecules, CARs or T cells expressing a CAR can be included in the kit.

The kit can include a container and a label or package insert on or associated with the container. Suitable containers include, for example, bottles, vials, syringes, etc. The containers may be formed from a variety of materials such as glass or plastic. The container typically holds a composition including one or more of the disclosed antibodies, antigen binding fragments, conjugates, nucleic acid molecules, CARs or T cells expressing a CAR. In several embodiments the container may have a sterile access port (for example the container may be an intravenous solution bag or a vial having a stopper pierceable by a hypodermic injection needle). A label or package insert indicates that the composition is used for treating the particular condition.

The label or package insert typically will further include instructions for use of a disclosed antibodies, antigen binding fragments, conjugates, nucleic acid molecules, CARs or T cells expressing a CAR, for example, in a method of treating or preventing a tumor or of making a CAR T cell. The package insert typically includes instructions customarily included in commercial packages of therapeutic products that contain information about the indications, usage, dosage, administration, contraindications and/or warnings concerning the use of such therapeutic products. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

EXAMPLES

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

Example 1A

Isolation of CD19-Specific Antibodies from a Fully Human Phage and Yeast-Displayed ScFv library Materials and Methods:

a) Production of Human ScFv and CD19-Specific Antibodies

A naïve human ScFv (recombinant single chain fragment variable of immunoglobulin) phage display library (approximate diversity, $10^{10}$ unique specificities), constructed from peripheral blood B cells of 50 healthy donors (Z. Y. Zhu and D. S. Dimitrov, unpublished data), were used for selection of ScFvs for recombinant human CD19 protein (Miltenyi Biotec, unpublished). Amplified libraries of $10^{12}$ phage-displayed ScFv were incubated with 5, 3, and 1, g of coated CD19 in a 5×100-μl volume, distributed equally in 5 wells of a 96-well plate for 2 h at room temperature during the first, second and third rounds of biopanning, respectively. After each round of incubation the wells were washed 5 times for the first round and 10 times for the later rounds with phosphate-buffered saline containing 0.05% Tween 20 (PBST) to remove nonspecifically bound phage, the bound phage were mixed with TG1 competent cells for 1 hour at 37° C., and the phage was amplified from the infected cells and used in the next round of biopanning. After the third round of biopanning, 380 clones were randomly picked from the infected TG1 cells and each inoculated into 150 μl 2YT medium containing 100 μg/ml carbenicillin and 0.2% glucose in 96-well plates by using the automated BioRobotics BioPick colony picking system (Genomic Solutions, Ann Arbor, Mich.). After the bacterial cultures reached an optical density at 600 nm (OD600) of 0.5, helper phage M13K07 at a multiplicity of infection (MOI) of 10 and kanamycin at 50 μg/ml (final concentration) were added to the medium, and the plates were further incubated at 30° C. overnight in a shaker at 250 rpm. The phage supernatants were mixed with 3% nonfat milk in PBS at a 4:1 volume ratio and used for enzyme-linked immunosorbent assay (ELISA) to identify clones of phage displaying ScFvs or VHs with high CD19 binding affinity. The supernatants were incubated for 2 h at room temperature with recombinant human CD19 coated at 50 ng per well in 96-well plates and washed five times with PBST, (after overnight incubation at 4° C. it was blocked with 3% nonfat milk in PBS and washed three times with PBS containing 0.05% Tween 20.) CD19-bound phage were detected using horseradish peroxidase-conjugated goat anti-M13 antibody. After incubation with the antibody, the nonspecifically bound antibody was removed by washing wells, and the 3,3',5,5'-tetramethylbenzidine (TMB) substrate was added, and solution absorbance at 450 nm (A450) measured. Clones that bound to CD19 with A450 of >1.0 were selected for further characterization.

b) Expression and Purification of Selected Soluble ScFvs.

The VH and VL of the selected clones were DNA sequenced, and the ScFvs encoded by clones with unique sequences were expressed and purified as described below. Plasmids extracted from these clones were used for transformation of HB2151 cells. A single colony was picked from the plate containing freshly transformed cells, inoculated into 200 ml 2YT medium containing 100 g/ml ampicillin and 0.2% glucose, and incubated at 37° C. with shaking at 250 rpm. When the culture OD at 600 nm reached 0.90, isopropyl-β-d-thiogalactopyranoside at a 0.5 mM final concentration was added, and the culture was further incubated overnight at 30° C. The bacterial pellet was collected after centrifugation at 8,000×g for 20 min and resuspended in PBS buffer containing 0.5 mU polymixin B (Sigma-Aldrich, St. Louis, Mo.). After 30 min incubation with rotation at 50 rpm at room temperature, the resuspended pellet was centrifuged at 25,000×g for 25 min at 4° C., and the supernatant was used for ScFv purification using the Ni-NTA resin following vendor protocol (Qiagen).

c) ELISA Binding Assay

ELISA binding assay 50 µl of the diluted recombinant human CD19 in PBS at 2 ug/ml was coated in a 96-well plate at 4° C. overnight. Purified ScFv with His and Flag tags were serially diluted and added into the target protein coated wells. After washing, a 1:3000 diluted HRP conjugated anti-Flag antibody was added for 1 hr at RT. After washing, 3, 3, 5, 5'-Tetramethylbenzidine (TMB) substrate was added, 1N $H_2SO_4$ was added to stop the reaction after incubation at room temperature for 10 minutes, and the O.D. was read at 450 nm to quantify the relative ability of ScFv to bind CD19.

d) Yeast Display of scFv Library.

The same ScFv starting material as for phage display was also incorporated into a yeast ScFv display system. To supplement phage-based scFv analysis, yeast libraries expressing the human scFv library were also screened. To enrich the yeast expressing scFvs that bind to both the recombinant CD19-Fc and the CD19 expressed on the cell surface of the CHOK1 cells, cell panning on CHOK1 transfected with CD19 cells was performed. For the first round of panning on the cell surface, two days prior to panning, the CHOK1-CD19 cells were seeded into 6-well plates and grown to 50% confluency in F12 K medium. $5 \times 10^7$ yeast cells were then washed 2× with PBSA buffer and resuspended into 3 mL F12 K medium, and then gently added dropwise to the CHOK1-CD19 cells. After rocking gently on ice for 2 hours, the CHOK1-CD19 cells were then washed 3 times with ice-cold PBSA to remove the yeast cells that did not bind to the CHOK1-CD19, and 0.05% Trypsin-EDTA (Gibco) was then used to dissociate the CHOK1-CD19 cells and bound yeast cells from the plate. The cell mix containing both the yeast and CHOK1 cells were then inoculated into 10 mL SDCAA medium and amplified overnight at 30° C. and then induced in SGCAA medium at 30° C. for 16 hours. For the second round of cell panning, a similar protocol as above was performed, but more stringent wash conditions were used. This method of panning yielded the m19217 binder. Further characterization of this binder as well as others from phage display indicated that affinity maturation was required, as the biological characteristics of the CAR created from this hit were still not optimal.

To increase the affinity of m19217, a yeast-display m19217 mutant scFv library was created by using error-prone PCR to create random point mutations in scFv gene sequences. After electroporation, the resulting mutant library was then grown overnight at 30° C. for 16 hours in SDCAA medium and then switched into SGCAA medium at 30° C. for another 16 hours. The mutant library was then sorted through MACS (immunomagentic column, Miltenyi Biotec) with CD19-Fc as the capture antigen to downsize the library and to increase the population of mutants that could bind to CD19-Fc. The strongest binders were then selected by double staining the pools with Anti-c-Myc-Alexa 488 and CD19-Fc/Anti-Hu-Fc and selecting for the binders that had the highest binding affinities as well as c-Myc expression levels. This process was then repeated two more times, until flow cytometry of yeast particles with fluorescently tagged antigen yielded average binding affinities of the mutant pools that were increased over the starting construct. Binding affinities were estimated by flow cytometry of yeast pools using decreasing amounts of labeled CD19. This process resulted in an increase of EC50 (Effective concentration for 50% binding of labeled CD19 on yeast displaying ScFv) for M19217 of 0.5 ug/ml to an affinity of <0.01 ug/ml for the affinity matured binders (M19217-1, 19217-2, M19217-7, M19217-23, M19217-29, M19217-38, M19217-40).

Results:

Due to the unique challenges of CD19 structure, phage display candidates did not yield biologically functional CAR constructs and thus ScFv identification that yielded biologically active binders were generated by yeast display. Based upon flow cytometry analysis of yeast-displayed ScFv, eight ScFv clones specific for recombinant human CD19 were identified and labeled as human anti-CD19 ScFv binders M19217 (LTG2050, founder clone, EC50 of 0.5 ug/ml), and the following affinity matured binders (EC50<0.01 ug/ml): M19217-1 (LTG2065), M19217-2 (LTG2066), M19217-7 (LTG2067), M19217-23 (LTG2068), M19217-29 (LTG2069), M19217-38 (LTG2070), and M19217-40 (LTG2071) respectively. The generation of a tandem CAR incorporating the anti-CD19 scFv M19217-1 sequence, is outlined in EXAMPLE 2, infra.

Example 1B

Isolation of CD22-Specific Antibodies from a Fully Human Phage and Yeast-Displayed ScFv Library Materials and Methods:

a) Production of Human ScFv and CD22-Specific Antibodies

A naïve human ScFv (recombinant single chain fragment variable of immunoglobulin) phage display library (approximate diversity, $10^{10}$ unique specificities), constructed from peripheral blood B cells of 50 healthy donors (Z. Y. Zhu and D. S. Dimitrov, unpublished data), were used for selection of ScFvs for recombinant human CD19 protein (Miltenyi Biotec, unpublished). Amplified libraries of $10^{12}$ phage-displayed ScFv were incubated with 5, 3, and 1, g of coated CD22 in a 5×100-µl volume, distributed equally in 5 wells of a 96-well plate for 2 h at room temperature during the first, second and third rounds of biopanning, respectively. After each round of incubation the wells were washed 5 times for the first round and 10 times for the later rounds with phosphate-buffered saline containing 0.05% Tween 20 (PBST) to remove nonspecifically bound phage, the bound phage were mixed with TG1 competent cells for 1 hour at 37° C., and the phage was amplified from the infected cells and used in the next round of biopanning. After the third round of biopanning, 380 clones were randomly picked from the infected TG1 cells and each inoculated into 150 µl 2YT medium containing 100 µg/ml carbenicillin and 0.2% glucose in 96-well plates by using the automated BioRobotics BioPick colony picking system (Genomic Solutions, Ann Arbor, Mich.). After the bacterial cultures reached an optical density at 600 nm (OD600) of 0.5, helper phage M13K07 at a multiplicity of infection (MOI) of 10 and kanamycin at 50 µg/ml (final concentration) were added to the medium, and the plates were further incubated at 30° C. overnight in a shaker at 250 rpm. The phage supernatants were mixed with 3% nonfat milk in PBS at a 4:1 volume ratio and used for enzyme-linked immunosorbent assay (ELISA) to identify clones of phage displaying ScFvs or VHs with high CD22 binding affinity. The supernatants were incubated for 2 h at room temperature with recombinant human CD22 coated at 50 ng per well in 96-well plates and washed five times with PBST, (after overnight incubation at 4° C. it was blocked with 3% nonfat milk in PBS and washed three times with PBS containing 0.05% Tween 20.) CD22-bound phage were detected using horseradish peroxidase-conjugated goat anti-M13 antibody. After incubation with the antibody, the nonspecifically bound antibody was removed by washing wells, and the 3,3',5,5'-tetramethylbenzidine (TMB) substrate was added, and solution absorbance at 450 nm (A450) measured. Clones that bound to CD22 with A450 of >1.0 were selected for further characterization.

b) Expression and Purification of Selected Soluble ScFvs

The VH and VL of the selected clones were DNA sequenced, and the ScFvs encoded by clones with unique sequences were expressed and purified as described below. Plasmids extracted from these clones were used for transformation of HB2151 cells. A single colony was picked from the plate containing freshly transformed cells, inoculated into 200 ml 2YT medium containing 100 µg/ml ampicillin and 0.2% glucose, and incubated at 37° C. with shaking at 250 rpm. When the culture OD at 600 nm reached 0.90, isopropyl-β-d-thiogalactopyranoside at a 0.5 mM final concentration was added, and the culture was further incubated overnight at 30° C. The bacterial pellet was collected after centrifugation at 8,000×g for 20 min and resuspended in PBS buffer containing 0.5 mU polymixin B (Sigma-Aldrich, St. Louis, Mo.). After 30 min incubation with rotation at 50 rpm at room temperature, the resuspended pellet was centrifuged at 25,000×g for 25 min at 4° C., and the supernatant was used for ScFv purification using the Ni-NTA resin following vendor protocol (Qiagen).

c) ELISA Binding Assay

For ELISA analysis 50 µl of the diluted recombinant human CD22 in PBS at 2 ug/ml was coated in a 96-well plate at 4° C. overnight. Purified ScFv with His and Flag tags were serially diluted and added into the target protein coated wells. After washing, a 1:3000 diluted HRP conjugated anti-Flag antibody was added for 1 hr at RT. After washing, 3, 3, 5, 5'-Tetramethylbenzidine (TMB) substrate was added, 1N $H_2SO_4$ was added to stop the reaction after incubation at room temperature for 10 minutes, and the O.D. was read at 450 nm to quantify the relative ability of ScFv to bind CD22.

d) Yeast Display of scFv Library

The same ScFv starting material as for phage display was also incorporated into a yeast ScFv display system. To supplement phage-based scFv analysis, yeast libraries expressing the human scFv library were also screened. To enrich the yeast expressing scFvs that bind to both the recombinant CD22-Fc and the CD19 expressed on the cell surface of the CHOK1 cells, cell panning on CHOK1 transfected with CD22 cells was performed. For the first round of panning on the cell surface, two days prior to panning, the CHOK1-CD22 cells were seeded into 6-well plates and grown to 50% confluency in F12 K medium. 5×10$^7$ yeast cells were then washed 2× with PBSA buffer and resuspended into 3 mL F12 K medium, and then gently added dropwise to the CHOK1-CD22 cells. After rocking gently on ice for 2 hours, the CHOK1-CD22 cells were then washed 3 times with ice-cold PBSA to remove the yeast cells that did not bind to the CHOK1-CD22, and 0.05% Trypsin-EDTA (Gibco) was then used to dissociate the CHOK1-CD22 cells and bound yeast cells from the plate. The cell mix containing both the yeast and CHOK1 cells were then inoculated into 10 mL SDCAA medium and amplified overnight at 30° C. and then induced in SGCAA medium at 30° C. for 16 hours. For the second round of cell panning, a similar protocol as above was performed, but more stringent wash conditions were used. This method of panning yielded the 16P, 24P, 25P, 11S and 12S binders. Binder sequences were incorporated into CART constructs as described in Example 2, infra, in a series of in vitro CART functional assays. Characterization of these binders from phage display in CART format revealed that only 16P binder had specific tumor-lytic activity in vitro, but it was low as compared to CAR positive control. Further, when 16P-based CART cells were tested in in vivo xenograft model, its antitumor function was very weak (Example 2, infra). Taken together, these results indicated that affinity maturation of anti-CD22 ScFv binders was required, as the biological characteristics of the CAR created from this binder set were still not optimal.

To increase the affinity of 16P, a yeast-display mutant scFv library was created by using error-prone PCR to create random point mutations in scFv gene sequences. After electroporation, the resulting mutant library was then grown overnight at 30° C. for 16 hours in SDCAA medium and then switched into SGCAA medium at 30° C. for another 16 hours. The mutant library was then sorted through MACS (immunomagnetic column, Miltenyi Biotec) with CD22-Fc as the capture antigen to downsize the library and to increase the population of mutants that could bind to CD22-Fc. The strongest binders were then selected by double staining the pools with Anti-c-Myc-Alexa 488 and CD19-Fc/Anti-Hu-Fc and selecting for the binders that had the highest binding affinities as well as c-Myc expression levels. This process was then repeated two more times, until flow cytometry of yeast particles with fluorescently tagged antigen yielded average binding affinities of the mutant pools that were increased over the starting construct. Binding affinities were estimated by flow cytometry of yeast pools using decreasing amounts of labeled CD22. This process resulted in an increase of EC50 (Effective concentration for 50% binding of labeled CD19 on yeast displaying ScFv) for 16P of 0.5 ug/ml to an affinity of <0.01 ug/ml for the affinity matured binders (16P1, 16P2, 16P3, 16P3v2, 16P6, 16P8, 16P10, 16P13, 16P15, 16P16, 16P17, 16P20, 16P20v2).

Results:

Due to the unique challenges of CD22 structure, phage display candidates did not yield sufficient functional CAR constructs with high biological activity and specificity. Thus, ScFv for biologically active and highly specific binders were generated by yeast display. Based upon flow cytometry analysis of yeast-displayed ScFv, thirteen ScFv clones specific for recombinant human CD22 were identified and labeled as human anti-CD22 ScFv binders 16P (LTG2202, founder clone, EC50 of 0.5 ug/ml), and the following affinity matured binders (EC50<0.01 ug/ml): 16P1, 16P2, 16P3, 16P3v2, 16P6, 16P8, 16P10, 16P13, 16P15, 16P17, 16P20, and 16P20v2 respectively. The generation of a tandem CAR incorporating the anti-CD22 scFv 16P17 sequence is outlined in EXAMPLE 2, infra.

Example 2

Dual-Targeting Tandem CARs Expressing Fully Human Anti-CD22 and Anti CD19 scFv Binding Sequences This example discusses the creation of a dual-targeting CAR, which targets tumor antigens CD19 and CD22 simultaneously. This approach has been postulated to help mitigate tumor antigen escape, which accounts for a significant portion of CAR therapy failures using single CAR approaches, namely anti-CD19 CAR, or anti-CD22 CAR therapy (Sotillo, Elena, et al. "Convergence of acquired mutations and alternative splicing of CD19 enables resistance to CART-19 immunotherapy." *Cancer discovery* (2015). Gardner, Rebecca, et al. "Acquisition of a CD19 negative myeloid phenotype allows immune escape of MLL-rearranged B-ALL from CD19 CAR-T cell therapy." *Blood* (2016): blood-2015., Fry, Terry J., et al. "CD22-targeted CAR T cells induce remission in B-ALL that is naive or resistant to CD19-targeted CAR immunotherapy." *Nature medicine* 24.1 (2018): 20.).

Utilization of mouse scFv sequences as CAR components has been shown to cause immune rejection or allergic anaphylactic reactions in patients, thus limiting the persistence and utility of CAR T treatment, and increasing the risk of toxicity. Therefore, utilization of fully human scFv binder sequences in CAR design is a high priority for future CAR development.

CD19 is a 85-95 kDa transmembrane cell surface glycoprotein receptor. CD19 is a member of immunoglobulin (Ig) superfamily of proteins, and contains two extracellular Ig-like domains, a transmembrane, and an intracellular signaling domain (Tedder T F, Isaacs, C M, 1989, J Immunol 143:712-171). CD19 modifies B cell receptor signaling, lowering the triggering threshold for the B cell receptor for antigen (Carter, R H, and Fearon, D T, 1992, Science, 256:105-107), and co-ordinates with CD81 and CD21 to regulate this essential B cell signaling complex (Bradbury, L E, Kansas G S, Levy S, Evans R L, Tedder T F, 1992, J Immunol, 149:2841-50). During B cell ontogeny CD19 is able to signal at the pro-B, pre-pre-B cell, pre-B, early B cell stages independent of antigen receptor, and is associated with Src family protein tyrosine kinases, is tyrosine phosphorylated, inducing both intracellular calcium mobilization and inositol phospholipid signaling (Uckun F M, Burkhardt A L, Jarvis L, Jun X, Stealy B, Dibirdik I, Myers D E, Tuel-Ahlgren L, Bolen J B, 1983, J Biol Chem 268:21172-84). The key point of relevance for treatment of B cell malignancies is that CD19 is expressed in a tightly regulated manner on normal B cells, being restricted to early B cell precursors at the stage of IgH gene rearrangement, mature B cells, but not expressed on hematopoietic stem cells, or mature plasma cells (Anderson, K C, Bates, M P, Slaughenhout B L, Pinkus G S, Schlossman S F, Nadler L M, 1984, Blood 63:1424-1433).

*Homo sapiens* CD22 (SIGLEC-2, Leu14) is a well-investigated cell surface glycoprotein expressed on B cell leukemias and lymphomas. At least two anti-CD22 antibody drug (Inotuzumab Ozogamicin) or immunotoxin conjugates (Moxetumomab Pasudotox) have been the subject of clinical trials (NCT02981628, NCT00659425). These approaches have had some success, and are still being investigated, for example in combination with other chemotherapeutic agents (Muller F, Stookey S, Cunningham T, Pastan I, 2017, Paclitaxel synergizes with exposure tume adjusted CD22-targeted immunotoxins against B-cell malignancies, Oncotarget 8:30644-30655). However, given the current advances with T-cell based therapy with CD19 CARs, the best approach to targeting CD22-expressing malignancies may be cell-based immunotherapy. Therapy featuring the m971-based anti-CD22 CAR is currently undergoing clinical trial at the National Cancer Institute (NCT02315612, P.I.: Terry Fry, M.D.). The tandem CD22 CD19-targeting CAR constructs presented here are an innovative new approach to creating and implementing new, fully human CD19 and CD22 binding moieties in one construct in order to achieve complete durable remissions and prevent tumor antigen escape.

Single CAR controls have been employed in this example as a comparison to the tandem CARs targeting CD19 and CD22. CAR Construct LTG1538 utilizing the mouse hybridoma FMC63-derived scFv is an activity control. This mouse-derived sequence is the current binder employed in commercial development (See KTE-C19, Kite Pharma, and CTL019, Novartis). The m971 CAR LTG2200 is equivalent to the CAR being evaluated at the NCI, and is used as an anti-CD22 CAR control.

Materials and Methods:

(a) Cell Lines

The Burkitt lymphoma cell line Raji, and the chronic myelogenous leukemia line K562 were purchased from American Tissue Culture Collection (ATCC, Manassass, Va.). The REH leukemia line was purchased from DSMZ (Leibniz Institute DSMZ, Braunschwieg, Germany). Cells were cultured in RPMI-1640 medium supplemented with 10% heat-inactivated fetal bovine serum (FBS, Hyclone, Logan, Utah) and 2 mM L-Glutamax (Thermo Fisher Scientific, Grand Island, N.Y.). Human Embryonic kidney line 293T was purchased from ATCC (Gibco/Thermo Fisher Scientific, Grand Island, N.Y.). Single-cell clones of luciferase-expressing cell lines were generated by stably transducing wild-type tumor lines with lentiviral vector encoding firefly luciferase (Lentigen Technology, Inc., Gaithersburg, Md.), followed by cloning and selection of luciferase-positive clones. The Raji clone was generated by passaging luciferase—transduced Raji cells in the mice and was selected for its proliferative capacity. Whole blood was collected from healthy volunteers at Oklahoma Blood Institute (OBI) with donors' written consent. Processed buffy coats were purchased from OBI (Oklahoma City, Okla.). The CD4-positive and CD8-positive human T cells were purified from buffy coats via positive selection using a 1:1 mixture of CD4− and CD8− MicroBeads (Miltenyi Biotec, Bergisch Gladbach, Germany) according to manufacturer's protocol.

(b) Creation of Chimeric Antigen Receptor (CAR)—Expression Vectors

CAR antigen-binding domains, ScFv, sequences were derived from human anti-CD22 ScFv or heavy chain variable fragments. CAR T constructs were generated by linking the binder sequence in frame to CD8a linking and transmembrane domains (aa 123-191, Ref sequence ID NP_001759.3), and then to 4-1BB (CD137, aa 214-255, UniProt sequence ID Q07011) signaling domain and CD3 zeta signaling domain (CD247, aa 52-163, Ref sequence ID: NP_000725.1).

CAR constructs sequences were cloned into a third generation lentiviral plasmid backbone (Lentigen Technology Inc., Gaithersburg, Md.). Lentiviral vector (LV) containing supernatants were generated by transient transfection of HEK 293T cells and vector pelleted by centrifugation of lentiviral vector-containing supernatants, and stored at −80° C.

(c) Primary T Cell Purification and Transduction

Human primary T cells from healthy volunteers were purified from whole blood or buffy coats (purchased from commercial provider with donor's written consent) using immunomagnetic bead selection of CD4$^+$ and CD8$^+$ cells according to manufacturer's protocol (Miltenyi Biotec, Bergisch Gladbach, Germany). T cells were cultivated in Tex-MACS medium supplemented with 200 IU/ml IL-2 at a density of 0.3 to 2×10$^6$ cells/ml, activated with CD3/CD28 MACS® GMP T Cell TransAct reagent (Miltenyi Biotec) and transduced on day 2 with lentiviral vectors encoding CAR constructs in the presence of 10 ug/ml protamine sulfate (Sigma-Aldrich, St. Louis, Mo.) overnight, and media exchanged on day 3. Cultures were propagated in TexMACS medium supplemented with 200 IU/ml IL-2 until harvest on day 8-13.

(d) Immune Effector Assays (CTL and Cytokine)

To determine cell-mediated cytotoxicity (CTL assay), 5,000 target cells stably transduced with firefly luciferase were combined with CAR T cells at various effector to target ratios and incubated overnight. SteadyGlo reagent (Promega, Madison Wis.) was added to each well and the resulting luminescence quantified as counts per second (sample CPS). Target only wells (max CPS) and target only wells plus 1% Tween-20 (min CPS) were used to determine assay range. Percent specific lysis was calculated as: (1-(sample CPS-min CPS)/(max CPS-min CPS)). Supernatants from co-cultures at E:T ratio of 10:1 were removed and analyzed by ELISA (eBioscience, San Diego, Calif.) for IFNγ, TNFα and IL-2 concentration.

(e) Flow Cytometric Analysis

For cell staining, half a million CAR T transduced cells were harvested from culture, washed two times in cold AutoMACS buffer supplemented with 0.5% bovine serum albumin (Miltenyi Biotec), and CAR surface expression detected by staining with CD22-Fc peptide followed by anti Fc-PE conjugate (Jackson ImmunoResearch, West Grove, Pa.). Anti-CD4 antibody conjugated to VioBlue fluorophore (Miltenyi Biotec) was used where indicated, as per vendors' protocol. Non-transduced cells were used as negative controls. Dead cells in all studies were excluded by 7AAD staining (BD Biosciences, San Jose, Calif.). Cells were washed twice and resuspended in 200 ul Staining Buffer before quantitative analysis by flow cytometry. Flow cytometric analysis was performed on a MACSQuant®10 Analyzer (Miltenyi Biotec), and data plots were generated using FlowJo software (Ashland, Oreg.).

Results

Tandem CAR constructs for dual targeting of CD22 and CD19 tumor antigens were developed in order to overcome tumor antigen escape. Shema of tandem CAR design is shown in FIGS. 1A and 1B. Fully human scFv binders targeting CD19 and CD22 were connected in tandem by a flexible linker, in either 22-19 or 19-22 orientation, noted membrane distal to proximal. Then, the resulting CAR binding segment was linked in frame to CD8 hinge and transmembrane domain, 4-1BB costimulatory domain and CD3 zeta activation domain to generate CAR 22-19 (LTG2681, FIG. 1A), or CAR19-22 (LTG2719, FIG. 1B). CAR sequences were incorporated into a 3rd generation lentiviral vectors and applied to primary human T cells for transduction.

Single CAR controls have been employed in this example as a comparison to the tandem CARs targeting CD19 and CD22. CAR Construct LTG1538 utilizing the mouse hybridoma FMC63-derived scFv is an activity control. This mouse-derived sequence is the current binder employed in commercial development (See KTE-C19, Kite Pharma, and CTL019, Novartis). The m971 CAR LTG2200 is equivalent to the CAR being evaluated at the NCI, and is used as an anti-CD22 CAR control.

Figure 2:
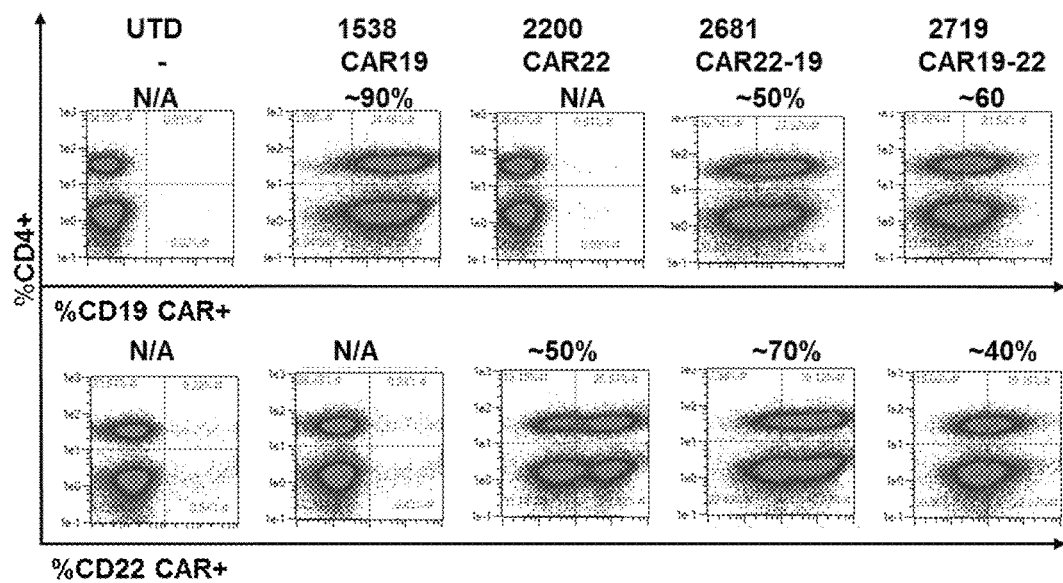
FIG. 2 depicts surface expression of tandem-CAR T constructs LTG 2681 (CAR22-19) and LTG2791 (CAR19-22) in human primary T cells. CAR T expression was determined by flow cytometry. T cells were activated with Miltenyi Biotec TransAct™ CD3 CD28 reagent in the presence of IL-2, and transduced with LV as described in Materials and Methods. On culture day 8, viable transduced T cells (7-AAD negative) were assayed for CAR surface expression using one of three staining methods: CD19 Fc followed by anti-Fc-AF647 (top panel), or CD22-his reagent followed by anti-his-PE staining (bottom panel). The LV used in transduction is listed on the top of each column.

The surface expression of anti-CD19/CD22 CARs incorporating single chain fragment variable (ScFv) sequences reactive with CD19/CD22 antigen, is shown in FIG. 2. The expression level for each ScFv-containing CAR was determined by flow cytometric analysis of LV-transduced T cells from healthy donors using one of two detection methods: i) CD22-his, followed anti-his-PE; ii) CD19 Fc recombinant protein, followed by anti Fc-A647. The ScFv-based anti-CD19/CD22 CAR constructs CAR22-19 LTG 2681, and CAR19-22 LTG2719, were highly expressed in human primary T cells as compared to non-transduced T cell controls.

As shown in FIG. 3, high cytolytic activity of the CD19/CD22 CARs was demonstrated: Human primary T cells were transduced with LV encoding CAR constructs (CAR 22-19 (LTG2681, D0023), CAR19-22 (LTG 2791, D0024), CAR19 (LTG1538), or CAR22 (LTG2200) see Methods), then incubated for 18 hours with the Raji, REH, or 293T cell lines, stably transduced with firefly luciferase, for luminescence based in vitro killing assays. Raji and Reh leukemia lines express CD19 and CD22 on their surface, while the negative controls, 293T do not. Raji and REH cells were lysed effectively by the tandem CAR 22-19 (LTG2681), tandem CAR19-22 (LTG27190), and the single-targeting controls CAR19 (LTG1538) and CAR22 (LTG2200), (FIG. 3). Therefore, both tandem CAR22-19 and CAR19-22 were functional in tumor lines co-expressing the CD19 and CD22 antigens, and had no spontaneous killing activity against CD19-CD22- cell line 293T, underscoring target specificity of these constructs.

Next, the functionality and specificity of each scFv in a tandem CAR in isolation was tested by using tumor lines A431 or 293T, engineered to express only a single target antigen (CD19 or CD22, or irrelevant antigen CD20). 293T-luc lines were created that express CD19 (293T luc CD-19+), or CD22 (293T luc-20+), and line CD20+(293T luc CD20) was used as an irrelevant target control (FIG. 4A). 293T-19+ were lysed by the CAR 19 (LTG1538) and tandem CAR 22-19 (LTG 2681), but not by CAR22 LTG 2200 or untransduced T cells control (FIG. 3). 293T-CD22+ were lysed by the tandem CAR 22-19 (LTG 2681) and the single CAR20 LTG2200, but not by the single CAR19 (LTG 1538), or untransduced control, demonstrating antigen specificity of the tandem CAR. Finally, no CAR construct lysed the 293T luc CD20 cells, since this antigen was not targeted (FIG. 4A). Similarly, tandem CAR T cells were tested in an overnight killing assay against A431 clones expressing only CD19 antigen (A431 luc CD19), or only CD22 antigen (A431 luc-CD22), or an irrelevant target control line A431 luc-CD20, expressing the antigen CD20, which the tandem CARs 19-22 and 22-19 are not intended to recognize (FIG. 4B). Again, A431 luc CD19 line was lysed only by the CAR 19 (LTG1538) and tandem CAR 22-19 (LTG 2681), but not by CAR22 LTG 2200 or untransduced T cells control, whereas line A431 luc CD22 was lysed by the tandem CAR 22-19 (LTG 2681) and the single CAR20 LTG2200, but not by the single CAR19 (LTG 1538), or untransduced control, demonstrating antigen specificity of the tandem CAR. Moreover, no CAR construct lysed A431 luc CD20 cells, since this antigen was not targeted (FIG. 4B). This results underscores the independent functionality and specificity of each targeting domain of the tandem CAR22-19 (FIGS. 4A-4B), and the potential of tandem CARs targeting the CD19 and CD22 antigens to mitigate tumor antigen escape.

The capacity of anti-CD19/CD22 CAR T cells for cytokine secretion was then evaluated (FIG. 5). The CD19+ CD22+ Raji tumor cells were co-incubated with the tandem 22-19 CAR T cells (LTG2681) or positive control CAR19 (LTG1538), positive control CAR22 (LTG2200), or negative control untransduced T cells (UTD) at effector to target ratio of 10:1 overnight, and culture supernatants were analyzed by ELISA for IFN gamma, TNF alpha, and IL-2. The tandem CAR 22-19 (LTG2681) strongly induced cytokines in response to tumor cells, whereas the negative control (untransduced, UTD.) yielded no appreciable cytokine induction. Notably, tandem CAR T-expressing cells LTG2681 showed similar levels of IFN gamma, TNF alpha, IL-2, to CAR22 control (LTG2200), and somewhat higher cytokine response than the single CAR19 (LTG1538) control, demonstrating the high potency of the tandem CAR. Importantly, CAR 22-19 produced no cytokine secretion in the absence of tumor cells (CART alone group), which further confirms CAR specificity, and indicates a lack of tonic signaling by the tandem car.

Example 3

Dual-Targeting CAR 22-19 Constructs Incorporating Various Co-Stimulatory Domains Demonstrate Robust Anti-Tumor Function This Example discusses tandem CD22– and CD19– dual targeting CAR constructs, which are incorporating various co-stimulatory domains. The co-stimulatory domains utilized in CAR 22-19 design in this example included ICOS, OX40, CD27, CD137/4-1BB, and CD28. These co-stimulatory domain sequences are derived from T cell surface molecules known to be involved in positive regulation of T cell function, including T cell activation, expansion, persistence, phenotypic differentiation, memory formation, and anti-tumor responses (Zhao Z, Condomines M, van der Stegen S J, et al: Structural design of engineered costimulation determines tumor rejection kinetics and persistence of CAR T cells. Cancer cell 28:415-428, 2015, Guedan S, Posey A D, Jr., Shaw C, et al: Enhancing CAR T cell persistence through ICOS and 4-1BB costimulation. JCI Insight 3, 2018, Song D-G, Ye Q, Poussin M, et al: CD27 costimulation augments the survival and antitumor activity of redirected human T cells in vivo. Blood 119:696-706, 2012, Hombach A A, Heiders J, Foppe M, et al: OX40 costimulation by a chimeric antigen receptor abrogates CD28 and IL-2 induced IL-10 secretion by redirected CD4+ T cells. Oncoimmunology 1:458-466, 2012, Yoshinaga S K, Whoriskey J S, Khare S D, et al: T-cell co-stimulation through B7RP-1 and ICOS. Nature 402:827-832, 1999). In some cases, CAR linker/hinge regions were also derived from the co-stimulatory domains utilized.

Concurrent dual targeting of CD19 and CD22 antigens is designed to mitigate tumor antigen escape, which has hindered therapeutic benefit in a sub-population of patients who have received either CD19 or CD22-targeted single CAR therapy (Sotillo, Elena, et al. "Convergence of acquired mutations and alternative splicing of CD19 enables resistance to CART-19 immunotherapy." *Cancer discovery* (2015). Gardner, Rebecca, et al. "Acquisition of a CD19 negative myeloid phenotype allows immune escape of MLL-rearranged B-ALL from CD19 CAR-T cell therapy." Blood (2016): blood-2015., Fry, Terry J., et al. "CD22-targeted CAR T cells induce remission in B-ALL that is naive or resistant to CD19-targeted CAR immunotherapy." *Nature medicine* 24.1 (2018): 20.).

Avoiding sequences of non-human origin, which may trigger host anti—"foreign" immune response, in CAR design, is thought to contribute to improved persistence of CAR T cells, and is preferred. All CAR components utilized in this example were of human origin. CAR binder configuration based on anti-CD 22-19 CAR (LTG2737), comprised of T cell membrane-distal human scFv targeting CD22 linked in frame to the T cell membrane-proximal human scFv targeting CD19, was utilized in all CAR constructs in Example 3.

Materials and Methods:
(a) Cell Lines

The Burkitt lymphoma cell line Raji, was purchased from American Tissue Culture Collection (ATCC, Manassass, Va.). Cells were cultured in RPMI-1640 medium supplemented with 10% heat-inactivated fetal bovine serum (FBS, Hyclone, Logan, Utah) and 2 mM L-Glutamax (Thermo Fisher Scientific, Grand Island, N.Y.). Human Embryonic kidney line 293T was purchased from ATCC (Gibco/Thermo Fisher Scientific, Grand Island, N.Y.). Single-cell clones of luciferase-expressing cell lines were generated by stably transducing wild-type tumor lines with lentiviral vector encoding firefly luciferase (Lentigen Technology, Inc., Gaithersburg, Md.), followed by cloning and selection of luciferase-positive clones. CD19 and CD22 expressing 293T cell line clones, designated 293TCD19 and 293TCD22, respectively, were generated by lentiviral transduction of human CD19 protein and human CD22 proteins into the parental 293T-luciferase expressing clone, following by single-cell cloning, selection and expansion of CD19- or CD22-positive target cell clones, as appropriate. Stable luciferase-expressing Raji clone was generated by passaging luciferase—transduced Raji cells in the mice and was selected for its proliferative capacity. Whole blood was collected from healthy volunteers at Oklahoma Blood Institute (OBI) with donors' written consent. Processed buffy coats were purchased from OBI (Oklahoma City, Okla.). The CD4-positive and CD8-positive human T cells were purified from buffy coats via positive selection using a 1:1 mixture of CD4– and CD8– MicroBeads (Miltenyi Biotec, Bergisch Gladbach, Germany) according to manufacturer's protocol.

(b) Creation of Chimeric Antigen Receptor (CAR)—Expression Vectors

The tandem CAR antigen-binding domain, was derived from a human anti-CD22 ScFv and human anti-CD19 scFv sequences, linked in tandem, in configuration anti-CD22 scFv-anti CD19-scFv-hinge-transmembrane domain-endodomain. Some CAR T constructs were generated by linking the CAR antigen-binding domain in frame to CD8a hinge and transmembrane domains (aa 123-191, Ref sequence ID NP_001759.3), and then to 4-1BB (CD137, aa 214-255, UniProt sequence ID Q07011) signaling domain and CD3 zeta signaling domain (CD247, aa 52-163, Ref sequence ID: NP_000725.1). In other constructs, the 4-1BB co-stimulatory domain was substituted for the human ICOS, CD27, CD28, OX-40 co-stimulatory domain, using the full signaling domain sequence of each molecule. In some embodiments, the CD8 transmembrane domain was substituted by transmembrane sequence derived from same protein as the co-stimulatory domain. In some embodiments, the endodomain of the CAR comprised two co-stimulatory domains connected in tandem. In some embodiments, no co-stimulatory domain was used, and the CD3ζ activation domain was linked in frame directly to the transmembrane domain. In some embodiments, two CAR chains were encoded in the same bicistronic expression cassette, separated by 2A ribosomal skip element, thus enabling co-expression of the two CAR chains in each T cell transduced with the lentiviral construct encoding the bicistronic CAR. CAR constructs sequences were cloned into a third generation lentiviral plasmid backbone under the control of the human EF-1α promoter (Lentigen Technology Inc., Gaithersburg, Md.). Lentiviral vector (LV) containing supernatants were generated by transient transfection of HEK 293T cells and vector pelleted by centrifugation of lentiviral vector-containing supernatants, and stored at −80° C.

(c) Primary T Cell Purification and Transduction

Human primary T cells from healthy volunteers were purified from whole blood or buffy coats (purchased from commercial provider with donor's written consent) using immunomagnetic bead selection of $CD4^+$ and $CD8^+$ cells according to manufacturer's protocol (Miltenyi Biotec, Bergisch Gladbach, Germany). T cells were cultivated in TexMACS medium supplemented with 200 IU/ml IL-2 at a density of 0.3 to 2×10$^6$ cells/ml, activated with CD3/CD28 MACS® GMP T Cell TransAct reagent (Miltenyi Biotec) and transduced on day 2 with lentiviral vectors encoding CAR constructs in the presence of 10 ug/ml protamine sulfate (Sigma-Aldrich, St. Louis, Mo.) overnight, and media exchanged on day 3. Cultures were propagated in TexMACS medium supplemented with 200 IU/ml IL-2 until harvest on day 8-13.

(d) Immune Effector Assays (CTL and Cytokine)

To determine cell-mediated cytotoxicity (CTL assay), 5,000 target cells stably transduced with firefly luciferase were combined with CAR T cells at various effector to target ratios and incubated overnight. SteadyGlo reagent (Promega, Madison Wis.) was added to each well and the resulting luminescence quantified as counts per second (sample CPS). Target only wells (max CPS) and target only wells plus 1% Tween-20 (min CPS) were used to determine assay range. Percent specific lysis was calculated as: (1-(sample CPS-min CPS)/(max CPS-min CPS)). Supernatants from co-cultures at E:T ratio of 10:1 were removed and analyzed by ELISA (eBioscience, San Diego, Calif.) for IFNγ, TNFα and IL-2 concentration.

(e) Flow Cytometric Analysis

For cell staining, half a million CAR T transduced cells were harvested from culture, washed two times in cold AutoMACS buffer supplemented with 0.5% bovine serum albumin (Miltenyi Biotec), and CAR surface expression detected by staining with CD22-His peptide followed by anti-His secondary detection reagent, simultaneously with CD19 Fc peptide followed by anti-Fc conjugate (the secondary detection reagents were purchased form Jackson ImmunoResearch, West Grove, Pa.). Anti-CD4 antibody conjugated to VioBlue fluorophore (Miltenyi Biotec) was used where indicated, as per vendors' protocol. Non-transduced cells were used as negative controls. Dead cells in all studies were excluded by 7AAD staining (BD Biosciences, San Jose, Calif.). Cells were washed twice and resuspended in 200 ul Staining Buffer before quantitative analysis by flow cytometry. Flow cytometric analysis was performed on a MACSQuant®10 Analyzer (Miltenyi Biotec), and data plots were generated using FlowJo software (Ashland, Oreg.).

Results

Dual-targeting CAR constructs comprised of different co-stimulatory domains were designed. CAR constructs are listed in Table 1. Schematic representation of CAR design configurations is provided in FIGS. 6A-6D. In some embodiments, the tandem CAR antigen-binding domain, comprised of anti-CD22 ScFv and anti-CD19 scFv sequences, were linked in tandem, in the following order: anti-CD22 scFv-anti CD19-scFv-hinge-transmembrane domain-endodomain (FIGS. 6A and 6B). The targeting tandem domain configuration was based on CAR 22-19 (LTG2681) in all cases. Anti-CD 22-19 CAR construct LTG2737 contained the CAR sequence identical to the Anti-CD 22-19 CAR construct LTG2681, but without use of the Woodchuck Hepatitis Virus (WHP) Posttranscriptional Regulatory Element (WPRE) during its construction. Several CAR T constructs were generated by linking the CAR antigen-binding domain in frame to CD8a hinge and transmembrane domains (constructs LTG2737, D0135, D0136, D0137, D0145, D0146, D0147, D0148, and D0149). In other constructs a transmembrane domain sequence matching the co-stimulatory domain was utilized: CD28 for D139, D140, OX40 for D0137, D0147, D0148. The transmembrane domain was linked in frame to a co-stimulatory domain derived from 4-1BB (LTG2737), CD28 (D0135, D0139, D0140), ICOS (D136, D146, D148, D149), OX40 (D0137, D0145, D0147, D0148) or CD27 (D0138, D0149). All CAR molecules contained the CD3 zeta signaling domain (CD247, aa 52-163, Ref sequence ID: NP_000725.1). In one embodiment, the endodomain of the CAR was comprised of two co-stimulatory domains, CD28 and 4-1BB, connected in tandem (D0140, FIG. 6B). In some embodiments, two distinct CAR molecules were co-expressed in the same T cell using a 2A ribosomal skip element for bicistronic expression (D146, D147, D148, D149, FIG. 6C, 6D). In this configuration, each CAR chain contained only one scFv, targeting either the CD19 or CD22 antigen, and both chains were co-expressed in each transduced T cell via transduction with a single lentiviral vector encoding the bicistronic sequence. In some embodiments, on at least one of the CAR chains, no co-stimulatory domain was used, so that the CD3 activation domain was linked in frame directly to the transmembrane domain of one of the CAR chains expressed concurrently in the same cell (D0146, D0147, FIG. 6C). CAR constructs sequences were cloned into a third generation lentiviral plasmid backbone under the control of the human EF-1α promoter (Lentigen Technology Inc., Gaithersburg, Md.).

TABLE 1

| CD22 and CD19 CAR T-Targeting Constructs and Controls | | |
|---|---|---|
| Construct designation | CAR Description | CAR Generation |
| LTG2737 | 22-19-CD8H&TM-41BB-CD3ζ | 2nd generation tandem |
| D0135 | 22-19-CD8H&TM-CD28-CD3ζ | 2nd generation tandem |
| D0136 | 22-19-CD8H&TM-ICOS-CD3ζ | 2nd generation tandem |
| D0137 | 22-19-CD8hinge-OX40TM-OX40-CD3ζ | 2nd generation tandem |
| D0138 | 22-19-CD8H&TM-CD27-CD3ζ | 2nd generation tandem |
| D0139 | 22-19-CD28H&TM-CD28-CD3ζ | 2nd generation tandem |
| D0145 | 22-19-CD8H&TM-OX40-CD3ζ | 2nd generation tandem |
| D0140 | 22-19-CD28H&TM-CD28-41BB-CD3ζ | 3rd generation tandem |
| D0146 | 19-CD8H&TM-ICOS-CD3ζ_22-CD8H&TM-CD3ζ | Bicistronic dual-targeting |
| D0147 | 19-CD8H-OX40TM-OX40-CD3ζ_22-CD8H&TM-CD3ζ | Bicistronic dual-targeting |
| D0148 | 19-CD8H-OX40TM-OX40-CD3ζ_22-CD8H&TM-ICOS-CD3ζ | Bicistronic dual-targeting |
| D0149 | 19-CD8H&TM-CD27-CD3ζ_22-CD8H&TM-ICOS-CD3ζ | Bicistronic dual-targeting |

The surface expression of anti-CD22-19 CAR incorporating various co-stimulatory domains, is shown in FIG. 7. The expression level for each ScFv-containing CAR was determined by flow cytometric analysis of LV-transduced T cells from healthy donors using simultaneous staining for the two scFv CAR targeting domains i) CD22-his, followed anti-his-PE; ii) CD19 Fc recombinant protein, followed by anti Fc-A647. All anti-CD22-19 CAR were highly expressed in human primary T cells as compared to non-transduced T cell controls. CAR expression levels ranged from 71%-90% (FIG. 7).

As shown in FIGS. 9A-9D, high cytolytic activity of the anti-CD22-19 CAR was demonstrated: Human primary T cells were transduced with LV encoding CAR constructs LTG2737, D0135, D0136, D0137, D0138, D0139, D0140, D0145, D0146), then incubated for 18 hours with the Raji, 293T, 293TCD19 or 293TCD22 cell lines, stably transduced with firefly luciferase, for luminescence based in vitro killing assays. Effector to target (ET) ratios of 2.5:1, 5:1 or 10:1 were used, as noted in the legend to the right of each plot. Raji cells express CD19 and CD22 on their surface, while the negative controls, 293T do not. The 293TCD19 and 293TCD22 target lines were generated to stably express either the CD19 or CD22 target antigen, respectively, and were used to evaluate the capability of the dual-targeting CAR constructs with different co-stimulatory domains to accomplish target lysis when triggered by each single target antigen, CD19 or CD22, independently of the other antigen.

Raji cells were lysed effectively by all dual targeting CARs, but not by the untransduced T cells, UTD, a negative control (FIG. 9A). By comparison, all dual-targeting CAR constructs lysed the single-antigens lines 293TCD19 and 293TCD22, demonstrating the capability of these CAR constructs to trigger their anti-tumor lytic function when activated either by CD19 antigen alone, or by CD22 antigen alone (FIGS. 9B and 9D, respectively). By contrast, none of the dual-targeting anti-CD22-19 CAR lysed the antigen-negative cell line 293T (FIG. 9C). Therefore, all anti-CD22-19 CAR were functional in tumor lines co-expressing the CD19 and CD22 antigens, and also in 293TCD19 and 293T CD22 lines expressing either CD19 or CD22 single antigen, and had no spontaneous killing activity against CD19– CD22– cell line 293T, underscoring the target specificity of these constructs.

The capacity of anti-CD22-19 CAR with various co-stimulatory domains for cytokine secretion was then evaluated (FIG. 8). The CD19+CD22+ Raji tumor cells were co-incubated with the tandem anti-CD22-19 CAR T cells expressing constructs LTG2737, D0135, D0136, D0137, D0138, D0139, D0140, D0145, D0146, or negative control untransduced T cells (UTD) at effector to target ratio of 10:1 overnight, and culture supernatants were analyzed by ELISA for IFN gamma, TNF alpha, and IL-2 (FIG. 8). All dual-targeting CARs strongly induced IL-2 and TNFα in response to tumor cells, whereas the negative control (untransduced, UTD) yielded no appreciable cytokine induction (FIG. 8). Notably, the elaborated levels of IFN gamma, were strongly induced in all CAR 22-19, but were especially high for CAR constructs D0146, D0139, D0136, indicating that the strength of cytokine response of the anti-CD22-19 CAR may be modulated by the composition of co-stimulatory domains utilized in CAR design. Overall, the induced secretion profiles of IFN gamma, TNF alpha, and IL-2 demonstrated the high potency of all CAR 22-19 constructs. Importantly, anti-CD22-19 CAR produced little to no cytokine secretion in the absence of tumor cells (CAR T alone group), which further confirms CAR specificity, and indicates a lack of tonic signaling by the tandem anti-CD22-19 CAR with various co-stimulatory domains.

EQUIVALENTS

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference, and may be employed in the practice of the invention. More generally, documents or references are cited in this text, either in a Reference List before the claims, or in the text itself; and, each of these documents or references ("herein cited references"), as well as each document or reference cited in each of the herein cited references (including any manufacturer's specifications, instructions, etc.), is hereby expressly incorporated herein by reference.

The foregoing description of some specific embodiments provides sufficient information that others can, by applying current knowledge, readily modify or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. In the drawings and the description, there have been disclosed exemplary embodiments and, although specific terms may have been employed, they are unless otherwise stated used in a generic and descriptive sense only and not for purposes of limitation, the scope of the claims therefore not being so limited. Moreover, one skilled in the art will appreciate that certain steps of the methods discussed herein may be sequenced in alternative order or steps may be combined. Therefore, it is intended that the appended claims not be limited to the particular embodiment disclosed herein. Those skilled in the art will recognize, or be able to ascertain using no more than routine experimentation, many equivalents to the embodiments of the invention described herein. Such equivalents are encompassed by the following claims.

SEQUENCE LISTING

The nucleic and amino acid sequences listed below are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NO: 1 nucleotide sequence of LTG2681 D0023 Leader-CD22 VH-(GGGGS)-3
CD22 VL (GGGGS)-5 CD19 VH (GGGGS)-3 CD19 VL CD8 hinge+TM-4-1BB-CD3z
(Construct CAR 2219)
ATGCTCTTGCTCGTGACTTCTTTGCTTTTGTGCGAACTTCCGCACCCAGCCTTCCT
TTTGATACCTCAGGTACAGCTTCAACAAAGCGGACCGGGACTTGTTAAGCATTCC
CAAACCCTTTCTCTCACGTGTGCAATTAGCGGCGATAGTGTATCCTCTAATTCTGC
GGCCTGGAACTGGATACGACAATCACCAAGCGGGGACTCGAGTGGTTGGGCCG
AACCTACTATCGGTCCAAATGGTATAATGACTACGCAGTATCCGTGAAATCTCGC
ATTACGATCAATCCAGACACCTCCAAAAATCAATTTTCTCTGCAGTTGAATAGCG
TGACTCCCGAGGACACGGCCGTTTACTATTGCGCCCAGGAAGTTGAACCCCACG
ATGCATTTGATATTTGGGGCCAGGGAACCATGGTGACAGTGAGTAGTGGGGGTG
GAGGATCTGGAGGAGGCGGTAGCGGCGGGGGCGGCAGTGATATCCAGATGACG
CAGTCACCTTCCAGCGTGTATGCGAGTGTGGGGGACAAGGTCACCATAACCTGTC
GCGCTAGCCAAGATGTCAGCGGGTGGCTGGCTTGGTACCAGCAGAAACCAGGTT
TGGCTCCTCAGCTTTTGATCTCAGGAGCGAGCACGCTTCAGGGTGAGGTCCCAAG
TCGCTTTAGTGGCTCTGGCTCCGGGACAGACTTCACGTTGACGATCAGCAGTTTG
CAGCCTGAGGATTTCGCGACCTACTACTGCCAGCAAGCGAAATATTTTCCGTACA
CTTTCGGTCAGGGGACCAAATTGGAGATCAAAGGTGGGGGTGGTTCAGGCGGCG
GAGGCTCAGGCGGCGGCGTAGCGGAGGAGGCGGAAGCGGGGGTGGCGGATCA
GAAGTGCAACTCGTTCAGAGTGGCGCGGAGGTTAAGAAACCCGGTGCATCTGTA
AAGGTTAGCTGTAAGGCATCAGGATACACTTTTACCAGCTATTACATGCATTGGG
TGAGACAGGCTCCCGGTCAGGGCTCGAATGGATGGGGTTGATCAACCCGAGTG
GTGGTTCAACATCTTACGCCCAGAAGTTTCAGGGCCGAGTAACAATGACTCGGG
ACACGTCTACCTCAACTGTGTATATGGAGCTTTCCAGCCTGCGCTCAGAGGATAC
AGCAGTCTATTACTGCGCACGGTCAGACAGAGGTATAACGGCCACTGATGCGTT
CGATATCTGGGGACAAGGGACTATGGTAACTGTGTCTTCCGGAGGAGGAGGTAG
TGGAGGGGGAGGAAGCGGTGGGGGGGGCTCACAGTCCGTTTTGACTCAGCCACC
AAGCGTCTCAGTCGCACCGGGGCGAATGGCGAAAATTACTTGCGGCGGGAGCGA
CATAGGCAACAAGAATGTGCATTGGTACCAACAGAAACCAGGTCAAGCACCTGT
TCTCGTGGTGTATGATGACTACGATCGCCCAAGCGGGATCCCGGAGCGGTTCTCT
GGATCAAATTCTGGTGATGCAGCCACTCTGACAATATCAACGGTGGAAGTCGGT
GACGAGGCTGATTACTTCTGCCAAGTATGGGATGGCAGCGGAGATCCCTACTGG
ATGTTTGGAGGAGGTACTCAACTGACAGTTCTGGGCGCGGCCGCAACGACCACT
CCTGCACCCCGCCCTCCGACTCCGGCCCCAACCATTGCCAGCCAGCCCCTGTCCC
TGCGGCCGGAAGCCTGCAGACCGGCTGCCGGCGGAGCCGTCCATACCCGGGGAC
TGGATTTCGCCTGCGATATCTATATCTGGGCACCACTCGCCGGAACCTGTGGAGT
GCTGCTGCTGTCCCTTGTGATCACCCTGTACTGCAAGCGCGGACGGAAGAAACTC
TTGTACATCTTCAAGCAGCCGTTCATGCGCCCTGTGCAAACCACCCAAGAAGAGG
ACGGGTGCTCCTCCGGTTCCCGGAAGAGGAAGAGGGCGGCTGGAACTGCGCG
TGAAGTTTTCCCGGTCCGCCGACGCTCCGGCGTACCAGCAGGGGCAAAACCAGC
TGTACAACGAACTTAACCTCGGTCGCCGGGAAGAATATGACGTGCTGGACAAGC
GGCGGGGAAGAGATCCCGAGATGGGTGGAAAGCCGCGGCGGAAGAACCCTCAG
GAGGGCTTGTACAACGAGCTGCAAAAGGACAAAATGGCCGAAGCCTACTCCGAG
ATTGGCATGAAGGGAGAGCGCAGACGCGGAAAGGGACACGATGGACTGTACCA
GGGACTGTCAACCGCGACTAAGGACACTTACGACGCCCTGCACATGCAGGCCCT
GCCCCCGCGC SEQ ID NO: 2 amino acid sequence of LTG2681 D0023 Leader-CD22 VH-(GGGGS)-3
CD22 VL (GGGGS)-5 CD19 VH (GGGGS)-3 CD19 VL CD8 hinge+TM-4-1BB- CD3z
(Construct CAR 2219)
MLLLVTSLLLCELPHPAFLLIPQVQLQQSGPGLVKHSQTLSLTCAISGDSVSSNSAAW
NWIRQSPSRGLEWLGRTYYRSKWYNDYAVSVKSRITINPDTSKNQFSLQLNSVTPED
TAVYYCAQEVEPHDAFDIWGQGTMVTVSSGGGGSGGGGSGGGGSDIQMTQSPSSV
YASVGDKVTITCRASQDVSGWLAWYQQKPGLAPQLLISGASTLQGEVPSRFSGSGSG
TDFTLTISSLQPEDFATYYCQQAKYFPYTFGQGTKLEIKGGGGSGGGGSGGGGSGGG
GSGGGGSEVQLVQSGAEVKKPGASVKVSCKASGYTFTSYYMHWVRQAPGQGLEW
MGLINPSGGSTSYAQKFQGRVTMTRDTSTSTVYMELSSLRSEDTAVYYCARSDRGIT
ATDAFDIWGQGTMVTVSSGGGGSGGGGSGGGGSQSVLTQPPSVSVAPGRMAKITCG
GSDIGNKNVHWYQQKPGQAPVLVVYDDYDRPSGIPERFSGSNSGDAATLTISTVEVG
DEADYFCQVWDGSGDPYWMFGGGTQLTVLGAAATTTPAPRPPTPAPTIASQPLSLRP
EACRPAAGGAVHTRGLDFACDIYIWAPLAGTCGVLLLSLVITLYCKRGRKKLLYIFK
QPFMRPVQTTQEEDGCSCRFPEEEEGGCELRVKFSRSADAPAYQQGQNQLYNELNL
GRREEYDVLDKRRGRDPEMGGKPRRKNPQEGLYNELQKDKMAEAYSEIGMKGERR
RGKGHDGLYQGLSTATKDTYDALHMQALPPR SEQ ID NO: 3 nucleotide sequence of LTG2791 D0024 Leader-CD19 VH
(GGGGS)3 CD19 VL-(GGGGS)5-CD22 VH (GGGGS)3-CD22 VH CD8
hinge+TM-4-1BB-CD3z (Construct CAR 1922)
ATGTTGCTTCTGGTTACTTCCCTTCTTCTTTGCGAGCTTCCACACCCAGCATTCCT
GCTCATTCCGGAGGTGCAACTCGTCCAATCCGGGGCCGAAGTTAAGAAGCCGGG
AGCATCTGTTAAAGTATCCTGTAAGGCCAGTGGGTATACTTTCACCTCATATTAT
ATGCACTGGGTGAGGCAGGCTCCAGGCCAAGGGTTGGAGTGGATGGGACTGATA
AACCCATCTGGGGGATCAACTTCTTATGCGCAAAAGTTCCAAGGTCGGGTCACTA
TGACAAGGGACACATCCACCAGCACTGTTTATATGGAACTGAGCAGCCTGAGAT
CTGAGGATACCGCAGTATATTACTGTGCACGCAGTGATAGAGGCATAACGGCGA
CTGACGCCTTCGACATTTGGGGCCAAGGGACAATGGTCACGGTTTCAAGTGGAG
GTGGAGGGTCTGGTGGCGGGGGTCTGGTGGTGGAGGCAGTCAGAGCGTCCTGA
CCCAGCCGCCTAGCGTCAGTGTGGCCCCCGGCCGCATGGCCAAGATAACGTGTG
GCGGAAGCGATATTGGGAATAAGAACGTCCACTGGTATCAGCAGAAGCCAGGGC
AGGCTCCCGTCCTCGTAGTATACGACGATTATGATCGGCCCAGTGGAATCCCCGA
GAGATTTAGCGGGAGTAACTCTGGGGATGCAGCGACACTTACTATCTCCACTGTT -continued

```
GAAGTAGGAGACGAGGCTGACTATTTTTGTCAGGTTTGGGACGGATCCGGAGAT
CCTTATTGGATGTTTGGCGGAGGTACTCAATTGACCGTGCTTGGAGGTGGCGGAG
GGAGCGGGGGTGGGGGCTCAGGGGGAGGTGGGTCAGGCGGGGGCGGAAGTGGT
GGCGGGGGGTTCCCAAGTCCAACTCCAGCAGTCAGGACCTGGACTGGTAAAACAC
TCTCAAACCCTGTCTCTCACGTGTGCCATATCTGGCGATAGTGTATCTTCAAACTC
TGCTGCATGGAACTGGATCAGGCAAAGTCCATCCCGCGGCCTTGAGTGGCTCGGT
CGAACCTATTACCGAAGCAAATGGTACAACGATTATGCGGTTTCAGTCAAGTCA
AGAATTACGATCAACCCTGATACGAGTAAGAACCAGTTTAGTTTGCAATTGAAC
AGTGTAACTCCCGAGGACACGGCGGTGTACTATTGTGCGCAAGAAGTCGAACCG
CATGATGCGTTCGATATCTGGGGGCAGGGCACAATGGTGACCGTATCTTCTGGCG
GCGGCGGCTCTGGAGGAGGAGGAAGCGGCGGAGGGGGATCTGACATACAAATG
ACACAATCCCCAAGTTCAGTATATGCTAGCGTCGGGGATAAAGTGACAATTACTT
GTAGGGCTTCTCAAGACGTAAGTGGCTGGTTGGCGTGGTACCAGCAAAAGCCGG
GTCTCGCCCCTCAACTCCTTATCAGCGGAGCTTCAACTCTTCAGGGAGAGGTCCC
AAGTCGATTCTCAGGCTCTGGCTCCGGGACAGATTTCACCTTGACAATTAGTTCA
CTGCAACCCGAGGATTTCGCAACTTACTACTGTCAACAGGCCAAGTACTTCCCGT
ATACGTTTGGTCAAGGCACAAAACTGGAGATTAAGGCGGCCGCAACGACCACTC
CTGCACCCCGCCCTCCGACTCCGGCCCCAACCATTGCCAGCCAGCCCCTGTCCCT
GCGGCCGGAAGCCTGCAGACCGGCTGCCGGCGGAGCCGTCCATACCCGGGGACT
GGATTTCGCCTGCGATATCTATATCTGGGCACCACTCGCCGGAACCTGTGGAGTG
CTGCTGCTGTCCCTTGTGATCACCCTGTACTGCAAGCGCGGACGGAAGAAACTCT
TGTACATCTTCAAGCAGCCGTTCATGCGCCCTGTGCAAACCACCCAAGAAGAGG
ACGGGTGCTCCTGCCGGTTCCCGGAAGAGGAAGAGGGCGGCTGCGAACTGCGCG
TGAAGTTTTCCCGGTCCGCCGACGCTCCGGCGTACCAGCAGGGGCAAAACCAGC
TGTACAACGAACTTAACCTCGGTCGCCGGGAAGAATATGACGTGCTGGACAAGC
GGCGGGGAAGAGATCCCGAGATGGGTGGAAAGCCGCGGCGGAAGAACCCTCAG
GAGGGCTTGTACAACGAGCTGCAAAAGGACAAAATGGCCGAAGCCTACTCCGAG
ATTGGCATGAAGGGAGAGCGCAGACGCGGGAAGGGACACGATGGACTGTACCA
GGGACTGTCAACCGCGACTAAGGACACTTACGACGCCCTGCACATGCAGGCCCT
GCCCCCGCGC
```

SEQ ID NO: 4 amino acid sequence of LTG2719 D0024 Leader-CD19 VH (GGGGS)3 CD19 VL-(GGGGS)5-CD22 VH (GGGGS)3-CD22 VH CD8 hinge+TM-4-1BB-CD3z (Construct CAR 1922)

```
MLLLVTSLLLCELPHPAFLLIPEVQLVQSGAEVKKPGASVKVSCKASGYTFTSYYMH
WVRQAPGQGLEWMGLINPSGGSTSYAQKFQGRVTMTRDTSTSTVYMELSSLRSEDT
AVYYCARSDRGITATDAFDIWGQGTMVTVSSGGGGSGGGGSGGGGSQSVLTQPPSV
SVAPGRMAKITCGGSDIGNKNVHWYQQKPGQAPVLVVYDDRPSGIPERFSGSNS
GDAATLTISTVEVGDEADYFCQVWDGSGDPYWMFGGGTQLTVLGGGGSGGGGS
GGGGSGGGGSGGGGSQVQLQQSGPGLVKHSQTLSLTCAISGDSVSSNSAAWNWIRQ
SPSRGLEWLGRTYYRSKWYNDYAVSVKSRITINPDTSKNQFSLQLNSVTPEDTAVYY
CAQEVEPHDAFDIWGQGTMVTVSSGGGGSGGGGSGGGGSDIQMTQSPSSVYASVG
DKVTITCRASQDVSGWLAWYQQKPGLAPQLLISGASTLQGEVPSRFSGSGSGTDFTL
TISSLQPEDFATYYCQQAKYFPYTFGQGTKLEIKAAATTTPAPRPPTPAPTIASQPLSL
RPEACRPAAGGAVHTRGLDFACDIYIWAPLAGTCGVLLLSLVITLYCKRGRKKLLYI
FKQPFMRPVQTTQEEDGCSCRFPEEEEGGCELRVKFSRSADAPAYQQGQNQLYNEL
NLGRREEYDVLDKRRGRDPEMGGKPRRKNPQEGLYNELQKDKMAEAYSEIGMKGE
RRRGKGHDGLYQGLSTATKDTYDALHMQALPPR
```

SEQ ID NO: 5 nucleotide sequence of fully human CAR19 LTG2065 (M19217-1-CD8 TM-4-1BB zeta)

```
ATGCTGCTGCTGGTGACCAGCCTGCTGCTGTGCGAACTGCCGCATCCGGCGTTTC
TGCTGATTCCGGAGGTCCAGCTGGTACAGTCTGGAGCTGAGGTGAAGAAGCCTG
GGGCCTCAGTGAAGGTCTCCTGCAAGGCTTCTGGATACACCTTCACCAGCTACTA
TATGCACTGGGTGCGACAGGCCCCTGGACAAGGGCTTGAGTGGATGGGATTAAT
CAACCCTAGTGGTGGTAGCACAAGCTACGCACAGAAGTTCCAGGGCAGAGTCAC
CATGACCAGGGACACGTCCACGAGCACAGTCTACATGGAGCTGAGCAGCCTGAG
ATCTGAGGACACGGCCGTGTATTACTGTGCGAGATCGGATCGGGGAATTACCGC
CACGGACGCTTTTGATATCTGGGGCCAAGGGACAATGGTCACCGTCTCTTCAGGC
GGAGGAGGCTCCGGGGGAGGAGGTTCCGGGGGCGGGGGTTCCCAGTCTGTGCTG
ACTCAGCCACCCTCGGTGTCAGTGGCCCCAGGGCGGATGGCAAGATTACCTGT
GGGGGAAGTGACATTGGAAATAAAAATGTCCACTGGTATCAGCAGAAGCCAGGC
CAGGCCCCTGTCCTGGTTGTCTATGATGATTACGACCGGCCCTCAGGGATCCCTG
AGCGATTCTCTGGCTCCAACTCTGGGGACGCGGCCACCCTGACGATCAGCACGGT
CGAAGTCGGGGATGAGGCCGACTATTCTGTCAGGTGTGGGACGGTAGTGGTGA
TCCTTATTGGATGTTCGGCGGAGGGACCCAGCTCACCGTTTTAGGTGCGGCCGCA
ACTACCACCCCTGCCCCTCGGCCGCCGACTCCGGCCCCAACCATCGCAAGCCAAC
CCCTCTCCTTGCGCCCCGAAGCTTGCCGCCCGGCCGCGGGTGGAGCCGTGCATAC
CCGGGGGCTGGACTTTGCCTGCGATATCTACATTTGGGCCCCGCTGGCCGGCACT
TGCGGCGTGCTCCTGCTGTCGCTGGTCATCACCCTTTACTGCAAGAGGGGCCGGA
AGAAGCTGCTTTACATCTTCAAGCAGCCGTTCATGCGGCCCGTGCAGACGACTCA
GGAAGAGGACGGATGCTCGTGCAGATTCCCTGAGGAGGAAGAGGGGGATGCG
AACTGCGCGTCAAGTTCTCACGGTCCGCCGACGCCCCGCATATCAACAGGGCC
AGAATCAGCTCTACAACGAGCTGAACCTGGGAAGGAGAGAGGAGTACGACGTG
CTGGACAAGCGACGCGGACGCGACCCGGAGATGGGGGGAAACCACGGCGGAA
AAACCCTCAGGAAGGACTGTACAACGAACTCCAGAAAGACAAGATGGCGGAAG
CCTACTCAGAAATCGGGATGAAGGGAGAGCGGAGGAGGGGAAAGGGTCACGAC
GGGCTGTACCAGGGACTGAGCACCGCCACTAAGGATACCTACGATGCCTTGCAT
ATGCAAGCACTCCCACCCCGG
```

SEQ ID NO: 6 amino acid sequence of fully human CAR19 LTG2065 (M19217-1-
CD8 TM-4-1 BB zeta)
MLLLVTSLLLCELPHPAFLLIPEVQLVQSGAEVKKPGASVKVSCKASGYTFTSYYMH
WVRQAPGQGLEWMGLINPSGGSTSYAQKFQGRVTMTRDTSTSTVYMELSSLRSEDT
AVYYCARSDRGITATDAFDIWGQGTMVTVSSGGGGSGGGGSGGGGSQSVLTQPPSV
SVAPGRMAKITCGGSDIGNKNVHWYQQKPGQAPVLVVYDDYDRPSGIPERFSGSNSG
DAATLTISTVEVGDEADYFCQVWDSGDPYWMFGGGTQLTVLGAAATTTPAPRPPT
PAPTIASQPLSLRPEACRPAAGGAVHTRGLDFACDIYIWAPLAGTCGVLLLSLVITLYC
KRGRKKLLYIFKQPFMRPVQTTQEEDGCSCRFPEEEEGGCELRVKFSRSADAPAYQQ
GQNQLYNELNLGRREEYDVLDKRRGRDPEMGGKPRRKNPQEGLYNELQKDKMAEA
YSEIGMKGERRRGKGHDGLYQGLSTATKDTYDALHMQALPPR SEQ ID NO: 7 nucleotide sequence of mouse scFv CAR19 LTG1538
ATGCTTCTCCTGGTCACCTCCCTGCTCCTCTGCGAACTGCCTCACCCTGCCTTCCT
TCTGATTCCTGACATTCAGATGACTCAGACCACCTCTTCCTTGTCCGCGTCACTG
GGAGACAGAGTGACCATCTCGTGTCGCGCAAGCCAGGATATCTCCAAGTACCTG
AACTGGTACCAACAGAAGCCCGACGGGACTGTGAAGCTGCTGATCTACCACACC
TCACGCCTGCACAGCGGAGTGCCAAGCAGATTCTCCGGCTCCGGCTCGGGAACC
GATTACTCGCTTACCATTAGCAACCTCGAGCAGGAGGACATCGCTACCTACTTCT
GCCAGCAAGGAAATACCCTGCCCTACACCTTCGGCGGAGGAACCAAATTGGAAA
TCACCGGCGGAGGAGGCTCCGGGGGAGGAGGTTCCGGGGGCGGGGGTTCCGAA
GTGAAGCTCCAGGAGTCCGGCCCCGGCCTGGTGGCGCCGTCGCAATCACTCTCT
GTGACCTGTACCGTGTCGGAGTGTCCCTGCCTGATTACGGCGTGAGCTGGATTC
GGCAGCCGCGCGGAAGGGCCTGGAATGGCTGGGTGTCATCGGGGATCCGAGA
CTACCTACTACAACTCGGCCCTGAAGTCCCGCCTGACTATCATCAAAGACAACTC
GAAGTCCCAGGTCTTTCTGAAGATGAACTCCCTGCAAACTGACGACACCGCCAT
CTATTACTGTGCTAAGCACTACTACTACGGTGGAAGCTATGCTATGGACTACTGG
GGGCAAGGCACTTCGGTGACTGTGTCAAGCGCGGCCGCAACTACCACCCCTGCC
CCTCGGCCGCCGACTCCGGCCCCAACCATCGCAAGCCAACCCCTCTCCTTGCGC
CCGAAGCTTGCCGCCCGGCCGCGGGTGGAGCCGTGCATACCCGGGGCTGGACT
TTGCCTGCGATATCTACATTTGGGCCCCGCTGGCCGGACACTTGCGGCGTGCTCCT
GCTGTCGCTGGTCATCACCCTTTACTGCAAGAGGGGCCGGAAGAAGCTGCTTTAC
ATCTTCAAGCAGCCGTTCATGCGGCCCGTGCAGACGACTCAGGAAGAGGACGGA
TGCTCGTGCAGATTCCCTGAGGAGGAAGAGGGGGGATGCGAACTGCGCGTCAAG
TTCTCACGGTCCGCCGACGCCCCCGCATATCAACAGGGCCAGAATCAGCTCTAC
AACGAGCTGAACCTGGGAAGGAGAGAGGAGTACGACGTGCTGGACAAGCGACG
CGGACGCGACCCGGAGATGGGGGGGAAACCACGGCGGAAAAACCCTCAGGAAG
GACTGTACAACGAACTCCAGAAAGACAAGATGGCGGAAGCCTACTCAGAAATC
GGGATGAAGGGAGAGCGGAGGAGGGGAAAGGGTCACGACGGGCTGTACCAGGG
ACTGAGCACCGCCACTAAGGATACCTACGATGCCTTGCATATGCAAGCACTCCC
ACCCCGG SEQ ID NO: 8 amino acid sequence of mouse scFv CAR19 LTG1538
MLLLVTSLLLCELPHPAFLLIPDIQMTQTTSSLSASLGDRVTISCRASQDISKYLNWYQ
QKPDGTVKLLIYHTSRLHSGVPSRFSGSGSGTDYSLTISNLEQEDIATYFCQQGNTLP
YTFGGGTKLEITGGGSGGGGSGGGGSEVKLQESGPGLVAPSQSLSVTCTVSGVSLP
DYGVSWIRQPPRKGLEWLGVIWGSETTYYNSALKSRLTIIKDNSKSQVFLKMNSLQT
DDTAIYYCAKHYYYGGSYAMDYWGQGTSVTVSSAAATTTPAPRPPTPAPTIASQPL
SLRPEACRPAAGGAVHTRGLDFACDIYIWAPLAGTCGVLLLSLVITLYCKRGRKKLL
YIFKQPFMRPVQTTQEEDGCSCRFPEEEEGGCELRVKFSRSADAPAYQQGQNQLYNE
LNLGRREEYDVLDKRRGRDPEMGGKPRRKNPQEGLYNELQKDKMAEAYSEIGMKG
ERRRGKGHDGLYQGLSTATKDTYDALHMQALPP SEQ ID NO: 9 nucleotide sequence of CAR22 LTG2209
ATGCTTCTTTTGGTGACTTCCCTTTTGCTGTGCGAGTTGCCACACCCCGCCTTCCT
GCTTATTCCCCAGGTACAGCTTCAACAGAGTGGGCCGGGACTGGTGAAACACTC
CCAAACACTTTCTCTGACGTGCGCTATATCAGGTGACTCTGTTTCATCTAATTCTG
CTGCGTGGAACTGGATTCGACAATCTCCCAGTCGCGGGTTGGAATGGCTGGGAC
GAACATATTATCGGTCTAAGTGGTATAACGATTATGCTGTATCTGTTAAATCTCG
AATTACGATTAATCCTGACACCTCCAAGAACCAGTTCTCCCTCCAGTTGAACTCA
GTCACACCGGAAGACACTGCGGTCTACTATTGCGCTCAAGAAGTCGAGCCACAT
GATGCATTCGACATCTGGGGCCAGGGAACGATGGTCACCGTCAGCAGTGGCGGC
GGCGGATCTGGGGTGGCGGTTCTGGCGGTGGAGGATCAGACATACAAATGACG
CAGAGTCCCTCAAGTGTGTACGCGAGTGTGGGGGATAAGGTAACTATTACGTGC
AGAGCGTCACAGGATGTTAGTGGATGGCTTGCCTGGTATCAGCAGAAGCCAGGC
CTTGCTCCACAGCTCCTTATCAGTGGTGCTTCTACACTTCAGGGCGAGGTTCCGA
GTAGATTCTCTGGTTCTGGATCTGGTACTGACTTCACTCTTACAATTTCTTCTTTG
CAACCAGAAGACTTTGCGACTTATTACTGCCAACAGGCCAAATACTTCCCTTATA
CATTTGGCCAAGGTACCAAGTTGGAGATAAAGGCGGCCGCAACTACCACCCCTG
CCCCTCGGCCGCCGACTCCGGCCCCAACCATCGCAAGCCAACCCCTCTCCTTGCG
CCCCGAAGCTTGCCGCCCGGCCGCGGGTGGAGCCGTGCATACCCGGGGGCTGGA
CTTTGCCTGCGATATCTACATTTGGGCCCCGTGGCCGGACACTTGCGGCGTGCTC
CTGCTGTCGCTGGTCATCACCCTTTACTGCAAGAGGGGCCGGAAGAAGCTGCTTT
ACATCTTCAAGCAGCCGTTCATGCGGCCCGTGCAGACGACTCAGGAAGAGGACG
GATGCTCGTGCAGATTCCCTGAGGAGGAAGAGGGGGGATGCGAACTGCGCGTCA
AGTTCTCACGGTCCGCCGACGCCCCCGCATATCAACAGGGCCAGAATCAGCTCTA
CAACGAGCTGAACCTGGGAAGGAGAGAGGAGTACGACGTGCTGGACAAGCGAC
GCGGACGCGACCCGGAGATGGGGGGGAAACCACGGCGGAAAAACCCTCAGGAA

```
GGACTGTACAACGAACTCCAGAAAGACAAGATGGCGGAAGCCTACTCAGAAATC
GGGATGAAGGGAGAGCGGAGGAGGGGAAAGGGTCACGACGGGCTGTACCAGGG
ACTGAGCACCGCCACTAAGGATACCTACGATGCCTTGCATATGCAAGCACTCCCA
CCCCGG

SEQ ID NO: 10 amino acid sequence of CD22A 1495 (CAR 20A)
MLLLVTSLLLCELPHPAFLLIPQVQLQQSGPGLVKHSQTLSLTCAISGDSVSSN
SAAWNWIRQSPSRGLEWLGRTYYRSKWYNDYAVSVKSRITINPDTSKNQFSL
QLNSVTPEDTAVYYCAQEVEPHDAFDIWGQGTMVTVSSGGGGSGGGGSGGG
GSDIQMTQSPSSVYASVGDKVTITCRASQDVSGWLAWYQQKPGLAPQLLISG
ASTLQGEVPSRFSGSGSGTDFTLTISSLQPEDFATYYCQQAKYFPYTFGQGTKL
EIKAAATTTPAPRPPTPAPTIASQPLSLRPEACRPAAGGAVHTRGLDFACDIYI
WAPLAGTCGVLLLSLVITLYCKRGRKKLLYIFKQPFMRPVQTTQEEDGCSCRF
PEEEEGGCELRVKFSRSADAPAYQQGQNQLYNELNLGRREEYDVLDKRRGR
DPEMGGKPRRKNPQEGLYNELQKDKMAEAYSEIGMKGERRRGKGHDGLYQ
GLSTATKDTYDALHMQALPPR SEQ ID NO: 11 nucleotide sequence of leader/signal peptide sequence (LP)
atgctgctgctggtgaccagcctgctgctgtgcgaactgccgcatccggcgtttctgctgattccg SEQ ID NO: 12 amino acid sequence of leader/signal peptide sequence (LP)
MLLLVTSLLLCELPHPAFLLIP SEQ ID NO: 35 nucleotide sequence of DNA CD8 transmembrane domain
atttgggccccgctggccggcacttgcggcgtgctcctgctgtcgctggtcatcacccttt
tactgc SEQ ID NO: 36 amino acid sequence of CD8 transmembrane domain
Ile Trp Ala Pro Leu Ala Gly Thr Cys Gly Val Leu Leu Leu Ser Leu
Val Ile Thr Leu Tyr Cys SEQ ID NO: 37 nucleotide sequence of DNA CD8 hinge domain
actaccaccctgcccctcggccgccgactccggccccaaccatcgcaagccaaccctc
tccttgcgccccgaagcttgccgcccggccgcgggtggagccgtgcatacccgggggctg
gactttgcctgcgatatctac SEQ ID NO: 38 amino acid sequence of CD8 hinge domain
Thr Thr Thr Pro Ala Pro Arg Pro Pro Thr Pro Ala Pro Thr Ile Ala
Ser Gln Pro Leu Ser Leu Arg Pro Glu Ala Cys Arg Pro Ala Ala Gly
Gly Ala Val His Thr Arg Gly Leu Asp Phe Ala Cys Asp Ile Tyr SEQ ID NO: 39 amino acid sequence of amino acid numbers 137 to 206 hinge and
transmembrane region of CD8.alpha. (NCBI RefSeq: NP.sub.--001759.3)
Thr Thr Thr Pro Ala Pro Arg Pro Pro Thr Pro Ala Pro Ile Ala Ser Gln Pro Leu
Ser Leu Arg Pro Glu Ala Cys Arg Pro Ala Ala Gly Gly Ala Val His Thr Arg Gly Leu
Asp Phe Ala Cys Asp Ile Tyr Ile Trp Ala Pro Leu Ala Gly Thr Cys Gly Val Leu Leu
Leu Ser Leu Val Ile Thr Leu Tyr Cys SEQ ID NO: 40 nucleotide sequence of DNA signaling domain of 4-1BB
aagaggggccggaagaagctgctttacatcttcaagcagccgttcatgcggcccgtgcag
acgactcaggaagaggacggatgctcgtgcagattccctgaggaggaagaggggggatgc
gaactg SEQ ID NO: 41 amino acid sequence of signaling domain of 4-1BB
Lys Arg Gly Arg Lys Lys Leu Leu Tyr Ile Phe Lys Gln Pro Phe Met
Arg Pro Val Gln Thr Thr Gln Glu Glu Asp Gly Cys Ser Cys Arg Phe
Pro Glu Glu Glu Glu Gly Gly Cys Glu Leu SEQ ID NO: 42 nucleotide sequence of DNA signaling domain of CD3-zeta
cgcgtcaagttctcacggtccgccgacgcccccgcatatcaacagggccagaatcagctc
tacaacgagctgaacctgggaaggagagaggagtacgacgtgctggacaagcgacgcgga
cgcgacccggagatggggggggaaaccacggcggaaaaaccctcaggaaggactgtacaac
gaactccagaaagacaagatggcggaagcctactcagaaatcgggatgaagggagagcgg
aggaggggaaagggtcacgacgggctgtaccagggactgagcaccgccactaaggatacc
tacgatgccttgcatatgcaagcactcccaccccgg SEQ ID NO: 43 amino acid sequence of CD3zeta
Arg Val Lys Phe Ser Arg Ser Ala Asp Ala Pro Ala Tyr Gln Gln Gly Gln Asn Gln Leu
Tyr Asn Glu Leu Asn Leu Gly Arg Arg Glu Glu Tyr Asp Val Leu Asp Lys Arg Arg
Gly Arg Asp Pro Glu Met Gly Gly Lys Pro Arg Arg Lys Asn Pro Gln Glu Gly Leu
Tyr Asn Glu Leu Gln Lys Asp Lys Met Ala Glu Ala Tyr Ser Glu Ile Gly Met Lys Gly
Glu Arg Arg Arg Gly Lys Gly His Asp Gly Leu Tyr Gln Gly Leu Ser Thr Ala Thr
Lys Asp Thr Tyr Asp Ala Leu His Met Gln Ala Leu Pro Pro Arg SEQ ID NO: 44 nucleotide sequence of ScFv CD19 (FMC63)
gacattcagatgactcagaccacctcttccttgtccgcgtcactgggagacagagtgaccat
ctcgtgtcgcgcaagccaggatatctccaagtacctgaactggtaccaacagaagcccga
cgggactgtgaagctgctgatctaccacacctcacgcctgcacagcggagtgccaagcag
attctccggctccggctcgggaaccgattactcgcttaccattagcaacctcgagcagga
```

```
ggacatcgctacctacttctgccagcaaggaaataccctgccctacaccttcggcggagg
aaccaaattggaaatcaccggcggaggaggctccggggaggaggitccggggcggggg
ttccgaagtgaagctccaggagtccggccccggcctggiggcgccgtcgcaatcactctc
tgtgacctgtaccgtgtcgggagtgtccctgcctgattacggcgtgagctggattcggca
gccgccgcggaagggcctggaatggctgggigtcatctgggatccgagactacctacta
caactcggccctgaagtcccgcctgactatcatcaaagacaactcgaagtcccaggictt
tctgaagatgaactccctgcaaactgacgacaccgccatctattactgtgctaagcacta
ctactacggtggaagctatgctatggactactgggggcaaggcacttcggtgactgtgtc
aagc
```

SEQ ID NO: 45 amino acid sequence of ScFv CD19 (FMC63)
Asp Ile Gln Met Thr Gln Thr Thr Ser Ser Leu Ser Ala Ser Leu Gly Asp Arg Val Thr
Ile Ser Cys Arg Ala Ser Gln Asp Ile Ser Lys Tyr Leu Asn Trp Tyr Gln Gln Lys Pro
Asp Gly Thr Val Lys Leu Leu Ile Tyr His Thr Ser Arg Leu His Ser Gly Val Pro Ser
Arg Phe Ser Gly Ser Gly Ser Gly Thr Asp Tyr Ser Leu Thr Ile Ser Asn Leu Glu Gln
Glu Asp Ile Ala Thr Tyr Phe Cys Gln Gln Gly Asn Thr Leu Pro Tyr Thr Phe Gly Gly
Gly Thr Lys Leu Glu Ile Thr Gly Gly Gly Ser Gly Gly Gly Ser Gly Gly Gly
Gly Ser Glu Val Lys Leu Gln Glu Ser Gly Pro Gly Leu Val Ala Pro Ser Gln Ser Leu
Ser Val Thr Cys Thr Val Ser Gly Val Ser Leu Pro Asp Tyr Gly Val Ser Trp Ile Arg
Gln Pro Pro Arg Lys Gly Leu Glu Trp Leu Gly Val Ile Trp Gly Ser Glu Thr Thr Tyr
Tyr Asn Ser Ala Leu Lys Ser Arg Leu Thr Ile Ile Lys Asp Asn Ser Lys Ser Gln Val
Phe Leu Lys Met Asn Ser Leu Gln Thr Asp Asp Thr Ala Ile Tyr Tyr Cys Ala Lys His
Tyr Tyr Tyr Gly Gly Ser Tyr Ala Met Asp Tyr Trp Gly Gln Gly Thr Ser Val Thr Val
Ser Ser SEQ ID NO: 46 nucleotide sequence of anti-CD33 CAR (LTG1936)
```
ATGCTGCTGCTGGTGACCAGCCTGCTGCTGTGCGAACTGCCGCATCCGGCGTTTC
TGCTGATTCCGCAGGTGCAGCTGGTGCAATCGGGGCAGAGGTGAAAAAGCCCG
GGGAGTCTCTGAGGATCTCCTGTAAGGGTTCTGGATTCAGTTTTCCCACCTACTG
GATCGGCTGGGTGCGCCAGATGCCCGGGAAAGGCCTGGAGTGGATGGGGATCAT
CTATCCTGGTGACTCTGATACCAGATACAGCCCGTCCTTCCAAGGCCAGGTCACC
ATCTCAGCCGACAAGTCCATCAGCACCGCCTACCTGCAGTGGAGCAGCCTGAAG
GCCTCGGACACCGCCATGTATTACTGTGCGAGACTAGTTGGAGATGGCTACAATA
CGGGGGCTTTTGATATCTGGGGCCAAGGGACAATGGTCACCGTCTCTTCAGGAG
GTGGCGGGTCTGGTGGTGGCGGTAGCGGTGGTGGCGGATCCGATATTGTGATGA
CCCACACTCCACTCTCTCTGTCCGTCACCCCTGGACAGCCGGCCTCCATCTCCTGC
AAGTCTAGTCAGAGCCTCCTGCATAGTAATGGAAAGACCTATTTGTATTGGTACC
TGCAGAAGCCAGGCCAGCCTCCACAGCTCCTGATCTATGGAGCTTCCAACCGGTT
CTCTGGAGTGCCAGACAGGTTCAGTGGCAGCGGGTCAGGGACAGATTTCACACT
GAAAATCAGCCGGGTGGAGGCTGAGGATGTTGGGGTTTATTACTGCATGCAAAG
TATACAGCTTCCTATCACCTTCGGCCAAGGGACACGACTGGAGATTAAAGCGGC
CGCAACTACCACCCCTGCCCCTCGGCCGCCGACTCCGGCCCCAACCATCGCAAGC
CAACCCCTCTCCTTGCGCCCCGAAGCTTGCCGCCCGGCCGCGGGTGGAGCCGTGC
ATACCCGGGGGCTGGACTTTGCCTGCGATATCTACATTTGGGCCCCGCTGGCCGG
CACTTGCGGCGTGCTCCTGCTGTCGCTGGTCATCACCCTTTACTGCAAGAGGGGC
CGGAAGAAGCTGCTTTACATCTTCAAGCAGCCGTTCATGCGGCCCGTGCAGACG
ACTCAGGAAGAGGACGGATGCTCGTGCAGATTCCCTGAGGAGGAAGGAGGGGGG
ATGCGAACTGCGCGTCAAGTTCTCACGGTCCGCCGACGCCCCCGCATATCAACAG
GGCCAGAATCAGCTCTACAACGAGCTGAACCTGGAAGGAGAGAGGAGTACGA
CGTGCTGGACAAGCGACGCGGACGCGACCCGGAGATGGGGGGGAAACCACGGC
GGAAAAACCCTCAGGAAGGACTGTACAACGAACTCCAGAAAGACAAGATGGCC
GAAGCCTACTCAGAAATCGGGATGAAGGGAGAGCGGAGGAGGGGAAAGGGTCA
CGACGGGCTGTACCAGGGACTGAGCACCGCCACTAAGGATACCTACGATGCCTT
GCATATGCAAGCACTCCCACCCCGG
```

SEQ ID NO: 47 amino acid sequence of anti-CD33 CAR (LTG1936)
MLLLVTSLLLCELPHPAFLLIPQVQLVQSGAEVKKPGESLRISCKGSGFSFPTYWIGW
VRQMPGKGLEWMGITYPGDSDTRYSPSFQGQVTISADKSISTAYLQWSSLKASDTAM
YYCARLVGDGYNTGAFDIWGQGTMVTVSSGGGGSGGGGSGGGGSDIVMTHTPLSL
SVTPGQPASISCKSSQSLLHSNGKTYLYWYLQKPGQPPQLLIYGASNRFSGVPDRFSG
SGSGTDFTLKISRVEAEDVGVYYCMQSIQLPITFGQGTRLEIKAAATTTPAPRPPTPAP
TIASQPLSLRPEACRPAAGGAVHTRGLDFACDIYIWAPLAGTCGVLLLSLVITLYCKR
GRKKLLYIFKQPFMRPVQTTQEEDGCSCRFPEEEEGGCELRVKFSRSADAPAYQQGQ
NQLYNELNLGRREEYDVLDKRRGRDPEMGGKPRRKNPQEGLYNELQKDKMAEAYS
EIGMKGERRRGKGHDGLYQGLSTATKDTYDALHMQALPP SEQ ID NO: 48 nucleotide sequence of anti-mesothelin CAR (LTG1904)
```
ATGCTGCTGCTGGTGACCAGCCTGCTGCTGTGCGAACTGCCGCATCCGGCGTTTC
TGCTGATTCCGGAGGTCCAGCTGGTACAGTCTGGGGAGGCTTGGTACAGCCTG
GGGGGTCCCTGAGACTCTCCTGTGCAGCCTCTGGATTCACCTTTGATGATTATGC
CATGCACTGGGTCCGGCAAGCTCCAGGGAAGGGCCTGGAGTGGGTCTCAGGTAT
TAGTTGGAATAGTGGTAGCATAGGCTATGCGGACTCTGTGAAGGGCCGATTCAC
CATCTCCAGAGACAACGCCAAGAACTCCCTGTATCTGCAAATGAACAGTCTGAG
AGCTGAGGACACGGCCTTGTATTACTGTGCAAAAGATTTATCGTCAGTGGCTGG
ACCCTTTAACTACTGGGGCCAGGGCACCCTGGTCACCGTCTCCTCAGGAGGTGGC
GGGTCTGGTGGAGGCGGTAGCGGCGGTGGCGGATCCTCTTCTGAGCTGACTCAG
GACCCTGCTGTGTCTGTGGCCTTGGGACAGACAGTCAGGATCACATGCCAAGGA
GACAGCCTCAGAAGCTATTATGCAAGCTGGTACCAGCAGAAGCCAGGACAGGCC
CCTGTACTTGTCATCTATGGTAAAAACAACCGGCCCTCAGGGATCCCAGACCGAT
```

```
TCTCTGGCTCCAGCTCAGGAAACACAGCTTCCTTGACCATCACTGGGGCTCAGGC
GGAGGATGAGGCTGACTATTACTGTAACTCCCGGGACAGCAGTGGTAACCATCT
GGTATTCGGCGGAGGCACCCAGCTGACCGTCCTCGGTGCGGCCGCAACTACCAC
CCCTGCCCCTCGGCCGCCGACTCCGGCCCCAACCATCGCAAGCCAACCCCTCTCC
TTGCGCCCCGAAGCTTGCCGCCCGGCCGCGGGTGGAGCCGTGCATACCCGGGGG
CTGGACTTTGCCTGCGATATCTACATTTGGGCCCCGCTGGCCGGCACTTGCGGCG
TGCTCCTGCTGTCGCTGGTCATCACCCTTTACTGCAAGAGGGGCCGGAAGAAGCT
GCTTTACATCTTCAAGCAGCCGTTCATGCGGCCCGTGCAGACGACTCAGGAAGA
GGACGGATGCTCGTGCAGATTCCCTGAGGAGGAAGAGGGGGATGCGAACTGC
GCGTCAAGTTCTCACGGTCCGCCGACGCCCCCGCATATCAACAGGGCCAGAATC
AGCTCTACAACGAGCTGAACCTGGGAAGGAGAGAGGAGTACGACGTGCTGGAC
AAGCGACGCGGACGCGACCCGGAGATGGGGGGAAACCACGGCGGAAAAACCC
TCAGGAAGGACTGTACAACGAACTCCAGAAAGACAAGATGGCGGAAGCCTACT
CAGAAATCGGGATGAAGGGAGAGCGGAGGAGGGGAAAGGGTCACGACGGGCTG
TACCAGGGACTGAGCACCGCCACTAAGGATACCTACGATGCCTTGCATATGCAA
GCACTCCCACCCCGG

SEQ ID NO: 49 amino acid sequence of anti-mesothelin CAR (LTG1904)
MLLLVTSLLLCELPHPAFLLIPEVQLVQSGGGLVQPGGSLRLSCAASGFTFDDYAMH
WVRQAPGKGLEWVSGISWNSGSIGYADSVKGRFTISRDNAKNSLYLQMNSLRAEDT
ALYYCAKDLSSVAGPFNYWGQGTLVTVSSGGGGSGGGGSGGGGSSSELTQDPAVS
VALGQTVRITCQGDSLRSYYASWYQQKPGQAPVLVIYGKNNRPSGIPDRFSGSSSGN
TASLTITGAQAEDEADYYCNSRDSSGNHLVFGGGTQLTVLGAAATTTPAPRPPTPAP
TIASQPLSLRPEACRPAAGGAVHTRGLDFACDIYIWAPLAGTCGVLLLSLVITLYCKR
GRKKLLYIFKQPFMRPVQTTQEEDGCSCRFPEEEEGGCELRVKFSRSADAPAYQQGQ
NQLYNELNLGRREEYDVLDKRRGRDPEMGGKPRRKNPQEGLYNELQKDKMAEAY
SEIGMKGERRRGKGHDGLYQGLSTATKDTYDALHMQALPPR SEQ ID NO: 50 nucleotide sequence of heavy chain scFv 16P17
CAGGTACAGCTTCAACAGAGTGGGCCGGGACTGGTGAAACACTCCCAAACACTT
TCTCTGACGTGCGCTATATCAGGTGACTCTGTTTCATCTAATTCTGCTGCGTGGA
ACTGGATTCGACAATCTCCCAGTCGCGGGTTGGAATGGCTGGGACGAACATATT
ATCGGTCTAAGTGGTATAACGATTATGCTGTATCTGTTAAATCTCGAATTACGAT
TAATCCTGACACCTCCAAGAACCAGTTCTCCCTCCAGTTGAACTCAGTCACACCG
GAAGACACTGCGGTCTACTATTGCGCTCAAGAAGTCGAGCCACATGATGCATTC
GACATCTGGGGCCAGGGAACGATGGTCACCGTCAGCAGT SEQ ID NO: 51 amino acid sequence of heavy chain scFv 16P17
QVQLQQSGPGLVKHSQTLSLTCAISGDSVSSNSAAWNWIRQSPSRGLEWLGRTYYR
SKWYNDYAVSVKSRITINPDTSKNQFSLQLNSVTPEDTAVYYCAQEVEPHDAFDIW
GQGTMVTVSS SEQ ID NO: 52 nucleotide sequence of light chain scFv 16P17
GACATACAAATGACGCAGAGTCCCTCAAGTGTGTACGCGAGTGTGGGGGATAAG
GTAACTATTACGTGCAGAGCGTCACAGGATGTTAGTGGATGGCTTGCCTGGTATC
AGCAGAAGCCAGGCCTTGCTCCACAGCTCCTTATCAGTGGTGCTTCTACACTTCA
GGGCGAGGTTCCGAGTAGATTCTCTGGTTCTGGATCTGGTACTGACTTCACTCTT
ACAATTTCTTCTTTGCAACCAGAAGACTTTGCGACTTATTACTGCCAACAGGCCA
AATACTTCCCTTATACATTTGGCCAAGGTACCAAGTTGGAGATAAAG SEQ ID NO: 53 amino acid sequence of light chain scFv 16P17
DIQMTQSPSSVYASVGDKVTITCRASQDVSGWLAWYQQKPGLAPQLLISGASTLQG
EVPSRFSGSGSGTDFTLTISSLQPEDFATYYCQQAKYFPYTFGQGTKLEIK SEQ ID NO: 54 nucleotide sequence of heavy chain scFv M19217-1
GAGGTCCAGCTGGTACAGTCTGGAGCTGAGGTGAAGAAGCCTGGGGCCTCAGTG
AAGGTCTCCTGCAAGGCTTCTGGATACACCTTCACCAGCTACTATATGCACTGGG
TGCGACAGGCCCCTGGACAAGGGCTTGAGTGGATGGGATTAATCAACCCTAGTG
GTGGTAGCACAAGCTACGCACAGAAGTTCCAGGGCAGAGTCACCATGACCAGGG
ACACGTCCACGAGCACAGTCTACATGGAGCTGAGCAGCCTGAGATCTGAGGACA
CGGCCGTGTATTACTGTGCGAGATCGGATCGGGGAATTACCGCCACGGACGCTT
TTGATATCTGGGGCCAAGGGACAATGGTCACCGTCTCTTCA SEQ ID NO: 55 nucleotide sequence of heavy chain scFv M19217-1
EVQLVQSGAEVKKPGASVKVSCKASGYTFTSYYMHWVRQAPGQGLEWMGLINPSG
GSTSYAQKFQGRVTMTRDTSTSTVYMELSSLRSEDTAVYYCARSDRGITATDAFDI
WGQGTMVTVSS SEQ ID NO: 56 nucleotide sequence of light chain scFv M19217-1
CAGTCTGTGCTGACTCAGCCACCCTCGGTGTCAGTGGCCCCAGGGCGGATGGCC
AAGATTACCTGTGGGGAAGTGACATTGGAAATAAAAATGTCCACTGGTATCAG
CAGAAGCCAGGCCAGGCCCCTGTCCTGGTTGTCTATGATGATTACGACCGGCCCT
CAGGGATCCCTGAGCGATTCTCTGGCTCCAACTCTGGGGACGCGGCCACCCTGA
CGATCAGCACGGTCGAAGTCGGGGATGAGGCCGACTATTTCTGTCAGGTGTGGG
ACGGTAGTGGTGATCCTTATTGGATGTTCGGCGGAGGGACCCAGCTCACCGTTTT
AGGT
```

SEQ ID NO: 57 amino acid sequence of light chain scFv M19217-1
QSVLTQPPSVSVAPGRMAKITCGGSDIGNKNVHWYQQKPGQAPVLVVYDDYDRPS
GIPERFSGSNSGDAATLTISTVEVGDEADYFCQVWDSGDPYWMFGGGTQLTVLG SEQ ID NO: 58 nucleotide sequence of CAR2 2LTG2200 (M971-CD8TM-4-1BB-zeta)
ATGCTTCTTTTGGTGACTTCCCTTTTGCTGTGCGAGTTGCCACACCCCGCCTTCCT
GCTTATTCCCCAGGTACAGCTCCAGCAGAGTGGCCCAGGGCTCGTGAAGCCAAG
CCAGACGCTGTCCCTGACTTGTGCAATTTCAGGGGATTCAGTTTCATCAAATAGC
GCGGCGTGGAATTGGATTCGACAATCTCCTTCCCGAGGGTTGGAATGGCTTGGA
CGAACATATTACAGATCCAAATGGTATAACGACTATGCGGTATCAGTAAAGTCA
AGAATAACCATTAACCCCGACACAAGCAAGAACCAATTCTCTTTGCAGCTTAAC
TCTGTCACGCCAGAAGACACGGCAGTCTATTATTGCGCTCGCGAGGTAACGGGT
GACCTGGAAGACGCTTTTGACATTTGGGGGCAGGGTACGATGGTGACAGTCAGT
TCAGGGGGCGGTGGGAGTGGGGGAGGGGGTAGCGGGGGGGGAGGGTCAGACAT
TCAGATGACCCAGTCCCCTTCATCCTTGTCTGCCTCCGTCGGTGACAGGGTGACA
ATAACATGCAGAGCAAGCCAAACAATCTGGAGCTATCTCAACTGGTACCAGCAG
CGACCAGGAAAAGCGCCAAACCTGCTGATTTACGCTGCTTCCTCCCTCCAATCAG
GCGTGCCTAGTAGATTTAGCGGTAGGGGCTCCGGCACCGATTTTACGCTCACTAT
AAGCTCTCTTCAAGCAGAAGATTTTGCGACTTATTACTGCCAGCAGTCCTATAGT
ATACCTCAGACTTTCGGACAGGGTACCAAGTTGGAGATTAAGGCGGCCGCAACT
ACCACCCCTGCCCCTCGGCCGCCGACTCCGGCCCCAACCATCGCAAGCCAACCC
CTCTCCTTGCGCCCCGAAGCTTGCCGCCCGGCCGCGGGTGGAGCCGTGCATACCC
GGGGGCTGGACTTTGCCTGCGATATCTACATTTGGGCCCCGCTGGCCGGCACTTG
CGGCGTGCTCCTGCTGTCGCTGGTCATCACCCTTTACTGCAAGAGGGGCCGGAAG
AAGCTGCTTTACATCTTCAAGCAGCCGTTCATGCGGCCCGTGCAGACGACTCAGG
AAGAGGACGGATGCTCGTGCAGATTCCCTGAGGAGGAAGAGGGGGGATGCGAA
CTGCGCGTCAAGTTCTCACGGTCCGCCGACGCCCCCGCATATCAACAGGGCCAG
AATCAGCTCTACAACGAGCTGAACCTGGGAAGGAGAGAGGAGTACGACGTGCT
GGACAAGCGACGCGGACGCGACCCGGAGATGGGGGGGAAACCACGGCGGAAAA
ACCCTCAGGAAGGACTGTACAACGAACTCCAGAAAGACAAGATGGCGGAAGCC
TACTCAGAAATCGGGATGAAGGGAGAGCGGAGGAGGGGAAAGGGTCACGACGG
GCTGTACCAGGGACTGAGCACCGCCACTAAGGATACCTACGATGCCTTGCATAT
GCAAGCACTCCCACCCCGG SEQ ID NO: 59 amino acid sequence of CAR22 LTG2200 (M971-CD8TM-4-1BB-zeta)
MLLLVTSLLLCELPHPAFLLIPQVQLQQSGPGLVKPSQTLSLTCAISGDSVSSNSAAW
NWIRQSPSRGLEWLGRTYYRSKWYNDYAVSVKSRITINPDTSKNQFSLQLNSVTPED
TAVYYCAREVTGDLEDAFDIWGQGTMVTVSSGGGGSGGGGSGGGGSDIQMTQSPS
SLSASVGDRVTITCRASQTIWSYLNWYQQRPGKAPNLLIYAASSLQSGVPSRFSGRGS
GTDFTLTISSLQAEDFATYYCQQSYSIPQTFGQGTKLEIKAAATTTPAPRPPTPAPTIAS
QPLSLRPEACRPAAGGAVHTRGLDFACDIYIWAPLAGTCGVLLLSLVITLYCKRGRK
KLLYIFKQPFMRPVQTTQEEDGCSCRFPEEEEGGCELRVKFSRSADAPAYQQGQNQL
YNELNLGRREEYDVLDKRRGRDPEMGGKPRRKNPQEGLYNELQKDKMAEAYSEIG
MKGERRRGKGHDGLYQGLSTATKDTYDALHMQALPPR SEQ ID NO: 60 nucleotide sequence of CAR LTG2737 (CD22-19 CD8 BBz)
ATGCTCTTGCTCGTGACTTCTTTGCTTTTGTGCGAACTTCCGCACCCAGCCTTCCT
TTTGATACCTCAGGTACAGCTTCAACAAAGCGGACCGGGACTTGTTAAGCATTC
CCAAACCCTTTCTCTCACGTGTGCAATTAGCGGCGATAGTGTATCCTCTAATTCT
GCGGCCTGGAACTGGATACGACAATCACCAAGCCGGGGACTCGAGTGGTTGGG
CCGAACCTACTATCGGTCCAAATGGTATAATGACTACGCAGTATCCGTGAAATC
TCGCATTACGATCAATCCAGACACCTCCAAAAATCAATTTTCTCTGCAGTTGAAT
AGCGTGACTCCCGAGGACACGGCCGTTTACTATTGCGCCCAGGAAGTTGAACCC
CACGATGCATTTGATATTTGGGGCCAGGGAACCATGGTGACAGTGAGTAGTGGG
GGTGGAGGATCTGGAGGAGGCGGTAGCGGCGGGGGCGGCAGTGATATCCAGAT
GACGCAGTCACCTTCCAGCGTGTATGCGAGTGTGGGGACAAGGTCACCATAAC
CTGTCGCGCTAGCCAAGATGTCAGCGGGTGGCTGGCTTGGTACCAGCAGAAACC
AGGTTTGGCTCCTCAGCTTTTGATCTCAGGAGCGAGCACGCTTCAGGGTGAGGT
CCCAAGTCGCTTTAGTGGCTCTGGCTCCGGGACAGACTTCACGTTGACGATCAG
CAGTTTGCAGCCTGAGGATTTCGCGACCTACTACTGCCAGCAAGCGAAATATTT
TCCGTACACTTTCGGTCAGGGGACCAAATTGGAGATCAAAGGTGGGGTGGTTC
AGGCGGCGGAGGCTCAGGCGGCGGCGGTAGCGGAGGAGGCGGAAGCGGGGGT
GGCGGATCAGAAGTGCAACTCGTTCAGAGTGGCGCGGAGGTTAAGAAACCCGG
TGCATCTGTAAAGGTTAGCTGTAAGGCATCAGGATACACTTTTACCAGCTATTA
CATGCATTGGGTGAGACAGGCTCCCGGTCAGGGGCTCGAATGGATGGGGTTGAT
CAACCCCGAGTGGTGGTTCAACATCTTACGCCCAGAAGTTTCAGGGCCGAGTAAC
AATGACTCGGGACACGTCTACCTCAACTGTGTATATGGAGCTTTCCAGCCTGCG
CTCAGAGGATACAGCAGTCTATTACTGCGCACGGTCAGACAGAGGTATAACGG
CCACTGATGCGTTCGATATCTGGGGACAAGGGACTATGGTAACTGTGTCTTCCG
GAGGAGGAGGTAGTGGAGGGGGAGGAAGCGGTGGGGGGGCTCACAGTCCGT
TTTGACTCAGCCACCAAGCGTCTCAGTCGCACCGGGGCGAATGGCGAAATTAC
TTGCGGCGGGAGCGACATAGGCAACAAGAATGTGCATTGGTACCAACAGAAAC
CAGGTCAAGCACCTGTTCTCGTGGTGTATGATGACTACGATCGCCCAAGCGGGA
TCCCGGAGCGGTTCTCTGGATCAAATTCTGGTGATGCAGCCACTCTGACAATAT
CAACGGTGGAAGTCGGTGACGAGGCTGATTACTTCTGCCAAGTATGGGATGGCA
GCGGAGATCCCTACTGGATGTTTGGAGGAGGTACTCAACTGACAGTTCTGGGCG
CGGCCGCAACGACCACTCCTGCACCCCGCCCTCCGACTCCGGCCCCAACCATTG
CCAGCCAGCCCCTGTCCCTGCGGCCGGAAGCCTGCAGACCGGCTGCCGGCGGA

```
GCCGTCCATACCCGGGGACTGGATTTCGCCTGCGATATCTATATCTGGGCACCA
CTCGCCGGAACCTGTGGAGTGCTGCTGCTGTCCCTTGTGATCACCCTGTACTGCA
AGCGCGGACGGAAGAAACTCTTGTACATCTTCAAGCAGCCGTTCATGCGCCCTG
TGCAAACCACCCAAGAAGAGGACGGGTGCTCCTGCCGGTTCCCGGAAGAGGAA
GAGGGCGGCTGCGAACTGCGCGTGAAGTTTTCCCGGTCCGCCGACGCTCCGGCG
TACCAGCAGGGGCAAAACCAGCTGTACAACGAACTTAACCTCGGTCGCCGGGA
AGAATATGACGTGCTGGACAAGCGGCGGGGAAGAGATCCCGAGATGGGTGGAA
AGCCGCGGCGGAAGAACCCTCAGGAGGGCTTGTACAACGAGCTGCAAAAGGAC
AAAATGGCCGAAGCCTACTCCGAGATTGGCATGAAGGGAGAGCGCAGACGCGG
GAAGGGACACGATGGACTGTACCAGGGACTGTCAACCGCGACTAAGGACACTT
ACGACGCCCTGCACATGCAGGCCCTGCCCCCGCGC

SEQ ID NO: 61 amino acid sequence of CAR LTG2737 CD22-19 CD8 BBz
MLLLVTSLLLCELPHPAFLLIPQVQLQQSGPGLVKHSQTLSLTCAISGDSVSSNSAA
WNWIRQSPSRGLEWLGRTYYRSKWYNDYAVSVKSRITINPDTSKNQFSLQLNSVTP
EDTAVYYCAQEVEPHDAFDIWGQGTMVTVSSGGGGSGGGGSGGGGSDIQMTQSPS
SVYASVGDKVTITCRASQDVSGWLAWYQQKPGLAPQLLISGASTLQGEVPSRFSGS
GSGTDFTLTISSLQPEDFATYYCQQAKYFPYTFGQGTKLEIKGGGGSGGGGSGGGGS
GGGGSGGGGSEVQLVQSGAEVKKPGASVKVSCKASGYTFTSYYMHWVRQAPGQG
LEWMGLINPSGGSTSYAQKFQGRVTMTRDTSTSTVYMELSSLRSEDTAVYYCARSD
RGITATDAFDIWGQGTMVTVSSGGGGSGGGGSGGGGSQSVLTQPPSVSVAPGRMA
KITCGGSDIGNKNVHWYQQKPGQAPVLVVYDDYDRPSGIPERFSGSNSGDAATLTI
STVEVGDEADYFCQVWDGSGDPYWMFGGGTQLTVLGAAATTTPAPRPPTPAPTIA
SQPLSLRPEACRPAAGGAVHTRGLDFACDIYIWAPLAGTCGVLLLSLVITLYCKRGR
KKLLYIFKQPFMRPVQTTQEEDGCSCRFPEEEEGGCELRVKFSRSADAPAYQQGQN
QLYNELNLGRREEYDVLDKRRGRDPEMGGKPRRKNPQEGLYNELQKDMAEAYS
EIGMKGERRRGKGHDGLYQGLSTATKDTYDALHMQALPPR SEQ ID NO: 62 nucleotide sequence of CAR D0135 CD22-19 CD8 CD28z
ATGCTCTTGCTCGTGACTTCTTTGCTTTTGTGCGAACTTCCGCACCCAGCCTTCCT
TTTGATACCTCAGGTACAGCTTCAACAAAGCGGACCGGGACTTGTTAAGCATTC
CCAAACCCTTTCTCTCACGTGTGCAATTAGCGGCGATAGTGTATCCTCTAATTCT
GCGGCCTGGAACTGGATACGACAATCACCAAGCCGGGGACTCGAGTGGTTGGG
CCGAACCTACTATCGGTCCAAATGGTATAATGACTACGCAGTATCCGTGAAATC
TCGCATTACGATCAATCCAGACACCTCCAAAAATCAATTTTCTCTGCAGTTGAAT
AGCGTGACTCCCGAGGACACGGCCGTTTACTATTGCGCCCAGGAAGTTGAACCC
CACGATGCATTTGATATTTGGGGCCAGGGAACCATGGTGACAGTGAGTAGTGGG
GGTGGAGGATCTGGAGGAGGCGGTAGCGGCGGGGGCGGCAGTGATATCCAGAT
GACGCAGTCACCTTCCAGCGTGTATGCGAGTGTGGGGGACAAGGTCACCATAAC
CTGTCGCGCTAGCCAAGATGTCAGCGGGTGCTGGCTTGGTACCAGCAGAAACC
AGGTTTGGCTCCTCAGCTTTTGATCTCAGGAGCGAGCACGCTTCAGGGTGAGGT
CCCAAGTCGCTTTAGTGGCTCTGGCTCCGGGACAGACTTCACGTTGACGATCAG
CAGTTTGCAGCCTGAGGATTTCGCGACCTACTACTGCCAGCAAGCGAAATATTT
TCCGTACACTTTCGGTCAGGGGACCAAATTGGAGATCAAAGGTGGGGGTGGTTC
AGGCGGCGGAGGCTCAGGCGGCGGCGGTAGCGGAGGAGGCGGAAGCGGGGGT
GGCGGATCAGAAGTGCAACTCGTTCAGAGTGGCGCGGAGGTTAAGAAACCCGG
TGCATCTGTAAAGGTTAGCTGTAAGGCATCAGGATACACTTTTACCAGCTATTA
CATGCATTGGGTGAGACAGGCTCCCGGTCAGGGGCTCGAATGGATGGGGTTGAT
CAACCCCGAGTGGTGGTTCAACATCTTACGCCCAGAAGTTTCAGGGCCGAGTAAC
AATGACTCGGGACACGTCTACCTCAACTGTGTATATGGAGCTTTCCAGCCTGCG
CTCAGAGAGGATCAGCAGTCTATTACTGCGCACGGTCAGACAGAGGTATAACGG
CCACTGATGCGTTCGATATCTGGGGACAAGGGACTATGGTAACTGTGTCTTCCG
GAGGAGGAGGTAGTGGAGGGGGAGGAAGCGGTGGGGGGGGCTCACAGTCCGT
TTTGACTCAGCCACCAAGCGTCTCAGTCGCACCGGGGCGAATGGCGAAAATTAC
TTGCGGCGGGAGCGACATAGGCAACAAGAATGTGCATTGGTACCAACAGAAAC
CAGGTCAAGCACCTGTTCTCGTGGTGTATGATGACTACGATCGCCCAAGCGGGA
TCCCGGAGCGGTTCTCTGGATCAAATTCTGGTGATGCAGCCACTCTGACAATAT
CAACGGTGGAAGTCGGTGACGAGGCTGATTACTTCTGCCAAGTATGGGATGGCA
GCGGAGATCCCTACTGGATGTTTGGAGGAGGTACTCAACTGACAGTTCTGGGCG
CGGCCGCGACTACCACTCCTGCACCACGGCCACCTACCCCAGCCCCACCATTG
CAAGCCAGCCACTTTCACTGCGCCCCGAAGCGTGTAGACCAGCTGCTGGAGGAG
CCGTGCATACCCGAGGGCTGGACTTCGCCTGTGACATCTACATCTGGGCCCCAT
TGGCTGGAACTTGCGGCGTGCTGCTCTTGTCTCTGGTCATTACCCTGTACTGCCG
GTCGAAGAGGTCCAGACTCTTGCACTCCGACTACATGAACATGACTCCTAGAAG
GCCCGGACCCACTAGAAAGCACTACCAGCCGTACGCCCCTCCTCGGGATTTCGC
CGCATACCGGTCCAGAGTGAAGTTCAGCCGCTCAGCCGATGCACCGGCCTACCA
GCAGGGACAGAACCAGCTCTACAACGAGCTCAACCTGGGTCGGCGGGAAGAAT
ATGACGTGCTGGACAAACGGCGCGGCAGAGATCCGGAGATGGGGGAAGCCG
AGGAGGAAGAACCCTCAAGAGGGCCTGTACAACGAACTGCAGAAGGACAAGAT
GGCGGAAGCCTACTCCGAGATCGGCATGAAGGGAGAACGCCGGAGAGGGAAG
GGTCATGACGGACTGTACCAGGGCCTGTCAACTGCCACTAAGGACACTTACGAT
GCGCTCCATATGCAAGCTTTGCCCCCGCGG SEQ ID NO: 63 amino acid sequence of CAR D0135 CD22-19 CD8 CD28z
MLLLVTSLLLCELPHPAFLLIPQVQLQQSGPGLVKHSQTLSLTCAISGDSVSSNSAA
WNWIRQSPSRGLEWLGRTYYRSKWYNDYAVSVKSRITINPDTSKNQFSLQLNSVTP
EDTAVYYCAQEVEPHDAFDIWGQGTMVTVSSGGGGSGGGGSGGGGSDIQMTQSPS
SVYASVGDKVTITCRASQDVSGWLAWYQQKPGLAPQLLISGASTLQGEVPSRFSGS
GSGTDFTLTISSLQPEDFATYYCQQAKYFPYTFGQGTKLEIKGGGGSGGGGSGGGGS
```

```
GGGGSGGGGSEVQLVQSGAEVKKPGASVKVSCKASGYTFTSYYMHWVRQAPGQG
LEWMGLINPSGGSTSYAQKFQGRVTMTRDTSTSTVYMELSSLRSEDTAVYYCARSD
RGITATDAFDIWGQGTMVTVSSGGGGSGGGGSGGGGSQSVLTQPPSVSVAPGRMA
KITCGGSDIGNKNVHWYQQKPGQAPVLVVYDDYDRPSGIPERFSGSNSGDAATLTI
STVEVGDEADYFCQVWDGSGDPYWMFGGGTQLTVLGAAATTTPAPRPPTPAPTIA
SQPLSLRPEACRPAAGGAVHTRGLDFACDIYIWAPLAGTCGVLLLSLVITLYCRSKR
SRLLHSDYMNMTPRRPGPTRKHYQPYAPPRDFAAYRSRVKFSRSADAPAYQQGQN
QLYNELNLGRREEYDVLDKRRGRDPEMGGKPRRKNPQEGLYNELQKDKMAEAYS
EIGMKGERRRGKGHDGLYQGLSTATKDTYDALHMQALPPR

SEQ ID NO: 64 nucleotide sequence of CAR D0136 CD22-19 CD8 ICOSz DNA
ATGCTCTTGCTCGTGACTTCTTTGCTTTTGTGCGAACTTCCGCACCCAGCCTTCC
TTTTGATACCTCAGGTACAGCTTCAACAAAGCGGACCGGGACTTGTTAAGCATT
CCCAAACCCTTTCTCTCACGTGTGCAATTAGCGGCGATAGTGTATCCTCTAATT
CTGCGGCCTGGAACTGGATACGACAATCACCAAGCCGGGGACTCGAGTGGTTG
GGCCGAACCTACTATCGGTCCAAATGGTATAATGACTACGCAGTATCCGTGAA
ATCTCGCATTACGATCAATCCAGACACCTCCAAAAATCAATTTTCTCTGCAGTT
GAATAGCGTGACTCCCGAGGACACGGCCGTTTACTATTGCGCCCAGGAAGTTG
AACCCCACGATGCATTTGATATTTGGGGCCAGGGAACCATGGTGACAGTGAGT
AGTGGGGGTGGAGGATCTGGAGGAGGCGGTAGCGGCGGGGGCGGCAGTGATA
TCCAGATGACGCAGTCACCTTCCAGCGTGTATGCGAGTGTGGGGACAAGGTC
ACCATAACCTGTCGCGCTAGCCAAGATGTCAGCGGGTGGCTGGCTTGGTACCA
GCAGAAACCAGGTTTGGCTCCTCAGCTTTTGATCTCAGGAGCGAGCACGCTTCA
GGGTGAGGTCCCAAGTCGCTTTAGTGGCTCTGGCTCCGGGACAGACTTCACGTT
GACGATCAGCAGTTTGCAGCCTGAGGATTTCGCGACCTACTACTGCCAGCAAG
CGAAATATTTTCCGTACACTTTCGGTCAGGGGACCAAATTGGAGATCAAAGGT
GGGGGTGGTTCAGGCGGCGGAGGCTCAGGCGGCGGCGGTAGCGGAGGAGGCG
GAAGCGGGGGTGGCGGATCAGAAGTGCAACTCGTTCAGAGTGGCGCGGAGGT
TAAGAAACCCGGTGCATCTGTAAAGGTTAGCTGTAAGGCATCAGGATACACTT
TTACCAGCTATTACATGCATTGGGTGAGACAGGCTCCCGGTCAGGGGCTCGAA
TGGATGGGGTTGATCAACCCGAGTGGTGGTTCAACATCTTACGCCCAGAAGTTT
CAGGGCCGAGTAACAATGACTCGGGACACGTCTACCTCAACTGTGTATATGGA
GCTTTCCAGCCTGCGCTCAGAGGATACAGCAGTCTATTACTGCGCACGGTCAG
ACAGAGGTATAACGGCCACTGATGCGTTCGATATCTGGGGACAAGGGACTATG
GTAACTGTGTCTTCCGGAGGAGGAGGTAGTGGAGGGGGAGGAAGCGGTGGGG
GGGGCTCACAGTCCGTTTTGACTCAGCCACCAAGCGTCTCAGTCGCACCGGGG
CGAATGGCGAAAATTACTTGCGGCGGGAGCGACATAGGCAACAAGAATGTGC
ATTGGTACCAACAGAAACCAGGTCAAGCACCTGTTCTCGTGGTGTATGATGAC
TACGATCGCCCAAGCGGGATCCCGGAGCGGTTCTCTGGATCAAATTCTGGTGA
TGCAGCCACTCTGACAATATCAACGGTGGAAGTCGGTGACGAGGCTGATTACT
TCTGCCAAGTATGGGATGGCAGCGGAGATCCCTACTGGATGTTTGGAGGAGGT
ACTCAACTGACAGTTCTGGGCGCGGCCGCGACTACCACTCCTGCACCACGGCC
ACCTACCCCAGCCCCCACCATTGCAAGCCAGCCACTTTCACTGCGCCCCGAAGC
GTGTAGACCAGCTGCTGGAGGAGCCGTGCATACCCGAGGGCTGGACTTCGCCT
GTGACATCTACATCTGGGCCCCATTGCTGGAACTTGCGGCGTGCTGCTCTTGT
CTCCTGGTCATTACCCTGTACTGCTGGCTGACAAAAAAGAAGTATTCATCTAGTG
TACATGATCCGAACGGTGAATACATGTTCATGCGCGCGGTGAACACGGCCAAG
AAGAGCAGACTGACCGACGTAACCCTTAGAGTGAAGTTCAGCCGCTCAGCCGA
TGCACCGGCCTACCAGCAGGGACAGAACCAGCTCTACAACGAGCTCAACCTGG
GTCGGCGGGAAGAATATGACGTGCTGGACAAACGGCGCGGCAGAGATCCGGA
GATGGGGGGAAAGCCGAGGAGGAAGAACCCTCAAGAGGGCCTGTACAACGAA
CTGCAGAAGGACAAGATGGCGGAAGCCTACTCCGAGATCGGCATGAAGGGAG
AACGCCGGAGAGGGAAGGGTCATGACGGACTGTACCAGGGCCTGTCAACTGCC
ACTAAGGACACTTACGATGCGCTCCATATGCAAGCTTTGCCCCCGCGG SEQ ID NO: 65 amino acid sequence of CAR D0136 CD22-19 CD8 ICOSz
MLLLVTSLLLCELPHPAFLLIPQVQLQQSGPGLVKHSQTLSLTCAISGDSVSSNSAA
WNWIRQSPSRGLEWLGRTYYRSKWYNDYAVSVKSRITINPDTSKNQFSLQLNSVTP
EDTAVYYCAQEVEPHDAFDIWGQGTMVTVSSGGGGSGGGGSGGGGSDIQMTQSPS
SVYASVGDKVTITCRASQDVSGWLAWYQQKPGLAPQLLISGASTLQGEVPSRFSGS
GSGTDFTLTISSLQPEDFATYYCQQAKYFPYTFGQGTKLEIKGGGGSGGGGSGGGGS
GGGGSGGGGSEVQLVQSGAEVKKPGASVKVSCKASGYTFTSYYMHWVRQAPGQG
LEWMGLINPSGGSTSYAQKFQGRVTMTRDTSTSTVYMELSSLRSEDTAVYYCARSD
RGITATDAFDIWGQGTMVTVSSGGGGSGGGGSGGGGSQSVLTQPPSVSVAPGRMA
KITCGGSDIGNKNVHWYQQKPGQAPVLVVYDDYDRPSGIPERFSGSNSGDAATLTI
STVEVGDEADYFCQVWDGSGDPYWMFGGGTQLTVLGAAATTTPAPRPPTPAPTIA
SQPLSLRPEACRPAAGGAVHTRGLDFACDIYIWAPLAGTCGVLLLSLVITLYCWLTK
KKYSSSVHDPNGEYMFMRAVNTAKKSRLTDVTLRVKFSRSADAPAYQQGQNQLY
NELNLGRREEYDVLDKRRGRDPEMGGKPRRKNPQEGLYNELQKDKMAEAYSEIG
MKGERRRGKGHDGLYQGLSTATKDTYDALHMQALPPR SEQ ID NO: 66 nucleotide sequence of CAR D0137 CD22-19 CD8 OX40TM
OX40z
ATGCTCTTGCTCGTGACTTCTTTGCTTTTGTGCGAACTTCCGCACCCAGCCTTC
CTTTTGATACCTCAGGTACAGCTTCAACAAAGCGGACCGGGACTTGTTAAGCA
TTCCCAAACCCTTTCTCTCACGTGTGCAATTAGCGGCGATAGTGTATCCTCTAA
TTCTGCGGCCTGGAACTGGATACGACAATCACCAAGCCGGGGACTCGAGTGG
TTGGGCCGAACCTACTATCGGTCCAAATGGTATAATGACTACGCAGTATCCGT
GAAATCTCGCATTACGATCAATCCAGACACCTCCAAAAATCAATTTTCTCTGC
```

```
AGTTGAATAGCGTGACTCCCGAGGACACGGCCGTTTACTATTGCGCCCAGGAA
GTTGAACCCCACGATGCATTTGATATTTGGGGCCAGGGAACCATGGTGACAGT
GAGTAGTGGGGGTGGAGGATCTGGAGGAGGCGGTAGCGGCGGGGGCGGCAG
TGATATCCAGATGACGCAGTCACCTTCCAGCGTGTATGCGAGTGTGGGGGACA
AGGTCACCATAACCTGTCGCGCTAGCCAAGATGTCAGCGGGTGGCTGGCTTGG
TACCAGCAGAAACCAGGTTTGGCTCCTCAGCTTTTGATCTCAGGAGCGAGCAC
GCTTCAGGGTGAGGTCCCAAGTCGCTTTAGTGGCTCTGGCTCCGGGACAGACT
TCACGTTGACGATCAGCAGTTTGCAGCCTGAGGATTTCGCGACCTACTACTGC
CAGCAAGCGAAATATTTTCCGTACACTTTCGGTCAGGGGACCAAATTGGAGAT
CAAAGGTGGGGGTGGTTCAGGCGGCGGAGGCTCAGGCGGCGGCGGTAGCGGA
GGAGGCGGAAGCGGGGGTGGCGGATCAGAAGTGCAACTCGTTCAGAGTGGCG
CGGAGGTTAAGAAACCCGGTGCATCTGTAAAGGTTAGCTGTAAGGCATCAGG
ATACACTTTTACCAGCTATTACATGCATTGGGTGAGACAGGCTCCCGGTCAGG
GGCTCGAATGGATGGGGTTGATCAACCCGAGTGGTGGTTCAACATCTTACGCC
CAGAAGTTTCAGGGCCGAGTAACAATGACTCGGGACACGTCTACCTCAACTGT
GTATATGGAGCTTTCCAGCCTGCGCTCAGAGGATACAGCAGTCTATTACTGCG
CACGGTCAGACAGAGGTATAACGGCCACTGATGCGTTCGATATCTGGGGACA
AGGGACTATGGTAACTGTGTCTTCCGGAGGAGGAGGTAGTGGAGGGGGAGGA
AGCGGTGGGGGGGGCTCACAGTCCGTTTTGACTCAGCCACCAAGCGTCTCAGT
CGCACCGGGGCGAATGGCGAAAATTACTTGCGGCGGGAGCGACATAGGCAAC
AAGAATGTGCATTGGTACCAACAGAAACCAGGTCAAGCACCTGTTCTCGTGGT
GTATGATGACTACGATCGCCCAAGCGGGATCCCGGAGCGGTTCTCTGGATCAA
ATTCTGGTGATGCAGCCACTCTGACAATATCAACGGTGGAAGTCGGTGACGAG
GCTGATTACTTCTGCCAAGTATGGGATGGCAGCGGAGATCCCTACTGGATGTT
TGGAGGAGGTACTCAACTGACAGTTCTGGGCGCGGCCGCAACGACCACTCCA
GCACCGAGACCGCCAACCCCCGCGCCTACCATCGCAAGTCAACCACTTTCTCT
CAGGCCTGAAGCGTGCCGACCTGCAGCTGGTGGGGCAGTACATACCAGGGGT
TTGGACTTCGCATGTGACGTGGCGGCAATTCTCGGCCTGGGACTTGTCCTTGG
TCTGCTTGGTCCGCTCGCAATACTTCTGGCCTTGTACCTGCTCCGCAGAGACCA
AAGACTTCCGCCCGACGCCCACAAGCCCCAGGAGGAGGTTCCTTCAGAACG
CCTATACAAGAAGAACAAGCAGATGCCCACTCTACCCTGGCTAAAATCAGGG
TGAAGTTTAGCCGGTCAGCTGATGCACCTGCATATCAGCAGGGACAGAACCA
GCTGTACAATGAGCTGAACCTCGGACAAGAGAGGAGTACGACGTGTTGGAC
AAAAGACGAGGTAGAGACCCCGAGATGGGCGGCAAGCCGAGAAGAAAAAAC
CCACAAGAAGGGCTTTATAATGAGCTTCAGAAAGATAAGATGGCAGAGGCCT
ACAGTGAGATTGGCATGAAGGGCGAAAGAAGGAGGGGCAAAGGACACGACG
GTCTCTACCAAGGCCTCAGCACGGCTACCAAAGATACGTATGACGCATTGCAT
ATGCAGGCATTGCCGCCCCGC

SEQ ID NO: 67 amino acid sequence of CAR D0137 CD22-19 CD8 OX40TM
OX40z
LLLVTSLLLCELPHPAFLLIPQVQLQQSGPGLVKHSQTLSLTCAISGDSVSSNSAAW
NWIRQSPSRGLEWLGRTYYRSKWYNDYAVSVKSRITINPDTSKNQFSLQLNSVTP
EDTAVYYCAQEVEPHDAFDIWGQGTMVTVSSGGGGSGGGGSGGGGSDIQMTQS
PSSVYASVGDKVTITCRASQDVSGWLAWYQQKPGLAPQLLISGASTLQGEVPSRF
SGSGSGTDFTLTISSLQPEDFATYYCQQAKYFPYTFGQGTKLEIKGGGGSGGGGSG
GGGSGGGGSEVQLVQSGAEVKKPGASVKVSCKASGYTFTSYYMHWVRQ
APGQGLEWMGLINPSGGSTSYAQKFQGRVTMTRDTSTSTVYMELSSLRSEDTAV
YYCARSDRGITATDAFDIWGQGTMVTVSSGGGGSGGGGSGGGGSQSVLTQPPSV
SVAPGRMAKITCGGSDIGNKNVHWYQQKPGQAPVLVVYDDYDRPSGIPERFSGS
NSGDAATLTISTVEVGDEADYFCQVWDGSGDPYWMFGGGTQLTVLGAAATTTP
APRPPTPAPTIASQPLSLRPEACRPAAGGAVHTRGLDFACDVAAILGLGLVLGLLG
PLAILLALYLLRRDQRLPPDAHKPPGGGSFRTPIQEEQADAHSTLAKIRVKFSRSAD
APAYQQGQNQLYNELNLGRREEYDVLDKRRGRDPEMGGKPRRKNPQEGLYNEL
QKDKMAEAYSEIGMKGERRRGKGHDGLYQGLSTATKDTYDALHMQALPPR SEQ ID NO: 68 nucleotide sequence of CAR D0138 CD22-19 CD8 CD27z
ATGCTCTTGCTCGTGACTTCTTTGCTTTTGTGCGAACTTCCGCACCCAGCCTTC
CTTTTGATACCTCAGGTACAGCTTCAACAAAGCGGACCGGGACTTGTTAAGCA
TTCCCAAACCCTTTCTCTCACGTGTGCAATTAGCGGCGATAGTGTATCCTCTAA
TTCTGCGGCCTGGAACTGGATACGACAATCACCAAGCCGGGGACTCGAGTGG
TTGGGCCGAACCTACTATCGGTCCAAATGGTATAATGACTACGCAGTATCCGT
GAAATCTCGCATTACGATCAATCCAGACACCTCCAAAAATCAATTTTCTCTGC
AGTTGAATAGCGTGACTCCCGAGGACACGGCCGTTTACTATTGCGCCCAGGAA
GTTGAACCCCACGATGCATTTGATATTTGGGGCCAGGGAACCATGGTGACAGT
GAGTAGTGGGGGTGGAGGATCTGGAGGAGGCGGTAGCGGCGGGGGCGGCAG
TGATATCCAGATGACGCAGTCACCTTCCAGCGTGTATGCGAGTGTGGGGGACA
AGGTCACCATAACCTGTCGCGCTAGCCAAGATGTCAGCGGGTGGCTGGCTTGG
TACCAGCAGAAACCAGGTTTGGCTCCTCAGCTTTTGATCTCAGGAGCGAGCAC
GCTTCAGGGTGAGGTCCCAAGTCGCTTTAGTGGCTCTGGCTCCGGGACAGACT
TCACGTTGACGATCAGCAGTTTGCAGCCTGAGGATTTCGCGACCTACTACTGC
CAGCAAGCGAAATATTTTCCGTACACTTTCGGTCAGGGGACCAAATTGGAGAT
CAAAGGTGGGGGTGGTTCAGGCGGCGGAGGCTCAGGCGGCGGCGGTAGCGGA
GGAGGCGGAAGCGGGGGTGGCGGATCAGAAGTGCAACTCGTTCAGAGTGGCG
CGGAGGTTAAGAAACCCGGTGCATCTGTAAAGGTTAGCTGTAAGGCATCAGG
ATACACTTTTACCAGCTATTACATGCATTGGGTGAGACAGGCTCCCGGTCAGG
GGCTCGAATGGATGGGGTTGATCAACCCGAGTGGTGGTTCAACATCTTACGCC
CAGAAGTTTCAGGGCCGAGTAACAATGACTCGGGACACGTCTACCTCAACTGT
GTATATGGAGCTTTCCAGCCTGCGCTCAGAGGATACAGCAGTCTATTACTGCG
```

```
CACGGTCAGACAGAGGTATAACGGCCACTGATGCGTTCGATATCTGGGACA
AGGGACTATGGTAACTGTGTCTTCCGGAGGAGGAGGTAGTGGAGGGGGAGGA
AGCGGTGGGGGGGGCTCACAGTCCGTTTTGACTCAGCCACCAAGCGTCTCAGT
CGCACCGGGGCGAATGGCGAAAATTACTTGCGGCGGGAGCGACATAGGCAAC
AAGAATGTGCATTGGTACCAACAGAAACCAGGTCAAGCACCTGTTCTCGTGGT
GTATGATGACTACGATCGCCCAAGCGGGATCCCGGAGCGGTTCTCTGGATCAA
ATTCTGGTGATGCAGCCACTCTGACAATATCAACGGTGGAAGTCGGTGACGAG
GCTGATTACTTCTGCCAAGTATGGGATGGCAGCGGAGATCCCTACTGGATGTT
TGGAGGAGGTACTCAACTGACAGTTCTGGGCGCGGCCGCGACTACCACTCCTG
CACCACGGCCACCTACCCCAGCCCCCACCATTGCAAGCCAGCCACTTTCACTG
CGCCCCGAAGCGTGTAGACCAGCTGCTGGAGGAGCCGTGCATACCCGAGGGC
TGGACTTCGCCTGTGACATCTACATCTGGGCCCCATTGGCTGGAACTTGCGGC
GTGCTGCTCTTGTCTCTGGTCATTACCCTGTACTGCCAACGGCGCAAATACCGC
TCCAATAAAGGCGAAAGTCCGGTAGAACCCGCAGAACCTTGCCACTACAGTT
GTCCCAGAGAAGAAGAGGGTTCTACAATACCTATTCAAGAGGACTATAGGAA
ACCAGAGCCCGCATGTAGTCCCAGAGTGAAGTTCAGCCGCTCAGCCGATGCA
CCGGCCTACCAGCAGGGACAGAACCAGCTCTACAACGAGCTCAACCTGGGTC
GGCGGGAAGAATATGACGTGCTGGACAAACGGCGCGGCAGAGATCCGGAGAT
GGGGGGGAAAGCCGAGGAGGAAGAACCCTCAAGAGGGCCTGTACAACGAACT
GCAGAAGGACAAGATGGCGGAAGCCTACTCCGAGATCGGCATGAAGGGAGA
ACGCCGGAGAGGGAAGGGTCATGACGGACTGTACCAGGGCCTGTCAACTGCC
ACTAAGGACACTTACGATGCGCTCCATATGCAAGCTTTGCCCCCGCGG

SEQ ID NO: 69 amino acid sequence of CAR D0138 CD22-19 CD8 CD27z
MLLLVTSLLLCELPHPAFLLIPQVQLQQSGPGLVKHSQTLSLTCAISGDSVSSNSAA
WNWIRQSPSRGLEWLGRTYYRSKWYNDYAVSVKSRITINPDTSKNQFSLQLNSVT
PEDTAVYYCAQEVEPHDAFDIWGQGTMVTVSSGGGGSGGGGSGGGGSDIQMTQ
SPSSVYASVGDKVTITCRASQDVSGWLAWYQQKPGLAPQLLISGASTLQGEVPSR
FSGSGSGTDFTLTISSLQPEDFATYYCQQAKYFPYTFGQGTKLEIKGGGGSGGGGS
GGGGSGGGGSGGGGSEVQLVQSGAEVKKPGASVKVSCKASGYTFTSYYMHWVR
QAPGQGLEWMGLINPSGGSTSYAQKFQGRVTMTRDTSTSTVYMELSSLRSEDTA
VYYCARSDRGITATDAFDIWGQGTMVTVSSGGGGSGGGGSGGGGSQSVLTQPPS
VSVAPGRMAKITCGGSDIGNKNVHWYQQKPGQAPVLVVYDDYDRPSGIPERFSG
SNSGDAATLTISTVEVGDEADYFCQVWDGSGDPYWMFGGGTQLTVLGAAATTT
PAPRPPTPAPTIASQPLSLRPEACRPAAGGAVHTRGLDFACDIYIWAPLAGTCGVL
LLSLVITLYCQRRKYRSNKGESPVEPAEPCHYSCPREEEGSTIPIQEDYRKPEPACSP
RVKFSRSADAPAYQQGQNQLYNELNLGRREEYDVLDKRRGRDPEMGGKPRRKN
PQEGLYNELQKDKMAEAYSEIGMKGERRRGKGHDGLYQGLSTATKDTYDALHM
QALPP SEQ ID NO: 70 nucleotide sequence of CAR D0139 CD22-19 CD28 CD28z
ATGCTCTTGCTCGTGACTTCTTTGCTTTTGTGCGAACTTCCGCACCCAGCCTTC
CTTTTGATACCTCAGGTACAGCTTCAACAAAGCGGACCGGGACTTGTTAAGCA
TTCCCAAACCCTTTCTCTCACGTGTGCAATTAGCGGCGATAGTGTATCCTCTAA
TTCTGCGGCCTGGAACTGGATACGACAATCACCAAGCCGGGGACTCGAGTGG
TTGGGCCGAACCTACTATCGGTCCAAATGGTATAATGACTACGCAGTATCCGT
GAAATCTCGCATTACGATCAATCCAGACACCTCCAAAAATCAATTTTCTCTGC
AGTTGAATAGCGTGACTCCCGAGGACACGGCCGTTTACTATTGCGCCCAGGAA
GTTGAACCCCACGATGCATTTGATATTTGGGGCCAGGGAACCATGGTGACAGT
GAGTAGTGGGGGTGGAGGATCTGGAGGAGGCGGTAGCGGCGGGGCGGCAG
TGATATCCAGATGACGCAGTCACCTTCCAGCGTGTATGCGAGTGTGGGGGACA
AGGTCACCATAACCTGTCGCGCTAGCCAAGATGTCAGCGGGTGGCTGGCTTGG
TACCAGCAGAAACCAGGTTTGGCTCCTCAGCTTTTGATCTCAGGAGCGAGCAC
GCTTCAGGGTGAGGTCCCAAGTCGCTTTAGTGGCTCTGGCTCCGGGACAGACT
TCACGTTGACGATCAGCAGTTTGCAGCCTGAGGATTTCGCGACCTACTACTGC
CAGCAAGCGAAATATTTTCCGTACACTTTCGGTCAGGGGACCAAATTGGAGAT
CAAAGGTGGGGGTGGTTCAGGCGGCGGAGGCTCAGGCGGCGGCGGTAGCGGA
GGAGGCGGAAGCGGGGGTGGCGGATCAGAAGTGCAACTCGTTCAGAGTGGCG
CGGAGGTTAAGAAACCCGGTGCATCTGTAAAGGTTAGCTGTAAGGCATCAGG
ATACACTTTTACCAGCTATTACATGCATTGGGTGAGACAGGCTCCCGGTCAGG
GGCTCGAATGGATGGGGTTGATCAACCCGAGTGGTGGTTCAACATCTTACGCC
CAGAAGTTTCAGGGCCGAGTAACAATGACTCGGGACACGTCTACCTCAACTGT
GTATATGGAGCTTTCCAGCCTGCGCTCAGAGGATACAGCAGTCTATTACTGCG
CACGGTCAGACAGAGGTATAACGGCCACTGATGCGTTCGATATCTGGGACA
AGGGACTATGGTAACTGTGTCTTCCGGAGGAGGAGGTAGTGGAGGGGGAGGA
AGCGGTGGGGGGGGCTCACAGTCCGTTTTGACTCAGCCACCAAGCGTCTCAGT
CGCACCGGGGCGAATGGCGAAAATTACTTGCGGCGGGAGCGACATAGGCAAC
AAGAATGTGCATTGGTACCAACAGAAACCAGGTCAAGCACCTGTTCTCGTGGT
GTATGATGACTACGATCGCCCAAGCGGGATCCCGGAGCGGTTCTCTGGATCAA
ATTCTGGTGATGCAGCCACTCTGACAATATCAACGGTGGAAGTCGGTGACGAG
GCTGATTACTTCTGCCAAGTATGGGATGGCAGCGGAGATCCCTACTGGATGTT
TGGAGGAGGTACTCAACTGACAGTTCTGGGCGCGGCCGCAATCGAAGTGATG
TATCCACCTCCGTACCTCGATAACGAGAAATCAAATGGAACGATCATTCATGT
GAAAGGGAAACATCTGTGCCCAAGCCCATTGTTCCCAGGTCCGTCAAAACCAT
TCTGGGTGCTTGTCGTTGTTGGGGGTGTACTCGCATGTTATTCTTTGCTGGTGA
CTGTGGCGTTTATCATCTTCTGGGTAAGGAGTAAACGCAGCCGCCTGCTGCAT
TCAGACTACATGAACATGACCCCACGGCGGCCCGGCCCAACGCGCAAACACT
ACCAACCTTACGCCCCACCGCGAGACTTTGCCGCCTACAGATCCCGCGTGAAG
TTTTCCCGGTCCGCCGACGCTCCGGCGTACCAGCAGGGGCAAAACCAGCTGTA
```

```
CAACGAACTTAACCTCGGTCGCCGGGAAGAATATGACGTGCTGGACAAGCGG
CGGGGAAGAGATCCCGAGATGGGTGGAAAGCCGCGGCGGAAGAACCCTCAG
GAGGGCTTGTACAACGAGCTGCAAAAGGACAAAATGGCCGAAGCCTACTCCG
AGATTGGCATGAAGGGAGAGCGCAGACGCGGGAAGGGACACGATGGACTGT
ACCAGGGACTGTCAACCGCGACTAAGGACACTTACGACGCCCTGCACATGCA
GGCCCTGCCCCCGCGC

SEQ ID NO: 71 amino acid sequence of CAR D0139 CD22-19 CD28 CD28z
MLLLVTSLLLCELPHPAFLLIPQVQLQQSGPGLVKHSQTLSLTCAISGDSVSSNSAA
WNWIRQSPSRGLEWLGRTYYRSKWYNDYAVSVKSRITINPDTSKNQFSLQLNSVT
PEDTAVYYCAQEVEPHDAFDIWGQGTMVTVSSGGGGSGGGGSGGGGSDIQMTQ
SPSSVYASVGDKVTITCRASQDVSGWLAWYQQKPGLAPQLLISGASTLQGEVPSR
FSGSGSGTDFTLTISSLQPEDFATYYCQQAKYFPYTFGQGTKLEIKGGGGSGGGGS
GGGGSGGGGSGGGGSEVQLVQSGAEVKKPGASVKVSCKASGYTFTSYYMHWVR
QAPGQGLEWMGLINPSGGSTSYAQKFQGRVTMTRDTSTSTVYMELSSLRSEDTA
VYYCARSDRGITATDAFDIWGQGTMVTVSSGGGGSGGGGSGGGGSQSVLTQPPS
VSVAPGRMAKITCGGSDIGNKNVHWYQQKPGQAPVLVVYDDYDRPSGIPERFSG
SNSGDAATLTISTVEVGDEADYFCQVWDGSGDPYWMFGGGTQLTVLGAAAIEV
MYPPPYLDNEKSNGTIIHVKGKHLCPSPLFPGPSKPFWVLVVVGGVLACYSLLVT
VAFIIFWVRSKRSRLLHSDYMNMTPRRPGPTRKHYQPYAPPRDFAAYRSRVKFSR
SADAPAYQQGQNQLYNELNLGRREEYDVLDKRRGRDPEMGGKPRRKNPQEGLY
NELQKDKMAEAYSEIGMKGERRRGKGHDGLYQGLSTATKDTYDALHMQALPPR SEQ ID NO: 72 nucleotide sequence of CAR D0145 CD22-19 CD8 OX40z
ATGCTCTTGCTCGTGACTTCTTTGCTTTTGTGCGAACTTCCGCACCCAGCCTTC
CTTTTGATACCTCAGGTACAGCTTCAACAAAGCGGACCGGGACTTGTTAAGCA
TTCCCAAACCCTTTCTCTCACGTGTGCAATTAGCGGCGATAGTGTATCCTCTAA
TTCTGCGGCCTGGAACTGGATACGACAATCACCAAGCCGGGGACTCGAGTGG
TTGGGCCGAACCTACTATCGGTCCAAATGGTATAATGACTACGCAGTATCCGT
GAAATCTCGCATTACGATCAATCCAGACACCTCCAAAAATCAATTTTCTCTGC
AGTTGAATAGCGTGACTCCCGAGGACACGGCCGTTTACTATTGCGCCCAGGAA
GTTGAACCCCACGATGCATTTGATATTTGGGCCAGGGAACCATGGTGACAGT
GAGTAGTGGGGGTGGAGGATCTGGAGGAGGCGGTAGCGGCGGGGCGGCAG
TGATATCCAGATGACGCAGTCCACCTTCCAGCGTGATGCGAGTGTGGGGGACA
AGGTCACCATAACCTGTCGCGCTAGCCAAGATGTCAGCGGGTGGCTGGCTTGG
TACCAGCAGAAACCAGGTTTGGCTCCTCAGCTTTTGATCTCAGGAGCGAGCAC
GCTTCAGGGTGAGGTCCCAAGTCGCTTTAGTGGCTCTGGCTCCGGGACAGACT
TCACGTTGACGATCAGCAGTTTGCAGCCTGAGGATTTCGCGACTACTACTGC
CAGCAAGCGAAATATTTTCCGTACACTTTCGGTCAGGGGACCAAATTGGAGAT
CAAAGGTGGGGGTGGTTCAGGCGGCGGAGGCTCAGGCGGCGGCGGTAGCGGA
GGAGGCGGAAGCGGGGGTGGCGGATCAGAAGTGCAACTCGTTCAGAGTGGCG
CGGAGGTTAAGAAACCCGGTGCATCTGTAAAGGTTAGCTGTAAGGCATCAGG
ATACACTTTTACCAGCTATTACATGCATTGGGTGAGACAGGCTCCCGGTCAGG
GGCTCGAATGGATGGGGTTGATCAACCCGAGTGGTGGTTCAACATCTTACGCC
CAGAAGTTTCAGGGCCGAGTAACAATGACTCGGGACACGTCTACCTCAACTGT
GTATATGGAGCTTTCCAGCCTGCGCTCAGAGGATACAGCAGTCTATTACTGCG
CACGGTCAGACAGAGGTATAACGGCCACTGATGCGTTCGATATCTGGGGACA
AGGGACTATGGTAACTGTGTCTTCCGGAGGAGGAGGTAGTGGAGGGGGAGGA
AGCGGTGGGGGGGGCTCACAGTCCGTTTTGACTCAGCCACCAAGCGTCTCAGT
CGCACCGGGGCGAATGGCGAAAATTACTTGCGGCGGGAGCGACATAGGCAAC
AAGAATGTGCATTGGTACCAACAGAAACCAGGTCAAGCACCTGTTCTCGTGGT
GTATGATGACTACGATCGCCCAAGCGGGATCCCGGAGCGGTTCTCTGGATCAA
ATTCTGGTGATGCAGCCACTCTGACAATATCAACGGTGGAAGTCGGTGACGAG
GCTGATTACTTCTGCCAAGTATGGGATGGCAGCGGAGATCCCTACTGGATGTT
TGGAGGAGGTACTCAACTGACAGTTCTGGGCGCGGCCGCAACAACCACTCCA
GCACCTAGACCGCCAACACCTGCACCTACCATCGCAAGTCAACCACTTTCTCT
CAGGCCTGAAGCGTGCCGACCTGCAGCTGGTGGGCAGTACATACCAGGGGT
TTGGACTTCGCATGTGACATCTACATCTGGGCCCCATTGGCTGGAACTTGCGG
CGTGCTGCTCTTGTCTCTGGTCATTACCCTGTACTGCGCCTTGTACCTGCTCCG
CAGAGACCAAAGACTTCCGCCCGACGCCCACAAGCCCCCAGGAGGAGGTTCC
TTCAGAACGCCTATACAAGAAGAACAAGCAGATGCCCACTCTACCCTGGCTA
AAATCAGGGTGAAGTTTAGCCGGTCAGCTGATGCACCTGCATATCAGCAGGG
ACAGAACCAGCTGTACAATGAGCTGAACCTCGGACGAAGAGAGGAGTACGAC
GTGTTGGACAAAAGACGAGGTAGAGACCCCGAGATGGGCGGCAAGCCGAGA
AGAAAAAACCCACAAGAAGGGCTTTATAATGAGCTTCAGAAAGATAAGATGG
CAGAGGCCTACAGTGAGATTGGCATGAAGGGCGAAAGAAGGAGGGGCAAAG
GACACGACGGTCTCTACCAAGGCCTCAGCACGGCTACCAAAGATACGTATGA
CGCATTGCATATGCAGGCATTGCCGCCCCGC SEQ ID NO: 73 amino acid sequence of CAR D0145 CD22-19 CD8 OX40z
MLLLVTSLLLCELPHPAFLLIPQVQLQQSGPGLVKHSQTLSLTCAISGDSVSSNSA
AWNWIRQSPSRGLEWLGRTYYRSKWYNDYAVSVKSRITINPDTSKNQFSLQLNS
VTPEDTAVYYCAQEVEPHDAFDIWGQGTMVTVSSGGGGSGGGGSGGGGSDIQM
TQSPSSVYASVGDKVTITCRASQDVSGWLAWYQQKPGLAPQLLISGASTLQGEV
PSRFSGSGSGTDFTLTISSLQPEDFATYYCQQAKYFPYTFGQGTKLEIKGGGGSGG
GGSGGGGSGGGGSEVQLVQSGAEVKKPGASVKVSCKASGYTFTSYYM
HWVRQAPGQGLEWMGLINPSGGSTSYAQKFQGRVTMTRDTSTSTVYMELSSLR
SEDTAVYYCARSDRGITATDAFDIWGQGTMVTVSSGGGGSGGGGSGGGGSQSV
LTQPPSVSVAPGRMAKITCGGSDIGNKNVHWYQQKPGQAPVLVVYDDYDRPSGI
```

PERFSGSNSGDAATLTISTVEVGDEADYFCQVWDGSGDPYWMFGGGTQLTVLG
AAATTTPAPRPPTPAPTIASQPLSLRPEACRPAAGGAVHTRGLDFACDIYIWAPLA
GTCGVLLLSLVITLYCALYLLRRDQRLPPDAHKPPGGGSFRTPIQEEQADAHSTL
AKIRVKFSRSADAPAYQQGQNQLYNELNLGRREEYDVLDKRRGRDPEMGKKPR
RKNPQEGLYNELQKDKMAEAYSEIGMKGERRRGKGHDGLYQGLSTATKDTYD
ALHMQALPPR

SEQ ID NO: 74 CAR nucleotide sequence of D0140 CD22-19 CD28 CD28 BBz
ATGCTCTTGCTCGTGACTTCTTTGCTTTTGTGCGAACTTCCGCACCCAGCCTTC
CTTTTGATACCTCAGGTACAGCTTCAACAAAGCGGACCGGGACTTGTTAAGC
ATTCCCAAACCCTTTCTCTCACGTGTGCAATTAGCGGCGATAGTGTATCCTCT
AATTCTGCGGCCTGGAACTGGATACGACAATCACCAAGCCGGGGACTCGAGT
GGTTGGGCCGAACCTACTATCGGTCCAAATGGTATAATGACTACGCAGTATC
CGTGAAATCTCGCATTACGATCAATCCAGACACCTCCAAAAATCAATTTTCTC
TGCAGTTGAATAGCGTGACTCCCGAGGACACGGCCGTTTACTATTGCGCCCA
GGAAGTTGAACCCCACGATGCATTTGATATTTGGGGCCAGGGAACCATGGTG
ACAGTGAGTAGTGGGGGTGGAGGATCTGGAGGAGGCGGTAGCGGCGGGGC
GGCAGTGATATCCAGATGACGCAGTCACCTTCCAGCGTGTATGCGAGTGTGG
GGGACAAGGTCACCATAACCTGTCGCGCTAGCCAAGATGTCAGCGGGTGGCT
GGCTTGGTACCAGCAGAAACCAGGTTTGGCTCCTCAGCTTTTGATCTCAGGAG
CGAGCACGCTTCAGGGTGAGGTCCCAAGTCGCTTTAGTGGCTCTGGCTCCGG
GACAGACTTCACGTTGACGATCAGCAGTTTGCAGCCTGAGGATTTCGCGACC
TACTACTGCCAGCAAGCGAAATATTTTCCGTACACTTTCGGTCAGGGGACCA
AATTGGAGATCAAAGGTGGGGGTGGTTCAGGCGGCGGAGGCTCAGGCGGCG
GCGGTAGCGGAGGAGGCGGAAGCGGGGGTGGCGGATCAGAAGTGCAACTCG
TTCAGAGTGGCGCGGAGGTTAAGAAACCCGGTGCATCTGTAAAGGTTAGCTG
TAAGGCATCAGGATACACTTTTACCAGCTATTACATGCATTGGGTGAGACAG
GCTCCCGGTCAGGGGCTCGAATGGATGGGGTTGATCAACCCGAGTGGTGGTT
CAACATCTTACGCCCAGAAGTTTCAGGGCCGAGTAACAATGACTCGGGACAC
GTCTACCTCAACTGTGTATATGGAGCTTTCCAGCCTGCGCTCAGAGGATACAG
CAGTCTATTACTGCGCACGGTCAGACAGAGGTATAACGGCCACTGATGCGTT
CGATATCTGGGGACAAGGGACTATGGTAACTGTGTCTTCCGGAGGAGGAGGT
AGTGGAGGGGAGGAAGCGGTGGGGGGGGCTCACAGTCCGTTTTGACTCAG
CCACCAAGCGTCTCAGTCGCACCGGGGCGAATGGCGAAAATTACTTGCGGCG
GGAGCGACATAGGCAACAAGAATGTGCATTGGTACCAACAGAAACCAGGTC
AAGCACCTGTTCTCGTGGTGTATGATGACTACGATCGCCCAAGCGGGATCCC
GGAGCGGTTCTCTGGATCAAATTCTGGTGATGCAGCCACTCTGACAATATCA
ACGGTGGAAGTCGGTGACGAGGCTGATTACTTCTGCCAAGTATGGGATGGCA
GCGGAGATCCCTACTGGATGTTTGGAGGAGGTACTCAACTGACAGTTCTGGG
CGCGGCCGCAATCGAAGTGATGTATCCACCTCCGTACCTCGATAACGAGAAA
TCAAATGGAACGATCATTCATGTGAAAGGGAAACATCTGTGCCCAAGCCCAT
TGTTCCCAGGTCCGTCAAAACCATTCTGGGTGCTTGTCGTTGTTGGGGGTGTA
CTCGCATGTTATTCTTTGCTGGTGACTGTGGCGTTTATCATCTTCTGGGTAAGG
AGTAAACGCAGCCGCCTGCTGCATTCAGACTACATGAACATGACCCCACGGC
GGCCCGGCCCAACGCGCAAACACTACCAACCTTACGCCCCACCGCGAGACTT
TGCCGCCTACAGATCCAAGCGCGGACGGAAGAAACTCTTGTACATCTTCAAG
CAGCCGTTCATGCGCCCTGTGCAAACCACCCAAGAAGAGGACGGTGCTCCT
GCCGGTTCCCGGAAGAGGAAGAGGGCGGCTGCGAACTGCGCGTGAAGTTTTC
CCGGTCCGCCGACGCTCCGGCGTACCAGCAGGGGCAAAACCAGCTGTACAAC
GAACTTAACCTCGGTCGCCGGGAAGAATATGACGTGCTGGACAAGCGGCGGG
GAAGAGATCCCGAGATGGGTGAAAGCCGCGGCGAAGAACCCTCAGGAGG
GCTTGTACAACGAGCTGCAAAAGGACAAAATGGCCGAAGCCTACTCCGAGAT
TGGCATGAAGGGAGAGCGCAGACGCGGGAAGGGACACGATGGACTGTACCA
GGGACTGTCAACCGCGACTAAGGACACTTACGACGCCCTGCACATGCAGGCC
CTGCCCCCGCGC SEQ ID NO: 75 amino acid sequence of CAR D0140 CD22-19 CD28 CD28 BBz
MLLLVTSLLLCELPHPAFLLIPQVQLQQSGPGLVKHSQTLSLTCAISGDSVSSNSA
AWNWIRQSPSRGLEWLGRTYYRSKWYNDYAVSVKSRITINPDTSKNQFSLQLNS
VTPEDTAVYYCAQEVEPHDAFDIWGQGTMVTVSSGGGGSGGGGSGGGGSDIQM
TQSPSSVYASVGDKVTITCRASQDVSGWLAWYQQKPGLAPQLLISGASTLQGEV
PSRFSGSGSGTDFTLTISSLQPEDFATYYCQQAKYFPYTFGQGTKLEIKGGGGSGG
GGSGGGGSGGGGSGGGGSEVQLVQSGAEVKKPGASVKVSCKASGYTFTSYYM
HWVRQAPGQGLEWMGLINPSGGSTSYAQKFQGRVTMTRDTSTSTVYMELSSLR
SEDTAVYYCARSDRGITATDAFDIWGQGTMVTVSSGGGGSGGGGSGGGGSQSV
LTQPPSVSVAPGRMAKITCGGSDIGNKNVHWYQQKPGQAPVLVVYDDYDRPSGI
PERFSGSNSGDAATLTISTVEVGDEADYFCQVWDGSGDPYWMFGGGTQLTVLG
AAAIEVMYPPPYLDNEKSNGTIIHVKGKHLCPSPLFPGPSKPFWVLVVVGGVLAC
YSLLVTVAFIIFWVRSKRSRLLHSDYMNMTPRRPGPTRKHYQPYAPPRDFAAYRS
KRGRKKLLYIFKQPFMRPVQTTQEEDGCSCRFPEEEEGGCELRVKFSRSADAPAY
QQGQNQLYNELNLGRREEYDVLDKRRGRDPEMGGKPRRKNPQEGLYNELQKD
KMAEAYSEIGMKGERRRGKGHDGLYQGLSTATKDTYDALHMQALPPR SEQ ID NO: 76 nucleotide sequence of CAR D0146 CD19 CD8H&TM ICOS z-
_CD22 CD8H&TM 3z
ATGCTGCTGCTGGTGACCAGCCTGCTGCTGTGCGAACTGCCGCATCCGGCGTT
TCTGCTGATTCCGGAGGTCCAGCTGGTACAGTCTGGAGCTGAGGTGAAGAAG
CCTGGGGCCTCAGTGAAGGTCTCCTGCAAGGCTTCTGGATACACCTTCACCA
GCTACTATATGCACTGGGTGCGACAGGCCCCTGGACAAGGGCTTGAGTGGAT

```
GGGATTAATCAACCCTAGTGGTGGTAGCACAAGCTACGCACAGAAGTTCCAG
GGCAGAGTCACCATGACCAGGGACACGTCCACGAGCACAGTCTACATGGAG
CTGAGCAGCCTGAGATCTGAGGACACGGCCGTGTATTACTGTGCGAGATCGG
ATCGGGGAATTACCGCCACGGACGCTTTTGATATCTGGGGCCAAGGGACAAT
GGTCACCGTCTCTTCAGGCGGAGGAGGCTCCGGGGGAGGAGGTTCCGGGGGC
GGGGGTTCCCAGTCTGTGCTGACTCAGCCACCCTCGGTGTCAGTGGCCCCAG
GCGGATGGCCAAGATTACCTGTGGGGGAAGTGACATTGGAAATAAAAATGT
CCACTGGTATCAGCAGAAGCCAGGCCAGGCCCCTGTCCTGGTTGTCTATGAT
GATTACGACCGGCCCTCAGGGATCCCTGAGCGATTCTCTGGCTCCAACTCTGG
GGACGCGGCCACCCTGACGATCAGCACGGTCGAAGTCGGGGATGAGGCCGA
CTATTTCTGTCAGGTGTGGGACGGTAGTGGTGATCCTTATTGGATGTTCGGCG
GAGGGACCCAGCTCACCGTTTTAGGTGCGGCCGCAACGACCACTCCTGCACC
ACGGCCACCTACCCCAGCCCCCACCATTGCAAGCCAGCCACTTTCACTGCGC
CCCGAAGCGTGTAGACCAGCTGCTGGAGGAGCCGTGCATACCCGAGGGCTGG
ACTTCGCCTGTGACATCTACATCTGGGCCCCATTGGCTGGAACTTGCGGCGTG
CTGCTCTTGTCTCTGGTCATTACCCTGTACTGCTGGCTGACAAAAAAGAAGTA
TTCATCTAGTGTACATGATCCGAACGGTGAATACATGTTCATGCGCGCGGTGA
ACACGGCCAAGAAGAGCAGACTGACCGACGTAACCCTTAGAGTGAAGTTTAG
CCGCTCAGCCGATGCACCGGCCTACCAGCAGGGACAGAACCAGCTCTACAAC
GAGCTCAACCTGGGTCGGCGGGAAGAATATGACGTGCTGGACAAACGGCGC
GGCAGAGATCCGGAGATGGGGGGAAAGCCGAGGAGGAAGAACCCTCAAGAG
GGCCTGTACAACGAACTGCAGAAGGACAAGATGGCGGAAGCCTACTCCGAG
ATCGGCATGAAGGGAGAACGCCGGAGAGGGAAGGGTCATGACGGACTGTAC
CAGGGCCTGTCAACTGCCACTAAGGACACTTACGATGCGCTCCATATGCAAG
CTTTGCCCCCGCGGCGCGCGAAACGCGGCAGCGGCGCGACCAACTTTAGCCT
GCTGAAACAGGCGGGCGATGTGGAAGAAAACCCGGGCCCGCGAGCAAAGAG
GAATATTATGGCTCTGCCTGTTACGGCACTGCTCCTTCCGCTTGCATTGTTGTT
GCACGCAGCGCGGCCCCAAGTGCAGCTGCAGCAGTCCGGTCCTGGACTGGTC
AAGCCGTCCCAGACTCTGAGCCTGACTTGCGCAATTAGCGGGGACTCAGTCT
CGTCCAATTCGGCGGCCTGGAACTGGATCCGGCAGTCACCATCAAGGGGCCT
GGAATGGCTCGGGCGCACTTACTACCGGTCCAAATGGTATACCGACTACGCC
GTGTCCGTGAAGAATCGGATCACCATTAACCCCGACACCTCGAAGAACCAGT
TCTCACTCCAACTGAACAGCGTGACCCCCGAGGATACCGCGGTGTACTACTG
CGCACAAGAAGTGGAACCGCAGGACGCCTTCGACATTTGGGGACAGGGAAC
GATGGTCACAGTGTCGTCCGGTGGAGGAGGTTCCGGAGGCGGTGGATCTGGA
GGCGGAGGTTCGGATATCCAGATGACCCAGAGCCCCTCCTCGGTGTCCGCAT
CCGTGGGCGATAAGGTCACCATTACCTGTAGAGCGTCCCAGGACGTGTCCGG
ATGGCTGGCCTGGTACCAGCAGAAGCCAGGCTTGGCTCCTCAACTGCTGATC
TTCGGCGCCAGCACTCTTCAGGGGGAAGTGCCATCACGCTTCTCCGGATCCG
GTTCCGGCACCGACTTCACCCTGACCATCAGCAGCCTCCAGCCTGAGGACTTC
GCCACTTACTACTGCCAACAGGCCAAGTACTTCCCCTATACCTTCGGAAGAG
GCACTAAGCTGGAAATCAAGGCTAGCGCAACCACTACGCCTGCTCCGCGGCC
TCCAACGCCCGCCCACGATAGCTAGCAGCCGTTGTCTCTCCGACCAGAG
GCGTGTAGACCGGCCGCTGGCGGAGCCGTACATACTCGCGGACTCGACTTCG
CTTGCGACATCTACATTTGGGCACCCTTGGCTGGGACCTGTGGGGTGCTGTTG
CTGTCCTTGGTTATTACGTTGTACTGCAGAGTCAAATTTTCCAGGTCCGCAGA
TGCCCCCGCGTACCAGCAAGGCCAGAACCAACTTTACAACGAACTGAACCTG
GGTCGCCGGGAGGAATATGATGTGCTGGATAAACGAAGGGGGAGGGACCCT
GAGATGGGAGGGAAACCTCGCAGGAAAAACCCGCAGGAAGGTTTGTACAAC
GAGTTGCAGAAGGATAAGATGGCTGAGGCTTACTCTGAAATAGGGATGAAG
GGAGAGAGACGGAGAGGAAAAGGCCATGATGGCCTTTACCAGGGCTTAAGC
ACAGCAACAAAGGATACTTACGACGCTCTTCACATGCAAGCTCTGCCACCAC
GG

SEQ ID NO: 77 amino acid sequence of CAR D0146 CD19 CD8H&TM ICOS
z_CD22 CD8H&TMz
MLLLVTSLLLCELPHPAFLLIPEVQLVQSGAEVKKPGASVKVSCKASGYTFTSYY
MHWVRQAPGQGLEWMGLINPSGGSTSYAQKFQGRVTMTRDTSTSTVYMELSS
LRSEDTAVYYCARSDRGITATDAFDIWGQGTMVTVSSGGGGSGGGGSGGGGSQ
SVLTQPPSVSVAPGRMAKITCGGSDIGNKNVHWYQQKPGQAPVLVVYDDYDRP
SGIPERFSGSNSGDAATLTISTVEVGDEADYFCQVWDGSGDPYWMFGGGTQLT
VLGAAATTTPAPRPPTPAPTIASQPLSLRPEACRPAAGGAVHTRGLDFACDIYIW
APLAGTCGVLLLSLVITLYCWLTKKKYSSSVHDPNGEYMFMRAVNTAKKSRLT
DVTLRVKFSRSADAPAYQQGQNQLYNELNLGRREEYDVLDKRRGRDPEMGGK
PRRKNPQEGLYNELQKDKMAEAYSEIGMKGERRRGKHDGLYQGLSTATKDT
YDALHMQALPPRRAKRGSGATNFSLLKQAGDVEENPGPRAKRNIMALPVTALL
LPLALLLHAARPQVQLQQSGPGLVKPSQTLSLTCAISGDSVSSNSAAWNWIRQS
PSRGLEWLGRTYYRSKWYTDYAVSVKNRITINPDTSKNQFSLQLNSVTPEDTAV
YYCAQEVEPQDAFDIWGQGTMVTVSSGGGGSGGGGSGGGGSDIQMTQSPSSVS
ASVGDKVTITCRASQDVSGWLAWYQQKPGLAPQLLIFGASTLQGEVPSRFSGSG
SGTDFTLTISSLQPEDFATYYCQQAKYFPYTFGRGTKLEIKASATTTPAPRPPTPA
PTIASQPLSLRPEACRPAAGGAVHTRGLDFACDIYIWAPLAGTCGVLLLSLVITL
YCRVKFSRSADAPAYQQGQNQLYNELNLGRREEYDVLDKRRGRDPEMGGKPR
RKNPQEGLYNELQKDKMAEAYSEIGMKGERRRGKHDGLYQGLSTATKDTYD
ALHMQALPPR SEQ ID NO: 78 nucleotide sequence of CAR D0147 CD19 CD8H OX40TM OX40
z_CD22 CD8H&TM z
ATGCACTGGGTGCGACAGGCCCCTGGACAAGGGCTTGAGTGGATGGGATTA
```

```
ATCAACCCTAGTGGTGGTAGCACAAGCTACGCACAGAAGTTCCAGGGCAGA
GTCACCATGACCAGGGACACGTCCACGAGCACAGTCTACATGGAGCTGAGC
AGCCTGAGATCTGAGGACACGGCCGTGTATTACTGTGCGAGATCGGATCGG
GGAATTACCGCCACGGACGCTTTTGATATCTGGGGCCAAGGGACAATGGTC
ACCGTCTCTTCAGGCGGAGGAGGCTCCGGGGGAGGAGGTTCCGGGGGCGGG
GGTTCCCAGTCTGTGCTGACTCAGCCACCCTCGGTGTCAGTGGCCCCAGGGC
GGATGGCCAAGATTACCTGTGGGGGAAGTGACATTGGAAATAAAAATGTCC
ACTGGTATCAGCAGAAGCCAGGCCAGGCCCCTGTCCTGGTTGTCTATGATGA
TTACGACCGGCCCTCAGGGATCCCTGAGCGATTCTCTGGCTCCAACTCTGGG
GACGCGGCCACCCTGACGATCAGCACGGTCGAAGTCGGGGATGAGGCCGAC
TATTTCTGTCAGGTGTGGGACGGTAGTGGTGATCCTTATTGGATGTTCGGCG
GAGGGACCCAGCTCACCGTTTTAGGTGCGGCCGCAACGACCACTCCAGCAC
CGAGACCGCCAACCCCCGCGCCTACCATCGCAAGTCAACCACTTTCTCTCAG
GCCTGAAGCGTGCCGACCTGCAGCTGGTGGGGCAGTACATACCAGGGGTTT
GGACTTCGCATGTGACGTGGCGGCAATTCTCGGCCTGGGACTTGTCCTTGGT
CTGCTTGGTCCGCTCGCAATACTTCTGGCCTTGTACCTGCTCCGCAGAGACC
AAAGACTTCCGCCCGACGCCCACAAGCCCCCAGGAGGAGGTTCCTTCAGAA
CGCCTATACAAGAAGAACAAGCAGATGCCCACTCTACCCTGGCTAAAATCA
GGGTGAAGTTTAGCCGCTCAGCCGATGCACCGGCCTACCAGCAGGGACAGA
ACCAGCTCTACAACGAGCTCAACCTGGGTCGGCGGGAAGAATATGACGTGC
TGGACAAACGGCGCGGCAGAGATCCGGAGATGGGGGGAAAGCCGAGGAGG
AAGAACCCTCAAGAGGGCCTGTACAACGAACTGCAGAAGGACAAGATGGCG
GAAGCCTACTCCGAGATCGGCATGAAGGGAGAACGCCGGAGAGGGAAGGG
TCATGACGGACTGTACCAGGGCCTGTCAACTGCCACTAAGGACACTTACGAT
GCGCTCCATATGCAAGCTTTGCCCCCGCGGCGCGCGAAACGCGGCAGCGGC
GCGACCAACTTTAGCCTGCTGAAACAGGCGGGCGATGTGGAAGAAAACCCG
GGCCCGCGAGCAAAGAGGAATATTATGGCTCTGCCTGTTACGGCACTGCTCC
TTCCGCTTGCATTGTTGTTGCACGCAGCGCGGCCCCAAGTGCAGCTGCAGCA
GTCCGGTCCTGGACTGGTCAAGCCGTCCCAGACTCTGAGCCTGACTTGCGCA
ATTAGCGGGGACTCAGTCTCGTCCAATTCGGCGGCCTGGAACTGGATCCGGC
AGTCACCATCAAGGGGCCTGGAATGGCTCGGCGCACTTACTACCGGTCCA
AATGGTATACCGACTACGCCGTGTCCGTGAAGAATCGGATCACCATTAACCC
CGACACCTCGAAGAACCAGTTCTCACTCCAACTGAACAGCGTGACCCCCGA
GGATACCGCGGTGTACTACTGCGCACAAGAAGTGGAACCGCAGGACGCCTT
CGACATTTGGGGACAGGGAACGATGGTCACAGTGTCGTCCGGTGGAGGAGG
TTCCGGAGGCGGTGGATCTGGAGGCGGAGGTTCGGATATCCAGATGACCCA
GAGCCCCTCCTCGGTGTCCGCATCCGTGGGCGATAAGGTCACCATTACCTGT
AGAGCGTCCCAGGACGTGTCCGGATGGCTGGCCTGGTACCAGCAGAAGCCA
GGCTTGGCTCCTCAACTGCTGATCTTCGGCGCCAGCACTCTTCAGGGGGAAG
TGCCATCACGCTTCTCCGGATCCGGTTCCGGCACCGACTTCACCCTGACCAT
CAGCAGCCTCCAGCCTGAGGACTTCGCCACTTACTACTGCCAACAGGCCAAG
TACTTCCCCTATACCTTCGGAAGAGGCACTAAGCTGGAAATCAAGGCTAGCG
CAACCACTACGCCTGCTCCGCGGCCTCCAACGCCCGCCCACGATAGCTAG
TCAGCCGTTGTCTCTCCGACCAGAGGCGTGTAGACCGGCCGCTGGCGGAGCC
GTACATACTCGCGGACTCGACTTCGCTTGCGACATCTACATTTGGGCACCCT
TGGCTGGGACCTGTGGGGTGCTGTTGCTGTCCTTGGTTATTACGTTGTACTGC
AGAGTCAAATTTTCCAGGTCCGCAGATGCCCCCGCGTACCAGCAAGGCCAG
AACCAACTTTACAACGAACTGAACCTGGGTCGCCGGGAGGAATATGATGTG
CTGGATAAACGAAGGGGGAGGGACCCTGAGATGGGAGGGAAACCTCGCAG
GAAAAACCCGCAGGAAGGTTTGTACAACGAGTTGCAGAAGGATAAGATGGC
TGAGGCTTACTCTGAAATAGGGATGAAGGGAGAGAGACGGAGGGAAAAG
GCCATGATGGCCTTTACCAGGGCTTAAGCACAGCAACAAAGGATACTTACG
ACGCTCTTCACATGCAAGCTCTGCCACCACGG

SEQ ID NO: 79 amino acid sequence of CAR D0147 CD19 CD8H OX40TM OX40
z_CD22 CD8H&TM 3z
MHWVRQAPGQGLEWMGLINPSGGSTSYAQKFQGRVTMTRDTSTSTVYMELSS
LRSEDTAVYYCARSDRGITATDAFDIWGQGTMVTVSSGGGGSGGGGSGGGGSQ
SVLTQPPSVSVAPGRMAKITCGGSDIGNKNVHWYQQKPGQAPVLVVYDDYDRP
SGIPERFSGSNSGDAATLTISTVEVGDEADYFCQVWDGSGDPYWMFGGGTQLT
VLGAAATTTPAPRPPTPAPTIASQPLSLRPEACRPAAGGAVHTRGLDFACDVAAI
LGLGLVLGLLGPLAILLALYLLRRDQRLPPDAHKPPGGGSFRTPIQEEQADAHST
LAKIRVKFSRSADAPAYQQGQNQLYNELNLGRREEYDVLDKRRGRDPEMGGK
PRRKNPQEGLYNELQKDKMAEAYSEIGMKGERRRGKGHDGLYQGLSTATKDT
YDALHMQALPPRRAKRGSGATNFSLLKQAGDVEENPGPRAKRNIMALPVTALL
LPLALLLHAARPQVQLQQSGPGLVKPSQTLSLTCAISGDSVSSNSAAWNWIRQS
PSRGLEWLGRTYYRSKWYTDYAVSVKNRITINPDTSKNQFSLQLNSVTPEDTAV
YYCAQEVEPQDAFDIWGQGTMVTVSSGGGGSGGGGSGGGGSDIQMTQSPSSVS
ASVGDKVTITCRASQDVSGWLAWYQQKPGLAPQLLIFGASTLQGEVPSRFSGSG
SGTDFTLTISSLQPEDFATYYCQQAKYFPYTFGRGTKLEIKASATTTPAPRPPTPA
PTIASQPLSLRPEACRPAAGGAVHTRGLDFACDIYIWAPLAGTCGVLLLSLVITL
YCRVKFSRSADAPAYQQGQNQLYNELNLGRREEYDVLDKRRGRDPEMGGKPR
RKNPQEGLYNELQKDKMAEAYSEIGMKGERRRGKGHDGLYQGLSTATKDTYD
ALHMQALPPR SEQ ID NO: 80 nucleotide sequence of CAR D0148 CD19 CD8H OX40TM OX40
z_CD22 CD8H&TM ICOS z
ATGCTGCTGCTGGTGACCAGCCTGCTGCTGTGCGAACTGCCGCATCCGGCGT
TTCTGCTGATTCCGGAGGTCCAGCTGGTACAGTCTGGAGCTGAGGTGAAGAA
```

```
GCCTGGGGCCTCAGTGAAGGTCTCCTGCAAGGCTTCTGGATACACCTTCACC
AGCTACTATATGCACTGGGTGCGACAGGCCCCTGGACAAGGGCTTGAGTGG
ATGGGATTAATCAACCCTAGTGGTGGTAGCACAAGCTACGCACAGAAGTTC
CAGGGCAGAGTCACCATGACCAGGGACACGTCCACGAGCACAGTCTACATG
GAGCTGAGCAGCCTGAGATCTGAGGACACGGCCGTGTATTACTGTGCGAGA
TCGGATCGGGGAATTACCGCCACGGACGCTTTTGATATCTGGGGCCAAGGG
ACAATGGTCACCGTCTCTTCAGGCGGAGGAGGCTCCGGGGGAGGAGGTTCC
GGGGGCGGGGGTTCCCAGTCTGTGCTGACTCAGCCACCCTCGGTGTCAGTG
GCCCCAGGGCGGATGGCCAAGATTACCTGTGGGGGAAGTGACATTGGAAATA
AAAATGTCCACTGGTATCAGCAGAAGCCAGGCCAGGCCCCTGTCCTGGTTGT
CTATGATGATTACGACCGGCCCTCAGGGATCCCTGAGCGATTCTCTGGCTCC
AACTCTGGGACGCGGCCACCCTGACGATCAGCACGGTCGAAGTCGGGGAT
GAGGCCGACTATTTCTGTCAGGTGTGGGACGGTAGTGGTGATCCTTATTGGA
TGTTCGGCGGAGGGACCCAGCTCACCGTTTTAGGTGCGGCCGCAACGACCAC
TCCAGCACCGAGACCGCCAACCCCCGCGCCTACCATCGCAAGTCAACCACTT
TCTCTCAGGCCTGAAGCGTGCCGACCTGCAGCTGGTGGGCAGTACATACCA
GGGGTTTGGACTTCGCATGTGACGTGGCGGCAATTCTCGGCCTGGGACTTGT
CCTTGGTCTGCTTGGTCCGCTCGCAATACTTCTGGCCTTGTACCTGCTCCGCA
GAGACCAAAGACTTCCGCCCGACGCCCACAAGCCCCCAGGAGGAGGTTCCT
TCAGAACGCCTATACAAGAAGAACAAGCAGATGCCCACTCTACCCTGGCTA
AAATCAGGGTGAAGTTTAGCCGCTCAGCCGATGCACCGGCCTACCAGCAGG
GACAGAACCAGCTCTACAACGAGCTCAACCTGGGTCGGCGGGAAGAATATG
ACGTGCTGGACAAACGGCGCGGCAGAGATCCGGAGATGGGGGGAAAGCCG
AGGAGGAAGAACCCTCAAGAGGGCCTGTACAACGAACTGCAGAAGGACAA
GATGGCGGAAGCCTACTCCGAGATCGGCATGAAGGGAGAACGCCGGAGAG
GGAAGGGTCATGACGGACTGTACCAGGGCCTGTCAACTGCCACTAAGGACA
CTTACGATGCGCTCCATATGCAAGCTTTGCCCCCGCGGCGCGCGAAACGCGG
CAGCGGCGCGACCAACTTTAGCCTGCTGAAACAGGCGGGCGATGTGGAAGA
AAACCCGGGCCCGCGAGCAAGAGGAATATTATGGCTCTGCCTGTTACGGC
ACTGCTCCTTCCGCTTGCATTGTTGTGCACGCAGCGCGCCCCAAGTGCAG
CTGCAGCAGTCCGGTCCTGGACTGGTCAAGCCGTCCCAGACTCTGAGCCTGA
CTTGCGCAATTAGCGGGGACTCAGTCTCGTCCAATTCGGCGGCCTGGAACTG
GATCCGGCAGTCACCATCAAGGGGCCTGGAATGGCTCGGGCGCACTTACTA
CCGGTCCAAATGGTATACCGACTACGCCGTGTCCGTGAAGAATCGGATCACC
ATTAACCCCGACACCTCGAAGAACCAGTTCTCACTCCAACTGAACAGCGTGA
CCCCCGAGGATACCGCGGTGTACTACTGCGCACAAGAAGTGGAACCGCAGG
ACGCCTTCGACATTTGGGGACAGGGAACGATGGTCACAGTGTCGTCCGGTG
GAGGAGGTTCCGGAGGCGGTGGATCTGGAGGCGGAGGTTCGGATATCCAGA
TGACCCAGAGCCCCTCCTCGGTGTCCGCATCCGTGGGCGATAAGGTCACCAT
TACCTGTAGAGCGTCCCAGGACGTGTCCGGATGGCTGGCCTGGTACCAGCAG
AAGCCAGGCTTGGCTCCTCAACTGCTGATCTTCGGCGCCAGCACTCTTCAGG
GGGAAGTGCCATCACGCTTCTCCGGATCCGGTTCCGGCACCGACTTCACCCT
GACCATCAGCAGCCTCCAGCCTGAGGACTTCGCCACTTACTACTGCCAACAG
GCCAAGTACTTCCCCTATACCTTCGGAAGAGGCACTAAGCTGGAAATCAAG
GCTAGCGCAACCACTACGCCTGCTCCGCGGCCTCCAACGCCCGCGCCCACGA
TAGCTAGTCAGCCGTTGTCTCTCCGACCAGAGGCGTGTAGACCGGCCGCTGG
CGGAGCCGTACATACTCGCGGACTCGACTTCGCTTGCGACATCTACATTTGG
GCACCCTTGGCTGGGACCTGTGGGGTGCTGTTGCTGTCCTTGGTTATTACGTT
GTACTGCTGGCTGACAAAAAAGAAGTATTCATCTAGTGTACATGATCCGAAC
GGTGAATACATGTTCATGCGCGCGGTGAACACGGCCAAGAAGAGCAGACTG
ACCGACGTAACCCTTAGAGTCAAATTTTCCAGGTCCGCAGATGCCCCCGCGT
ACCAGCAAGGCCAGAACCAACTTTACAACGAACTGAACCTGGGTCGCCGGG
AGGAATATGATGTGCTGGATAAACGAAGGGGGAGGGACCCTGAGATGGGA
GGGAAACCTCGCAGGAAAAACCCGCAGGAAGGTTTGTACAACGAGTTGCAG
AAGGATAAGATGGCTGAGGCTTACTCTGAAATAGGGATGAAGGGAGAGAGA
CGGAGAGGAAAAGGCCATGATGGCCTTTACCAGGGCTTGAGCACAGCAACA
AAGGATACTTACGACGCTCTTCACATGCAAGCTCTGCCACCACGG

SEQ ID NO: 81 amino acid sequence of CAR D0148 CD19 CD8H OX40TM OX40
z_CD22 CD8H&TM ICOS z
MLLLVTSLLLCELPHPAFLLIPEVQLVQSGAEVKKPGASVKVSCKASGYTFTSYY
MHWVRQAPGQGLEWMGLINPSGGSTSYAQKFQGRVTMTRDTSTSTVYMELSS
LRSEDTAVYYCARSDRGITATDAFDIWGQGTMVTVSSGGGGSGGGGSGGGGSQ
SVLTQPPSVSVAPGRMAKITCGGSDIGNKNVHWYQQKPGQAPVLVVYDDYDRP
SGIPERFSGSNSGDAATLTISTVEVGDEADYFCQVWDGSGDPYWMFGGGTQLT
VLGAAATTTPAPRPPTPAPTIASQPLSLRPEACRPAAGGAVHTRGLDFACDVAAI
LGLGLVLGLLGPLAILLALYLLRRDQRLPPDAHKPPGGGSFRTPIQEEQADAHST
LAKIRVKFSRSADAPAYQQGQNQLYNELNLGRREEYDVLDKRRGRDPEMGGK
PRRKNPQEGLYNELQKDKMAEAYSEIGMKGERRRGKGHDGLYQGLSTATKDT
YDALHMQALPPRRAKRGSGATNFSLLKQAGDVEENPGPRAKRNIMALPVTALL
LPLALLLHAARPQVQLQQSGPGLVKPSQTLSLTCAISGDSVSSNSAAWNWIRQS
PSRGLEWLGRTYYRSKWYTDYAVSVKNRITINPDTSKNQFSLQLNSVTPEDTAV
YYCAQEVEPQDAFDIWGQGTMVTVSSGGGGSGGGGSGGGGSDIQMTQSPSSVS
ASVGDKVTITCRASQDVSGWLAWYQQKPGLAPQLLIFGASTLQGEVPSRFSGSG
SGTDFTLTISSLQPEDFATYYCQQAKYFPYTFGRGTKLEIKASATTTPAPRPPTPA
PTIASQPLSLRPEACRPAAGGAVHTRGLDFACDIYIWAPLAGTCVLLLSLVITL
YCWLTKKKYSSSVHDPNGEYMFMRAVNTAKKSRLTDVTLRVKFSRSADAPAY
QQGQNQLYNELNLGRREEYDVLDKRRGRDPEMGGKPRRKNPQEGLYNELQKD
KMAEAYSEIGMKGERRRGKGHDGLYQGLSTATKDTYDALHMQALPPR
```

SEQ ID NO: 82 nucleotide sequence of CAR D0149 CD19 CD8H&TM CD27
z_CD22 CD8H&TM ICOS3 z
ATGCACTGGGTGCGACAGGCCCCTGGACAAGGGCTTGAGTGGATGGGATTA
ATCAACCCTAGTGGTGGTAGCACAAGCTACGCACAGAAGTTCCAGGGCAGA
GTCACCATGACCAGGGACACGTCCACGAGCACAGTCTACATGGAGCTGAGC
AGCCTGAGATCTGAGGACACGGCCGTGTATTACTGTGCGAGATCGGATCGG
GGAATTACCGCCACGGACGCTTTTGATATCTGGGGCCAAGGGACAATGGTC
ACCGTCTCTTCAGGCGGAGGAGGCTCCGGGGGAGGAGGTTCCGGGGGCGGG
GGTTCCCAGTCTGTGCTGACTCAGCCACCCTCGGTGTCAGTGGCCCCAGGGC
GGATGGCCAAGATTACCTGTGGGGGAAGTGACATTGGAAATAAAAATGTCC
ACTGGTATCAGCAGAAGCCAGGCCAGGCCCCTGTCCTGGTTGTCTATGATGA
TTACGACCGGCCCTCAGGGATCCCTGAGCGATTCTCTGGCTCCAACTCTGGG
GACGCGGCCACCCTGACGATCAGCACGGTCGAAGTCGGGGATGAGGCCGAC
TATTTCTGTCAGGTGTGGGACGGTAGTGGTGATCCTTATTGGATGTTCGGCG
GAGGGACCCAGCTCACCGTTTTAGGTGCGGCCGCGACTACCACTCCTGCACC
ACGGCCACCTACCCCAGCCCCCACCATTGCAAGCCAGCCACTTTCACTGCGC
CCCGAAGCGTGTAGACCAGCTGCTGGAGGAGCCGTGCATACCCGAGGGCTG
GACTTCGCCTGTGACATCTACATCTGGGCCCCATTGGCTGGAACTTGCGGCG
TGCTGCTCTTGTCTCTGGTCATTACCCTGTACTGCCAACGGCGCAAATACCGC
TCCAATAAAGGCGAAAGTCCGGTAGAACCCGCAGAACCTTGCCACTACAGT
TGTCCCAGAGAAGAAGAGGGTTCTACAATACCTATTCAAGAGGACTATAGG
AAACCAGAGCCCGCATGTAGTCCCAGAGTGAAGTTCAGCCGCTCAGCCGAT
GCACCGGCCTACCAGCAGGGACAGAACCAGCTCTACAACGAGCTCAACCTG
GGTCGGCGGGAAGAATATGACGTGCTGGACAAACGGCGCGGCAGAGATCCG
GAGATGGGGGAAAGCCGAGGAGGAAGAACCCTCAAGAGGGCCTGTACAA
CGAACTGCAGAAGGACAAGATGGCGGAAGCCTACTCCGAGATCGGCATGAA
GGGAGAACGCCGGAGAGGGAAGGGTCATGACGGACTGTACCAGGGCCTGTC
AACTGCCACTAAGGACACTTACGATGCGCTCCATATGCAAGCTTTGCCCCCG
CGGCGCGCGAAACGCGGCAGCGGCGCGACCAACTTTAGCCTGCTGAAACAG
GCGGGCGATGTGGAAGAAAACCCGGGCCCGCGAGCAAAGAGGAATATTATG
GCTCTGCCTGTTACGGCACTGCTCCTTCCGCTTGCATTGTTGTTGCACGCAGC
GCGGCCCCAAGTGCAGCTGCAGCAGTCCGGTCCTGGACTGGTCAAGCCGTCC
CAGACTCTGAGCCTGACTTGCGCAATTAGCGGGGACTCAGTCTCGTCCAATT
CGGCGGCCTGGAACTGGATCCGGCAGTCACCATCAAGGGGCCTGGAATGGC
TCGGGCGCACTTACTACCGGTCCAAATGGTATACCGACTACGCCGTGTCCGT
GAAGAATCGGATCACCATTAACCCCGACACCTCGAAGAACCAGTTCTCACTC
CAACTGAACAGCGTGACCCCCGAGGATACCGCGGTGTACTACTGCGCACAA
GAAGTGGAACCGCAGGACGCCTTCGACATTTGGGGACAGGGAACGATGGTC
ACAGTCTCGTCCGGTGGAGGAGGTTCCGGAGGCGGTGGATCTGGAGGCGGA
GGTTCGGATATCCAGATGACCCAGAGCCCCTCCTCGGTGTCCGCATCCGTGG
GCGATAAGGTCACCATTACCTGTAGAGCGTCCCAGGACGTGTCCGGATGGCT
GGCCTGGTACCAGAAGCCAGGCTTGGCTCCTCAACTGCTGATCTTCGGC
GCCAGCACTCTTCAGGGGGAAGTGCCATCACGCTTCTCCGGATCCGGTTCCG
GCACCGACTTCACCCTGACCATCAGCAGCCTCCAGCCTGAGGACTTCGCCAC
TTACTACTGCCAACAGGCCAAGTACTTCCCCTATACCTTCGGAAGAGGCACT
AAGCTGGAAATCAAGGCTAGCGCAACCACTACGCCTGCTCCGGCCTCCA
ACGCCCCGCGCCCACGATAGCTAGTCAGCCGTTGTCTCTCCGACCAGAGGCGT
GTAGACCGGCCGCTGCGGAGCCGTACATACTCGCGGACTCGACTTCGCTTG
CGACATCTACATTTGGGCACCCTTGGCTGGGACCTGTGGGGTGCTGTTGCTG
TCCTTGGTTATTACGTTGTACTGCTGGCTGACAAAAAGAAGTATTCATCTA
GTGTACATGATCCGAACGGTGAATACATGTTCATGCGCGCGGTGAACACGG
CCAAGAAGAGCAGACTGACCGACGTAACCCTTAGAGTCAAATTTTCCAGGT
CCGCAGATGCCCCCGCGTACCAGCAAGGCCAGAACCAACTTTACAACGAAC
TGAACCTGGGTCGCCGGGAGGAATATGATGTGCTGGATAAACGAAGGGGGA
GGGACCCTGAGATGGGAGGGAAACCTCGCAGGAAAAACCCGCAGGAAGGT
TTGTACAACGAGTTGCAGAAGGATAAGATGGCTGAGGCTTACTCTGAAATA
GGGATGAAGGGAGAGAGACGGAGAGGAAAAGGCCATGATGGCCTTTACCA
GGGCTTGAGCACAGCAACAAAGGATACTTACGACGCTCTTCACATGCAAGC
TCTGCCACCACGG SEQ ID NO: 83 amino acid sequence of CAR D0149 CD19 CD8H&TM ICOS z
CD22 CD8H&TM ICOS z
MHWVRQAPGQGLEWMGLINPSGGSTSYAQKFQGRVTMTRDTSTSTVYMELSS
LRSEDTAVYYCARSDRGITATDAFDIWGQGTMVTVSSGGGGSGGGGSGGGGS
QSVLTQPPSVSVAPGRMAKITCGGSDIGNKNVHWYQQKPGQAPVLVVYDDYD
RPSGIPERFSGSNSGDAATLTISTVEVGDEADYFCQVWDGSGDPYWMFGGGTQ
LTVLGAAATTTPAPRPPTPAPTIASQPLSLRPEACRPAAGGAVHTRGLDFACDIY
IWAPLAGTCGVLLLSLVITLYCQRRKYRSNKGESPVEPAEPCHYSCPREEEGSTI
PIQEDYRKPEPACSPRVKFSRSADAPAYQQGQNQLYNELNLGRREEYDVLDKR
RGRDPEMGGKPRRKNPQEGLYNELQKDKMAEAYSEIGMKGERRRGKGHDGL
YQGLSTATKDTYDALHMQALPPRRAKRGSGATNFSLLKQAGDVEENPGPRAK
RNIMALPVTALLLPLALLLHAARPQVQLQQSGPGLVKPSQTLSLTCAISGDSVS
SNSAAWNWIRQSPSRGLEWLGRTYYRSKWYTDYAVSVKNRITINPDTSKNQFS
LQLNSVTPEDTAVYYCAQEVEPQDAFDIWGQGTMVTVSSGGGGSGGGGSGGG
GSDIQMTQSPSSVSASVGDKVTITCRASQDVSGWLAWYQQKPGLAPQLLIFGA
STLQGEVPSRFSGSGSGTDFTLTISSLQPEDFATYYCQQAKYFPYTFGRGTKLEI
KASATTTPAPRPPTPAPTIASQPLSLRPEACRPAAGGAVHTRGLDFACDIYIWAP
LAGTCGVLLLSLVITLYCWLTKKKYSSSVHDPNGEYMFMRAVNTAKKSRLTD VTLRVKFSRSADAPAYQQGQNQLYNELNLGRREEYDVLDKRRGRDPEMGGKP
RRKNPQEGLYNELQKDKMAEAYSEIGMKGERRRGKGHDGLYQGLSTATKDT
YDALHMQALPPR

What is claimed is:

1. A method of treating a cancer in a human subject in need thereof, the method comprising administering to the human subject a pharmaceutical composition comprising an anti-tumor effective amount of a population of autologous T cells, wherein the autologous T cells comprise a nucleic acid sequence that encodes a CD19/CD22 tandem chimeric antigen receptor (CAR), comprising an extracellular antigen binding domain comprising a CD19/CD22 antigen binding domain, a transmembrane domain, and an intracellular signaling domain, wherein the CD19/CD22 tandem CAR comprises the amino acid sequence comprising SEQ ID NO: 2, 4, 61, 63, 65, 67, 69, 71, 73, 75, 77, 79, 81, or 83, thereby treating the cancer of the human subject.

2. The method of claim 1, wherein the transmembrane domain comprises a transmembrane domain of the alpha, the beta or the zeta chain of a T-cell receptor, a CD8, a CD28, a CD3 epsilon, a CD45, a CD4, a CD5, a CD8, a CD9, a CD16, a CD22, a CD33, a CD37, a CD64, a CD80, a CD86, a CD134, a CD137 and a CD154.

3. The method of claim 1, wherein the extracellular antigen binding domain comprising the CD19/CD22 antigen binding domain, the intracellular signaling domain, or both are connected to the transmembrane domain by a linker or a spacer domain.

4. The method of claim 3, wherein the linker or the spacer domain is derived from the extracellular domain of CD8 or CD28, and is linked to the transmembrane domain.

5. The method of claim 1, wherein the extracellular antigen binding domain comprising the CD19/CD22 antigen binding domain is preceded by a leader nucleotide sequence encoding a leader peptide.

6. The method of claim 1, wherein the intracellular signaling domain comprises a costimulatory domain comprising a functional signaling domain of a protein selected from the group consisting of OX40, CD70, CD27, CD28, CD5, ICAM-1, LFA-1 (CD11a/CD18), ICOS (CD278), DAP10, DAP12, 4-1BB (CD137), and a combination thereof.

7. The method of claim 1, wherein the nucleic acid sequence encoding the CD19/CD22 tandem chimeric antigen receptor (CAR) is encoded by a nucleotide sequence comprising SEQ ID NO. 1, 3, 60, 62, 64, 66, 68, 70, 72, 74, 76, 78, 80, or 82, or a sequence with 85%, 90%, 95%, 96%, 97%, 98% or 99% identity thereof.

8. The method of claim 1, wherein the intracellular signaling domain comprises a costimulatory domain, a primary signaling domain, or any combination thereof.

9. The method of claim 1, wherein the intracellular signaling domain comprises a CD3 zeta intracellular domain.

10. The method of claim 1, wherein the cancer is a hematological cancer.

11. The method of claim 10, wherein the hematological cancer is leukemia or lymphoma.

12. The method of claim 11, wherein the leukemia is chronic lymphocytic leukemia (CLL), acute lymphocytic leukemia (ALL), or chronic myelogenous leukemia (CML).

13. The method of claim 11, wherein the lymphoma is mantle cell lymphoma, non-Hodgkin's lymphoma or Hodgkin's lymphoma.

14. The method of claim 1, wherein the cancer is an adult carcinoma, selected from the group consisting of: an oral and pharynx cancer, a digestive system cancer, a respiratory system cancer, bones and joint cancers, a soft tissue cancer, a skin cancer, a cancer of the central nervous system, a breast cancer, a genital cancer, an urinary cancer, a cancer of the eye and orbit, an endocrine cancer, and a brain cancer.

* * * * *

SEQUENCE LISTING

<160> NUMBER OF SEQ ID NOS: 83

<210> SEQ ID NO 1
<211> LENGTH: 2292
<212> TYPE: DNA
<213> ORGANISM: Artificial Sequence
<220> FEATURE:
<223> OTHER INFORMATION: LTG2681 D0023 Leader - Construct CAR 2219

<400> SEQUENCE: 1

```
atgctcttgc tcgtgacttc tttgcttttg tgcgaacttc cgcacccagc cttccttttg      60
atacctcagg tacagcttca acaaagcgga ccgggacttg ttaagcattc ccaaacccct     120
tctctcacgt gtgcaattag cggcgatagt gtatcctcta attctgcggc ctggaactgg     180
atacgacaat caccaagccg gggactcgag tggttgggcc gaacctacta tcggtccaaa     240
tggtataatg actacgcagt atccgtgaaa tctcgcatta cgatcaatcc agacacctcc     300
aaaaatcaat tttctctgca gttgaatagc gtgactcccg aggacacggc cgtttactat     360
tgcgcccagg aagttgaacc ccacgatgca tttgatattt ggggccaggg aaccatggtg     420
acagtgagta gtgggggtgg aggatctgga ggaggcggta gcggcggggg cggcagtgat     480
atccagatga cgcagtcacc ttccagcgtg tatgcgagtg tggggacaa ggtcaccata     540
acctgtcgcg ctagccaaga tgtcagcggg tggctggctt ggtaccagca gaaaccaggt     600
ttggctcctc agcttttgat ctcaggagcg agcacgcttc agggtgaggt cccaagtcgc     660
tttagtggct ctggctccgg gacagacttc acgttgacga tcagcagttt gcagcctgag     720
gatttcgcga cctactactg ccagcaagcg aaatattttc cgtacacttt cggtcagggg     780
accaaattgg agatcaaagg tggggggtggt tcaggcggcg aggctcagg cggcggcgt     840
agcggaggag gcggaagcgg gggtggcgga tcagaagtgc aactcgttca gagtggcgcg     900
gaggttaaga aacccggtgc atctgtaaag gttagctgta aggcatcagg atacactttt     960
accagctatt acatgcattg ggtgagacag gctcccggtc aggggctcga atggatgggg    1020
ttgatcaacc cgagtggtgg ttcaacatct tacgcccaga gtttcagggg ccagtaaca    1080
atgactcggg acacgtctac ctcaactgtg tatatggagc tttccagcct gcgctcagag    1140
gatacagcag tctattactg cgcacggtca gacagaggta taacggccac tgatgcgttc    1200
gatatctggg gacaagggac tatggtaact gtgtcttccg gaggaggagg tagtggaggg    1260
ggaggaagcg gtgggggggg ctcacagtcc gttttgactc agccaccaag cgtctcagtc    1320
gcaccggggc gaatggcgaa aattacttgc ggcgggagcg acataggcaa caagaatgtg    1380
cattggtacc aacagaaacc aggtcaagca cctgttctcg tggtgtatga tgactacgat    1440
cgcccaagcg ggatcccgga gcggttctct ggatcaaatt ctggtgatgc agccactctg    1500
acaatatcaa cggtggaagt cggtgacgag gctgattact ctgccaagt atgggatggc    1560
agcggagatc cctactggat gttggagga ggtactcaac tgacagttct gggcgcggcc    1620
gcaacgacca ctcctgcacc ccgccctccg actccgggccc caaccattgc cagcagccc    1680
ctgtccctgc ggccggaagc ctgcagaccg gctgccggcg gagccgtcca tacccgggga    1740
```

```
ctggatttcg cctgcgatat ctatatctgg gcaccactcg ccggaacctg tggagtgctg    1800
ctgctgtccc ttgtgatcac cctgtactgc aagcgcggac ggaagaaact cttgtacatc    1860
ttcaagcagc cgttcatgcg ccctgtgcaa accacccaag aagaggacgg tgctcctgc     1920 cggttcccgg aagaggaaga gggcggctgc gaactgcgcg tgaagttttc ccggtccgcc    1980
gacgctccgg cgtaccagca ggggcaaaac cagctgtaca cgaacttaa cctcggtcgc     2040 cgggaagaat atgacgtgct ggacaagcgg cggggaagag atcccgagat gggtggaaag    2100
ccgcggcgga agaaccctca ggagggcttg tacaacgagc tgcaaaagga caaaatggcc    2160
gaagcctact ccgagattgg catgaaggga gagcgcagac gcgggaaggg acacgatgga    2220
ctgtaccagg gactgtcaac cgcgactaag gacacttacg acgccctgca catgcaggcc    2280 ctgccccgc gc                                                         2292
```

<210> SEQ ID NO 2
<211> LENGTH: 764
<212> TYPE: PRT
<213> ORGANISM: Artificial Sequence
<220> FEATURE:
<223> OTHER INFORMATION: LTG2681 D0023 Leader - Construct CAR 2219

<400> SEQUENCE: 2

```
Met Leu Leu Leu Val Thr Ser Leu Leu Cys Glu Leu Pro His Pro
1               5                   10                  15

Ala Phe Leu Leu Ile Pro Gln Val Gln Leu Gln Ser Gly Pro Gly
                20                  25                  30

Leu Val Lys His Ser Gln Thr Leu Ser Leu Thr Cys Ala Ile Ser Gly
            35                  40                  45

Asp Ser Val Ser Ser Asn Ser Ala Ala Trp Asn Trp Ile Arg Gln Ser
        50                  55                  60

Pro Ser Arg Gly Leu Glu Trp Leu Gly Arg Thr Tyr Tyr Arg Ser Lys
65                  70                  75                  80

Trp Tyr Asn Asp Tyr Ala Val Ser Val Lys Ser Arg Ile Thr Ile Asn
                85                  90                  95

Pro Asp Thr Ser Lys Asn Gln Phe Ser Leu Gln Leu Asn Ser Val Thr
            100                 105                 110

Pro Glu Asp Thr Ala Val Tyr Tyr Cys Ala Gln Glu Val Glu Pro His
        115                 120                 125

Asp Ala Phe Asp Ile Trp Gly Gln Gly Thr Met Val Thr Val Ser Ser
    130                 135                 140

Gly Gly Gly Gly Ser Gly Gly Gly Ser Gly Gly Gly Gly Ser Asp
145                 150                 155                 160

Ile Gln Met Thr Gln Ser Pro Ser Ser Val Tyr Ala Ser Val Gly Asp
                165                 170                 175

Lys Val Thr Ile Thr Cys Arg Ala Ser Gln Asp Val Ser Gly Trp Leu
            180                 185                 190

Ala Trp Tyr Gln Gln Lys Pro Gly Leu Ala Pro Gln Leu Leu Ile Ser
        195                 200                 205

Gly Ala Ser Thr Leu Gln Gly Glu Val Pro Ser Arg Phe Ser Gly Ser
    210                 215                 220

Gly Ser Gly Thr Asp Phe Thr Leu Thr Ile Ser Ser Leu Gln Pro Glu
225                 230                 235                 240

Asp Phe Ala Thr Tyr Tyr Cys Gln Gln Ala Lys Tyr Phe Pro Tyr Thr
                245                 250                 255

Phe Gly Gln Gly Thr Lys Leu Glu Ile Lys Gly Gly Gly Gly Ser Gly
```

```
                260                 265                 270
Gly Gly Gly Ser Gly Gly Gly Ser Gly Gly Gly Ser Gly Gly
            275                 280                 285
Gly Gly Ser Glu Val Gln Leu Val Gln Ser Gly Ala Glu Val Lys Lys
290                 295                 300
Pro Gly Ala Ser Val Lys Val Ser Cys Lys Ala Ser Gly Tyr Thr Phe
305                 310                 315                 320
Thr Ser Tyr Tyr Met His Trp Val Arg Gln Ala Pro Gly Gln Gly Leu
                325                 330                 335
Glu Trp Met Gly Leu Ile Asn Pro Ser Gly Gly Ser Thr Ser Tyr Ala
            340                 345                 350
Gln Lys Phe Gln Gly Arg Val Thr Met Thr Arg Asp Thr Ser Thr Ser
        355                 360                 365
Thr Val Tyr Met Glu Leu Ser Ser Leu Arg Ser Glu Asp Thr Ala Val
    370                 375                 380
Tyr Tyr Cys Ala Arg Ser Asp Arg Gly Ile Thr Ala Thr Asp Ala Phe
385                 390                 395                 400
Asp Ile Trp Gly Gln Gly Thr Met Val Thr Val Ser Ser Gly Gly Gly
                405                 410                 415
Gly Ser Gly Gly Gly Gly Ser Gly Gly Gly Ser Gln Ser Val Leu
            420                 425                 430
Thr Gln Pro Pro Ser Val Ser Val Ala Pro Gly Arg Met Ala Lys Ile
        435                 440                 445
Thr Cys Gly Gly Ser Asp Ile Gly Asn Lys Asn Val His Trp Tyr Gln
    450                 455                 460
Gln Lys Pro Gly Gln Ala Pro Val Leu Val Val Tyr Asp Asp Tyr Asp
465                 470                 475                 480
Arg Pro Ser Gly Ile Pro Glu Arg Phe Ser Gly Ser Asn Ser Gly Asp
                485                 490                 495
Ala Ala Thr Leu Thr Ile Ser Thr Val Glu Val Gly Asp Glu Ala Asp
            500                 505                 510
Tyr Phe Cys Gln Val Trp Asp Gly Ser Gly Asp Pro Tyr Trp Met Phe
        515                 520                 525
Gly Gly Gly Thr Gln Leu Thr Val Leu Gly Ala Ala Ala Thr Thr Thr
    530                 535                 540
Pro Ala Pro Arg Pro Pro Thr Pro Ala Pro Thr Ile Ala Ser Gln Pro
545                 550                 555                 560
Leu Ser Leu Arg Pro Glu Ala Cys Arg Pro Ala Ala Gly Gly Ala Val
                565                 570                 575
His Thr Arg Gly Leu Asp Phe Ala Cys Asp Ile Tyr Ile Trp Ala Pro
            580                 585                 590
Leu Ala Gly Thr Cys Gly Val Leu Leu Leu Ser Leu Val Ile Thr Leu
        595                 600                 605
Tyr Cys Lys Arg Gly Arg Lys Lys Leu Leu Tyr Ile Phe Lys Gln Pro
    610                 615                 620
Phe Met Arg Pro Val Gln Thr Thr Gln Glu Glu Asp Gly Cys Ser Cys
625                 630                 635                 640
Arg Phe Pro Glu Glu Glu Glu Gly Gly Cys Glu Leu Arg Val Lys Phe
                645                 650                 655
Ser Arg Ser Ala Asp Ala Pro Ala Tyr Gln Gln Gly Gln Asn Gln Leu
            660                 665                 670
Tyr Asn Glu Leu Asn Leu Gly Arg Arg Glu Glu Tyr Asp Val Leu Asp
        675                 680                 685
```

```
Lys Arg Arg Gly Arg Asp Pro Glu Met Gly Gly Lys Pro Arg Arg Lys
        690                 695                 700
Asn Pro Gln Glu Gly Leu Tyr Asn Glu Leu Gln Lys Asp Lys Met Ala
705                 710                 715                 720
Glu Ala Tyr Ser Glu Ile Gly Met Lys Gly Glu Arg Arg Arg Gly Lys
                725                 730                 735
Gly His Asp Gly Leu Tyr Gln Gly Leu Ser Thr Ala Thr Lys Asp Thr
            740                 745                 750
Tyr Asp Ala Leu His Met Gln Ala Leu Pro Pro Arg
        755                 760
```

<210> SEQ ID NO 3
<211> LENGTH: 2292
<212> TYPE: DNA
<213> ORGANISM: Artificial Sequence
<220> FEATURE:
<223> OTHER INFORMATION: LTG2791 D0024 Leader - construct CAR 1922

<400> SEQUENCE: 3

```
atgttgcttc tggttacttc ccttcttctt tgcgagcttc cacacccagc attcctgctc      60
attccggagg tgcaactcgt ccaatccggg gccgaagtta agaagccggg agcatctgtt     120
aaagtatcct gtaaggccag tgggtatact ttcacctcat attatatgca ctgggtgagg     180
caggctccag gccaagggtt ggagtggatg ggactgataa acccatctgg gggatcaact     240
tcttatgcgc aaaagttcca aggtcgggtc actatgacaa gggacacatc caccagcact     300
gtttatatgg aactgagcag cctgagatct gaggataccg cagtatatta ctgtgcacgc     360
agtgatagag gcataacggc gactgacgcc ttcgacattt ggggccaagg acaatggtc     420
acggtttcaa gtggaggtgg agggtctggt ggcgggggggt ctggtggtgg aggcagtcag     480
agcgtcctga cccagccgcc tagcgtcagt gtggcccccg gccgcatggc aagataacg     540
tgtggcggaa gcgatattgg gaataagaac gtccactggt atcagcagaa gccagggcag     600
gctcccgtcc tcgtagtata cgacgattat gatcggccca gtggaatccc cgagagattt     660
agcggagta actctgggga tgcagcgaca cttactatct ccactgttga agtaggagac     720
gaggctgact atttttgtca ggtttgggac ggatccggag atccttattg gatgtttggc     780
ggaggtactc aattgaccgt gcttggaggt ggcggaggga gcggggggtgg gggctcaggg     840
ggaggtgggt caggcggggg cggaagtggt ggcgggggtt cccaagtcca actccagcag     900
tcaggacctg gactggtaaa acactctcaa accctgtctc tcacgtgtgc catatctggc     960
gatagtgtat cttcaaactc tgctgcatgg aactggatca ggcaaagtcc atcccgcggc    1020
cttgagtggc tcggtcgaac ctattaccga agcaaatggt acaacgatta tgcggtttca    1080
gtcaagtcaa gaattacgat caaccctgat acgagtaaga accagtttag tttgcaattg    1140
aacagtgtaa ctcccgagga cacggcggtg tactattgtg cgcaagaagt cgaaccgcat    1200
gatgcgttcg atatctgggg gcagggcaca atggtgaccg tatcttctgg cggcggcggc    1260
tctggaggag gaggaagcgg cggagggggga tctgacatac aaatgacaca atccccaagt    1320
tcagtatatg ctagcgtcgg ggataaagtg acaattactt gtagggcttc tcaagacgta    1380
agtggctggt tggcgtggta ccagcaaaag ccgggtctcg cccctcaact ccttatcagc    1440
ggagcttcaa ctcttcaggg agaggtccca agtcgattct caggctctgg ctccgggaca    1500
gatttcaccc tgacaattag ttcactgcaa cccgaggatt tcgcaactta ctactgtcaa    1560
caggccaagt acttcccgta tacgtttggt caaggcacaa aactggagat taggcggcc    1620
```

```
gcaacgacca ctcctgcacc ccgccctccg actccggccc caaccattgc cagccagccc   1680
ctgtccctgc ggccggaagc ctgcagaccg gctgccggcg gagccgtcca tacccgggga   1740
ctggatttcg cctgcgatat ctatatctgg gcaccactcg ccggaacctg tggagtgctg   1800
ctgctgtccc ttgtgatcac cctgtactgc aagcgcggac ggaagaaact cttgtacatc   1860
ttcaagcagc cgttcatgcg ccctgtgcaa accacccaag aagaggacgg gtgctcctgc   1920
cggttcccgg aagaggaaga gggcggctgc gaactgcgcg tgaagttttc ccggtccgcc   1980
gacgctccgg cgtaccagca ggggcaaaac cagctgtaca cgaacttaa cctcggtcgc    2040 cgggaagaat atgacgtgct ggacaagcgg cggggaagag atcccgagat gggtggaaag   2100
ccgcggcgga agaaccctca ggagggcttg tacaacgagc tgcaaaagga caaaatggcc   2160
gaagcctact ccgagattgg catgaaggga gagcgcagac gcgggaaggg acacgatgga   2220
ctgtaccagg gactgtcaac cgcgactaag gacacttacg acgccctgca catgcaggcc   2280 ctgccccgc gc                                                        2292
```

<210> SEQ ID NO 4
<211> LENGTH: 764
<212> TYPE: PRT
<213> ORGANISM: Artificial Sequence
<220> FEATURE:
<223> OTHER INFORMATION: LTG2719 D0024 Leader - Construct CAR 1922

<400> SEQUENCE: 4

```
Met Leu Leu Leu Val Thr Ser Leu Leu Cys Glu Leu Pro His Pro
1               5                   10                  15

Ala Phe Leu Leu Ile Pro Glu Val Gln Leu Val Gln Ser Gly Ala Glu
            20                  25                  30

Val Lys Lys Pro Gly Ala Ser Val Lys Val Ser Cys Lys Ala Ser Gly
        35                  40                  45

Tyr Thr Phe Thr Ser Tyr Tyr Met His Trp Val Arg Gln Ala Pro Gly
    50                  55                  60

Gln Gly Leu Glu Trp Met Gly Leu Ile Asn Pro Ser Gly Gly Ser Thr
65                  70                  75                  80

Ser Tyr Ala Gln Lys Phe Gln Gly Arg Val Thr Met Thr Arg Asp Thr
                85                  90                  95

Ser Thr Ser Thr Val Tyr Met Glu Leu Ser Ser Leu Arg Ser Glu Asp
            100                 105                 110

Thr Ala Val Tyr Tyr Cys Ala Arg Ser Asp Arg Gly Ile Thr Ala Thr
        115                 120                 125

Asp Ala Phe Asp Ile Trp Gly Gln Gly Thr Met Val Thr Val Ser Ser
    130                 135                 140

Gly Gly Gly Gly Ser Gly Gly Gly Ser Gly Gly Gly Gly Ser Gln
145                 150                 155                 160

Ser Val Leu Thr Gln Pro Pro Ser Val Ser Val Ala Pro Gly Arg Met
                165                 170                 175

Ala Lys Ile Thr Cys Gly Gly Ser Asp Ile Gly Asn Lys Asn Val His
            180                 185                 190

Trp Tyr Gln Gln Lys Pro Gly Gln Ala Pro Val Leu Val Val Tyr Asp
        195                 200                 205

Asp Tyr Asp Arg Pro Ser Gly Ile Pro Glu Arg Phe Ser Gly Ser Asn
    210                 215                 220

Ser Gly Asp Ala Ala Thr Leu Thr Ile Ser Thr Val Glu Val Gly Asp
225                 230                 235                 240
```

```
Glu Ala Asp Tyr Phe Cys Gln Val Trp Asp Gly Ser Gly Asp Pro Tyr
                245                 250                 255

Trp Met Phe Gly Gly Gly Thr Gln Leu Thr Val Leu Gly Gly Gly Gly
            260                 265                 270

Gly Ser Gly Gly Gly Gly Ser Gly Gly Gly Ser Gly Gly Gly Gly
        275                 280                 285

Ser Gly Gly Gly Ser Gln Val Gln Leu Gln Gln Ser Gly Pro Gly
        290                 295                 300

Leu Val Lys His Ser Gln Thr Leu Ser Leu Thr Cys Ala Ile Ser Gly
305                 310                 315                 320

Asp Ser Val Ser Ser Asn Ser Ala Ala Trp Asn Trp Ile Arg Gln Ser
                325                 330                 335

Pro Ser Arg Gly Leu Glu Trp Leu Gly Arg Thr Tyr Tyr Arg Ser Lys
            340                 345                 350

Trp Tyr Asn Asp Tyr Ala Val Ser Val Lys Ser Arg Ile Thr Ile Asn
            355                 360                 365

Pro Asp Thr Ser Lys Asn Gln Phe Ser Leu Gln Leu Asn Ser Val Thr
370                 375                 380

Pro Glu Asp Thr Ala Val Tyr Tyr Cys Ala Gln Glu Val Glu Pro His
385                 390                 395                 400

Asp Ala Phe Asp Ile Trp Gly Gln Gly Thr Met Val Thr Val Ser Ser
            405                 410                 415

Gly Gly Gly Gly Ser Gly Gly Gly Ser Gly Gly Gly Gly Ser Asp
            420                 425                 430

Ile Gln Met Thr Gln Ser Pro Ser Ser Val Tyr Ala Ser Val Gly Asp
            435                 440                 445

Lys Val Thr Ile Thr Cys Arg Ala Ser Gln Asp Val Ser Gly Trp Leu
450                 455                 460

Ala Trp Tyr Gln Gln Lys Pro Gly Leu Ala Pro Gln Leu Leu Ile Ser
465                 470                 475                 480

Gly Ala Ser Thr Leu Gln Gly Glu Val Pro Ser Arg Phe Ser Gly Ser
            485                 490                 495

Gly Ser Gly Thr Asp Phe Thr Leu Thr Ile Ser Ser Leu Gln Pro Glu
            500                 505                 510

Asp Phe Ala Thr Tyr Tyr Cys Gln Gln Ala Lys Tyr Phe Pro Tyr Thr
            515                 520                 525

Phe Gly Gln Gly Thr Lys Leu Glu Ile Lys Ala Ala Thr Thr Thr
            530                 535                 540

Pro Ala Pro Arg Pro Pro Thr Pro Ala Pro Thr Ile Ala Ser Gln Pro
545                 550                 555                 560

Leu Ser Leu Arg Pro Glu Ala Cys Arg Pro Ala Ala Gly Gly Ala Val
            565                 570                 575

His Thr Arg Gly Leu Asp Phe Ala Cys Asp Ile Tyr Ile Trp Ala Pro
            580                 585                 590

Leu Ala Gly Thr Cys Gly Val Leu Leu Leu Ser Leu Val Ile Thr Leu
            595                 600                 605

Tyr Cys Lys Arg Gly Arg Lys Lys Leu Leu Tyr Ile Phe Lys Gln Pro
610                 615                 620

Phe Met Arg Pro Val Gln Thr Thr Gln Glu Glu Asp Gly Cys Ser Cys
625                 630                 635                 640

Arg Phe Pro Glu Glu Glu Glu Gly Gly Cys Glu Leu Arg Val Lys Phe
                645                 650                 655
```

```
Ser Arg Ser Ala Asp Ala Pro Ala Tyr Gln Gln Gly Gln Asn Gln Leu
            660                 665                 670

Tyr Asn Glu Leu Asn Leu Gly Arg Arg Glu Glu Tyr Asp Val Leu Asp
        675                 680                 685

Lys Arg Arg Gly Arg Asp Pro Glu Met Gly Gly Lys Pro Arg Arg Lys
690                 695                 700

Asn Pro Gln Glu Gly Leu Tyr Asn Glu Leu Gln Lys Asp Lys Met Ala
705                 710                 715                 720

Glu Ala Tyr Ser Glu Ile Gly Met Lys Gly Glu Arg Arg Arg Gly Lys
                725                 730                 735

Gly His Asp Gly Leu Tyr Gln Gly Leu Ser Thr Ala Thr Lys Asp Thr
            740                 745                 750

Tyr Asp Ala Leu His Met Gln Ala Leu Pro Pro Arg
        755                 760
```

<210> SEQ ID NO 5
<211> LENGTH: 1485
<212> TYPE: DNA
<213> ORGANISM: Artificial Sequence
<220> FEATURE:
<223> OTHER INFORMATION: human CAR19 LTG2065

<400> SEQUENCE: 5

```
atgctgctgc tggtgaccag cctgctgctg tgcgaactgc cgcatccggc gtttctgctg      60
attccggagg tccagctggt acagtctgga gctgaggtga agaagcctgg ggcctcagtg     120
aaggtctcct gcaaggcttc tggatacacc ttcaccagct actatatgca ctgggtgcga    180
caggcccctg gacaagggct tgagtggatg ggattaatca accctagtgg tggtagcaca    240
agctacgcac agaagttcca gggcagagtc accatgacca gggacacgtc cacgagcaca    300
gtctacatgg agctgagcag cctgagatct gaggacacgg ccgtgtatta ctgtgcgaga    360
tcggatcggg gaattaccgc cacggacgct tttgatatct ggggccaagg gacaatggtc    420
accgtctctt caggcggagg aggctccggg ggaggaggtt ccggggggcgg gggttcccag    480
tctgtgctga ctcagccacc ctcggtgtca gtggccccag gcggatggc aagattacc      540
tgtgggggaa gtgacattgg aaataaaaat gtccactggt atcagcagaa gccaggccag    600
gcccctgtcc tggttgtcta tgatgattac gaccggccct cagggatccc tgagcgattc    660
tctggctcca actctgggga cgcggccacc ctgacgatca gcacggtcga agtcggggat    720
gaggccgact atttctgtca ggtgtgggac ggtagtggtg atccttattg gatgttcggc    780
ggagggaccc agctcaccgt tttaggtgcg gccgcaacta ccacccctgc ccctcggccg    840
ccgactccgg ccccaaccat cgcaagccaa cccctctcct tgcgccccga agcttgccgc    900
ccggccgcgg tgagccgt gcatacccgg gggctggact tgcctgcga tatctacatt       960
tgggcccgc tggccggcac ttgcggcgtg ctcctgctgt cgctggtcat caccctttac    1020
tgcaagaggg gccggaagaa gctgctttac atcttcaagc agccgttcat gcggcccgtg    1080
cagacgactc aggaagagga cggatgctcg tgcagattcc ctgaggagga gaggggggga    1140
tgcgaactgc gcgtcaagtt ctcacggtcc gccgacgccc ccgcatatca cagggccag    1200
aatcagctct acaacgagct gaacctggga aggagagag agtacgacgt gctggacaag    1260
cgacgcggac gcgacccgga gatgggggg aaaccacggc ggaaaaaccc tcaggaagga    1320
ctgtacaacg aactccagaa agacaagatg gcggaagcct actcagaaat cgggatgaag    1380
ggagagcgga ggaggggaaa gggtcacgac gggctgtacc agggactgag caccgccact    1440
```

-continued

```
aaggatacct acgatgcctt gcatatgcaa gcactcccac cccgg         1485
```

<210> SEQ ID NO 6
<211> LENGTH: 495
<212> TYPE: PRT
<213> ORGANISM: Artificial Sequence
<220> FEATURE:
<223> OTHER INFORMATION: human CAR19 LTG2065

<400> SEQUENCE: 6

```
Met Leu Leu Leu Val Thr Ser Leu Leu Leu Cys Glu Leu Pro His Pro
1               5                   10                  15

Ala Phe Leu Leu Ile Pro Glu Val Gln Leu Val Gln Ser Gly Ala Glu
            20                  25                  30

Val Lys Lys Pro Gly Ala Ser Val Lys Val Ser Cys Lys Ala Ser Gly
        35                  40                  45

Tyr Thr Phe Thr Ser Tyr Tyr Met His Trp Val Arg Gln Ala Pro Gly
    50                  55                  60

Gln Gly Leu Glu Trp Met Gly Leu Ile Asn Pro Ser Gly Gly Ser Thr
65                  70                  75                  80

Ser Tyr Ala Gln Lys Phe Gln Gly Arg Val Thr Met Thr Arg Asp Thr
                85                  90                  95

Ser Thr Ser Thr Val Tyr Met Glu Leu Ser Ser Leu Arg Ser Glu Asp
            100                 105                 110

Thr Ala Val Tyr Tyr Cys Ala Arg Ser Asp Arg Gly Ile Thr Ala Thr
        115                 120                 125

Asp Ala Phe Asp Ile Trp Gly Gln Gly Thr Met Val Thr Val Ser Ser
    130                 135                 140

Gly Gly Gly Gly Ser Gly Gly Gly Ser Gly Gly Gly Gly Ser Gln
145                 150                 155                 160

Ser Val Leu Thr Gln Pro Pro Ser Val Ser Val Ala Pro Gly Arg Met
                165                 170                 175

Ala Lys Ile Thr Cys Gly Gly Ser Asp Ile Gly Asn Lys Asn Val His
            180                 185                 190

Trp Tyr Gln Gln Lys Pro Gly Gln Ala Pro Val Leu Val Val Tyr Asp
        195                 200                 205

Asp Tyr Asp Arg Pro Ser Gly Ile Pro Glu Arg Phe Ser Gly Ser Asn
    210                 215                 220

Ser Gly Asp Ala Ala Thr Leu Thr Ile Ser Thr Val Glu Val Gly Asp
225                 230                 235                 240

Glu Ala Asp Tyr Phe Cys Gln Val Trp Asp Gly Ser Gly Asp Pro Tyr
                245                 250                 255

Trp Met Phe Gly Gly Gly Thr Gln Leu Thr Val Leu Gly Ala Ala Ala
            260                 265                 270

Thr Thr Thr Pro Ala Pro Arg Pro Pro Thr Pro Ala Pro Thr Ile Ala
        275                 280                 285

Ser Gln Pro Leu Ser Leu Arg Pro Glu Ala Cys Arg Pro Ala Ala Gly
    290                 295                 300

Gly Ala Val His Thr Arg Gly Leu Asp Phe Ala Cys Asp Ile Tyr Ile
305                 310                 315                 320

Trp Ala Pro Leu Ala Gly Thr Cys Gly Val Leu Leu Leu Ser Leu Val
                325                 330                 335

Ile Thr Leu Tyr Cys Lys Arg Gly Arg Lys Lys Leu Leu Tyr Ile Phe
            340                 345                 350

Lys Gln Pro Phe Met Arg Pro Val Gln Thr Thr Gln Glu Glu Asp Gly
```

```
            355                 360                 365
Cys Ser Cys Arg Phe Pro Glu Glu Glu Gly Gly Cys Glu Leu Arg
        370                 375                 380

Val Lys Phe Ser Arg Ser Ala Asp Ala Pro Ala Tyr Gln Gln Gly Gln
385                 390                 395                 400

Asn Gln Leu Tyr Asn Glu Leu Asn Leu Gly Arg Arg Glu Glu Tyr Asp
                405                 410                 415

Val Leu Asp Lys Arg Arg Gly Arg Asp Pro Glu Met Gly Gly Lys Pro
            420                 425                 430

Arg Arg Lys Asn Pro Gln Glu Gly Leu Tyr Asn Glu Leu Gln Lys Asp
        435                 440                 445

Lys Met Ala Glu Ala Tyr Ser Glu Ile Gly Met Lys Gly Glu Arg Arg
    450                 455                 460

Arg Gly Lys Gly His Asp Gly Leu Tyr Gln Gly Leu Ser Thr Ala Thr
465                 470                 475                 480

Lys Asp Thr Tyr Asp Ala Leu His Met Gln Ala Leu Pro Pro Arg
                485                 490                 495

<210> SEQ ID NO 7
<211> LENGTH: 1470
<212> TYPE: DNA
<213> ORGANISM: Artificial Sequence
<220> FEATURE:
<223> OTHER INFORMATION: mouse scFv CAR19 LTG1538

<400> SEQUENCE: 7
atgcttctcc tggtcaccct cctgctcctc tgcgaactgc ctcaccctgc cttccttctg      60
attcctgaca ttcagatgac tcagaccacc tcttccttgt ccgcgtcact gggagacaga     120
gtgaccatct cgtgtcgcgc aagccaggat atctccaagt acctgaactg gtaccaacag    180
aagcccgacg ggactgtgaa gctgctgatc taccacacct cacgcctgca cagcggagtg    240
ccaagcagat tctccggctc cggctcggga accgattact cgcttaccat agcaacctc     300
gagcaggagg acatcgctac ctacttctgc cagcaaggaa ataccctgcc ctacaccttc    360
ggcggaggaa ccaaattgga aatcaccggc ggaggaggct ccggggagg aggttccggg    420
ggcgggggtt ccgaagtgaa gctccaggag tccggccccg gcctggtggc cgtcgcaa     480
tcactctctg tgacctgtac cgtgtcggga gtgtccctgc ctgattacgg cgtgagctgg    540
attcggcagc cgccgcggaa gggcctggaa tggctgggtg tcatctgggg atccgagact    600
acctactaca actcggccct gaagtccgc ctgactatca tcaaagacaa ctcgaagtcc    660
caggtctttc tgaagatgaa ctccctgcaa actgacgaca ccgccatcta ttactgtgct    720
aagcactact actacggtgg aagctatgct atggactact gggggcaagg cacttcggtg    780
actgtgtcaa gcgcggccgc aactaccacc cctgcccctc ggccgccgac tccggcccca    840
accatcgcaa gccaacccct ctccttgcgc cccgaagctt gccgcccggc cgcgggtgga    900
gccgtgcata cccgggggct ggactttgcc tgcgatatct catttgggc cccgctggcc    960
ggcacttgcg gcgtgctcct gctgtcgctg gtcatcaccc tttactgcaa gagggccgg   1020
aagaagctgc tttacatctt caagcagccg ttcatgcggc ccgtcagac gactcaggaa   1080
gaggacggat gctcgtgcag attccctgag gaggaagagg ggggatgcga actgcgcgtc   1140
aagttctcac ggtccgccga cgccccgca tatcaacagg gccagaatca gctctacaac   1200
gagctgaact ggaaggag agaggagtac gacgtgctgg acaagcgacg cggacgcgac   1260
ccggagatgg gggggaaacc acggcggaaa aaccctcagg aaggactgta caacgaactc   1320
```

```
cagaaagaca agatggcgga agcctactca gaaatcggga tgaagggaga gcggaggagg    1380
ggaaagggtc acgacgggct gtaccaggga ctgagcaccg ccactaagga tacctacgat    1440
gccttgcata tgcaagcact cccaccccgg                                    1470
```

<210> SEQ ID NO 8
<211> LENGTH: 489
<212> TYPE: PRT
<213> ORGANISM: Artificial Sequence
<220> FEATURE:
<223> OTHER INFORMATION: mouse scFv CAR19 LTG1538

<400> SEQUENCE: 8

```
Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Gly Gly Gly Ser Gly Gly Gly Ser Gly Gly Gly Ser
    130                 135                 140

Glu Val Lys Leu Gln Glu Ser Gly Pro Gly Leu Val Ala Pro Ser Gln
145                 150                 155                 160

Ser Leu Ser Val Thr Cys Thr Val Ser Gly Val Ser Leu Pro Asp Tyr
                165                 170                 175

Gly Val Ser Trp Ile Arg Gln Pro Pro Arg Lys Gly Leu Glu Trp Leu
            180                 185                 190

Gly Val Ile Trp Gly Ser Glu Thr Thr Tyr Tyr Asn Ser Ala Leu Lys
        195                 200                 205

Ser Arg Leu Thr Ile Ile Lys Asp Asn Ser Lys Ser Gln Val Phe Leu
    210                 215                 220

Lys Met Asn Ser Leu Gln Thr Asp Asp Thr Ala Ile Tyr Tyr Cys Ala
225                 230                 235                 240

Lys His Tyr Tyr Tyr Gly Gly Ser Tyr Ala Met Asp Tyr Trp Gly Gln
                245                 250                 255

Gly Thr Ser Val Thr Val Ser Ser Ala Ala Thr Thr Thr Pro Ala
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
    290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335
```

Lys Arg Gly Arg Lys Lys Leu Leu Tyr Ile Phe Lys Gln Pro Phe Met
            340                 345                 350

Arg Pro Val Gln Thr Thr Gln Glu Glu Asp Gly Cys Ser Cys Arg Phe
            355                 360                 365

Pro Glu Glu Glu Glu Gly Gly Cys Glu Leu Arg Val Lys Phe Ser Arg
            370                 375                 380

Ser Ala Asp Ala Pro Ala Tyr Gln Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
            420                 425                 430

Gln Glu Gly Leu Tyr Asn Glu Leu Gln Lys Asp Lys Met Ala Glu Ala
            435                 440                 445

Tyr Ser Glu Ile Gly Met Lys Gly Glu Arg Arg Arg Gly Lys Gly His
            450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro
                485

<210> SEQ ID NO 9
<211> LENGTH: 1476
<212> TYPE: DNA
<213> ORGANISM: Artificial Sequence
<220> FEATURE:
<223> OTHER INFORMATION: CAR22 LTG2209

<400> SEQUENCE: 9

```
atgcttcttt tggtgacttc cctttttgctg tgcgagttgc cacacccgc cttcctgctt      60 attccccagg tacagcttca acagagtggg ccgggactgg tgaaacactc ccaaacactt     120
tctctgacgt gcgctatatc aggtgactct gtttcatcta attctgctgc gtggaactgg     180 attgacaat ctcccagtcg cgggttggaa tggctgggac gaacatatta tcggtctaag     240
tggtataacg attatgctgt atctgttaaa tctcgaatta cgattaatcc tgacacctcc     300
aagaaccagt tctccctcca gttgaactca gtcacaccgg aagacactgc ggtctactat     360
tgcgctcaag aagtcgagcc acatgatgca ttcgacatct ggggccaggg aacgatggtc     420
accgtcagca gtggcggcgg cggatctggg ggtggcggtt ctggcggtgg aggatcagac     480
atacaaatga cgcagagtcc ctcaagtgtg tacgcgagtg tgggggataa ggtaactatt     540
acgtgcagag cgtcacagga tgttagtgga tggcttgcct ggtatcagca gaagccaggc     600
cttgctccac agctccttat cagtggtgct tctacacttc agggcgaggt tccgagtaga     660
ttctctggtt ctggatctgg tactgacttc actcttacaa tttcttcttt gcaaccagaa     720
gactttgcga cttattactg ccaacaggcc aaatacttcc cttatacatt tggccaaggt     780
accaagttgg agataaaggc ggccgcaact accacccctg cccctcggcc gccgactccg     840
gccccaacca tcgcaagcca acccctctcc ttgcgcccg aagcttgccg cccggccgcg     900
ggtggagccg tgcatacccg ggggctggac tttgcctgcg atatctacat ttgggccccg     960
ctggccggca cttgcggcgt gctcctgctg tcgctggtca tcacccttta ctgcaagagg    1020
ggccggaaga gctgctttta catcttcaag cagccgttca tgcggcccgt gcagacgact    1080
caggaagagg acggatgctc gtgcagattc cctgaggagg aagagggggg atgcgaactg    1140
```

-continued

```
cgcgtcaagt tctcacggtc cgccgacgcc cccgcatatc aacagggcca gaatcagctc     1200
tacaacgagc tgaacctggg aaggagagag gagtacgacg tgctggacaa gcgacgcgga     1260
cgcgacccgg agatgggggg gaaaccacgg cggaaaaacc ctcaggaagg actgtacaac     1320
gaactccaga agacaagat ggcggaagcc tactcagaaa tcgggatgaa gggagagcgg      1380
aggaggggaa agggtcacga cgggctgtac cagggactga gcaccgccac taaggatacc     1440
tacgatgcct tgcatatgca agcactccca ccccgg                              1476
```

<210> SEQ ID NO 10
<211> LENGTH: 492
<212> TYPE: PRT
<213> ORGANISM: Artificial Sequence
<220> FEATURE:
<223> OTHER INFORMATION: CD22A 1495

<400> SEQUENCE: 10

```
Met Leu Leu Leu Val Thr Ser Leu Leu Cys Glu Leu Pro His Pro
1               5                   10                  15

Ala Phe Leu Leu Ile Pro Gln Val Gln Leu Gln Gln Ser Gly Pro Gly
                20                  25                  30

Leu Val Lys His Ser Gln Thr Leu Ser Leu Thr Cys Ala Ile Ser Gly
            35                  40                  45

Asp Ser Val Ser Ser Asn Ser Ala Ala Trp Asn Trp Ile Arg Gln Ser
        50                  55                  60

Pro Ser Arg Gly Leu Glu Trp Leu Gly Arg Thr Tyr Tyr Arg Ser Lys
65                  70                  75                  80

Trp Tyr Asn Asp Tyr Ala Val Ser Val Lys Ser Arg Ile Thr Ile Asn
                85                  90                  95

Pro Asp Thr Ser Lys Asn Gln Phe Ser Leu Gln Leu Asn Ser Val Thr
            100                 105                 110

Pro Glu Asp Thr Ala Val Tyr Tyr Cys Ala Gln Glu Val Glu Pro His
        115                 120                 125

Asp Ala Phe Asp Ile Trp Gly Gln Gly Thr Met Val Thr Val Ser Ser
    130                 135                 140

Gly Gly Gly Gly Ser Gly Gly Gly Ser Gly Gly Gly Gly Ser Asp
145                 150                 155                 160

Ile Gln Met Thr Gln Ser Pro Ser Ser Val Tyr Ala Ser Val Gly Asp
                165                 170                 175

Lys Val Thr Ile Thr Cys Arg Ala Ser Gln Asp Val Ser Gly Trp Leu
            180                 185                 190

Ala Trp Tyr Gln Gln Lys Pro Gly Leu Ala Pro Gln Leu Leu Ile Ser
        195                 200                 205

Gly Ala Ser Thr Leu Gln Gly Glu Val Pro Ser Arg Phe Ser Gly Ser
    210                 215                 220

Gly Ser Gly Thr Asp Phe Thr Leu Thr Ile Ser Ser Leu Gln Pro Glu
225                 230                 235                 240

Asp Phe Ala Thr Tyr Tyr Cys Gln Gln Ala Lys Tyr Phe Pro Tyr Thr
                245                 250                 255

Phe Gly Gln Gly Thr Lys Leu Glu Ile Lys Ala Ala Ala Thr Thr Thr
            260                 265                 270

Pro Ala Pro Arg Pro Pro Thr Pro Ala Pro Thr Ile Ala Ser Gln Pro
        275                 280                 285

Leu Ser Leu Arg Pro Glu Ala Cys Arg Pro Ala Ala Gly Gly Ala Val
    290                 295                 300
```

His Thr Arg Gly Leu Asp Phe Ala Cys Asp Ile Tyr Ile Trp Ala Pro
305                 310                 315                 320

Leu Ala Gly Thr Cys Gly Val Leu Leu Ser Leu Val Ile Thr Leu
                325                 330                 335

Tyr Cys Lys Arg Gly Lys Lys Leu Leu Tyr Ile Phe Lys Gln Pro
            340                 345                 350

Phe Met Arg Pro Val Gln Thr Thr Gln Glu Glu Asp Gly Cys Ser Cys
                355                 360                 365

Arg Phe Pro Glu Glu Glu Gly Gly Cys Glu Leu Arg Val Lys Phe
    370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
                420                 425                 430

Asn Pro Gln Glu Gly Leu Tyr Asn Glu Leu Gln Lys Asp Lys Met Ala
                435                 440                 445

Glu Ala Tyr Ser Glu Ile Gly Met Lys Gly Glu Arg Arg Arg Gly Lys
450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490

<210> SEQ ID NO 11
<211> LENGTH: 66
<212> TYPE: DNA
<213> ORGANISM: Artificial Sequence
<220> FEATURE:
<223> OTHER INFORMATION: leader/signal peptide sequence

<400> SEQUENCE: 11
atgctgctgc tggtgaccag cctgctgctg tgcgaactgc cgcatccggc gtttctgctg    60
attccg                                                               66

<210> SEQ ID NO 12
<211> LENGTH: 22
<212> TYPE: PRT
<213> ORGANISM: Artificial Sequence
<220> FEATURE:
<223> OTHER INFORMATION: leader/signal peptide sequence

<400> SEQUENCE: 12

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 13

<400> SEQUENCE: 13

000

<210> SEQ ID NO 14

<400> SEQUENCE: 14

000

<210> SEQ ID NO 15

<400> SEQUENCE: 15

000

<210> SEQ ID NO 16

<400> SEQUENCE: 16

000

<210> SEQ ID NO 17

<400> SEQUENCE: 17

000

<210> SEQ ID NO 18

<400> SEQUENCE: 18

000

<210> SEQ ID NO 19

<400> SEQUENCE: 19

000

<210> SEQ ID NO 20

<400> SEQUENCE: 20

000

<210> SEQ ID NO 21

<400> SEQUENCE: 21

000

<210> SEQ ID NO 22

<400> SEQUENCE: 22

000

<210> SEQ ID NO 23

<400> SEQUENCE: 23

000

<210> SEQ ID NO 24

<400> SEQUENCE: 24

000

<210> SEQ ID NO 25

<400> SEQUENCE: 25

000

```
<210> SEQ ID NO 26
<400> SEQUENCE: 26
000

<210> SEQ ID NO 27
<400> SEQUENCE: 27
000

<210> SEQ ID NO 28
<400> SEQUENCE: 28
000

<210> SEQ ID NO 29
<400> SEQUENCE: 29
000

<210> SEQ ID NO 30
<400> SEQUENCE: 30
000

<210> SEQ ID NO 31
<400> SEQUENCE: 31
000

<210> SEQ ID NO 32
<400> SEQUENCE: 32
000

<210> SEQ ID NO 33
<400> SEQUENCE: 33
000

<210> SEQ ID NO 34
<400> SEQUENCE: 34
000

<210> SEQ ID NO 35
<211> LENGTH: 66
<212> TYPE: DNA
<213> ORGANISM: Artificial Sequence
<220> FEATURE:
<223> OTHER INFORMATION: DNA CD8 transmembrane domain

<400> SEQUENCE: 35
atttgggccc cgctggccgg cacttgcggc gtgctcctgc tgtcgctggt catcacccTT    60
tactgc                                                              66

<210> SEQ ID NO 36
<211> LENGTH: 22
```

<212> TYPE: PRT
<213> ORGANISM: Artificial Sequence
<220> FEATURE:
<223> OTHER INFORMATION: CD8 transmembrane domain

<400> SEQUENCE: 36

Ile Trp Ala Pro Leu Ala Gly Thr Cys Gly Val Leu Leu Leu Ser Leu
1               5                   10                  15

Val Ile Thr Leu Tyr Cys
            20

<210> SEQ ID NO 37
<211> LENGTH: 141
<212> TYPE: DNA
<213> ORGANISM: Artificial Sequence
<220> FEATURE:
<223> OTHER INFORMATION: DNA CD8 hinge domain

<400> SEQUENCE: 37
actaccaccc ctgcccctcg gcgccgact ccggccccaa ccatcgcaag ccaaccctc      60 tccttgcgcc ccgaagcttg ccgcccggcc gcgggtggag ccgtgcatac ccgggggctg    120
gactttgcct gcgatatcta c                                             141

<210> SEQ ID NO 38
<211> LENGTH: 47
<212> TYPE: PRT
<213> ORGANISM: Artificial Sequence
<220> FEATURE:
<223> OTHER INFORMATION: CD8 hinge domain

<400> SEQUENCE: 38

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp Ile Tyr
            35                  40                  45

<210> SEQ ID NO 39
<211> LENGTH: 69
<212> TYPE: PRT
<213> ORGANISM: Artificial Sequence
<220> FEATURE:
<223> OTHER INFORMATION: amino acid numbers 137 to 206 hinge and
      transmembrane region of CD8.alpha.

<400> SEQUENCE: 39

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp Ile Tyr Ile
            35                  40                  45

Trp Ala Pro Leu Ala Gly Thr Cys Gly Val Leu Leu Leu Ser Leu Val
        50                  55                  60

Ile Thr Leu Tyr Cys
65

<210> SEQ ID NO 40
<211> LENGTH: 126
<212> TYPE: DNA
<213> ORGANISM: Artificial Sequence

```
<220> FEATURE:
<223> OTHER INFORMATION: signaling domain of 4-1BB

<400> SEQUENCE: 40
aagaggggcc ggaagaagct gctttacatc ttcaagcagc cgttcatgcg gcccgtgcag        60
acgactcagg aagaggacgg atgctcgtgc agattccctg aggaggaaga gggggatgc        120 gaactg                                                                  126

<210> SEQ ID NO 41
<211> LENGTH: 42
<212> TYPE: PRT
<213> ORGANISM: Artificial Sequence
<220> FEATURE:
<223> OTHER INFORMATION: signaling domain of 4-1BB

<400> SEQUENCE: 41

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 42
<211> LENGTH: 336
<212> TYPE: DNA
<213> ORGANISM: Artificial Sequence
<220> FEATURE:
<223> OTHER INFORMATION: signaling domain of CD3-zeta

<400> SEQUENCE: 42
cgcgtcaagt tctcacggtc cgccgacgcc cccgcatatc aacagggcca gaatcagctc        60
tacaacgagc tgaacctggg aaggagagag gagtacgacg tgctggacaa gcgacgcgga       120
cgcgacccgg agatgggggg gaaaccacgg cggaaaaacc ctcaggaagg actgtacaac       180
gaactccaga aagacaagat ggcggaagcc tactcagaaa tcgggatgaa gggagagcgg       240 aggagggaa agggtcacga cgggctgtac cagggactga gcaccgccac taaggatacc       300
tacgatgcct tgcatatgca agcactccca ccccgg                                 336

<210> SEQ ID NO 43
<211> LENGTH: 112
<212> TYPE: PRT
<213> ORGANISM: Artificial Sequence
<220> FEATURE:
<223> OTHER INFORMATION: CD3zeta

<400> SEQUENCE: 43

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95
```

Thr Lys Asp Thr Tyr Asp Ala Leu His Met Gln Ala Leu Pro Pro Arg
            100                 105                 110

<210> SEQ ID NO 44
<211> LENGTH: 726
<212> TYPE: DNA
<213> ORGANISM: Artificial Sequence
<220> FEATURE:
<223> OTHER INFORMATION: ScFv CD19 (FMC63)

<400> SEQUENCE: 44

```
gacattcaga tgactcagac cacctcttcc ttgtccgcgt cactgggaga cagagtgacc      60
atctcgtgtc gcgcaagcca ggatatctcc aagtacctga actggtacca acagaagccc    120
gacgggactg tgaagctgct gatctaccac acctcacgcc tgcacagcgg agtgccaagc    180
agattctccg gctccggctc gggaaccgat tactcgctta ccattagcaa cctcgagcag    240
gaggacatcg ctacctactt ctgccagcaa ggaaataccc tgccctacac cttcggcgga    300
ggaaccaaat tggaaatcac cggcggagga ggctccgggg aggaggttc cggggggcggg    360
ggttccgaag tgaagctcca ggagtccggc cccggcctgg tggcgccgtc gcaatcactc    420
tctgtgacct gtaccgtgtc gggagtgtcc ctgcctgatt acggcgtgag ctggattcgg    480
cagccgccgc ggaagggcct ggaatggctg gtgtcatct ggggatccga gactacctac    540
tacaactcgg ccctgaagtc ccgcctgact atcatcaaag acaactcgaa gtcccaggtc    600
tttctgaaga tgaactccct gcaaactgac gacaccgcca tctattactg tgctaagcac    660
tactactacg gtggaagcta tgctatggac tactggggc aaggcacttc ggtgactgtg    720
tcaagc                                                               726
```

<210> SEQ ID NO 45
<211> LENGTH: 242
<212> TYPE: PRT
<213> ORGANISM: Artificial Sequence
<220> FEATURE:
<223> OTHER INFORMATION: ScFv CD19 (FMC63)

<400> SEQUENCE: 45

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Gly Gly Gly Ser
            100                 105                 110

Gly Gly Gly Gly Ser Gly Gly Gly Ser Glu Val Lys Leu Gln Glu
        115                 120                 125

Ser Gly Pro Gly Leu Val Ala Pro Ser Gln Ser Leu Ser Val Thr Cys
    130                 135                 140

Thr Val Ser Gly Val Ser Leu Pro Asp Tyr Gly Val Ser Trp Ile Arg
145                 150                 155                 160

Gln Pro Pro Arg Lys Gly Leu Glu Trp Leu Gly Val Ile Trp Gly Ser
            165                 170                 175

Glu Thr Thr Tyr Tyr Asn Ser Ala Leu Lys Ser Arg Leu Thr Ile Ile
        180                 185                 190

Lys Asp Asn Ser Lys Ser Gln Val Phe Leu Lys Met Asn Ser Leu Gln
    195                 200                 205

Thr Asp Asp Thr Ala Ile Tyr Tyr Cys Ala Lys His Tyr Tyr Gly
    210                 215                 220

Gly Ser Tyr Ala Met Asp Tyr Trp Gly Gln Gly Thr Ser Val Thr Val
225                 230                 235                 240

Ser Ser

<210> SEQ ID NO 46
<211> LENGTH: 1491
<212> TYPE: DNA
<213> ORGANISM: Artificial Sequence
<220> FEATURE:
<223> OTHER INFORMATION: anti-CD33 CAR (LTG1936)

<400> SEQUENCE: 46

| | | | | | |
|---|---|---|---|---|---|
| atgctgctgc | tggtgaccag | cctgctgctg | tgcgaactgc | cgcatccggc | gtttctgctg | 60 |
| attccgcagg | tgcagctggt | gcaatctggg | gcagaggtga | aaaagcccgg | ggagtctctg | 120 |
| aggatctcct | gtaagggttc | tggattcagt | tttcccacct | actggatcgg | ctgggtgcgc | 180 |
| cagatgcccg | ggaaaggcct | ggagtggatg | gggatcatct | atcctggtga | ctctgatacc | 240 |
| agatacagcc | cgtccttcca | aggccaggtc | accatctcag | ccgacaagtc | catcagcacc | 300 |
| gcctacctgc | agtggagcag | cctgaaggcc | tcggacaccg | ccatgtatta | ctgtgcgaga | 360 |
| ctagttggag | atggctacaa | tacggggggct | tttgatatct | ggggccaagg | gacaatggtc | 420 |
| accgtctctt | caggaggtgg | cgggtctggt | ggtggcggta | gcggtggtgg | cggatccgat | 480 |
| attgtgatga | cccacactcc | actctctctg | tccgtcaccc | ctggacagcc | ggcctccatc | 540 |
| tcctgcaagt | ctagtcagag | cctcctgcat | agtaatggaa | agacctattt | gtattggtac | 600 |
| ctgcagaagc | caggccagcc | tccacagctc | ctgatctatg | agcttccaa | ccggttctct | 660 |
| ggagtgccag | acaggttcag | tggcagcggg | tcaggacag | atttcacact | gaaaatcagc | 720 |
| cgggtggagc | tgaggatgt | tgggggtttat | tactgcatgc | aaagtataca | gcttcctatc | 780 |
| accttcggcc | aagggacacg | actggagatt | aaagcggccg | caactaccac | ccctgcccct | 840 |
| cggccgccga | ctccggcccc | aaccatcgca | agccaacccc | tctccttgcg | ccccgaagct | 900 |
| tgccgcccgg | ccgcgggtgg | agccgtgcat | acccgggggc | tggactttgc | ctgcgatatc | 960 |
| tacatttggg | ccccgctggc | cggcacttgc | ggcgtgctcc | tgctgtcgct | ggtcatcacc | 1020 |
| ctttactgca | gaggggccg | gaagaagctg | ctttacatct | tcaagcagcc | gttcatgcgg | 1080 |
| cccgtgcaga | cgactcagga | agaggacgga | tgctcgtgca | gattccctga | ggaggaagag | 1140 |
| gggggatgcg | aactgcgcgt | caagttctca | cggtccgccg | acgccccgc | atatcaacag | 1200 |
| ggccagaatc | agctctacaa | cgagctgaac | ctgggaagga | gaggagta | cgacgtgctg | 1260 |
| gacaagcgac | gcgacgcgcga | cccggagatg | ggggggaaac | cacggcggaa | aaaccctcag | 1320 |
| gaaggactgt | acaacgaact | ccagaaagac | aagatggcgg | aagcctactc | agaaatcggg | 1380 |
| atgaagggag | agcggaggag | gggaaagggt | cacgacgggc | tgtaccaggg | actgagcacc | 1440 |
| gccactaagg | atacctacga | tgccttgcat | atgcaagcac | tcccaccccg | g | 1491 |

<210> SEQ ID NO 47
<211> LENGTH: 496
<212> TYPE: PRT
<213> ORGANISM: Artificial Sequence
<220> FEATURE:
<223> OTHER INFORMATION: anti-CD33 CAR (LTG1936)

<400> SEQUENCE: 47

```
Met Leu Leu Leu Val Thr Ser Leu Leu Leu Cys Glu Leu Pro His Pro
1               5                   10                  15

Ala Phe Leu Leu Ile Pro Gln Val Gln Leu Val Gln Ser Gly Ala Glu
            20                  25                  30

Val Lys Lys Pro Gly Glu Ser Leu Arg Ile Ser Cys Lys Gly Ser Gly
        35                  40                  45

Phe Ser Phe Pro Thr Tyr Trp Ile Gly Trp Val Arg Gln Met Pro Gly
    50                  55                  60

Lys Gly Leu Glu Trp Met Gly Ile Ile Tyr Pro Gly Asp Ser Asp Thr
65                  70                  75                  80

Arg Tyr Ser Pro Ser Phe Gln Gly Gln Val Thr Ile Ser Ala Asp Lys
                85                  90                  95

Ser Ile Ser Thr Ala Tyr Leu Gln Trp Ser Ser Leu Lys Ala Ser Asp
            100                 105                 110

Thr Ala Met Tyr Tyr Cys Ala Arg Leu Val Gly Asp Gly Tyr Asn Thr
        115                 120                 125

Gly Ala Phe Asp Ile Trp Gly Gln Gly Thr Met Val Thr Val Ser Ser
    130                 135                 140

Gly Gly Gly Gly Ser Gly Gly Gly Ser Gly Gly Gly Gly Ser Asp
145                 150                 155                 160

Ile Val Met Thr His Thr Pro Leu Ser Leu Ser Val Thr Pro Gly Gln
                165                 170                 175

Pro Ala Ser Ile Ser Cys Lys Ser Ser Gln Ser Leu Leu His Ser Asn
            180                 185                 190

Gly Lys Thr Tyr Leu Tyr Trp Tyr Leu Gln Lys Pro Gly Gln Pro Pro
        195                 200                 205

Gln Leu Leu Ile Tyr Gly Ala Ser Asn Arg Phe Ser Gly Val Pro Asp
    210                 215                 220

Arg Phe Ser Gly Ser Gly Ser Gly Thr Asp Phe Thr Leu Lys Ile Ser
225                 230                 235                 240

Arg Val Glu Ala Glu Asp Val Gly Val Tyr Tyr Cys Met Gln Ser Ile
                245                 250                 255

Gln Leu Pro Ile Thr Phe Gly Gln Gly Thr Arg Leu Glu Ile Lys Ala
            260                 265                 270

Ala Ala Thr Thr Thr Pro Ala Pro Arg Pro Pro Thr Pro Ala Pro Thr
        275                 280                 285

Ile Ala Ser Gln Pro Leu Ser Leu Arg Pro Glu Ala Cys Arg Pro Ala
    290                 295                 300

Ala Gly Gly Ala Val His Thr Arg Gly Leu Asp Phe Ala Cys Asp Ile
305                 310                 315                 320

Tyr Ile Trp Ala Pro Leu Ala Gly Thr Cys Gly Val Leu Leu Leu Ser
                325                 330                 335

Leu Val Ile Thr Leu Tyr Cys Lys Arg Gly Arg Lys Lys Leu Leu Tyr
            340                 345                 350

Ile Phe Lys Gln Pro Phe Met Arg Pro Val Gln Thr Thr Gln Glu Glu
        355                 360                 365

Asp Gly Cys Ser Cys Arg Phe Pro Glu Glu Glu Glu Gly Gly Cys Glu
```

| | | | | | | | | | | | |
|---|---|---|---|---|---|---|---|---|---|---|---|
| | | | 370 | | | 375 | | | 380 | | |
| Leu | Arg | Val | Lys | Phe | Ser | Arg | Ser | Ala | Asp | Ala | Pro | Ala | Tyr | Gln | Gln |
| 385 | | | | | 390 | | | | | 395 | | | | | 400 |

| Gly | Gln | Asn | Gln | Leu | Tyr | Asn | Glu | Leu | Asn | Leu | Gly | Arg | Arg | Glu | Glu |
|---|---|---|---|---|---|---|---|---|---|---|---|---|---|---|---|
| | | | | 405 | | | | | 410 | | | | | 415 | |

| Tyr | Asp | Val | Leu | Asp | Lys | Arg | Arg | Gly | Arg | Asp | Pro | Glu | Met | Gly | Gly |
|---|---|---|---|---|---|---|---|---|---|---|---|---|---|---|---|
| | | | 420 | | | | | 425 | | | | | 430 | | |

| Lys | Pro | Arg | Arg | Lys | Asn | Pro | Gln | Glu | Gly | Leu | Tyr | Asn | Glu | Leu | Gln |
|---|---|---|---|---|---|---|---|---|---|---|---|---|---|---|---|
| | | | 435 | | | | | 440 | | | | | 445 | | |

| Lys | Asp | Lys | Met | Ala | Glu | Ala | Tyr | Ser | Glu | Ile | Gly | Met | Lys | Gly | Glu |
|---|---|---|---|---|---|---|---|---|---|---|---|---|---|---|---|
| | | | 450 | | | | | 455 | | | | | 460 | | |

| Arg | Arg | Arg | Gly | Lys | Gly | His | Asp | Gly | Leu | Tyr | Gln | Gly | Leu | Ser | Thr |
|---|---|---|---|---|---|---|---|---|---|---|---|---|---|---|---|
| 465 | | | | | 470 | | | | | 475 | | | | | 480 |

| Ala | Thr | Lys | Asp | Thr | Tyr | Asp | Ala | Leu | His | Met | Gln | Ala | Leu | Pro | Pro |
|---|---|---|---|---|---|---|---|---|---|---|---|---|---|---|---|
| | | | | 485 | | | | | 490 | | | | | 495 | |

<210> SEQ ID NO 48
<211> LENGTH: 1476
<212> TYPE: DNA
<213> ORGANISM: Artificial Sequence
<220> FEATURE:
<223> OTHER INFORMATION: anti-mesothelin CAR (LTG1904)

<400> SEQUENCE: 48

```
atgctgctgc tggtgaccag cctgctgctg tgcgaactgc cgcatccggc gtttctgctg      60
attccggagg tccagctggt acagtctggg ggaggcttgg tacagcctgg ggggtccctg     120
agactctcct gtgcagcctc tggattcacc tttgatgatt atgccatgca ctgggtccgg     180
caagctccag ggaagggcct ggagtgggtc tcaggtatta gttggaatag tggtagcata     240
ggctatgcgg actctgtgaa gggccgattc accatctcca gagacaacgc caagaactcc     300
ctgtatctgc aaatgaacag tctgagagct gaggacacgg ccttgtatta ctgtgcaaaa     360
gatttatcgt cagtggctgg acccttttaac tactggggcc agggcaccct ggtcaccgtc     420
tcctcaggag gtggcgggtc tggtggaggc ggtagcggcg gtggcggatc ctcttctgag     480
ctgactcagg accctgctgt gtctgtggcc ttggacagag cagtcaggat cacatgccaa     540
ggagacagcc tcagaagcta ttatgcaagc tggtaccagc agaagccagg acaggcccct     600
gtacttgtca tctatggtaa aaacaaccgg ccctcaggga tcccagaccg attctctggc     660
tccagctcag gaaacacagc ttccttgacc atcactgggg ctcaggcgga ggatgaggct     720
gactattact gtaactcccg ggacagcagt ggtaaccatc tggtattcgg cggaggcacc     780
cagctgaccg tcctcggtgc ggccgcaact accacccctg cccctcggcc gccgactccg     840
gccccaacca tcgcaagcca acccctctcc ttgcgccccg aagcttgccg cccggccgcg     900
ggtggagccg tgcatacccg ggggctggac tttgcctgcg atatctacat ttgggccccg     960
ctggccggca cttgcggcgt gctcctgctg tcgctggtca tcaccctttta ctgcaagagg    1020
ggccggaaga agctgctttta catcttcaag cagccgttca tgcggcccgt gcagacgact    1080
caggaagagg acggatgctc gtgcagattc cctgaggagg aagaggggggg atgcgaactg    1140
cgcgtcaagt tctcacggtc cgccgacgcc ccgcatatc aacagggcca gaatcagctc    1200
tacaacgagc tgaacctggg aaggagagag gagtacgacg tgctggacaa gcgacgcgga    1260
cgcgaccccg agatgggggg gaaaccacgc cggaaaaaacc ctcaggaagg actgtacaac    1320
gaactccaga agacaagat ggcggaagcc tactcagaaa tcgggatgaa gggagagcgg    1380
```

-continued

```
aggagggaa aaggtcacga cgggctgtac cagggactga gcaccgccac taaggatacc    1440
tacgatgcct tgcatatgca agcactccca ccccgg                             1476
```

<210> SEQ ID NO 49
<211> LENGTH: 492
<212> TYPE: PRT
<213> ORGANISM: Artificial Sequence
<220> FEATURE:
<223> OTHER INFORMATION: anti-mesothelin CAR (LTG1904)

<400> SEQUENCE: 49

```
Met Leu Leu Leu Val Thr Ser Leu Leu Cys Glu Leu Pro His Pro
1               5                   10                  15

Ala Phe Leu Leu Ile Pro Glu Val Gln Leu Val Gln Ser Gly Gly
                20                  25                  30

Leu Val Gln Pro Gly Gly Ser Leu Arg Leu Ser Cys Ala Ala Ser Gly
                35                  40                  45

Phe Thr Phe Asp Asp Tyr Ala Met His Trp Val Arg Gln Ala Pro Gly
    50                  55                  60

Lys Gly Leu Glu Trp Val Ser Gly Ile Ser Trp Asn Ser Gly Ser Ile
65                  70                  75                  80

Gly Tyr Ala Asp Ser Val Lys Gly Arg Phe Thr Ile Ser Arg Asp Asn
                85                  90                  95

Ala Lys Asn Ser Leu Tyr Leu Gln Met Asn Ser Leu Arg Ala Glu Asp
                100                 105                 110

Thr Ala Leu Tyr Tyr Cys Ala Lys Asp Leu Ser Ser Val Ala Gly Pro
            115                 120                 125

Phe Asn Tyr Trp Gly Gln Gly Thr Leu Val Thr Val Ser Ser Gly Gly
    130                 135                 140

Gly Gly Ser Gly Gly Gly Ser Gly Gly Gly Ser Ser Ser Glu
145                 150                 155                 160

Leu Thr Gln Asp Pro Ala Val Ser Val Ala Leu Gly Gln Thr Val Arg
                165                 170                 175

Ile Thr Cys Gln Gly Asp Ser Leu Arg Ser Tyr Tyr Ala Ser Trp Tyr
                180                 185                 190

Gln Gln Lys Pro Gly Gln Ala Pro Val Leu Val Ile Tyr Gly Lys Asn
            195                 200                 205

Asn Arg Pro Ser Gly Ile Pro Asp Arg Phe Ser Gly Ser Ser Ser Gly
    210                 215                 220

Asn Thr Ala Ser Leu Thr Ile Thr Gly Ala Gln Ala Glu Asp Glu Ala
225                 230                 235                 240

Asp Tyr Tyr Cys Asn Ser Arg Asp Ser Ser Gly Asn His Leu Val Phe
                245                 250                 255

Gly Gly Gly Thr Gln Leu Thr Val Leu Gly Ala Ala Ala Thr Thr Thr
                260                 265                 270

Pro Ala Pro Arg Pro Pro Thr Pro Ala Pro Thr Ile Ala Ser Gln Pro
            275                 280                 285

Leu Ser Leu Arg Pro Glu Ala Cys Arg Pro Ala Ala Gly Gly Ala Val
    290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Leu
                325                 330                 335

Tyr Cys Lys Arg Gly Arg Lys Lys Leu Leu Tyr Ile Phe Lys Gln Pro
                340                 345                 350
```

Phe Met Arg Pro Val Gln Thr Thr Gln Glu Glu Asp Gly Cys Ser Cys
          355                 360                 365

Arg Phe Pro Glu Glu Glu Gly Gly Cys Glu Leu Arg Val Lys Phe
    370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Tyr Asp Val Leu Asp
            405                 410                 415

Lys Arg Arg Gly Arg Asp Pro Glu Met Gly Gly Lys Pro Arg Arg Lys
            420                 425                 430

Asn Pro Gln Glu Gly Leu Tyr Asn Glu Leu Gln Lys Asp Lys Met Ala
                435                 440                 445

Glu Ala Tyr Ser Glu Ile Gly Met Lys Gly Glu Arg Arg Arg Gly Lys
            450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490

<210> SEQ ID NO 50
<211> LENGTH: 366
<212> TYPE: DNA
<213> ORGANISM: Artificial Sequence
<220> FEATURE:
<223> OTHER INFORMATION: heavy chain scFv 16P17

<400> SEQUENCE: 50
caggtacagc ttcaacagag tgggccggga ctggtgaaac actcccaaac actttctctg     60
acgtgcgcta tatcaggtga ctctgtttca tctaattctg ctgcgtggaa ctggattcga    120
caatctccca gtcgcgggtt ggaatggctg gacgaacat attatcggtc taagtggtat     180
aacgattatg ctgtatctgt taaatctcga attacgatta atcctgacac ctccaagaac    240
cagttctccc tccagttgaa ctcagtcaca ccggaagaca ctgcggtcta ctattgcgct    300
caagaagtcg agccacatga tgcattcgac atctggggcc agggaacgat ggtcaccgtc    360
agcagt                                                              366

<210> SEQ ID NO 51
<211> LENGTH: 122
<212> TYPE: PRT
<213> ORGANISM: Artificial Sequence
<220> FEATURE:
<223> OTHER INFORMATION: heavy chain scFv 16P17

<400> SEQUENCE: 51

Gln Val Gln Leu Gln Gln Ser Gly Pro Gly Leu Val Lys His Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Gln Glu Val Glu Pro His Asp Ala Phe Asp Ile Trp
            100                 105                 110
Gly Gln Gly Thr Met Val Thr Val Ser Ser
        115                 120

<210> SEQ ID NO 52
<211> LENGTH: 321
<212> TYPE: DNA
<213> ORGANISM: Artificial Sequence
<220> FEATURE:
<223> OTHER INFORMATION: light chain scFv 16P17

<400> SEQUENCE: 52
gacatacaaa tgacgcagag tccctcaagt gtgtacgcga gtgtggggga taaggtaact      60
attacgtgca gagcgtcaca ggatgttagt ggatggcttg cctggtatca gcagaagcca     120
ggccttgctc cacagctcct tatcagtggt gcttctacac ttcagggcga ggttccgagt     180
agattctctg gttctggatc tggtactgac ttcactctta caatttcttc tttgcaacca     240
gaagactttg cgacttatta ctgccaacag gccaaatact tcccttatac atttggccaa     300
ggtaccaagt tggagataaa g                                               321

<210> SEQ ID NO 53
<211> LENGTH: 107
<212> TYPE: PRT
<213> ORGANISM: Artificial Sequence
<220> FEATURE:
<223> OTHER INFORMATION: light chain scFv 16P17

<400> SEQUENCE: 53

Asp Ile Gln Met Thr Gln Ser Pro Ser Ser Val Tyr Ala Ser Val Gly
1               5                   10                  15

Asp Lys Val Thr Ile Thr Cys Arg Ala Ser Gln Asp Val Ser Gly Trp
            20                  25                  30

Leu Ala Trp Tyr Gln Gln Lys Pro Gly Leu Ala Pro Gln Leu Leu Ile
        35                  40                  45

Ser Gly Ala Ser Thr Leu Gln Gly Glu Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Lys Tyr Phe Pro Tyr
                85                  90                  95

Thr Phe Gly Gln Gly Thr Lys Leu Glu Ile Lys
            100                 105

<210> SEQ ID NO 54
<211> LENGTH: 366
<212> TYPE: DNA
<213> ORGANISM: Artificial Sequence
<220> FEATURE:
<223> OTHER INFORMATION: heavy chain scFv M19217-1

<400> SEQUENCE: 54
gaggtccagc tggtacagtc tggagctgag gtgaagaagc tggggcctc agtgaaggtc       60 tcctgcaagg cttctggata caccttcacc agctactata tgcactgggt gcgacaggcc     120
cctggacaag gcttgagtg gatgggatta atcaaccta gtggtggtag cacaagctac       180
gcacagaagt tccagggcag agtcaccatg accagggaca cgtccacgag cacagtctac     240
atggagctga gcagcctgag atctgaggac acggccgtgt attactgtgc gagatcggat     300

```
cggggaatta ccgccacgga cgcttttgat atctggggcc aagggacaat ggtcaccgtc    360
tcttca                                                              366

<210> SEQ ID NO 55
<211> LENGTH: 122
<212> TYPE: PRT
<213> ORGANISM: Artificial Sequence
<220> FEATURE:
<223> OTHER INFORMATION: heavy chain scFv M19217-1

<400> SEQUENCE: 55

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Leu Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Asp Arg Gly Ile Thr Ala Thr Asp Ala Phe Asp Ile Trp
            100                 105                 110

Gly Gln Gly Thr Met Val Thr Val Ser Ser
        115                 120

<210> SEQ ID NO 56
<211> LENGTH: 330
<212> TYPE: DNA
<213> ORGANISM: Artificial Sequence
<220> FEATURE:
<223> OTHER INFORMATION: light chain scFv M19217-1

<400> SEQUENCE: 56
cagtctgtgc tgactcagcc accctcggtg tcagtggccc cagggcggat ggccaagatt     60
acctgtgggg gaagtgacat tggaaataaa aatgtccact ggtatcagca gaagccaggc    120
caggcccctg tcctggttgt ctatgatgat tacgaccggc cctcagggat ccctgagcga    180
ttctctggct ccaactctgg gacgcggcc accctgacga tcagcacggt cgaagtcggg    240
gatgaggccg actatttctg tcaggtgtgg acggtagtg gtgatcctta ttggatgttc    300
ggcggaggga cccagctcac cgttttaggt                                     330

<210> SEQ ID NO 57
<211> LENGTH: 110
<212> TYPE: PRT
<213> ORGANISM: Artificial Sequence
<220> FEATURE:
<223> OTHER INFORMATION: light chain scFv M19217-1

<400> SEQUENCE: 57

Gln Ser Val Leu Thr Gln Pro Pro Ser Val Ser Val Ala Pro Gly Arg
1               5                   10                  15

Met Ala Lys Ile Thr Cys Gly Gly Ser Asp Ile Gly Asn Lys Asn Val
            20                  25                  30

His Trp Tyr Gln Gln Lys Pro Gly Gln Ala Pro Val Leu Val Val Tyr
        35                  40                  45
```

Asp Asp Tyr Asp Arg Pro Ser Gly Ile Pro Glu Arg Phe Ser Gly Ser
        50                  55                  60

Asn Ser Gly Asp Ala Ala Thr Leu Thr Ile Ser Thr Val Glu Val Gly
 65                  70                  75                  80

Asp Glu Ala Asp Tyr Phe Cys Gln Val Trp Asp Gly Ser Gly Asp Pro
                 85                  90                  95

Tyr Trp Met Phe Gly Gly Gly Thr Gln Leu Thr Val Leu Gly
            100                 105                 110

<210> SEQ ID NO 58
<211> LENGTH: 1482
<212> TYPE: DNA
<213> ORGANISM: Artificial Sequence
<220> FEATURE:
<223> OTHER INFORMATION: CAR22 LTG2200 (M971-CD8TM-4-1BB-zeta)

<400> SEQUENCE: 58

```
atgcttcttt tggtgacttc ccttttgctg tgcgagttgc cacacccgc cttcctgctt      60
attccccagg tacagctcca gcagagtggc ccagggctcg tgaagccaag ccagacgctg    120
tccctgactt gtgcaatttc aggggattca gtttcatcaa atagcgcggc gtggaattgg    180
attcgacaat ctccttcccg agggttggaa tggcttggac gaacatatta cagatccaaa    240
tggtataacg actatgcggt atcagtaaag tcaagaataa ccattaaccc cgacacaagc    300
aagaaccaat tctctttgca gcttaactct gtcacgccag aagacacggc agtctattat    360
tgcgctcgcg aggtaacggg tgacctgaaa acgcttttg acatttgggg cagggtacg     420
atggtgacag tcagttcagg gggcggtggg agtggggag gggtagcgg ggggggaggg    480
tcagacattc agatgaccca gtccccttca tccttgtctg cctccgtcgg tgacagggtg    540
acaataacat gcagagcaag ccaaacaatc tggagctatc tcaactggta ccagcagcga    600
ccaggaaaag cgccaaacct gctgatttac gctgcttcct ccctccaatc aggcgtgcct    660
agtagattta gcggtagggg ctccggcacc gattttacgc tcactataag ctctcttcaa    720
gcagaagatt ttgcgactta ttactgccag cagtcctata gtatacctca gacttctcgga   780
cagggtacca agttggagat taaggcggcc gcaactacca ccctgcccc tcggccgccg    840
actccggccc caaccatcgc aagccaaccc ctctccttgc ccccgaagc ttgccgcccg    900
gccgcgggtg agccgtgca cccgggggg ctggactttg cctgcgatat ctacatttgg    960
gccccgctgg ccggcacttg cggcgtgctc ctgctgtcgc tggtcatcac cctttactgc   1020
aagagggggcc ggaagaagct gctttacatc ttcaagcagc cgttcatgcg gcccgtgcag   1080
acgactcagg aagaggacgg atgctcgtgc agattccctg aggaggaaga ggggggatgc   1140
gaactgcgcg tcaagttctc acggtccgcc gacgcccccg catatcaaca gggccagaat   1200
cagctctaca acgagctgaa cctgggaagg agagaggagt acgacgtgct ggacaagcga   1260
cgcggacgcg acccggagat ggggggggaaa ccacggcgga aaaaccctca ggaaggactg   1320
tacaacgaac tccagaaaga caagatggcg gaagcctact cagaaatcgg gatgaaggga   1380
gagcggagga ggggaaaggg tcacgacggg ctgtaccagg gactgagcac cgccactaag   1440
gatacctacg atgccttgca tatgcaagca ctcccacccc gg                      1482
```

<210> SEQ ID NO 59
<211> LENGTH: 494
<212> TYPE: PRT
<213> ORGANISM: Artificial Sequence
<220> FEATURE:

<223> OTHER INFORMATION: CAR22 LTG2200 (M971-CD8TM-4-1BB-zeta)

<400> SEQUENCE: 59

```
Met Leu Leu Leu Val Thr Ser Leu Leu Leu Cys Glu Leu Pro His Pro
1               5                   10                  15

Ala Phe Leu Leu Ile Pro Gln Val Gln Leu Gln Gln Ser Gly Pro Gly
            20                  25                  30

Leu Val Lys Pro Ser Gln Thr Leu Ser Leu Thr Cys Ala Ile Ser Gly
        35                  40                  45

Asp Ser Val Ser Ser Asn Ser Ala Ala Trp Asn Trp Ile Arg Gln Ser
    50                  55                  60

Pro Ser Arg Gly Leu Glu Trp Leu Gly Arg Thr Tyr Tyr Arg Ser Lys
65                  70                  75                  80

Trp Tyr Asn Asp Tyr Ala Val Ser Val Lys Ser Arg Ile Thr Ile Asn
                85                  90                  95

Pro Asp Thr Ser Lys Asn Gln Phe Ser Leu Gln Leu Asn Ser Val Thr
            100                 105                 110

Pro Glu Asp Thr Ala Val Tyr Tyr Cys Ala Arg Glu Val Thr Gly Asp
        115                 120                 125

Leu Glu Asp Ala Phe Asp Ile Trp Gly Gln Gly Thr Met Val Thr Val
    130                 135                 140

Ser Ser Gly Gly Gly Gly Ser Gly Gly Gly Gly Ser Gly Gly Gly Gly
145                 150                 155                 160

Ser Asp Ile Gln Met Thr Gln Ser Pro Ser Ser Leu Ser Ala Ser Val
                165                 170                 175

Gly Asp Arg Val Thr Ile Thr Cys Arg Ala Ser Gln Thr Ile Trp Ser
            180                 185                 190

Tyr Leu Asn Trp Tyr Gln Gln Arg Pro Gly Lys Ala Pro Asn Leu Leu
        195                 200                 205

Ile Tyr Ala Ala Ser Ser Leu Gln Ser Gly Val Pro Ser Arg Phe Ser
    210                 215                 220

Gly Arg Gly Ser Gly Thr Asp Phe Thr Leu Thr Ile Ser Ser Leu Gln
225                 230                 235                 240

Ala Glu Asp Phe Ala Thr Tyr Tyr Cys Gln Gln Ser Tyr Ser Ile Pro
                245                 250                 255

Gln Thr Phe Gly Gln Gly Thr Lys Leu Glu Ile Lys Ala Ala Ala Thr
            260                 265                 270

Thr Thr Pro Ala Pro Arg Pro Pro Thr Pro Ala Pro Thr Ile Ala Ser
        275                 280                 285

Gln Pro Leu Ser Leu Arg Pro Glu Ala Cys Arg Pro Ala Ala Gly Gly
    290                 295                 300

Ala Val His Thr Arg Gly Leu Asp Phe Ala Cys Asp Ile Tyr Ile Trp
305                 310                 315                 320

Ala Pro Leu Ala Gly Thr Cys Gly Val Leu Leu Leu Ser Leu Val Ile
                325                 330                 335

Thr Leu Tyr Cys Lys Arg Gly Arg Lys Lys Leu Leu Tyr Ile Phe Lys
            340                 345                 350

Gln Pro Phe Met Arg Pro Val Gln Thr Thr Gln Glu Glu Asp Gly Cys
        355                 360                 365

Ser Cys Arg Phe Pro Glu Glu Glu Glu Gly Gly Cys Glu Leu Arg Val
    370                 375                 380

Lys Phe Ser Arg Ser Ala Asp Ala Pro Ala Tyr Gln Gln Gly Gln Asn
385                 390                 395                 400
```

```
Gln Leu Tyr Asn Glu Leu Asn Leu Gly Arg Arg Glu Tyr Asp Val
                405                 410                 415
Leu Asp Lys Arg Arg Gly Arg Asp Pro Glu Met Gly Gly Lys Pro Arg
            420                 425                 430
Arg Lys Asn Pro Gln Glu Gly Leu Tyr Asn Glu Leu Gln Lys Asp Lys
        435                 440                 445
Met Ala Glu Ala Tyr Ser Glu Ile Gly Met Lys Gly Glu Arg Arg Arg
    450                 455                 460
Gly Lys Gly His Asp Gly Leu Tyr Gln Gly Leu Ser Thr Ala Thr Lys
465                 470                 475                 480
Asp Thr Tyr Asp Ala Leu His Met Gln Ala Leu Pro Pro Arg
                485                 490
```

<210> SEQ ID NO 60
<211> LENGTH: 2292
<212> TYPE: DNA
<213> ORGANISM: Artificial Sequence
<220> FEATURE:
<223> OTHER INFORMATION: CAR LTG2737 (CD22-19 CD8 BBz)

<400> SEQUENCE: 60

```
atgctcttgc tcgtgacttc tttgcttttg tgcgaacttc cgcacccagc cttccttttg      60
ataccctcagg tacagcttca acaaagcgga ccgggacttg ttaagcattc ccaaaccctt    120
tctctcacgt gtgcaattag cggcgatagt gtatcctcta attctgcggc ctggaactgg    180
atacgacaat caccaagccg gggactcgag tggttgggcc gaacctacta tcggtccaaa    240
tggtataatg actacgcagt atccgtgaaa tctcgcatta cgatcaatcc agacacctcc    300
aaaaatcaat tttctctgca gttgaatagc gtgactcccg aggacacggc cgtttactat    360
tgcgcccagg aagttgaacc ccacgatgca tttgatattt ggggccaggg aaccatggtg    420
acagtgagta gtggggggtgg aggatctgga ggaggcggta gcggcggggg cggcagtgat    480
atccagatga cgcagtcacc ttccagcgtg tatgcgagtg tggggacaa ggtcaccata    540
acctgtcgcg ctagccaaga tgtcagcggg tggctggctt ggtaccagca gaaaccaggt    600
ttggctcctc agcttttgat ctcaggagcg agcacgcttc agggtgaggt cccaagtcgc    660
tttagtggct ctggctccgg gacagacttc acgttgacga tcagcagttt gcagcctgag    720
gatttcgcga cctactactg ccagcaagcg aaatattttc cgtacacttt cggtcagggg    780
accaaattgg agatcaaagg tggggggtggt tcaggcggcg gaggctcagg cggcggcggt    840
agcggaggag cgggaagcgg gggtggcgga tcagaagtgc aactcgttca gagtggcgcg    900
gaggttaaga aacccggtgc atctgtaaag gttagctgta aggcatcagg atacactttt    960
accagctatt acatgcattg ggtgagacag gctcccggtc aggggctcga atggatgggg   1020
ttgatcaacc cgagtggtgg ttcaacatct tacgcccaga gtttcagggc cgagtaaca    1080
atgactcggg acacgtctac ctcaactgtg tatatggagc tttccagcct gcgctcagag   1140
gatacagcag tctattactg cgcacggtca gacagaggta taacgccac tgatgcgttc    1200
gatatctggg gacaagggac tatggtaact gtgtcttccg gaggaggagg tagtggaggg   1260
ggaggaagcg gtgggggggg ctcacagtcc gttttgactc agccaccaag cgtctcagtc   1320
gcaccggggc gaatggcgaa aattacttgc ggcgggagcg acataggcaa caagaatgtg   1380
cattggtacc aacagaaacc aggtcaagca cctgttctcg tggtgtatga tgactacgat   1440
cgcccaagcg ggatcccgga gcggttctct ggatcaaatt ctggtgatgc agccactctg   1500
acaatatcaa cggtggaagt cggtgacgag gctgattact tctgccaagt atgggatggc   1560
```

-continued

```
agcggagatc cctactggat gtttggagga ggtactcaac tgacagttct gggcgcggcc    1620
gcaacgacca ctcctgcacc ccgccctccg actccggccc caaccattgc cagccagccc    1680
ctgtccctgc ggccggaagc ctgcagaccg gctgccggcg agccgtcca tacccgggga    1740 ctggatttcg cctgcgatat ctatatctgg gcaccactcg ccggaacctg tggagtgctg    1800
ctgctgtccc ttgtgatcac cctgtactgc aagcgcggac ggaagaaact cttgtacatc    1860
ttcaagcagc cgttcatgcg ccctgtgcaa accacccaag aagaggacgg gtgctcctgc    1920
cggttcccgg aagaggaaga gggcggctgc gaactgcgcg tgaagttttc ccggtccgcc    1980
gacgctccgg cgtaccagca ggggcaaaac cagctgtaca acgaacttaa cctcggtcgc    2040
cgggaagaat atgacgtgct ggacaagcgg cggggaagag atcccgagat gggtggaaag    2100
ccgcggcgga agaaccctca ggagggcttg tacaacgagc tgcaaaagga caaaatggcc    2160
gaagcctact ccgagattgg catgaaggga gagcgcagac gcgggaaggg acacgatgga    2220
ctgtaccagg gactgtcaac cgcgactaag gacacttacg acgccctgca catgcaggcc    2280
ctgccccccg gc                                                         2292
```

<210> SEQ ID NO 61
<211> LENGTH: 764
<212> TYPE: PRT
<213> ORGANISM: Artificial Sequence
<220> FEATURE:
<223> OTHER INFORMATION: CAR LTG2737 CD22-19 CD8 BBz

<400> SEQUENCE: 61

```
Met Leu Leu Leu Val Thr Ser Leu Leu Leu Cys Glu Leu Pro His Pro
1               5                   10                  15

Ala Phe Leu Leu Ile Pro Gln Val Gln Leu Gln Gln Ser Gly Pro Gly
            20                  25                  30

Leu Val Lys His Ser Gln Thr Leu Ser Leu Thr Cys Ala Ile Ser Gly
        35                  40                  45

Asp Ser Val Ser Ser Asn Ser Ala Ala Trp Asn Trp Ile Arg Gln Ser
    50                  55                  60

Pro Ser Arg Gly Leu Glu Trp Leu Gly Arg Thr Tyr Tyr Arg Ser Lys
65                  70                  75                  80

Trp Tyr Asn Asp Tyr Ala Val Ser Val Lys Ser Arg Ile Thr Ile Asn
                85                  90                  95

Pro Asp Thr Ser Lys Asn Gln Phe Ser Leu Gln Leu Asn Ser Val Thr
            100                 105                 110

Pro Glu Asp Thr Ala Val Tyr Tyr Cys Ala Gln Glu Val Glu Pro His
        115                 120                 125

Asp Ala Phe Asp Ile Trp Gly Gln Gly Thr Met Val Thr Val Ser Ser
    130                 135                 140

Gly Gly Gly Gly Ser Gly Gly Gly Ser Gly Gly Gly Gly Ser Asp
145                 150                 155                 160

Ile Gln Met Thr Gln Ser Pro Ser Ser Val Tyr Ala Ser Val Gly Asp
                165                 170                 175

Lys Val Thr Ile Thr Cys Arg Ala Ser Gln Asp Val Ser Gly Trp Leu
            180                 185                 190

Ala Trp Tyr Gln Gln Lys Pro Gly Leu Ala Pro Gln Leu Leu Ile Ser
        195                 200                 205

Gly Ala Ser Thr Leu Gln Gly Glu Val Pro Ser Arg Phe Ser Gly Ser
    210                 215                 220
```

```
Gly Ser Gly Thr Asp Phe Thr Leu Thr Ile Ser Ser Leu Gln Pro Glu
225                 230                 235                 240

Asp Phe Ala Thr Tyr Tyr Cys Gln Gln Ala Lys Tyr Phe Pro Tyr Thr
            245                 250                 255

Phe Gly Gln Gly Thr Lys Leu Glu Ile Lys Gly Gly Gly Gly Ser Gly
                260                 265                 270

Gly Gly Gly Ser Gly Gly Gly Ser Gly Gly Gly Ser Gly Gly
        275                 280                 285

Gly Gly Ser Glu Val Gln Leu Val Gln Ser Gly Ala Glu Val Lys Lys
        290                 295                 300

Pro Gly Ala Ser Val Lys Val Ser Cys Lys Ala Ser Gly Tyr Thr Phe
305                 310                 315                 320

Thr Ser Tyr Tyr Met His Trp Val Arg Gln Ala Pro Gly Gln Gly Leu
                325                 330                 335

Glu Trp Met Gly Leu Ile Asn Pro Ser Gly Gly Ser Thr Ser Tyr Ala
                340                 345                 350

Gln Lys Phe Gln Gly Arg Val Thr Met Thr Arg Asp Thr Ser Thr Ser
            355                 360                 365

Thr Val Tyr Met Glu Leu Ser Ser Leu Arg Ser Glu Asp Thr Ala Val
370                 375                 380

Tyr Tyr Cys Ala Arg Ser Asp Arg Gly Ile Thr Ala Thr Asp Ala Phe
385                 390                 395                 400

Asp Ile Trp Gly Gln Gly Thr Met Val Thr Val Ser Ser Gly Gly Gly
                405                 410                 415

Gly Ser Gly Gly Gly Gly Ser Gly Gly Gly Gly Ser Gln Ser Val Leu
            420                 425                 430

Thr Gln Pro Pro Ser Val Ser Val Ala Pro Gly Arg Met Ala Lys Ile
            435                 440                 445

Thr Cys Gly Gly Ser Asp Ile Gly Asn Lys Asn Val His Trp Tyr Gln
450                 455                 460

Gln Lys Pro Gly Gln Ala Pro Val Leu Val Val Tyr Asp Asp Tyr Asp
465                 470                 475                 480

Arg Pro Ser Gly Ile Pro Glu Arg Phe Ser Gly Ser Asn Ser Gly Asp
                485                 490                 495

Ala Ala Thr Leu Thr Ile Ser Thr Val Glu Val Gly Asp Glu Ala Asp
            500                 505                 510

Tyr Phe Cys Gln Val Trp Asp Gly Ser Gly Asp Pro Tyr Trp Met Phe
        515                 520                 525

Gly Gly Gly Thr Gln Leu Thr Val Leu Gly Ala Ala Ala Thr Thr Thr
        530                 535                 540

Pro Ala Pro Arg Pro Pro Thr Pro Ala Pro Thr Ile Ala Ser Gln Pro
545                 550                 555                 560

Leu Ser Leu Arg Pro Glu Ala Cys Arg Pro Ala Ala Gly Gly Ala Val
                565                 570                 575

His Thr Arg Gly Leu Asp Phe Ala Cys Asp Ile Tyr Ile Trp Ala Pro
            580                 585                 590

Leu Ala Gly Thr Cys Gly Val Leu Leu Leu Ser Leu Val Ile Thr Leu
                595                 600                 605

Tyr Cys Lys Arg Gly Arg Lys Lys Leu Leu Tyr Ile Phe Lys Gln Pro
            610                 615                 620

Phe Met Arg Pro Val Gln Thr Thr Gln Glu Glu Asp Gly Cys Ser Cys
625                 630                 635                 640

Arg Phe Pro Glu Glu Glu Glu Gly Gly Cys Glu Leu Arg Val Lys Phe
```

```
                    645                 650                 655
Ser Arg Ser Ala Asp Ala Pro Ala Tyr Gln Gln Gly Gln Asn Gln Leu
            660                 665                 670

Tyr Asn Glu Leu Asn Leu Gly Arg Arg Glu Glu Tyr Asp Val Leu Asp
        675                 680                 685

Lys Arg Arg Gly Arg Asp Pro Glu Met Gly Gly Lys Pro Arg Arg Lys
690                 695                 700

Asn Pro Gln Glu Gly Leu Tyr Asn Glu Leu Gln Lys Asp Lys Met Ala
705                 710                 715                 720

Glu Ala Tyr Ser Glu Ile Gly Met Lys Gly Glu Arg Arg Arg Gly Lys
                725                 730                 735

Gly His Asp Gly Leu Tyr Gln Gly Leu Ser Thr Ala Thr Lys Asp Thr
                740                 745                 750

Tyr Asp Ala Leu His Met Gln Ala Leu Pro Pro Arg
            755                 760
```

<210> SEQ ID NO 62
<211> LENGTH: 2289
<212> TYPE: DNA
<213> ORGANISM: Artificial Sequence
<220> FEATURE:
<223> OTHER INFORMATION: CAR D0135 CD22-19 CD8 CD28z

<400> SEQUENCE: 62

```
atgctcttgc tcgtgacttc tttgcttttg tgcgaacttc cgcacccagc cttccttttg      60
atacctcagg tacagcttca acaaagcgga ccgggacttg ttaagcattc ccaaacccttt    120
tctctcacgt gtgcaattag cggcgatagt gtatcctcta attctgcggc ctggaactgg     180
atacgacaat caccaagccg ggactcgag  tggttgggcc gaacctacta tcggtccaaa    240
tggtataatg actacgcagt atccgtgaaa tctcgcatta cgatcaatcc agacacctcc     300
aaaaatcaat tttctctgca gttgaatagc gtgactcccg aggacacggc cgtttactat     360
tgcgcccagg aagttgaacc ccacgatgca tttgatattt ggggccaggg aaccatggtg    420
acagtgagta gtggggggtgg aggatctgga ggaggcggta gcggcggggg cggcagtgat    480
atccagatga cgcagtcacc ttccagcgtg tatgcgagtg tggggacaa  ggtcaccata    540
acctgtcgcg ctagccaaga tgtcagcggg tggctggctt ggtaccagca gaaaccaggt    600
ttggctcctc agctttgat  ctcaggagcg agcacgcttc agggtgaggt cccagtcgc      660
tttagtggct ctggctccgg gacagacttc acgttgacga tcagcagttt gcagcctgag    720
gattttcgcga cctactactg ccagcaagcg aaatattttc gtacacttt  cggtcagggg    780
accaaattgg agatcaaagg tggggggtggt tcaggcggcg gaggctcagg cggcggcggt    840
agcggaggag gcggaagcgg gggtggcgga tcagaagtgc aactcgttca gagtggcgcg    900
gaggttaaga aacccggtgc atctgtaaag gttagctgta aggcatcagg atacactttt    960
accagctatt acatgcattg ggtgagacag gctcccggtc aggggctcga atggatgggg    1020
ttgatcaacc cgagtggtgg ttcaacatct tacgcccaga gtttcagggg ccgagtaaca    1080
atgactcggg acacgtctac ctcaactgtg tatatggagc tttccagcct gcgctcagag    1140
gatacagcag tctattactg cgcacggtca gacagaggta taacgccac  tgatgcgttc    1200
gatatctggg gacaagggac tatggtaact gtgtcttccg gaggaggagg tagtggaggg    1260
ggaggaagcg gtggggggggg ctcacagtcc gttttgactc agccaccaag cgtctcagtc    1320
gcaccggggc gaatggcgaa aattacttgc ggcgggagcg acataggcaa caagaatgtg    1380
```

```
cattggtacc aacagaaacc aggtcaagca cctgttctcg tggtgtatga tgactacgat    1440
cgcccaagcg ggatcccgga gcggttctct ggatcaaatt ctggtgatgc agccactctg    1500
acaatatcaa cggtggaagt cggtgacgag gctgattact tctgccaagt atgggatggc    1560
agcggagatc cctactggat gtttggagga ggtactcaac tgacagttct gggcgcggcc    1620
gcgactacca ctcctgcacc acggccacct accccagccc ccaccattgc aagccagcca    1680
ctttcactgc gccccgaagc gtgtagacca gctgctggag gagccgtgca tacccgaggg    1740
ctggacttcg cctgtgacat ctacatctgg gccccattgg ctggaacttg cggcgtgctg    1800
ctcttgtctc tggtcattac cctgtactgc cggtcgaaga ggtccagact cttgcactcc    1860
gactacatga acatgactcc tagaaggccc ggacccacta gaaagcacta ccagccgtac    1920
gcccctcctc gggatttcgc cgcataccgg tccagagtga agttcagccg ctcagccgat    1980
gcaccggcct accagcaggg acagaaccag ctctacaacg agctcaacct gggtcggcgg    2040
gaagaatatg acgtgctgga caacggcgc ggcagagatc cggagatggg gggaaagccg    2100
aggaggaaga accctcaaga gggcctgtac aacgaactgc agaaggacaa gatggcggaa    2160
gcctactccg agatcggcat gaagggagaa cgccggagag ggaagggtca tgacggactg    2220
taccagggcc tgtcaactgc cactaaggac acttacgatg cgctccatat gcaagctttg    2280
ccccccgcgg                                                             2289
```

<210> SEQ ID NO 63
<211> LENGTH: 763
<212> TYPE: PRT
<213> ORGANISM: Artificial Sequence
<220> FEATURE:
<223> OTHER INFORMATION: CAR D0135 CD22-19 CD8 CD28z

<400> SEQUENCE: 63

```
Met Leu Leu Leu Val Thr Ser Leu Leu Leu Cys Glu Leu Pro His Pro
1               5                   10                  15

Ala Phe Leu Leu Ile Pro Gln Val Gln Leu Gln Gln Ser Gly Pro Gly
            20                  25                  30

Leu Val Lys His Ser Gln Thr Leu Ser Leu Thr Cys Ala Ile Ser Gly
        35                  40                  45

Asp Ser Val Ser Ser Asn Ser Ala Ala Trp Asn Trp Ile Arg Gln Ser
    50                  55                  60

Pro Ser Arg Gly Leu Glu Trp Leu Gly Arg Thr Tyr Tyr Arg Ser Lys
65                  70                  75                  80

Trp Tyr Asn Asp Tyr Ala Val Ser Val Lys Ser Arg Ile Thr Ile Asn
                85                  90                  95

Pro Asp Thr Ser Lys Asn Gln Phe Ser Leu Gln Leu Asn Ser Val Thr
            100                 105                 110

Pro Glu Asp Thr Ala Val Tyr Tyr Cys Ala Gln Glu Val Glu Pro His
        115                 120                 125

Asp Ala Phe Asp Ile Trp Gly Gln Gly Thr Met Val Thr Val Ser Ser
    130                 135                 140

Gly Gly Gly Gly Ser Gly Gly Gly Ser Gly Gly Gly Gly Ser Asp
145                 150                 155                 160

Ile Gln Met Thr Gln Ser Pro Ser Ser Val Tyr Ala Ser Val Gly Asp
                165                 170                 175

Lys Val Thr Ile Thr Cys Arg Ala Ser Gln Asp Val Ser Gly Trp Leu
            180                 185                 190

Ala Trp Tyr Gln Gln Lys Pro Gly Leu Ala Pro Gln Leu Leu Ile Ser
```

-continued

```
            195                 200                 205
Gly Ala Ser Thr Leu Gln Gly Glu Val Pro Ser Arg Phe Ser Gly Ser
210                 215                 220

Gly Ser Gly Thr Asp Phe Thr Leu Thr Ile Ser Ser Leu Gln Pro Glu
225                 230                 235                 240

Asp Phe Ala Thr Tyr Tyr Cys Gln Gln Ala Lys Tyr Phe Pro Tyr Thr
                245                 250                 255

Phe Gly Gln Gly Thr Lys Leu Glu Ile Lys Gly Gly Gly Ser Gly
            260                 265                 270

Gly Gly Gly Ser Gly Gly Gly Ser Gly Gly Gly Ser Gly Gly
        275                 280                 285

Gly Gly Ser Glu Val Gln Leu Val Gln Ser Gly Ala Glu Val Lys Lys
290                 295                 300

Pro Gly Ala Ser Val Lys Val Ser Cys Lys Ala Ser Gly Tyr Thr Phe
305                 310                 315                 320

Thr Ser Tyr Tyr Met His Trp Val Arg Gln Ala Pro Gly Gln Gly Leu
                325                 330                 335

Glu Trp Met Gly Leu Ile Asn Pro Ser Gly Gly Ser Thr Ser Tyr Ala
            340                 345                 350

Gln Lys Phe Gln Gly Arg Val Thr Met Thr Arg Asp Thr Ser Thr Ser
        355                 360                 365

Thr Val Tyr Met Glu Leu Ser Ser Leu Arg Ser Glu Asp Thr Ala Val
370                 375                 380

Tyr Tyr Cys Ala Arg Ser Asp Arg Gly Ile Thr Ala Thr Asp Ala Phe
385                 390                 395                 400

Asp Ile Trp Gly Gln Gly Thr Met Val Thr Val Ser Ser Gly Gly Gly
                405                 410                 415

Gly Ser Gly Gly Gly Gly Ser Gly Gly Gly Gly Ser Gln Ser Val Leu
            420                 425                 430

Thr Gln Pro Pro Ser Val Ser Val Ala Pro Gly Arg Met Ala Lys Ile
        435                 440                 445

Thr Cys Gly Gly Ser Asp Ile Gly Asn Lys Asn Val His Trp Tyr Gln
450                 455                 460

Gln Lys Pro Gly Gln Ala Pro Val Leu Val Val Tyr Asp Asp Tyr Asp
465                 470                 475                 480

Arg Pro Ser Gly Ile Pro Glu Arg Phe Ser Gly Ser Asn Ser Gly Asp
                485                 490                 495

Ala Ala Thr Leu Thr Ile Ser Thr Val Glu Val Gly Asp Glu Ala Asp
            500                 505                 510

Tyr Phe Cys Gln Val Trp Asp Gly Ser Gly Asp Pro Tyr Trp Met Phe
        515                 520                 525

Gly Gly Gly Thr Gln Leu Thr Val Leu Gly Ala Ala Ala Thr Thr Thr
530                 535                 540

Pro Ala Pro Arg Pro Pro Thr Pro Ala Pro Thr Ile Ala Ser Gln Pro
545                 550                 555                 560

Leu Ser Leu Arg Pro Glu Ala Cys Arg Pro Ala Ala Gly Gly Ala Val
                565                 570                 575

His Thr Arg Gly Leu Asp Phe Ala Cys Asp Ile Tyr Ile Trp Ala Pro
            580                 585                 590

Leu Ala Gly Thr Cys Gly Val Leu Leu Leu Ser Leu Val Ile Thr Leu
        595                 600                 605

Tyr Cys Arg Ser Lys Arg Ser Arg Leu Leu His Ser Asp Tyr Met Asn
610                 615                 620
```

```
Met Thr Pro Arg Arg Pro Gly Pro Thr Arg Lys His Tyr Gln Pro Tyr
625                 630                 635                 640

Ala Pro Pro Arg Asp Phe Ala Ala Tyr Arg Ser Arg Val Lys Phe Ser
            645                 650                 655

Arg Ser Ala Asp Ala Pro Ala Tyr Gln Gln Gly Gln Asn Gln Leu Tyr
        660                 665                 670

Asn Glu Leu Asn Leu Gly Arg Arg Glu Glu Tyr Asp Val Leu Asp Lys
            675                 680                 685

Arg Arg Gly Arg Asp Pro Glu Met Gly Gly Lys Pro Arg Arg Lys Asn
        690                 695                 700

Pro Gln Glu Gly Leu Tyr Asn Glu Leu Gln Lys Asp Lys Met Ala Glu
705                 710                 715                 720

Ala Tyr Ser Glu Ile Gly Met Lys Gly Glu Arg Arg Arg Gly Lys Gly
            725                 730                 735

His Asp Gly Leu Tyr Gln Gly Leu Ser Thr Ala Thr Lys Asp Thr Tyr
        740                 745                 750

Asp Ala Leu His Met Gln Ala Leu Pro Pro Arg
        755                 760
```

<210> SEQ ID NO 64
<211> LENGTH: 2277
<212> TYPE: DNA
<213> ORGANISM: Artificial Sequence
<220> FEATURE:
<223> OTHER INFORMATION: CAR D0136 CD22-19 CD8 ICOSz DNA

<400> SEQUENCE: 64

```
atgctcttgc tcgtgacttc tttgcttttg tgcgaacttc cgcacccagc cttccttttg      60
atacctcagg tacagcttca acaaagcgga ccgggacttg ttaagcattc ccaaacccct     120
tctctcacgt gtgcaattag cggcgatagt gtatcctcta attctgcggc ctggaactgg     180
atacgacaat caccaagccg gggactcgag tggttgggcc gaacctacta tcggtccaaa     240
tggtataatg actacgcagt atccgtgaaa tctcgcatta cgatcaatcc agacacctcc     300
aaaaatcaat tttctctgca gttgaatagc gtgactcccg aggacacggc cgtttactat     360
tgcgcccagg aagttgaacc ccacgatgca tttgatattt ggggccaggg aaccatggtg     420
acagtgagta gtgggggtgg aggatctgga ggaggcggta gcggcggggg cggcagtgat     480
atccagatga cgcagtcacc ttccagcgtg tatgcgagtg tggggacaa ggtcaccata      540
acctgtcgcg ctagccaaga tgtcagcggg tggctggctt ggtaccagca gaaaccaggt     600
ttggctcctc agcttttgat ctcaggagcg agcacgcttc agggtgaggt cccaagtcgc     660
tttagtggct ctggctccgg gacagacttc acgttgacga tcagcagttt gcagcctgag     720
gatttcgcga cctactactg ccagcaagcg aaatattttc cgtacacttt cggtcagggg     780
accaaattgg agatcaaagg tgggggtggt tcaggcggcg gaggctcagg cggcggcgt      840
agcggaggag gcggaagcgg gggtggcgga tcagaagtgc aactcgttca gagtggcgcg     900
gaggttaaga acccggtgc atctgtaaag gttagctgta aggcatcagg atacacttt      960
accagctatt acatgcattg ggtgagacag gctcccggtc aggggctcga atggatgggg    1020
ttgatcaacc cgagtggtgg ttcaacatct tacgcccaga gtttcagggg ccgagtaaca    1080
atgactcggg acacgtctac ctcaactgtg tatatggagc tttccagcct gcgctcagag    1140
gatacagcag tctattactg cgcacggtca gacagaggta taacggccac tgatgcgttc    1200
gatatctggg gacaagggac tatggtaact gtgtcttccg gaggaggagg tagtgaggg     1260
```

```
ggaggaagcg gtggggggggg ctcacagtcc gttttgactc agccaccaag cgtctcagtc   1320
gcaccggggc gaatggcgaa aattacttgc ggcgggagcg acataggcaa caagaatgtg   1380
cattggtacc aacagaaacc aggtcaagca cctgttctcg tggtgtatga tgactacgat   1440
cgcccaagcg ggatcccgga gcggttctct ggatcaaatt ctggtgatgc agccactctg   1500
acaatatcaa cggtggaagt cggtgacgag gctgattact tctgccaagt atgggatggc   1560
agcggagatc cctactggat gtttggagga ggtactcaac tgacagttct gggcgcggcc   1620
gcgactacca ctcctgcacc acggccacct accccagccc ccaccattgc aagccagcca   1680
ctttcactgc gccccgaagc gtgtagacca gctgctggag gagccgtgca tacccgaggg   1740
ctggacttcg cctgtgacat ctacatctgg gccccattgg ctggaacttg cggcgtgctg   1800
ctcttgtctc tggtcattac cctgtactgc tggctgacaa aaagaagta ttcatctagt    1860 gtacatgatc cgaacggtga atacatgttc atgcgcgcgg tgaacacggc caagaagagc   1920
agactgaccg acgtaaccct tagagtgaag ttcagccgct cagccgatgc accggcctac   1980
cagcagggac agaaccagct ctacaacgag ctcaacctgg gtcggcggga agaatatgac   2040
gtgctggaca acggcgcgg cagagatccg gagatggggg gaaagccgag gaggaagaac    2100
cctcaagagg gcctgtacaa cgaactgcag aaggacaaga tggcggaagc ctactccgag   2160
atcggcatga aggagaacg ccggagaggg aagggtcatg acggactgta ccagggcctg    2220
tcaactgcca ctaaggacac ttacgatgcg ctccatatgc aagctttgcc cccgcgg      2277
```

<210> SEQ ID NO 65
<211> LENGTH: 759
<212> TYPE: PRT
<213> ORGANISM: Artificial Sequence
<220> FEATURE:
<223> OTHER INFORMATION: CAR D0136 CD22-19 CD8 ICOSz

<400> SEQUENCE: 65

```
Met Leu Leu Leu Val Thr Ser Leu Leu Leu Cys Glu Leu Pro His Pro
1               5                   10                  15

Ala Phe Leu Leu Ile Pro Gln Val Gln Leu Gln Gln Ser Gly Pro Gly
            20                  25                  30

Leu Val Lys His Ser Gln Thr Leu Ser Leu Thr Cys Ala Ile Ser Gly
        35                  40                  45

Asp Ser Val Ser Ser Asn Ser Ala Ala Trp Asn Trp Ile Arg Gln Ser
    50                  55                  60

Pro Ser Arg Gly Leu Glu Trp Leu Gly Arg Thr Tyr Tyr Arg Ser Lys
65                  70                  75                  80

Trp Tyr Asn Asp Tyr Ala Val Ser Val Lys Ser Arg Ile Thr Ile Asn
                85                  90                  95

Pro Asp Thr Ser Lys Asn Gln Phe Ser Leu Gln Leu Asn Ser Val Thr
            100                 105                 110

Pro Glu Asp Thr Ala Val Tyr Tyr Cys Ala Gln Glu Val Glu Pro His
        115                 120                 125

Asp Ala Phe Asp Ile Trp Gly Gln Gly Thr Met Val Thr Val Ser Ser
    130                 135                 140

Gly Gly Gly Gly Ser Gly Gly Gly Ser Gly Gly Gly Gly Ser Asp
145                 150                 155                 160

Ile Gln Met Thr Gln Ser Pro Ser Ser Val Tyr Ala Ser Val Gly Asp
                165                 170                 175

Lys Val Thr Ile Thr Cys Arg Ala Ser Gln Asp Val Ser Gly Trp Leu
```

-continued

```
                180                 185                 190
Ala Trp Tyr Gln Gln Lys Pro Gly Leu Ala Pro Gln Leu Leu Ile Ser
                195                 200                 205
Gly Ala Ser Thr Leu Gln Gly Glu Val Pro Ser Arg Phe Ser Gly Ser
                210                 215                 220
Gly Ser Gly Thr Asp Phe Thr Leu Thr Ile Ser Ser Leu Gln Pro Glu
225                 230                 235                 240
Asp Phe Ala Thr Tyr Tyr Cys Gln Gln Ala Lys Tyr Phe Pro Tyr Thr
                245                 250                 255
Phe Gly Gln Gly Thr Lys Leu Glu Ile Lys Gly Gly Gly Gly Ser Gly
                260                 265                 270
Gly Gly Gly Ser Gly Gly Gly Ser Gly Gly Gly Ser Gly Gly
                275                 280                 285
Gly Gly Ser Glu Val Gln Leu Val Gln Ser Gly Ala Glu Val Lys Lys
                290                 295                 300
Pro Gly Ala Ser Val Lys Val Ser Cys Lys Ala Ser Gly Tyr Thr Phe
305                 310                 315                 320
Thr Ser Tyr Tyr Met His Trp Val Arg Gln Ala Pro Gly Gln Gly Leu
                325                 330                 335
Glu Trp Met Gly Leu Ile Asn Pro Ser Gly Gly Ser Thr Ser Tyr Ala
                340                 345                 350
Gln Lys Phe Gln Gly Arg Val Thr Met Thr Arg Asp Thr Ser Thr Ser
                355                 360                 365
Thr Val Tyr Met Glu Leu Ser Ser Leu Arg Ser Glu Asp Thr Ala Val
                370                 375                 380
Tyr Tyr Cys Ala Arg Ser Asp Arg Gly Ile Thr Ala Thr Asp Ala Phe
385                 390                 395                 400
Asp Ile Trp Gly Gln Gly Thr Met Val Thr Val Ser Ser Gly Gly Gly
                405                 410                 415
Gly Ser Gly Gly Gly Gly Ser Gly Gly Gly Gly Ser Gln Ser Val Leu
                420                 425                 430
Thr Gln Pro Pro Ser Val Ser Val Ala Pro Gly Arg Met Ala Lys Ile
                435                 440                 445
Thr Cys Gly Gly Ser Asp Ile Gly Asn Lys Asn Val His Trp Tyr Gln
                450                 455                 460
Gln Lys Pro Gly Gln Ala Pro Val Leu Val Val Tyr Asp Asp Tyr Asp
465                 470                 475                 480
Arg Pro Ser Gly Ile Pro Glu Arg Phe Ser Gly Ser Asn Ser Gly Asp
                485                 490                 495
Ala Ala Thr Leu Thr Ile Ser Thr Val Glu Val Gly Asp Glu Ala Asp
                500                 505                 510
Tyr Phe Cys Gln Val Trp Asp Gly Ser Gly Asp Pro Tyr Trp Met Phe
                515                 520                 525
Gly Gly Gly Thr Gln Leu Thr Val Leu Gly Ala Ala Ala Thr Thr Thr
                530                 535                 540
Pro Ala Pro Arg Pro Pro Thr Pro Ala Pro Thr Ile Ala Ser Gln Pro
545                 550                 555                 560
Leu Ser Leu Arg Pro Glu Ala Cys Arg Pro Ala Ala Gly Gly Ala Val
                565                 570                 575
His Thr Arg Gly Leu Asp Phe Ala Cys Asp Ile Tyr Ile Trp Ala Pro
                580                 585                 590
Leu Ala Gly Thr Cys Gly Val Leu Leu Leu Ser Leu Val Ile Thr Leu
                595                 600                 605
```

```
Tyr Cys Trp Leu Thr Lys Lys Tyr Ser Ser Val His Asp Pro
        610                 615                 620

Asn Gly Glu Tyr Met Phe Met Arg Ala Val Asn Thr Ala Lys Lys Ser
625                 630                 635                 640

Arg Leu Thr Asp Val Thr Leu Arg Val Lys Phe Ser Arg Ser Ala Asp
                645                 650                 655

Ala Pro Ala Tyr Gln Gln Gly Gln Asn Gln Leu Tyr Asn Glu Leu Asn
                660                 665                 670

Leu Gly Arg Arg Glu Glu Tyr Asp Val Leu Asp Lys Arg Arg Gly Arg
            675                 680                 685

Asp Pro Glu Met Gly Gly Lys Pro Arg Arg Lys Asn Pro Gln Glu Gly
        690                 695                 700

Leu Tyr Asn Glu Leu Gln Lys Asp Lys Met Ala Glu Ala Tyr Ser Glu
705                 710                 715                 720

Ile Gly Met Lys Gly Glu Arg Arg Gly Lys Gly His Asp Gly Leu
                725                 730                 735

Tyr Gln Gly Leu Ser Thr Ala Thr Lys Asp Thr Tyr Asp Ala Leu His
                740                 745                 750

Met Gln Ala Leu Pro Pro Arg
        755
```

<210> SEQ ID NO 66
<211> LENGTH: 2283
<212> TYPE: DNA
<213> ORGANISM: Artificial Sequence
<220> FEATURE:
<223> OTHER INFORMATION: CAR D0137 CD22-19 CD8 OX40TM OX40z

<400> SEQUENCE: 66

```
atgctcttgc tcgtgacttc tttgcttttg tgcgaacttc cgcacccagc cttccttttg      60
atacctcagg tacagcttca acaaagcgga ccgggacttg ttaagcattc ccaaaccctt     120
tctctcacgt gtgcaattag cggcgatagt gtatcctcta attctgcggc ctggaactgg     180
atacgacaat caccaagccg ggactcgag tggttgggcc gaacctacta tcggtccaaa      240
tggtataatg actacgcagt atccgtgaaa tctcgcatta cgatcaatcc agacacctcc     300
aaaaatcaat tttctctgca gttgaatagc gtgactcccg aggacacggc cgtttactat     360
tgcgcccagg aagttgaacc ccacgatgca tttgatattt ggggcaggg aaccatggtg      420
acagtgagta gtggggggtgg aggatctgga ggaggcggta gcggcggggg cggcagtgat     480
atccagatga cgcagtcacc ttccagcgtg tatgcgagtg tggggacaa ggtcaccata      540
acctgtcgcg ctagccaaga tgtcagcggg tggctggctt ggtaccagca gaaaccaggt     600
ttggctcctc agcttttgat ctcaggagcg agcacgcttc agggtgaggt cccaagtcgc     660
tttagtggct ctggctccgg gacagacttc acgttgacga tcagcagttt gcagcctgag     720
gatttcgcga cctactactg ccagcaagcg aaatatttc cgtacacttt cggtcagggg      780
accaaattgg agatcaaagg tgggggtggt tcaggcggcg gaggctcagg cggcggcggt     840
agcggaggag cggaagcgg gggtggcgga tcagaagtgc aactcgttca gagtggcgcg     900
gaggttaaga aacccggtgc atctgtaaag gttagctgta aggcatcagg atacactttt     960
accagctatt acatgcattg ggtgagacag gctcccggtc aggggctcga atggatgggg    1020
ttgatcaacc cgagtggtgg ttcaacatct tacgcccaga gtttcagggc cagtaacaca    1080
atgactcggg acacgtctac ctcaactgtg tatatggagc tttccagcct gcgctcagag    1140
```

```
gatacagcag tctattactg cgcacggtca gacagaggta taacggccac tgatgcgttc    1200
gatatctggg gacaagggac tatggtaact gtgtcttccg gaggaggagg tagtggaggg    1260
ggaggaagcg gtgggggggg ctcacagtcc gttttgactc agccaccaag cgtctcagtc    1320 gcaccgggc  gaatggcgaa aattacttgc ggcgggagcg acataggcaa caagaatgtg    1380
cattggtacc aacagaaacc aggtcaagca cctgttctcg tggtgtatga tgactacgat    1440
cgcccaagcg ggatcccgga gcggttctct ggatcaaatt ctggtgatgc agccactctg    1500
acaatatcaa cggtggaagt cggtgacgag gctgattact tctgccaagt atgggatggc    1560
agcggagatc cctactggat gtttggagga ggtactcaac tgacagttct gggcgcggcc    1620
gcaacgacca ctccagcacc gagaccgcca accccgcgc  ctaccatcgc aagtcaacca    1680
ctttctctca ggcctgaagc gtgccgacct gcagctggtg gggcagtaca taccaggggt    1740
ttggacttcg catgtgacgt ggcggcaatt ctcggcctgg acttgtcct  tggtctgctt    1800 ggtccgctcg caatacttct ggccttgtac ctgctccgca gagaccaaag acttccgccc    1860
gacgcccaca agcccccagg aggaggttcc ttcagaacgc ctatacaaga gaacaagca    1920 gatgcccact ctaccctggc taaaatcagg gtgaagttta gccggtcagc tgatgcacct    1980
gcatatcagc agggacagaa ccagctgtac aatgagctga acctcggacg aagagaggag    2040
tacgacgtgt tggacaaaag acgaggtaga gaccccgaga tgggcggcaa gccgagaaga    2100
aaaaacccac aagaagggct ttataatgag cttcagaaag ataagatggc agaggcctac    2160
agtgagattg gcatgaaggg cgaaagaagg aggggcaaag gacacgacgg tctctaccaa    2220
ggcctcagca cggctaccaa agatacgtat gacgcattgc atatgcaggc attgccgccc    2280
cgc                                                                 2283
```

<210> SEQ ID NO 67
<211> LENGTH: 760
<212> TYPE: PRT
<213> ORGANISM: Artificial Sequence
<220> FEATURE:
<223> OTHER INFORMATION: CAR D0137 CD22-19 CD8 OX40TM OX40z

<400> SEQUENCE: 67

```
Leu Leu Leu Val Thr Ser Leu Leu Leu Cys Glu Leu Pro His Pro Ala
 1               5                  10                  15

Phe Leu Leu Ile Pro Gln Val Gln Leu Gln Gln Ser Gly Pro Gly Leu
             20                  25                  30

Val Lys His Ser Gln Thr Leu Ser Leu Thr Cys Ala Ile Ser Gly Asp
         35                  40                  45

Ser Val Ser Ser Asn Ser Ala Ala Trp Asn Trp Ile Arg Gln Ser Pro
     50                  55                  60

Ser Arg Gly Leu Glu Trp Leu Gly Arg Thr Tyr Tyr Arg Ser Lys Trp
 65                  70                  75                  80

Tyr Asn Asp Tyr Ala Val Ser Val Lys Ser Arg Ile Thr Ile Asn Pro
                 85                  90                  95

Asp Thr Ser Lys Asn Gln Phe Ser Leu Gln Leu Asn Ser Val Thr Pro
            100                 105                 110

Glu Asp Thr Ala Val Tyr Tyr Cys Ala Gln Glu Val Glu Pro His Asp
        115                 120                 125

Ala Phe Asp Ile Trp Gly Gln Gly Thr Met Val Thr Val Ser Ser Gly
    130                 135                 140

Gly Gly Gly Ser Gly Gly Gly Gly Ser Gly Gly Gly Gly Ser Asp Ile
145                 150                 155                 160
```

```
Gln Met Thr Gln Ser Pro Ser Val Tyr Ala Ser Val Gly Asp Lys
                165                 170                 175

Val Thr Ile Thr Cys Arg Ala Ser Gln Asp Val Ser Gly Trp Leu Ala
            180                 185                 190

Trp Tyr Gln Gln Lys Pro Gly Leu Ala Pro Gln Leu Leu Ile Ser Gly
        195                 200                 205

Ala Ser Thr Leu Gln Gly Glu Val Pro Ser Arg Phe Ser Gly Ser Gly
    210                 215                 220

Ser Gly Thr Asp Phe Thr Leu Thr Ile Ser Ser Leu Gln Pro Glu Asp
225                 230                 235                 240

Phe Ala Thr Tyr Tyr Cys Gln Gln Ala Lys Tyr Phe Pro Tyr Thr Phe
                245                 250                 255

Gly Gln Gly Thr Lys Leu Glu Ile Lys Gly Gly Gly Ser Gly Gly
                260                 265                 270

Gly Gly Ser Gly Gly Gly Ser Gly Gly Gly Ser Gly Gly Gly
            275                 280                 285

Gly Ser Glu Val Gln Leu Val Gln Ser Gly Ala Glu Val Lys Lys Pro
        290                 295                 300

Gly Ala Ser Val Lys Val Ser Cys Lys Ala Ser Gly Tyr Thr Phe Thr
305                 310                 315                 320

Ser Tyr Tyr Met His Trp Val Arg Gln Ala Pro Gly Gln Gly Leu Glu
                325                 330                 335

Trp Met Gly Leu Ile Asn Pro Ser Gly Gly Ser Thr Ser Tyr Ala Gln
            340                 345                 350

Lys Phe Gln Gly Arg Val Thr Met Thr Arg Asp Thr Ser Thr Ser Thr
        355                 360                 365

Val Tyr Met Glu Leu Ser Ser Leu Arg Ser Glu Asp Thr Ala Val Tyr
    370                 375                 380

Tyr Cys Ala Arg Ser Asp Arg Gly Ile Thr Ala Thr Asp Ala Phe Asp
385                 390                 395                 400

Ile Trp Gly Gln Gly Thr Met Val Thr Val Ser Ser Gly Gly Gly Gly
                405                 410                 415

Ser Gly Gly Gly Gly Ser Gly Gly Gly Gly Ser Gln Ser Val Leu Thr
            420                 425                 430

Gln Pro Pro Ser Val Ser Val Ala Pro Gly Arg Met Ala Lys Ile Thr
        435                 440                 445

Cys Gly Gly Ser Asp Ile Gly Asn Lys Asn Val His Trp Tyr Gln Gln
    450                 455                 460

Lys Pro Gly Gln Ala Pro Val Leu Val Val Tyr Asp Asp Tyr Asp Arg
465                 470                 475                 480

Pro Ser Gly Ile Pro Glu Arg Phe Ser Gly Ser Asn Ser Gly Asp Ala
                485                 490                 495

Ala Thr Leu Thr Ile Ser Thr Val Glu Val Gly Asp Glu Ala Asp Tyr
            500                 505                 510

Phe Cys Gln Val Trp Asp Gly Ser Gly Asp Pro Tyr Trp Met Phe Gly
        515                 520                 525

Gly Gly Thr Gln Leu Thr Val Leu Gly Ala Ala Thr Thr Thr Pro
    530                 535                 540

Ala Pro Arg Pro Pro Thr Pro Ala Pro Thr Ile Ala Ser Gln Pro Leu
545                 550                 555                 560

Ser Leu Arg Pro Glu Ala Cys Arg Pro Ala Ala Gly Gly Ala Val His
                565                 570                 575
```

```
Thr Arg Gly Leu Asp Phe Ala Cys Asp Val Ala Ala Ile Leu Gly Leu
            580                 585                 590
Gly Leu Val Leu Gly Leu Leu Gly Pro Leu Ala Ile Leu Leu Ala Leu
        595                 600                 605
Tyr Leu Leu Arg Arg Asp Gln Arg Leu Pro Pro Asp Ala His Lys Pro
    610                 615                 620
Pro Gly Gly Gly Ser Phe Arg Thr Pro Ile Gln Glu Glu Gln Ala Asp
625                 630                 635                 640
Ala His Ser Thr Leu Ala Lys Ile Arg Val Lys Phe Ser Arg Ser Ala
                645                 650                 655
Asp Ala Pro Ala Tyr Gln Gln Gly Gln Asn Gln Leu Tyr Asn Glu Leu
            660                 665                 670
Asn Leu Gly Arg Arg Glu Glu Tyr Asp Val Leu Asp Lys Arg Arg Gly
        675                 680                 685
Arg Asp Pro Glu Met Gly Gly Lys Pro Arg Arg Lys Asn Pro Gln Glu
    690                 695                 700
Gly Leu Tyr Asn Glu Leu Gln Lys Asp Lys Met Ala Glu Ala Tyr Ser
705                 710                 715                 720
Glu Ile Gly Met Lys Gly Glu Arg Arg Arg Gly Lys Gly His Asp Gly
                725                 730                 735
Leu Tyr Gln Gly Leu Ser Thr Ala Thr Lys Asp Thr Tyr Asp Ala Leu
            740                 745                 750
His Met Gln Ala Leu Pro Pro Arg
        755                 760

<210> SEQ ID NO 68
<211> LENGTH: 2310
<212> TYPE: DNA
<213> ORGANISM: Artificial Sequence
<220> FEATURE:
<223> OTHER INFORMATION: CAR D0138 CD22-19 CD8 CD27z

<400> SEQUENCE: 68
atgctcttgc tcgtgacttc tttgcttttg tgcgaacttc cgcacccagc cttccttttg      60
atacctcagg tacagcttca acaaagcgga ccgggacttg ttaagcattc ccaaacccTt     120
tctctcacgt gtgcaattag cggcgatagt gtatcctcta attctgcggc ctggaactgg     180
atacgacaat caccaagccg gggactcgag tggttgggcc gaacctacta tcggtccaaa     240
tggtataatg actacgcagt atccgtgaaa tctcgcatta cgatcaatcc agacacctcc     300
aaaaatcaat tttctctgca gttgaatagc gtgactcccg aggacacggc cgtttactat     360
tgcgcccagg aagttgaacc ccacgatgca tttgatattt ggggccaggg aaccatggtg     420
acagtgagta gtggggggtgg aggatctgga ggaggcggta gcggcggggg cggcagtgat     480
atccagatga cgcagtcacc ttccagcgtg tatgcgagtg tggggacaa ggtcaccata     540
acctgtcgcg ctagccaaga tgtcagcggg tggctggctt ggtaccagca gaaaccaggt     600
ttggctcctc agcttttgat ctcaggagcg agcacgcttc agggtgaggt cccaagtcgc     660
tttagtggct ctggctccgg gacagacttc acgttgacga tcagcagttt gcagcctgag     720
gatttcgcga cctactactg ccagcaagcg aaatatttc cgtacacttt cggtcagggg     780
accaaattgg agatcaaagg tgggggtggt tcaggcggcg aggctcagg cggcggcggt     840
agcggaggag gcggaagcgg gggtggcgga tcagaagtgc aactcgttca gagtggcgcg     900
gaggttaaga aacccggtgc atctgtaaag gttagctgta aggcatcagg atacacttt     960
accagctatt acatgcattg ggtgagacag gctcccggtc aggggctcga atggatgggg    1020
```

```
ttgatcaacc cgagtggtgg ttcaacatct tacgcccaga agtttcaggg ccgagtaaca      1080
atgactcggg acacgtctac ctcaactgtg tatatggagc tttccagcct gcgctcagag      1140
gatacagcag tctattactg cgcacggtca gacagaggta taacggccac tgatgcgttc      1200
gatatctggg gacaagggac tatggtaact gtgtcttccg gaggaggagg tagtggaggg      1260
ggaggaagcg gtggggggggg ctcacagtcc gttttgactc agccaccaag cgtctcagtc      1320
gcaccggggc gaatggcgaa aattacttgc ggcgggagcg acataggcaa caagaatgtg      1380
cattggtacc aacagaaacc aggtcaagca cctgttctcg tggtgtatga tgactacgat      1440
cgcccaagcg ggatcccgga gcggttctct ggatcaaatt ctggtgatgc agccactctg      1500
acaatatcaa cggtggaagt cggtgacgag gctgattact tctgccaagt atgggatggc      1560
agcggagatc cctactggat gtttggagga ggtactcaac tgacagttct gggcgcggcc      1620
gcgactacca ctcctgcacc acggccacct accccagccc ccaccattgc aagccagcca      1680
ctttcactgc gccccgaagc gtgtagacca gctgctggag gagccgtgca tacccgaggg      1740
ctggacttcg cctgtgacat ctacatctgg gccccattgg ctggaacttg cggcgtgctg      1800
ctcttgtctc tggtcattac cctgtactgc aacggcgca aataccgctc aataaaggc      1860
gaaagtccgg tagaacccgc agaaccttgc cactacagtt gtcccagaga agagggt      1920
tctacaatac ctattcaaga ggactatagg aaaccagagc ccgcatgtag tcccagagtg      1980
aagttcagcc gctcagccga tgcaccggcc taccagcagg acagaaccca gctctacaac      2040
gagctcaacc tgggtcggcg ggaagaatat gacgtgctgg acaaacgcgc ggcagagat      2100
ccggagatgg ggggaaagcc gaggaggaag aaccctcaag agggcctgta caacgaactg      2160
cagaaggaca gatggcgga agcctactcc gagatcggca tgaagggaga acgccggaga      2220
gggaagggtc atgacggact gtaccagggc ctgtcaactg ccactaagga cacttacgat      2280
gcgctccata tgcaagcttt gccccgcgg                                        2310
```

<210> SEQ ID NO 69
<211> LENGTH: 769
<212> TYPE: PRT
<213> ORGANISM: Artificial Sequence
<220> FEATURE:
<223> OTHER INFORMATION: CAR D0138 CD22-19 CD8 CD27z

<400> SEQUENCE: 69

```
Met Leu Leu Leu Val Thr Ser Leu Leu Cys Glu Leu Pro His Pro
1               5                  10                  15

Ala Phe Leu Leu Ile Pro Gln Val Gln Leu Gln Gln Ser Gly Pro Gly
                20                  25                  30

Leu Val Lys His Ser Gln Thr Leu Ser Leu Thr Cys Ala Ile Ser Gly
            35                  40                  45

Asp Ser Val Ser Ser Asn Ser Ala Ala Trp Asn Trp Ile Arg Gln Ser
        50                  55                  60

Pro Ser Arg Gly Leu Glu Trp Leu Gly Arg Thr Tyr Tyr Arg Ser Lys
65                  70                  75                  80

Trp Tyr Asn Asp Tyr Ala Val Ser Val Lys Ser Arg Ile Thr Ile Asn
                85                  90                  95

Pro Asp Thr Ser Lys Asn Gln Phe Ser Leu Gln Leu Asn Ser Val Thr
            100                 105                 110

Pro Glu Asp Thr Ala Val Tyr Tyr Cys Ala Gln Glu Val Glu Pro His
        115                 120                 125
```

-continued

Asp Ala Phe Asp Ile Trp Gly Gln Gly Thr Met Val Thr Val Ser Ser
130                 135                 140

Gly Gly Gly Gly Ser Gly Gly Gly Ser Gly Gly Gly Gly Ser Asp
145                 150                 155                 160

Ile Gln Met Thr Gln Ser Pro Ser Ser Val Tyr Ala Ser Val Gly Asp
            165                 170                 175

Lys Val Thr Ile Thr Cys Arg Ala Ser Gln Asp Val Ser Gly Trp Leu
            180                 185                 190

Ala Trp Tyr Gln Gln Lys Pro Gly Leu Ala Pro Gln Leu Leu Ile Ser
        195                 200                 205

Gly Ala Ser Thr Leu Gln Gly Glu Val Pro Ser Arg Phe Ser Gly Ser
210                 215                 220

Gly Ser Gly Thr Asp Phe Thr Leu Thr Ile Ser Ser Leu Gln Pro Glu
225                 230                 235                 240

Asp Phe Ala Thr Tyr Tyr Cys Gln Gln Ala Lys Tyr Phe Pro Tyr Thr
                245                 250                 255

Phe Gly Gln Gly Thr Lys Leu Glu Ile Lys Gly Gly Gly Gly Ser Gly
            260                 265                 270

Gly Gly Gly Ser Gly Gly Gly Gly Ser Gly Gly Gly Gly Ser Gly Gly
        275                 280                 285

Gly Gly Ser Glu Val Gln Leu Val Gln Ser Gly Ala Glu Val Lys Lys
290                 295                 300

Pro Gly Ala Ser Val Lys Val Ser Cys Lys Ala Ser Gly Tyr Thr Phe
305                 310                 315                 320

Thr Ser Tyr Tyr Met His Trp Val Arg Gln Ala Pro Gly Gln Gly Leu
                325                 330                 335

Glu Trp Met Gly Leu Ile Asn Pro Ser Gly Gly Ser Thr Ser Tyr Ala
            340                 345                 350

Gln Lys Phe Gln Gly Arg Val Thr Met Thr Arg Asp Thr Ser Thr Ser
        355                 360                 365

Thr Val Tyr Met Glu Leu Ser Ser Leu Arg Ser Glu Asp Thr Ala Val
370                 375                 380

Tyr Tyr Cys Ala Arg Ser Asp Arg Gly Ile Thr Ala Thr Asp Ala Phe
385                 390                 395                 400

Asp Ile Trp Gly Gln Gly Thr Met Val Thr Val Ser Ser Gly Gly Gly
                405                 410                 415

Gly Ser Gly Gly Gly Gly Ser Gly Gly Gly Gly Ser Gln Ser Val Leu
            420                 425                 430

Thr Gln Pro Pro Ser Val Ser Val Ala Pro Gly Arg Met Ala Lys Ile
        435                 440                 445

Thr Cys Gly Gly Ser Asp Ile Gly Asn Lys Asn Val His Trp Tyr Gln
450                 455                 460

Gln Lys Pro Gly Gln Ala Pro Val Leu Val Val Tyr Asp Asp Tyr Asp
465                 470                 475                 480

Arg Pro Ser Gly Ile Pro Glu Arg Phe Ser Gly Ser Asn Ser Gly Asp
                485                 490                 495

Ala Ala Thr Leu Thr Ile Ser Thr Val Glu Val Gly Asp Glu Ala Asp
            500                 505                 510

Tyr Phe Cys Gln Val Trp Asp Gly Ser Gly Asp Pro Tyr Trp Met Phe
        515                 520                 525

Gly Gly Gly Thr Gln Leu Thr Val Leu Gly Ala Ala Ala Thr Thr Thr
530                 535                 540

Pro Ala Pro Arg Pro Pro Thr Pro Ala Pro Thr Ile Ala Ser Gln Pro

```
          545                 550                 555                 560
Leu Ser Leu Arg Pro Glu Ala Cys Arg Pro Ala Ala Gly Gly Ala Val
                565                 570                 575
His Thr Arg Gly Leu Asp Phe Ala Cys Asp Ile Tyr Ile Trp Ala Pro
                580                 585                 590
Leu Ala Gly Thr Cys Gly Val Leu Leu Leu Ser Leu Val Ile Thr Leu
                595                 600                 605
Tyr Cys Gln Arg Arg Lys Tyr Arg Ser Asn Lys Gly Glu Ser Pro Val
                610                 615                 620
Glu Pro Ala Glu Pro Cys His Tyr Ser Cys Pro Arg Glu Glu Glu Gly
625                 630                 635                 640
Ser Thr Ile Pro Ile Gln Glu Asp Tyr Arg Lys Pro Glu Pro Ala Cys
                645                 650                 655
Ser Pro Arg Val Lys Phe Ser Arg Ser Ala Asp Ala Pro Ala Tyr Gln
                660                 665                 670
Gln Gly Gln Asn Gln Leu Tyr Asn Glu Leu Asn Leu Gly Arg Arg Glu
                675                 680                 685
Glu Tyr Asp Val Leu Asp Lys Arg Arg Gly Arg Asp Pro Glu Met Gly
                690                 695                 700
Gly Lys Pro Arg Arg Lys Asn Pro Gln Glu Gly Leu Tyr Asn Glu Leu
705                 710                 715                 720
Gln Lys Asp Lys Met Ala Glu Ala Tyr Ser Glu Ile Gly Met Lys Gly
                725                 730                 735
Glu Arg Arg Arg Gly Lys Gly His Asp Gly Leu Tyr Gln Gly Leu Ser
                740                 745                 750
Thr Ala Thr Lys Asp Thr Tyr Asp Ala Leu His Met Gln Ala Leu Pro
                755                 760                 765
Pro
```

<210> SEQ ID NO 70
<211> LENGTH: 2280
<212> TYPE: DNA
<213> ORGANISM: Artificial Sequence
<220> FEATURE:
<223> OTHER INFORMATION: CAR D0139 CD22-19 CD28 CD28z

<400> SEQUENCE: 70

```
atgctcttgc tcgtgacttc tttgcttttg tgcgaacttc cgcacccagc cttccttttg      60
atacctcagg tacagcttca acaaagcgga ccgggacttg ttaagcattc ccaaaccctt     120
tctctcacgt gtgcaattag cggcgatagt gtatcctcta attctgcggc ctggaactgg     180
atacgacaat caccaagccg gggactcgag tggttgggcc gaacctacta tcggtccaaa     240
tggtataatg actacgcagt atccgtgaaa tctcgcatta cgatcaatcc agacacctcc     300
aaaaatcaat tttctctgca gttgaatagc gtgactcccg aggacacggc cgtttactat     360
tgcgcccagg aagttgaacc ccacgatgca tttgatattt ggggccaggg aaccatggtg     420
acagtgagta gtggggggtgg aggatctgga ggaggcggta gcggcggggg cggcagtgat     480
atccagatga cgcagtcacc ttccagcgtg tatgcgagtg tggggacaa ggtcaccata     540
acctgtcgcg ctagccaaga tgtcagcggg tggctggctt gtaccagca gaaaccaggt     600
ttggctcctc agcttttgat ctcaggagcg agcacgcttc agggtgaggt cccaagtcgc     660
tttagtggct ctggctccgg gacagacttc acgttgacga tcagcagttt gcagcctgag     720
gatttcgcga cctactactg ccagcaagcg aaatattttc cgtacacttt cggtcagggg     780
```

```
accaaattgg agatcaaagg tgggggtggt tcaggcggcg gaggctcagg cggcggcggt    840
agcggaggag gcggaagcgg gggtggcgga tcagaagtgc aactcgttca gagtggcgcg    900
gaggttaaga aacccggtgc atctgtaaag gttagctgta aggcatcagg atacactttt    960
accagctatt acatgcattg ggtgagacag gctcccggtc aggggctcga atggatgggg   1020
ttgatcaacc cgagtggtgg ttcaacatct tacgcccaga agtttcaggg ccgagtaaca   1080
atgactcggg acacgtctac ctcaactgtg tatatggagc tttccagcct gcgctcagag   1140
gatacagcag tctattactg cgcacggtca gacagaggta taacggccac tgatgcgttc   1200
gatatctggg gacaagggac tatggtaact gtgtcttccg gaggaggagg tagtggaggg   1260
ggaggaagcg gtgggggggg ctcacagtcc gttttgactc agccaccaag cgtctcagtc   1320
gcaccgggc gaatggcgaa aattacttgc ggcgggagcg acataggcaa caagaatgtg   1380
cattggtacc aacagaaacc aggtcaagca cctgttctcg tggtgtatga tgactacgat   1440
cgcccaagcg ggatcccgga gcggttctct ggatcaaatt ctggtgatgc agccactctg   1500
acaatatcaa cggtggaagt cggtgacgag gctgattact tctgccaagt atgggatggc   1560
agcggagatc cctactggat gtttggagga ggtactcaac tgacagttct gggcgcggcc   1620
gcaatcgaag tgatgtatcc acctccgtac ctcgataacg agaaatcaaa tggaacgatc   1680
attcatgtga agggaaaaca tctgtgccca agcccattgt tcccaggtcc gtcaaaacca   1740
ttctgggtgc ttgtcgttgt tggggtgta ctcgcatgtt attctttgct ggtgactgtg    1800
gcgtttatca tcttctgggt aaggagtaaa cgcagccgcc tgctgcattc agactacatg   1860
aacatgaccc cacggcggcc cggcccaacg cgcaaacact accaaccta cgccccaccg     1920
cgagactttg ccgcctacag atcccgcgtg aagttttccc ggtccgccga cgctccggcg   1980
taccagcagg gcaaaaacca gctgtacaac gaacttaacc tcggtcgccg ggaagaatat   2040
gacgtgctgg acaagcggcg gggaagagat cccgagatgg gtggaaagcc gcggcggaag   2100
aaccctcagg agggcttgta caacgagctg caaaaggaca aaatggccga agcctactcc   2160
gagattggca tgaagggaga gcgcagacgc gggaagggac acgatggact gtaccaggga   2220
ctgtcaaccg cgactaagga cacttacgac gccctgcaca tgcaggccct gccccccgcgc  2280
```

<210> SEQ ID NO 71
<211> LENGTH: 760
<212> TYPE: PRT
<213> ORGANISM: Artificial Sequence
<220> FEATURE:
<223> OTHER INFORMATION: CAR D0139 CD22-19 CD28 CD28z

<400> SEQUENCE: 71

```
Met Leu Leu Leu Val Thr Ser Leu Leu Cys Glu Leu Pro His Pro
1               5                   10                  15

Ala Phe Leu Leu Ile Pro Gln Val Gln Leu Gln Gln Ser Gly Pro Gly
            20                  25                  30

Leu Val Lys His Ser Gln Thr Leu Ser Leu Thr Cys Ala Ile Ser Gly
        35                  40                  45

Asp Ser Val Ser Ser Asn Ser Ala Ala Trp Asn Trp Ile Arg Gln Ser
    50                  55                  60

Pro Ser Arg Gly Leu Glu Trp Leu Gly Arg Thr Tyr Tyr Arg Ser Lys
65                  70                  75                  80

Trp Tyr Asn Asp Tyr Ala Val Ser Val Lys Ser Arg Ile Thr Ile Asn
                85                  90                  95

Pro Asp Thr Ser Lys Asn Gln Phe Ser Leu Gln Leu Asn Ser Val Thr
```

```
                100                 105                 110
Pro Glu Asp Thr Ala Val Tyr Tyr Cys Ala Gln Glu Val Glu Pro His
            115                 120                 125
Asp Ala Phe Asp Ile Trp Gly Gln Gly Thr Met Val Thr Val Ser Ser
130                 135                 140
Gly Gly Gly Ser Gly Gly Gly Ser Gly Gly Gly Ser Asp
145                 150                 155                 160
Ile Gln Met Thr Gln Ser Pro Ser Ser Val Tyr Ala Ser Val Gly Asp
            165                 170                 175
Lys Val Thr Ile Thr Cys Arg Ala Ser Gln Asp Val Ser Gly Trp Leu
            180                 185                 190
Ala Trp Tyr Gln Gln Lys Pro Gly Leu Ala Pro Gln Leu Leu Ile Ser
            195                 200                 205
Gly Ala Ser Thr Leu Gln Gly Glu Val Pro Ser Arg Phe Ser Gly Ser
            210                 215                 220
Gly Ser Gly Thr Asp Phe Thr Leu Thr Ile Ser Ser Leu Gln Pro Glu
225                 230                 235                 240
Asp Phe Ala Thr Tyr Tyr Cys Gln Gln Ala Lys Tyr Phe Pro Tyr Thr
            245                 250                 255
Phe Gly Gln Gly Thr Lys Leu Glu Ile Lys Gly Gly Gly Gly Ser Gly
            260                 265                 270
Gly Gly Gly Ser Gly Gly Gly Ser Gly Gly Gly Ser Gly Gly
            275                 280                 285
Gly Gly Ser Glu Val Gln Leu Val Gln Ser Gly Ala Glu Val Lys Lys
            290                 295                 300
Pro Gly Ala Ser Val Lys Val Ser Cys Lys Ala Ser Gly Tyr Thr Phe
305                 310                 315                 320
Thr Ser Tyr Tyr Met His Trp Val Arg Gln Ala Pro Gly Gln Gly Leu
            325                 330                 335
Glu Trp Met Gly Leu Ile Asn Pro Ser Gly Gly Ser Thr Ser Tyr Ala
            340                 345                 350
Gln Lys Phe Gln Gly Arg Val Thr Met Thr Arg Asp Thr Ser Thr Ser
            355                 360                 365
Thr Val Tyr Met Glu Leu Ser Ser Leu Arg Ser Glu Asp Thr Ala Val
            370                 375                 380
Tyr Tyr Cys Ala Arg Ser Asp Arg Gly Ile Thr Ala Thr Asp Ala Phe
385                 390                 395                 400
Asp Ile Trp Gly Gln Gly Thr Met Val Thr Val Ser Ser Gly Gly Gly
            405                 410                 415
Gly Ser Gly Gly Gly Gly Ser Gly Gly Gly Ser Gln Ser Val Leu
            420                 425                 430
Thr Gln Pro Pro Ser Val Ser Ala Pro Gly Arg Met Ala Lys Ile
            435                 440                 445
Thr Cys Gly Gly Ser Asp Ile Gly Asn Lys Asn Val His Trp Tyr Gln
            450                 455                 460
Gln Lys Pro Gly Gln Ala Pro Val Leu Val Val Tyr Asp Asp Tyr Asp
465                 470                 475                 480
Arg Pro Ser Gly Ile Pro Glu Arg Phe Ser Gly Ser Asn Ser Gly Asp
            485                 490                 495
Ala Ala Thr Leu Thr Ile Ser Thr Val Glu Val Gly Asp Glu Ala Asp
            500                 505                 510
Tyr Phe Cys Gln Val Trp Asp Gly Ser Gly Asp Pro Tyr Trp Met Phe
            515                 520                 525
```

```
Gly Gly Gly Thr Gln Leu Thr Val Leu Gly Ala Ala Ala Ile Glu Val
            530                 535                 540
Met Tyr Pro Pro Pro Tyr Leu Asp Asn Glu Lys Ser Asn Gly Thr Ile
545                 550                 555                 560
Ile His Val Lys Gly Lys His Leu Cys Pro Ser Pro Leu Phe Pro Gly
                565                 570                 575
Pro Ser Lys Pro Phe Trp Val Leu Val Val Val Gly Gly Val Leu Ala
            580                 585                 590
Cys Tyr Ser Leu Leu Val Thr Val Ala Phe Ile Ile Phe Trp Val Arg
        595                 600                 605
Ser Lys Arg Ser Arg Leu Leu His Ser Asp Tyr Met Asn Met Thr Pro
    610                 615                 620
Arg Arg Pro Gly Pro Thr Arg Lys His Tyr Gln Pro Tyr Ala Pro Pro
625                 630                 635                 640
Arg Asp Phe Ala Ala Tyr Arg Ser Arg Val Lys Phe Ser Arg Ser Ala
                645                 650                 655
Asp Ala Pro Ala Tyr Gln Gln Gly Gln Asn Gln Leu Tyr Asn Glu Leu
            660                 665                 670
Asn Leu Gly Arg Arg Glu Glu Tyr Asp Val Leu Asp Lys Arg Arg Gly
        675                 680                 685
Arg Asp Pro Glu Met Gly Gly Lys Pro Arg Arg Lys Asn Pro Gln Glu
690                 695                 700
Gly Leu Tyr Asn Glu Leu Gln Lys Asp Lys Met Ala Glu Ala Tyr Ser
705                 710                 715                 720
Glu Ile Gly Met Lys Gly Glu Arg Arg Arg Gly Lys Gly His Asp Gly
                725                 730                 735
Leu Tyr Gln Gly Leu Ser Thr Ala Thr Lys Asp Thr Tyr Asp Ala Leu
            740                 745                 750
His Met Gln Ala Leu Pro Pro Arg
        755                 760

<210> SEQ ID NO 72
<211> LENGTH: 2292
<212> TYPE: DNA
<213> ORGANISM: Artificial Sequence
<220> FEATURE:
<223> OTHER INFORMATION: CAR D0145 CD22-19 CD8 OX40z

<400> SEQUENCE: 72
atgctcttgc tcgtgacttc tttgcttttg tgcgaacttc cgcacccagc cttcctttttg     60 atacctcagg tacagcttca acaaagcgga ccgggacttg ttaagcattc ccaaacccct    120
tctctcacgt gtgcaattag cggcgatagt gtatcctcta attctgcggc ctggaactgg    180
atacgacaat caccaagccg gggactcgag tggttgggcc gaacctacta tcggtccaaa    240
tggtataatg actacgcagt atccgtgaaa tctcgcatta cgatcaatcc agacacctcc    300
aaaaatcaat tttctctgca gttgaatagc gtgactcccg aggacacggc cgtttactat    360
tgcgcccagg aagttgaacc ccacgatgca tttgatattt ggggccaggg aaccatggtg    420
acagtgagta gtggggtgg aggatctgga ggaggcggta gcggcggggg cggcagtgat    480
atccagatga cgcagtcacc ttccagcgtg tatgcgagtg tggggacaa ggtcaccata    540 acctgtcgcg ctagccaaga tgtcagcggg tggctggctt ggtaccagca gaaaccaggt    600
ttggctcctc agcttttgat ctcaggagcg agcacgcttc agggtgaggt cccaagtcgc    660
tttagtggct ctggctccgg gacagacttc acgttgacga tcagcagttt gcagcctgag    720
```

```
gatttcgcga cctactactg ccagcaagcg aaatattttc cgtacacttt cggtcagggg    780
accaaattgg agatcaaagg tgggggtggt tcaggcggcg gaggctcagg cggcggcggt    840
agcggaggag gcggaagcgg gggtggcgga tcagaagtgc aactcgttca gagtggcgcg    900
gaggttaaga aacccggtgc atctgtaaag gttagctgta aggcatcagg atacactttt    960
accagctatt acatgcattg ggtgagacag gctcccggtc aggggctcga atggatgggg   1020
ttgatcaacc cgagtggtgg ttcaacatct tacgcccaga agtttcaggg ccgagtaaca   1080
atgactcggg acacgtctac ctcaactgtg tatatggagc tttccagcct gcgctcagag   1140
gatacagcag tctattactg cgcacggtca gacagaggta taacggccac tgatgcgttc   1200
gatatctggg gacaagggac tatggtaact gtgtcttccg gaggaggagg tagtggaggg   1260
ggaggaagcg gtgggggggg ctcacagtcc gttttgactc agccaccaag cgtctcagtc   1320
gcaccggggc gaatggcgaa aattacttgc ggcgggagcg acataggcaa caagaatgtg   1380
cattggtacc aacagaaacc aggtcaagca cctgttctcg tggtgtatga tgactacgat   1440
cgcccaagcg ggatcccgga gcggttctct ggatcaaatt ctggtgatgc agccactctg   1500
acaatatcaa cggtggaagt cggtgacgag gctgattact tctgccaagt atgggatggc   1560
agcggagatc cctactggat gtttggagga ggtactcaac tgacagttct gggcgcggcc   1620
gcaacaacca ctccagcacc tagaccgcca acacctgcac ctaccatcgc aagtcaacca   1680
ctttctctca ggcctgaagc gtgccgacct gcagctggtg gggcagtaca taccaggggt   1740
ttggacttcg catgtgacat ctacatctgg gccccattgg ctggaacttg cggcgtgctg   1800
ctcttgtctc tggtcattac cctgtactgc gccttgtacc tgctccgcag agaccaaaga   1860
cttccgcccg acgcccacaa gcccccagga ggaggttcct tcagaacgcc tatacaagaa   1920
gaacaagcag atgcccactc taccctggct aaaatcaggg tgaagtttag ccggtcagct   1980
gatgcacctg catatcagca gggacagaac cagctgtaca atgagctgaa cctcggacga   2040
agagaggagt acgacgtgtt ggacaaaaga cgaggtagag accccgagat gggcggcaag   2100
ccgagaagaa aaaacccaca agaagggctt tataatgagc ttcagaaaga taagatggca   2160
gaggcctaca gtgagattgg catgaaggcc gaaagaagga gggcaaagg acacgacggt   2220 ctctaccaag gcctcagcac ggctaccaaa gatacgtatg acgcattgca tatgcaggca   2280
ttgccgcccc gc                                                       2292
```

<210> SEQ ID NO 73
<211> LENGTH: 764
<212> TYPE: PRT
<213> ORGANISM: Artificial Sequence
<220> FEATURE:
<223> OTHER INFORMATION: CAR D0145 CD22-19 CD8 OX40z

<400> SEQUENCE: 73

```
Met Leu Leu Leu Val Thr Ser Leu Leu Cys Glu Leu Pro His Pro
1               5                   10                  15

Ala Phe Leu Leu Ile Pro Gln Val Gln Leu Gln Gln Ser Gly Pro Gly
                20                  25                  30

Leu Val Lys His Ser Gln Thr Leu Ser Leu Thr Cys Ala Ile Ser Gly
            35                  40                  45

Asp Ser Val Ser Ser Asn Ser Ala Ala Trp Asn Trp Ile Arg Gln Ser
        50                  55                  60

Pro Ser Arg Gly Leu Glu Trp Leu Gly Arg Thr Tyr Tyr Arg Ser Lys
65                  70                  75                  80
```

Trp Tyr Asn Asp Tyr Ala Val Ser Val Lys Ser Arg Ile Thr Ile Asn
                85                  90                  95

Pro Asp Thr Ser Lys Asn Gln Phe Ser Leu Gln Leu Asn Ser Val Thr
            100                 105                 110

Pro Glu Asp Thr Ala Val Tyr Tyr Cys Ala Gln Glu Val Glu Pro His
        115                 120                 125

Asp Ala Phe Asp Ile Trp Gly Gln Gly Thr Met Val Thr Val Ser Ser
130                 135                 140

Gly Gly Gly Gly Ser Gly Gly Gly Ser Gly Gly Gly Ser Asp
145                 150                 155                 160

Ile Gln Met Thr Gln Ser Pro Ser Ser Val Tyr Ala Ser Val Gly Asp
                165                 170                 175

Lys Val Thr Ile Thr Cys Arg Ala Ser Gln Asp Val Ser Gly Trp Leu
            180                 185                 190

Ala Trp Tyr Gln Gln Lys Pro Gly Leu Ala Pro Gln Leu Leu Ile Ser
        195                 200                 205

Gly Ala Ser Thr Leu Gln Gly Glu Val Pro Ser Arg Phe Ser Gly Ser
210                 215                 220

Gly Ser Gly Thr Asp Phe Thr Leu Thr Ile Ser Ser Leu Gln Pro Glu
225                 230                 235                 240

Asp Phe Ala Thr Tyr Tyr Cys Gln Gln Ala Lys Tyr Phe Pro Tyr Thr
                245                 250                 255

Phe Gly Gln Gly Thr Lys Leu Glu Ile Lys Gly Gly Gly Gly Ser Gly
            260                 265                 270

Gly Gly Gly Ser Gly Gly Gly Ser Gly Gly Gly Ser Gly Gly
        275                 280                 285

Gly Gly Ser Glu Val Gln Leu Val Gln Ser Gly Ala Glu Val Lys Lys
290                 295                 300

Pro Gly Ala Ser Val Lys Val Ser Cys Lys Ala Ser Gly Tyr Thr Phe
305                 310                 315                 320

Thr Ser Tyr Tyr Met His Trp Val Arg Gln Ala Pro Gly Gln Gly Leu
                325                 330                 335

Glu Trp Met Gly Leu Ile Asn Pro Ser Gly Gly Ser Thr Ser Tyr Ala
            340                 345                 350

Gln Lys Phe Gln Gly Arg Val Thr Met Thr Arg Asp Thr Ser Thr Ser
        355                 360                 365

Thr Val Tyr Met Glu Leu Ser Ser Leu Arg Ser Glu Asp Thr Ala Val
370                 375                 380

Tyr Tyr Cys Ala Arg Ser Asp Arg Gly Ile Thr Ala Thr Asp Ala Phe
385                 390                 395                 400

Asp Ile Trp Gly Gln Gly Thr Met Val Thr Val Ser Ser Gly Gly Gly
                405                 410                 415

Gly Ser Gly Gly Gly Gly Ser Gly Gly Gly Ser Gln Ser Val Leu
            420                 425                 430

Thr Gln Pro Pro Ser Val Ser Val Ala Pro Gly Arg Met Ala Lys Ile
        435                 440                 445

Thr Cys Gly Gly Ser Asp Ile Gly Asn Lys Asn Val His Trp Tyr Gln
450                 455                 460

Gln Lys Pro Gly Gln Ala Pro Val Leu Val Val Tyr Asp Asp Tyr Asp
465                 470                 475                 480

Arg Pro Ser Gly Ile Pro Glu Arg Phe Ser Gly Ser Asn Ser Gly Asp
                485                 490                 495

```
Ala Ala Thr Leu Thr Ile Ser Thr Val Glu Val Gly Asp Glu Ala Asp
                500                 505                 510

Tyr Phe Cys Gln Val Trp Asp Gly Ser Gly Asp Pro Tyr Trp Met Phe
            515                 520                 525

Gly Gly Gly Thr Gln Leu Thr Val Leu Gly Ala Ala Thr Thr Thr
        530                 535                 540

Pro Ala Pro Arg Pro Pro Thr Pro Ala Pro Thr Ile Ala Ser Gln Pro
545                 550                 555                 560

Leu Ser Leu Arg Pro Glu Ala Cys Arg Pro Ala Ala Gly Gly Ala Val
                565                 570                 575

His Thr Arg Gly Leu Asp Phe Ala Cys Asp Ile Tyr Ile Trp Ala Pro
            580                 585                 590

Leu Ala Gly Thr Cys Gly Val Leu Leu Leu Ser Leu Val Ile Thr Leu
        595                 600                 605

Tyr Cys Ala Leu Tyr Leu Leu Arg Arg Asp Gln Arg Leu Pro Pro Asp
610                 615                 620

Ala His Lys Pro Pro Gly Gly Gly Ser Phe Arg Thr Pro Ile Gln Glu
625                 630                 635                 640

Glu Gln Ala Asp Ala His Ser Thr Leu Ala Lys Ile Arg Val Lys Phe
                645                 650                 655

Ser Arg Ser Ala Asp Ala Pro Ala Tyr Gln Gln Gly Gln Asn Gln Leu
            660                 665                 670

Tyr Asn Glu Leu Asn Leu Gly Arg Arg Glu Glu Tyr Asp Val Leu Asp
        675                 680                 685

Lys Arg Arg Gly Arg Asp Pro Glu Met Gly Gly Lys Pro Arg Arg Lys
690                 695                 700

Asn Pro Gln Glu Gly Leu Tyr Asn Glu Leu Gln Lys Asp Lys Met Ala
705                 710                 715                 720

Glu Ala Tyr Ser Glu Ile Gly Met Lys Gly Glu Arg Arg Arg Gly Lys
                725                 730                 735

Gly His Asp Gly Leu Tyr Gln Gly Leu Ser Thr Ala Thr Lys Asp Thr
            740                 745                 750

Tyr Asp Ala Leu His Met Gln Ala Leu Pro Pro Arg
        755                 760

<210> SEQ ID NO 74
<211> LENGTH: 2406
<212> TYPE: DNA
<213> ORGANISM: Artificial Sequence
<220> FEATURE:
<223> OTHER INFORMATION: D0140 CD22-19 CD28 CD28 BBz

<400> SEQUENCE: 74
atgctcttgc tcgtgacttc tttgcttttg tgcgaacttc cgcacccagc cttcctttg      60 atacctcagg tacagcttca acaaagcgga ccgggacttg ttaagcattc ccaaaccctt    120
tctctcacgt gtgcaattag cggcgatagt gtatcctcta attctgcggc ctggaactgg    180
atacgacaat caccaagccg gggactcgag tggttgggcc gaacctacta tcggtccaaa    240
tggtataatg actacgcagt atccgtgaaa tctcgcatta cgatcaatcc agacacctcc    300
aaaaatcaat tttctctgca gttgaatagc gtgactcccg aggacacggc cgtttactat    360
tgcgcccagg aagttgaacc ccacgatgca tttgatattt ggggccaggg aaccatggtg    420
acagtgagta gtggggtgg aggatctgga ggaggcggta gcggcggggg cggcagtgat    480
atccagatga cgcagtcacc ttccagcgtg tatgcgagtg tggggacaa ggtcaccata    540
```

```
acctgtcgcg ctagccaaga tgtcagcggg tggctggctt ggtaccagca gaaaccaggt    600
ttggctcctc agcttttgat ctcaggagcg agcacgcttc agggtgaggt cccaagtcgc    660
tttagtggct ctggctccgg gacagacttc acgttgacga tcagcagttt gcagcctgag    720
gatttcgcga cctactactg ccagcaagcg aaatattttc cgtacacttt cggtcagggg    780
accaaattgg agatcaaagg tgggggtggt tcaggcggcg gaggctcagg cggcggcggt    840
agcggaggag gcggaagcgg gggtggcgga tcagaagtgc aactcgttca gagtggcgcg    900
gaggttaaga aacccggtgc atctgtaaag gttagctgta aggcatcagg atacactttt    960
accagctatt acatgcattg ggtgagacag gctcccggtc aggggctcga atggatgggg   1020
ttgatcaacc cgagtggtgg ttcaacatct tacgcccaga gtttcagggg ccgagtaaca   1080
atgactcggg acacgtctac ctcaactgtg tatatggagc tttccagcct gcgctcagag   1140
gatacagcag tctattactg cgcacggtca gacagaggta taacggccac tgatgcgttc   1200
gatatctggg gacaagggac tatggtaact gtgtcttccg gaggaggagg tagtggaggg   1260
ggaggaagcg gtgggggggg ctcacagtcc gttttgactc agccaccaag cgtctcagtc   1320
gcaccggggc gaatggcgaa aattacttgc ggcgggagcg acataggcaa caagaatgtg   1380
cattggtacc aacagaaacc aggtcaagca cctgttctcg tggtgtatga tgactacgat   1440
cgcccaagcg ggatcccgga gcggttctct ggatcaaatt ctggtgatgc agccactctg   1500
acaatatcaa cggtggaagt cggtgacgag gctgattact tctgccaagt atgggatggc   1560
agcggagatc cctactggat gtttggagga ggtactcaac tgacagttct gggcgcggcc   1620
gcaatcgaag tgatgtatcc acctccgtac ctcgataacg agaaatcaaa tggaacgatc   1680
attcatgtga agggaaacat ctgtgcccca gcccattgt tcccaggtcc gtcaaaacca   1740
ttctgggtgc ttgtcgttgt tgggggtgta ctcgcatgtt attctttgct ggtgactgtg   1800
gcgtttatca tcttctgggt aaggagtaaa cgcagccgcc tgctgcattc agactacatg   1860
aacatgaccc cacggcggcc cggcccaacg cgcaaacact accaaccttg cgccccaccg   1920
cgagactttg ccgcctacag atccaagcgc ggacggaaga aactcttgta catcttcaag   1980
cagccgttca tgcgccctgt gcaaaccacc aagaagagg acgggtgctc ctgccggttc   2040
ccggaagagg aagagggcgg ctgcgaactg cgcgtgaagt tttcccggtc cgccgacgct   2100
ccggcgtacc agcaggggca aaaccagctg tacaacgaac ttaacctcgg tcgccgggaa   2160
gaatatgacg tgctggacaa gcggcgggga agagatcccg agatgggtgg aaagccgcgg   2220
cggaagaacc ctcaggaggg cttgtacaac gagctgcaaa aggacaaaat ggccgaagcc   2280
tactccgaga ttggcatgaa gggagagcgc agacgcggga agggacacga tggactgtac   2340
cagggactgt caaccgcgac taaggacact tacgacgccc tgcacatgca ggccctgccc   2400
ccgcgc                                                               2406
```

<210> SEQ ID NO 75  
<211> LENGTH: 802  
<212> TYPE: PRT  
<213> ORGANISM: Artificial Sequence  
<220> FEATURE:  
<223> OTHER INFORMATION: CAR D0140 CD22-19 CD28 CD28 BBz
<400> SEQUENCE: 75

```
Met Leu Leu Leu Val Thr Ser Leu Leu Cys Glu Leu Pro His Pro
1               5                   10                  15

Ala Phe Leu Leu Ile Pro Gln Val Gln Leu Gln Gln Ser Gly Pro Gly
            20                  25                  30
```

```
Leu Val Lys His Ser Gln Thr Leu Ser Leu Thr Cys Ala Ile Ser Gly
             35                  40                  45

Asp Ser Val Ser Ser Asn Ser Ala Ala Trp Asn Trp Ile Arg Gln Ser
         50                  55                  60

Pro Ser Arg Gly Leu Glu Trp Leu Gly Arg Thr Tyr Tyr Arg Ser Lys
 65                  70                  75                  80

Trp Tyr Asn Asp Tyr Ala Val Ser Val Lys Ser Arg Ile Thr Ile Asn
                 85                  90                  95

Pro Asp Thr Ser Lys Asn Gln Phe Ser Leu Gln Leu Asn Ser Val Thr
                100                 105                 110

Pro Glu Asp Thr Ala Val Tyr Tyr Cys Ala Gln Val Glu Pro His
                115                 120                 125

Asp Ala Phe Asp Ile Trp Gly Gln Gly Thr Met Val Thr Val Ser Ser
            130                 135                 140

Gly Gly Gly Gly Ser Gly Gly Gly Ser Gly Gly Gly Ser Asp
145                 150                 155                 160

Ile Gln Met Thr Gln Ser Pro Ser Ser Val Tyr Ala Ser Val Gly Asp
                165                 170                 175

Lys Val Thr Ile Thr Cys Arg Ala Ser Gln Asp Val Ser Gly Trp Leu
            180                 185                 190

Ala Trp Tyr Gln Gln Lys Pro Gly Leu Ala Pro Gln Leu Leu Ile Ser
        195                 200                 205

Gly Ala Ser Thr Leu Gln Gly Glu Val Pro Ser Arg Phe Ser Gly Ser
    210                 215                 220

Gly Ser Gly Thr Asp Phe Thr Leu Thr Ile Ser Ser Leu Gln Pro Glu
225                 230                 235                 240

Asp Phe Ala Thr Tyr Tyr Cys Gln Gln Ala Lys Tyr Phe Pro Tyr Thr
                245                 250                 255

Phe Gly Gln Gly Thr Lys Leu Glu Ile Lys Gly Gly Gly Gly Ser Gly
            260                 265                 270

Gly Gly Gly Ser Gly Gly Gly Ser Gly Gly Gly Ser Gly Gly
        275                 280                 285

Gly Gly Ser Glu Val Gln Leu Val Gln Ser Gly Ala Glu Val Lys Lys
    290                 295                 300

Pro Gly Ala Ser Val Lys Val Ser Cys Lys Ala Ser Gly Tyr Thr Phe
305                 310                 315                 320

Thr Ser Tyr Tyr Met His Trp Val Arg Gln Ala Pro Gly Gln Gly Leu
                325                 330                 335

Glu Trp Met Gly Leu Ile Asn Pro Ser Gly Gly Ser Thr Ser Tyr Ala
            340                 345                 350

Gln Lys Phe Gln Gly Arg Val Thr Met Thr Arg Asp Thr Ser Thr Ser
        355                 360                 365

Thr Val Tyr Met Glu Leu Ser Ser Leu Arg Ser Glu Asp Thr Ala Val
    370                 375                 380

Tyr Tyr Cys Ala Arg Ser Asp Arg Gly Ile Thr Ala Thr Asp Ala Phe
385                 390                 395                 400

Asp Ile Trp Gly Gln Gly Thr Met Val Thr Val Ser Ser Gly Gly Gly
                405                 410                 415

Gly Ser Gly Gly Gly Gly Ser Gly Gly Gly Gly Ser Gln Ser Val Leu
            420                 425                 430

Thr Gln Pro Pro Ser Val Ser Val Ala Pro Gly Arg Met Ala Lys Ile
        435                 440                 445
```

-continued

Thr Cys Gly Gly Ser Asp Ile Gly Asn Lys Asn Val His Trp Tyr Gln
    450                 455                 460

Gln Lys Pro Gly Gln Ala Pro Val Leu Val Val Tyr Asp Asp Tyr Asp
465                 470                 475                 480

Arg Pro Ser Gly Ile Pro Glu Arg Phe Ser Gly Ser Asn Ser Gly Asp
                485                 490                 495

Ala Ala Thr Leu Thr Ile Ser Thr Val Glu Val Gly Asp Glu Ala Asp
                500                 505                 510

Tyr Phe Cys Gln Val Trp Asp Gly Ser Gly Asp Pro Tyr Trp Met Phe
            515                 520                 525

Gly Gly Gly Thr Gln Leu Thr Val Leu Gly Ala Ala Ala Ile Glu Val
    530                 535                 540

Met Tyr Pro Pro Pro Tyr Leu Asp Asn Glu Lys Ser Asn Gly Thr Ile
545                 550                 555                 560

Ile His Val Lys Gly Lys His Leu Cys Pro Ser Pro Leu Phe Pro Gly
                565                 570                 575

Pro Ser Lys Pro Phe Trp Val Leu Val Val Val Gly Gly Val Leu Ala
                580                 585                 590

Cys Tyr Ser Leu Leu Val Thr Val Ala Phe Ile Ile Phe Trp Val Arg
            595                 600                 605

Ser Lys Arg Ser Arg Leu Leu His Ser Asp Tyr Met Asn Met Thr Pro
    610                 615                 620

Arg Arg Pro Gly Pro Thr Arg Lys His Tyr Gln Pro Tyr Ala Pro Pro
625                 630                 635                 640

Arg Asp Phe Ala Ala Tyr Arg Ser Lys Arg Gly Arg Lys Lys Leu Leu
                645                 650                 655

Tyr Ile Phe Lys Gln Pro Phe Met Arg Pro Val Gln Thr Thr Gln Glu
                660                 665                 670

Glu Asp Gly Cys Ser Cys Arg Phe Pro Glu Glu Glu Glu Gly Gly Cys
            675                 680                 685

Glu Leu Arg Val Lys Phe Ser Arg Ser Ala Asp Ala Pro Ala Tyr Gln
    690                 695                 700

Gln Gly Gln Asn Gln Leu Tyr Asn Glu Leu Asn Leu Gly Arg Arg Glu
705                 710                 715                 720

Glu Tyr Asp Val Leu Asp Lys Arg Arg Gly Arg Asp Pro Glu Met Gly
                725                 730                 735

Gly Lys Pro Arg Arg Lys Asn Pro Gln Glu Gly Leu Tyr Asn Glu Leu
                740                 745                 750

Gln Lys Asp Lys Met Ala Glu Ala Tyr Ser Glu Ile Gly Met Lys Gly
            755                 760                 765

Glu Arg Arg Arg Gly Lys Gly His Asp Gly Leu Tyr Gln Gly Leu Ser
    770                 775                 780

Thr Ala Thr Lys Asp Thr Tyr Asp Ala Leu His Met Gln Ala Leu Pro
785                 790                 795                 800

Pro Arg

<210> SEQ ID NO 76
<211> LENGTH: 2913
<212> TYPE: DNA
<213> ORGANISM: Artificial Sequence
<220> FEATURE:
<223> OTHER INFORMATION: CAR D0146 CD19 CD8H&TM ICOS z_CD22 CD8H&TM 3z

<400> SEQUENCE: 76
atgctgctgc tggtgaccag cctgctgctg tgcgaactgc cgcatccggc gtttctgctg      60

-continued

| | |
|---|---|
| attccggagg tccagctggt acagtctgga gctgaggtga agaagcctgg ggcctcagtg | 120 |
| aaggtctcct gcaaggcttc tggatacacc ttcaccagct actatatgca ctgggtgcga | 180 |
| caggcccctg gacaagggct tgagtggatg ggattaatca accctagtgg tggtagcaca | 240 |
| agctacgcac agaagttcca gggcagagtc accatgacca gggacacgtc cacgagcaca | 300 |
| gtctacatgg agctgagcag cctgagatct gaggacacgg ccgtgtatta ctgtgcgaga | 360 |
| tcggatcggg gaattaccgc cacgacgct tttgatatct ggggccaagg acaatggtc | 420 |
| accgtctctt caggcggagg aggctccggg ggaggaggtt ccggggggcgg gggttcccag | 480 |
| tctgtgctga ctcagccacc ctcggtgtca gtggccccag gcggatggc caagattacc | 540 |
| tgtgggggaa gtgacattgg aaataaaaat gtccactggt atcagcagaa gccaggccag | 600 |
| gcccctgtcc tggttgtcta tgatgattac gaccggccct cagggatccc tgagcgattc | 660 |
| tctggctcca actctgggga cgcggccacc ctgacgatca gcacggtcga agtcggggat | 720 |
| gaggccgact atttctgtca ggtgtgggac ggtagtggtg atccttattg gatgttcggc | 780 |
| ggagggaccc agctcaccgt tttaggtgcg gccgcaacga ccactcctgc accacggcca | 840 |
| cctaccccag cccccaccat tgcaagccag ccactttcac tgcgcccga agcgtgtaga | 900 |
| ccagctgctg gaggagccgt gcatacccga gggctggact cgcctgtga catctacatc | 960 |
| tgggccccat tggctggaac ttgcggcgtg ctgctcttgt ctctggtcat taccctgtac | 1020 |
| tgctggctga caaaaaagaa gtattcatct agtgtacatg atccgaacgg tgaatacatg | 1080 |
| ttcatgcgcg cggtgaacac ggccaagaag agcagactga ccgacgtaac ccttagagtg | 1140 |
| aagtttagcc gctcagccga tgcaccggcc taccagcagg acagaaccca gctctacaac | 1200 |
| gagctcaacc tgggtcggcg ggaagaatat gacgtgctgg acaaacggcg cggcagagat | 1260 |
| ccggagatgg ggggaaagcc gaggaggaag aaccctcaag agggcctgta caacgaactg | 1320 |
| cagaaggaca agatggcgga agcctactcc gagatcggca tgaagggaga acgccggaga | 1380 |
| gggaagggtc atgacggact gtaccagggc ctgtcaactg ccactaagga cacttacgat | 1440 |
| gcgctccata tgcaagcttt gcccccgcgg cgcgcgaaac gcggcagcgg cgcgaccaac | 1500 |
| tttagcctgc tgaaacaggc gggcgatgtg aagaaaacc cgggcccgcg agcaaagagg | 1560 |
| aatattatgg ctctgcctgt tacggcactg ctccttccgc ttgcattgtt gttgcacgca | 1620 |
| gcgcggcccc aagtgcagct gcagcagtcc ggtcctggac tggtcaagcc gtcccagact | 1680 |
| ctgagcctga cttgcgcaat tagcggggac tcagtctcgt ccaattcggc ggcctggaac | 1740 |
| tggatccggc agtcaccatc aaggggcctg gaatggctcg ggcgcactta ctaccggtcc | 1800 |
| aaatggtata ccgactacgc cgtgtccgtg aagaatcgga tcaccattaa ccccgacacc | 1860 |
| tcgaagaacc agttctcact ccaactgaac agcgtgaccc cgaggatac cgcggtgtac | 1920 |
| tactgcgcac aagaagtgga accgcaggac gccttcgaca tttggggaca gggaacgatg | 1980 |
| gtcacagtgt cgtccggtgg aggaggttcc ggaggcggtg gatctggagg cggaggttcg | 2040 |
| gatatccaga tgacccagag cccctcctcg gtgtccgcat ccgtgggcga taaggtcacc | 2100 |
| attacctgta gagcgtccca ggacgtgtcc ggatggctgg cctggtacca gcagaagcca | 2160 |
| ggcttggctc ctcaactgct gatcttcggc gccagcactc ttcaggggga agtgccatca | 2220 |
| cgcttctccg gatccggttc cggcaccgac ttcaccctga ccatcagcag cctccagcct | 2280 |
| gaggacttcg ccacttacta ctgccaacag gccaagtact ccccctatac cttcggaaga | 2340 |
| ggcactaagc tggaaatcaa ggctagcgca accactacgc ctgctccgcg gcctccaacg | 2400 |

```
cccgcgccca cgatagctag tcagccgttg tctctccgac cagaggcgtg tagaccggcc    2460
gctggcggag ccgtacatac tcgcggactc gacttcgctt gcgacatcta catttgggca    2520
cccttggctg ggacctgtgg ggtgctgttg ctgtccttgg ttattacgtt gtactgcaga    2580
gtcaaatttt ccaggtccgc agatgccccc gcgtaccagc aaggccagaa ccaactttac    2640
aacgaactga acctgggtcg ccgggaggaa tatgatgtgc tggataaacg aaggggagg    2700 gaccctgaga tggagggaa acctcgcagg aaaaacccgc aggaaggttt gtacaacgag    2760
ttgcagaagg ataagatggc tgaggcttac tctgaaatag ggatgaaggg agagagacgg    2820
agaggaaaag gccatgatgg cctttaccag ggcttaagca cagcaacaaa ggatacttac    2880
gacgctcttc acatgcaagc tctgccacca cgg                                 2913
```

<210> SEQ ID NO 77
<211> LENGTH: 971
<212> TYPE: PRT
<213> ORGANISM: Artificial Sequence
<220> FEATURE:
<223> OTHER INFORMATION: CAR D0146 CD19 CD8H&TM ICOS z_CD22 CD8H&TMz
<400> SEQUENCE: 77

```
Met Leu Leu Leu Val Thr Ser Leu Leu Cys Glu Leu Pro His Pro
1               5                   10                  15

Ala Phe Leu Leu Ile Pro Glu Val Gln Leu Val Gln Ser Gly Ala Glu
            20                  25                  30

Val Lys Lys Pro Gly Ala Ser Val Lys Val Ser Cys Lys Ala Ser Gly
        35                  40                  45

Tyr Thr Phe Thr Ser Tyr Tyr Met His Trp Val Arg Gln Ala Pro Gly
    50                  55                  60

Gln Gly Leu Glu Trp Met Gly Leu Ile Asn Pro Ser Gly Gly Ser Thr
65                  70                  75                  80

Ser Tyr Ala Gln Lys Phe Gln Gly Arg Val Thr Met Thr Arg Asp Thr
                85                  90                  95

Ser Thr Ser Thr Val Tyr Met Glu Leu Ser Ser Leu Arg Ser Glu Asp
            100                 105                 110

Thr Ala Val Tyr Tyr Cys Ala Arg Ser Asp Arg Gly Ile Thr Ala Thr
        115                 120                 125

Asp Ala Phe Asp Ile Trp Gly Gln Gly Thr Met Val Thr Val Ser Ser
    130                 135                 140

Gly Gly Gly Gly Ser Gly Gly Gly Ser Gly Gly Gly Gly Ser Gln
145                 150                 155                 160

Ser Val Leu Thr Gln Pro Pro Ser Val Ser Val Ala Pro Gly Arg Met
                165                 170                 175

Ala Lys Ile Thr Cys Gly Gly Ser Asp Ile Gly Asn Lys Asn Val His
            180                 185                 190

Trp Tyr Gln Gln Lys Pro Gly Gln Ala Pro Val Leu Val Val Tyr Asp
        195                 200                 205

Asp Tyr Asp Arg Pro Ser Gly Ile Pro Glu Arg Phe Ser Gly Ser Asn
    210                 215                 220

Ser Gly Asp Ala Ala Thr Leu Thr Ile Ser Thr Val Glu Val Gly Asp
225                 230                 235                 240

Glu Ala Asp Tyr Phe Cys Gln Val Trp Asp Gly Ser Gly Asp Pro Tyr
                245                 250                 255

Trp Met Phe Gly Gly Gly Thr Gln Leu Thr Val Leu Gly Ala Ala Ala
            260                 265                 270
```

```
Thr Thr Thr Pro Ala Pro Arg Pro Pro Thr Pro Ala Pro Thr Ile Ala
        275                 280                 285
Ser Gln Pro Leu Ser Leu Arg Pro Glu Ala Cys Arg Pro Ala Ala Gly
    290                 295                 300
Gly Ala Val His Thr Arg Gly Leu Asp Phe Ala Cys Asp Ile Tyr Ile
305                 310                 315                 320
Trp Ala Pro Leu Ala Gly Thr Cys Gly Val Leu Leu Leu Ser Leu Val
                325                 330                 335
Ile Thr Leu Tyr Cys Trp Leu Thr Lys Lys Tyr Ser Ser Ser Val
            340                 345                 350
His Asp Pro Asn Gly Glu Tyr Met Phe Met Arg Ala Val Asn Thr Ala
        355                 360                 365
Lys Lys Ser Arg Leu Thr Asp Val Thr Leu Arg Val Lys Phe Ser Arg
    370                 375                 380
Ser Ala Asp Ala Pro Ala Tyr Gln Gln Gly Gln Asn Gln Leu Tyr Asn
385                 390                 395                 400
Glu Leu Asn Leu Gly Arg Arg Glu Glu Tyr Asp Val Leu Asp Lys Arg
                405                 410                 415
Arg Gly Arg Asp Pro Glu Met Gly Gly Lys Pro Arg Arg Lys Asn Pro
            420                 425                 430
Gln Glu Gly Leu Tyr Asn Glu Leu Gln Lys Asp Lys Met Ala Glu Ala
        435                 440                 445
Tyr Ser Glu Ile Gly Met Lys Gly Glu Arg Arg Arg Gly Lys Gly His
    450                 455                 460
Asp Gly Leu Tyr Gln Gly Leu Ser Thr Ala Thr Lys Asp Thr Tyr Asp
465                 470                 475                 480
Ala Leu His Met Gln Ala Leu Pro Pro Arg Arg Ala Lys Arg Gly Ser
                485                 490                 495
Gly Ala Thr Asn Phe Ser Leu Leu Lys Gln Ala Gly Asp Val Glu Glu
            500                 505                 510
Asn Pro Gly Pro Arg Ala Lys Arg Asn Ile Met Ala Leu Pro Val Thr
        515                 520                 525
Ala Leu Leu Leu Pro Leu Ala Leu Leu Leu His Ala Ala Arg Pro Gln
    530                 535                 540
Val Gln Leu Gln Gln Ser Gly Pro Gly Leu Val Lys Pro Ser Gln Thr
545                 550                 555                 560
Leu Ser Leu Thr Cys Ala Ile Ser Gly Asp Ser Val Ser Ser Asn Ser
                565                 570                 575
Ala Ala Trp Asn Trp Ile Arg Gln Ser Pro Ser Arg Gly Leu Glu Trp
            580                 585                 590
Leu Gly Arg Thr Tyr Tyr Arg Ser Lys Trp Tyr Thr Asp Tyr Ala Val
        595                 600                 605
Ser Val Lys Asn Arg Ile Thr Ile Asn Pro Asp Thr Ser Lys Asn Gln
    610                 615                 620
Phe Ser Leu Gln Leu Asn Ser Val Thr Pro Glu Asp Thr Ala Val Tyr
625                 630                 635                 640
Tyr Cys Ala Gln Glu Val Glu Pro Gln Asp Ala Phe Asp Ile Trp Gly
                645                 650                 655
Gln Gly Thr Met Val Thr Val Ser Ser Gly Gly Gly Gly Ser Gly Gly
            660                 665                 670
Gly Gly Ser Gly Gly Gly Ser Asp Ile Gln Met Thr Gln Ser Pro
    675                 680                 685
Ser Ser Val Ser Ala Ser Val Gly Asp Lys Val Thr Ile Thr Cys Arg
```

| | 690 | | | | 695 | | | | 700 | | |
|---|---|---|---|---|---|---|---|---|---|---|---|

Ala Ser Gln Asp Val Ser Gly Trp Leu Ala Trp Tyr Gln Gln Lys Pro
705 710 715 720

Gly Leu Ala Pro Gln Leu Leu Ile Phe Gly Ala Ser Thr Leu Gln Gly
725 730 735

Glu Val Pro Ser Arg Phe Ser Gly Ser Gly Ser Gly Thr Asp Phe Thr
740 745 750

Leu Thr Ile Ser Ser Leu Gln Pro Glu Asp Phe Ala Thr Tyr Tyr Cys
755 760 765

Gln Gln Ala Lys Tyr Phe Pro Tyr Thr Phe Gly Arg Gly Thr Lys Leu
770 775 780

Glu Ile Lys Ala Ser Ala Thr Thr Thr Pro Ala Pro Arg Pro Pro Thr
785 790 795 800

Pro Ala Pro Thr Ile Ala Ser Gln Pro Leu Ser Leu Arg Pro Glu Ala
805 810 815

Cys Arg Pro Ala Ala Gly Gly Ala Val His Thr Arg Gly Leu Asp Phe
820 825 830

Ala Cys Asp Ile Tyr Ile Trp Ala Pro Leu Ala Gly Thr Cys Gly Val
835 840 845

Leu Leu Leu Ser Leu Val Ile Thr Leu Tyr Cys Arg Val Lys Phe Ser
850 855 860

Arg Ser Ala Asp Ala Pro Ala Tyr Gln Gln Gly Gln Asn Gln Leu Tyr
865 870 875 880

Asn Glu Leu Asn Leu Gly Arg Arg Glu Glu Tyr Asp Val Leu Asp Lys
885 890 895

Arg Arg Gly Arg Asp Pro Glu Met Gly Gly Lys Pro Arg Arg Lys Asn
900 905 910

Pro Gln Glu Gly Leu Tyr Asn Glu Leu Gln Lys Asp Lys Met Ala Glu
915 920 925

Ala Tyr Ser Glu Ile Gly Met Lys Gly Glu Arg Arg Arg Gly Lys Gly
930 935 940

His Asp Gly Leu Tyr Gln Gly Leu Ser Thr Ala Thr Lys Asp Thr Tyr
945 950 955 960

Asp Ala Leu His Met Gln Ala Leu Pro Pro Arg
965 970

<210> SEQ ID NO 78
<211> LENGTH: 2754
<212> TYPE: DNA
<213> ORGANISM: Artificial Sequence
<220> FEATURE:
<223> OTHER INFORMATION: CAR D0147 CD19 CD8H OX40TM OX40 z_CD22
      CD8H&TM z

<400> SEQUENCE: 78

| | | | | |
|---|---|---|---|---|
| atgcactggg tgcgacaggc ccctggacaa gggcttgagt ggatgggatt aatcaaccct | | | | 60 |
| agtggtggta gcacaagcta cgcacagaag ttccagggca gagtcaccat gaccagggac | | | | 120 |
| acgtccacga gcacagtcta catggagctg agcagcctga gatctgagga cacggccgtg | | | | 180 |
| tattactgtg cgagatcgga tcggggaatt accgccacgg acgcttttga tatctggggc | | | | 240 |
| caagggacaa tggtcaccgt ctcttcaggc ggaggaggct ccggggagg aggttccggg | | | | 300 |
| ggcgggggtt cccagtctgt gctgactcag ccaccctcgg tgtcagtggc cccaggcgg | | | | 360 |
| atggccaaga ttacctgtgg gggaagtgac attggaaata aaaatgtcca ctggtatcag | | | | 420 |
| cagaagccag gccaggcccc tgtcctggtt gtctatgatg attacgaccg gccctcaggg | | | | 480 |

```
atccctgagc gattctctgg ctccaactct ggggacgcgg ccaccctgac gatcagcacg      540
gtcgaagtcg gggatgaggc cgactatttc tgtcaggtgt gggacggtag tggtgatcct      600
tattggatgt tcggcggagg gacccagctc accgttttag gtgcggccgc aacgaccact      660
ccagcaccga gaccgccaac ccccgcgcct accatcgcaa gtcaaccact ttctctcagg      720
cctgaagcgt gccgacctgc agctggtggg gcagtacata ccaggggttt ggacttcgca      780
tgtgacgtgc cggcaattct cggcctggga cttgtccttg gtctgcttgg tccgctcgca      840
atacttctgg ccttgtacct gctccgcaga gaccaaagac ttccgcccga cgcccacaag      900
cccccaggag gaggttcctt cagaacgcct atacaagaag aacaagcaga tgcccactct      960
accctggcta aaatcagggt gaagtttagc cgctcagccg atgcaccggc ctaccagcag     1020
ggacagaacc agctctacaa cgagctcaac ctgggtcggc gggaagaata tgacgtgctg     1080
gacaaacggc gcggcagaga tccggagatg gggggaaagc cgaggaggaa gaaccctcaa     1140
gagggcctgt acaacgaact gcagaaggac aagatggcgg aagcctactc cgagatcggc     1200
atgaagggag aacgccggag agggaagggt catgacggac tgtaccaggg cctgtcaact     1260
gccactaagg acacttacga tgcgctccat atgcaagctt gccccccgcg cgcgcgcgaaa    1320 cgcggcagcg gcgcgaccaa ctttagcctg ctgaaacagg cgggcgatgt ggaagaaaac     1380
ccgggcccgc gagcaaagag gaatattatg gctctgcctg ttacggcact gctccttccg     1440
cttgcattgt tgttgcacgc agcgcggccc caagtgcagc tgcagcagtc cggtcctgga     1500
ctggtcaagc cgtcccagac tctgagcctg acttgcgcaa ttagcgggga ctcagtctcg     1560
tccaattcgg cggcctggaa ctggatccgg cagtcaccat caaggggcct ggaatggctc     1620
gggcgcactt actaccggtc caaatggtat accgactacg ccgtgtccgt gaagaatcgg     1680
atcaccatta accccgacac ctcgaagaac cagttctcac tccaactgaa cagcgtgacc     1740
cccgaggata ccgcggtgta ctactgcgca caagaagtgg aaccgcagga cgccttcgac     1800
atttggggac agggaacgat ggtcacagtg tcgtccggtg gaggaggttc cggaggcggt     1860
ggatctggag gcggaggttc ggatatccag atgacccaga gccctcctc ggtgtccgca     1920 tccgtgggcg ataaggtcac cattacctgt agagcgtccc aggacgtgtc cggatggctg     1980
gcctggtacc agcagaagcc aggcttggct cctcaactgc tgatcttcgg cgccagcact     2040
cttcaggggg aagtgccatc acgcttctcc ggatccggtt ccggcaccga cttcaccctg     2100
accatcagca gcctccagcc tgaggacttc gccacttact actgccaaca ggccaagtac     2160
ttcccctata ccttcggaag aggcactaag ctggaaatca aggctagcgc aaccactacg     2220
cctgctccgc ggcctccaac gcccgcgccc acgatagcta gtcagccgtt gtctctccga     2280
ccagaggcgt gtagaccggc cgctggcgga gccgtacata tcgcggact cgacttcgct     2340 tgcgacatct acatttgggc cccttggct gggacctgtg gggtgctgtt gctgtccttg     2400
gttattacgt tgtactgcag agtcaaattt tccaggtccg cagatgcccc cgcgtaccag     2460
caaggccaga accaactta caacgaactg aacctgggtc gccgggagga atatgatgtg     2520
ctggataaac gaaggggag ggaccctgag atgggaggga acctcgcag gaaaaacccg     2580 caggaaggtt tgtacaacga gttgcagaag gataagatgg ctgaggctta ctctgaaata     2640
gggatgaagg gagagagacg gagaggaaaa ggccatgatg gcctttacca gggcttaagc     2700
acagcaacaa aggatactta cgacgctctt cacatgcaag ctctgccacc acgg           2754
```

<210> SEQ ID NO 79

```
<211> LENGTH: 918
<212> TYPE: PRT
<213> ORGANISM: Artificial Sequence
<220> FEATURE:
<223> OTHER INFORMATION: CAR D0147 CD19 CD8H OX40TM OX40 z _CD22
      CD8H&TM 3z

<400> SEQUENCE: 79

Met His Trp Val Arg Gln Ala Pro Gly Gln Gly Leu Glu Trp Met Gly
1               5                   10                  15

Leu Ile Asn Pro Ser Gly Gly Ser Thr Ser Tyr Ala Gln Lys Phe Gln
            20                  25                  30

Gly Arg Val Thr Met Thr Arg Asp Thr Ser Thr Ser Thr Val Tyr Met
        35                  40                  45

Glu Leu Ser Ser Leu Arg Ser Glu Asp Thr Ala Val Tyr Tyr Cys Ala
    50                  55                  60

Arg Ser Asp Arg Gly Ile Thr Ala Thr Asp Ala Phe Asp Ile Trp Gly
65                  70                  75                  80

Gln Gly Thr Met Val Thr Val Ser Ser Gly Gly Gly Ser Gly Gly
                85                  90                  95

Gly Gly Ser Gly Gly Gly Gly Ser Gln Ser Val Leu Thr Gln Pro Pro
            100                 105                 110

Ser Val Ser Val Ala Pro Gly Arg Met Ala Lys Ile Thr Cys Gly Gly
        115                 120                 125

Ser Asp Ile Gly Asn Lys Asn Val His Trp Tyr Gln Gln Lys Pro Gly
    130                 135                 140

Gln Ala Pro Val Leu Val Val Tyr Asp Asp Tyr Asp Arg Pro Ser Gly
145                 150                 155                 160

Ile Pro Glu Arg Phe Ser Gly Ser Asn Ser Gly Asp Ala Ala Thr Leu
                165                 170                 175

Thr Ile Ser Thr Val Glu Val Gly Asp Glu Ala Asp Tyr Phe Cys Gln
            180                 185                 190

Val Trp Asp Gly Ser Gly Asp Pro Tyr Trp Met Phe Gly Gly Gly Thr
        195                 200                 205

Gln Leu Thr Val Leu Gly Ala Ala Ala Thr Thr Thr Pro Ala Pro Arg
    210                 215                 220

Pro Pro Thr Pro Ala Pro Thr Ile Ala Ser Gln Pro Leu Ser Leu Arg
225                 230                 235                 240

Pro Glu Ala Cys Arg Pro Ala Ala Gly Gly Ala Val His Thr Arg Gly
                245                 250                 255

Leu Asp Phe Ala Cys Asp Val Ala Ala Ile Leu Gly Leu Gly Leu Val
            260                 265                 270

Leu Gly Leu Leu Gly Pro Leu Ala Ile Leu Leu Ala Leu Tyr Leu Leu
        275                 280                 285

Arg Arg Asp Gln Arg Leu Pro Pro Asp Ala His Lys Pro Pro Gly Gly
    290                 295                 300

Gly Ser Phe Arg Thr Pro Ile Gln Glu Glu Gln Ala Asp Ala His Ser
305                 310                 315                 320

Thr Leu Ala Lys Ile Arg Val Lys Phe Ser Arg Ser Ala Asp Ala Pro
                325                 330                 335

Ala Tyr Gln Gln Gly Gln Asn Gln Leu Tyr Asn Glu Leu Asn Leu Gly
            340                 345                 350

Arg Arg Glu Glu Tyr Asp Val Leu Asp Lys Arg Arg Gly Arg Asp Pro
        355                 360                 365

Glu Met Gly Gly Lys Pro Arg Arg Lys Asn Pro Gln Glu Gly Leu Tyr
```

```
            370                 375                 380
Asn Glu Leu Gln Lys Asp Lys Met Ala Glu Ala Tyr Ser Glu Ile Gly
385                 390                 395                 400

Met Lys Gly Glu Arg Arg Gly Lys Gly His Asp Gly Leu Tyr Gln
                405                 410                 415

Gly Leu Ser Thr Ala Thr Lys Asp Thr Tyr Asp Ala Leu His Met Gln
                420                 425                 430

Ala Leu Pro Pro Arg Arg Ala Lys Arg Gly Ser Gly Ala Thr Asn Phe
                435                 440                 445

Ser Leu Leu Lys Gln Ala Gly Asp Val Glu Glu Asn Pro Gly Pro Arg
                450                 455                 460

Ala Lys Arg Asn Ile Met Ala Leu Pro Val Thr Ala Leu Leu Leu Pro
465                 470                 475                 480

Leu Ala Leu Leu Leu His Ala Ala Arg Pro Gln Val Gln Leu Gln Gln
                485                 490                 495

Ser Gly Pro Gly Leu Val Lys Pro Ser Gln Thr Leu Ser Leu Thr Cys
                500                 505                 510

Ala Ile Ser Gly Asp Ser Val Ser Ser Asn Ser Ala Ala Trp Asn Trp
                515                 520                 525

Ile Arg Gln Ser Pro Ser Arg Gly Leu Glu Trp Leu Gly Arg Thr Tyr
                530                 535                 540

Tyr Arg Ser Lys Trp Tyr Thr Asp Tyr Ala Val Ser Val Lys Asn Arg
545                 550                 555                 560

Ile Thr Ile Asn Pro Asp Thr Ser Lys Asn Gln Phe Ser Leu Gln Leu
                565                 570                 575

Asn Ser Val Thr Pro Glu Asp Thr Ala Val Tyr Tyr Cys Ala Gln Glu
                580                 585                 590

Val Glu Pro Gln Asp Ala Phe Asp Ile Trp Gly Gln Gly Thr Met Val
                595                 600                 605

Thr Val Ser Ser Gly Gly Gly Ser Gly Gly Gly Ser Gly Gly
                610                 615                 620

Gly Gly Ser Asp Ile Gln Met Thr Gln Ser Pro Ser Ser Val Ser Ala
625                 630                 635                 640

Ser Val Gly Asp Lys Val Thr Ile Thr Cys Arg Ala Ser Gln Asp Val
                645                 650                 655

Ser Gly Trp Leu Ala Trp Tyr Gln Gln Lys Pro Gly Leu Ala Pro Gln
                660                 665                 670

Leu Leu Ile Phe Gly Ala Ser Thr Leu Gln Gly Glu Val Pro Ser Arg
                675                 680                 685

Phe Ser Gly Ser Gly Ser Gly Thr Asp Phe Thr Leu Thr Ile Ser Ser
                690                 695                 700

Leu Gln Pro Glu Asp Phe Ala Thr Tyr Tyr Cys Gln Gln Ala Lys Tyr
705                 710                 715                 720

Phe Pro Tyr Thr Phe Gly Arg Gly Thr Lys Leu Glu Ile Lys Ala Ser
                725                 730                 735

Ala Thr Thr Thr Pro Ala Pro Arg Pro Pro Thr Pro Ala Pro Thr Ile
                740                 745                 750

Ala Ser Gln Pro Leu Ser Leu Arg Pro Glu Ala Cys Arg Pro Ala Ala
                755                 760                 765

Gly Gly Ala Val His Thr Arg Gly Leu Asp Phe Ala Cys Asp Ile Tyr
                770                 775                 780

Ile Trp Ala Pro Leu Ala Gly Thr Cys Gly Val Leu Leu Leu Ser Leu
785                 790                 795                 800
```

```
Val Ile Thr Leu Tyr Cys Arg Val Lys Phe Ser Arg Ser Ala Asp Ala
            805                 810                 815

Pro Ala Tyr Gln Gln Gly Gln Asn Gln Leu Tyr Asn Glu Leu Asn Leu
        820                 825                 830

Gly Arg Arg Glu Glu Tyr Asp Val Leu Asp Lys Arg Arg Gly Arg Asp
        835                 840                 845

Pro Glu Met Gly Gly Lys Pro Arg Arg Lys Asn Pro Gln Glu Gly Leu
    850                 855                 860

Tyr Asn Glu Leu Gln Lys Asp Lys Met Ala Glu Ala Tyr Ser Glu Ile
865                 870                 875                 880

Gly Met Lys Gly Glu Arg Arg Arg Gly Lys Gly His Asp Gly Leu Tyr
                885                 890                 895

Gln Gly Leu Ser Thr Ala Thr Lys Asp Thr Tyr Asp Ala Leu His Met
            900                 905                 910

Gln Ala Leu Pro Pro Arg
        915

<210> SEQ ID NO 80
<211> LENGTH: 3030
<212> TYPE: DNA
<213> ORGANISM: Artificial Sequence
<220> FEATURE:
<223> OTHER INFORMATION: CAR D0148 CD19 CD8H OX40TM OX40 z_CD22 CD8H&TM
      ICOS z

<400> SEQUENCE: 80
atgctgctgc tggtgaccag cctgctgctg tgcgaactgc cgcatccggc gtttctgctg      60
attccggagg tccagctggt acagtctgga gctgaggtga agaagcctgg ggcctcagtg     120
aaggtctcct gcaaggcttc tggatacacc ttcaccagct actatatgca ctgggtgcga    180
caggcccctg gacaagggct tgagtggatg ggattaatca accctagtgg tggtagcaca    240
agctacgcac agaagttcca gggcagagtc accatgacca gggacacgtc cacgagcaca    300
gtctacatgg agctgagcag cctgagatct gaggacacgg ccgtgtatta ctgtgcgaga    360
tcggatcggg gaattaccgc cacggacgct tttgatatct ggggccaagg gacaatggtc    420
accgtctctt caggcggagg aggctccggg ggaggaggtt ccggggggcgg gggttcccag    480 tctgtgctga ctcagccacc ctcggtgtca gtggccccag gcggatggc caagattacc    540 tgtgggggaa gtgacattgg aaataaaaat gtccactggt atcagcagaa gccaggccag    600
gcccctgtcc tggttgtcta tgatgattac accggccct cagggatccc tgagcgattc    660
tctggctcca actctgggga cgcggccacc ctgacgatca gcacggtcga agtcggggat    720
gaggccgact atttctgtca ggtgtgggac ggtagtggtg atccttattg gatgttcggc    780
ggagggaccc agctcaccgt tttaggtgcg gccgcaacga ccactccagc accgagaccg    840 ccaaccccg cgcctaccat cgcaagtcaa ccactttctc tcaggcctga gcgtgccga    900 cctgcagctg gtggggcagt acataccagg ggtttggact cgcatgtga cgtggcggca    960 attctcggcc tgggacttgt ccttggtctg cttggtccgc tcgcaatact tctggccttg   1020
tacctgctcc gcagagacca agacttccg cccgacgccc acaagccccc aggaggaggt   1080
tccttcagaa cgcctataca agaagaacaa gcagatgccc actctaccct ggctaaaatc   1140
agggtgaagt ttagccgctc agccgatgca ccggcctacc agcagggaca gaaccagctc   1200
tacaacgagc tcaacctggg tcggcgggaa gaatatgacg tgctggacaa cggcgcggc   1260 agagatccgg agatgggggg aaagccgagg aggaagaacc ctcaagaggg cctgtacaac   1320
```

```
gaactgcaga aggacaagat ggcggaagcc tactccgaga tcggcatgaa gggagaacgc   1380
cggagaggga agggtcatga cggactgtac cagggcctgt caactgccac taaggacact   1440
tacgatgcgc tccatatgca agctttgccc ccgcggcgcg cgaaacgcgg cagcggcgcg   1500
accaacttta gcctgctgaa acaggcgggc gatgtggaag aaaacccggg cccgcgagca   1560
aagaggaata ttatggctct gcctgttacg gcactgctcc ttccgcttgc attgttgttg   1620
cacgcagcgc ggcccaagt gcagctgcag cagtccggtc ctggactggt caagccgtcc   1680
cagactctga gcctgacttg cgcaattagc ggggactcag tctcgtccaa ttcggcggcc   1740
tggaactgga tccggcagtc accatcaagg ggcctggaat ggctcgggcg cacttactac   1800
cggtccaaat ggtataccga ctacgccgtg tccgtgaaga tcggatcac cattaaccccc   1860 gacacctcga gaaccagtt ctcactccaa ctgaacagcg tgaccccga ggataccgcg   1920 gtgtactact gcgcacaaga agtggaaccg caggacgcct tcgacatttg ggacaggga   1980 acgatggtca cagtgtcgtc cggtggagga ggttccggag cggtggatc tggaggcgga   2040 ggttcggata tccagatgac ccagagcccc tcctcggtgt ccgcatccgt gggcgataag   2100
gtcaccatta cctgtagagc gtcccaggac gtgtccggat ggctggcctg gtaccagcag   2160
aagccaggct tggctcctca actgctgatc ttcggcgcca gcactcttca gggggaagtg   2220
ccatcacgct ctccggatc cggttccggc accgacttca ccctgaccat cagcagcctc   2280
cagcctgagg acttcgccac ttactactgc caacaggcca agtacttccc ctataccttc   2340
ggaagaggga ctaagctgga aatcaaggct agcgcaacca ctacgcctgc tccgcggcct   2400
ccaacgcccg cgcccacgat agctagtcag ccgttgtctc tccgaccaga ggcgtgtaga   2460
ccggccgctg gcggagccgt acatactcgc ggactcgact tcgcttgcga catctacatt   2520
tgggcaccct ggctgggac ctgtggggtg ctgttgctgt ccttggttat tacgttgtac   2580
tgctggctga caaaaaagaa gtattcatct agtgtacatg atccgaacgg tgaatacatg   2640
ttcatgcgcg cggtgaacac ggccaagaag agcagactga ccgacgtaac ccttagagtc   2700
aaatttccca ggtccgcaga tgccccccgcg taccagcaag gccagaacca actttacaac   2760
gaactgaacc tgggtcgccg ggaggaatat gatgtgctgg ataaacgaag ggggagggac   2820
cctgagatgg gagggaaacc tcgcaggaaa acccgcagg aaggttttgta caacgagttg   2880 cagaaggata agatggctga ggcttactct gaaataggga tgaagggaga gagacggaga   2940
ggaaaaggcc atgatggcct ttaccagggc ttgagcacag caacaaagga tacttacgac   3000
gctcttcaca tgcaagctct gccaccacgg                                    3030
```

<210> SEQ ID NO 81
<211> LENGTH: 1010
<212> TYPE: PRT
<213> ORGANISM: Artificial Sequence
<220> FEATURE:
<223> OTHER INFORMATION: CAR D0148 CD19 CD8H OX40TM OX40 z _CD22 CD8H&TM
    ICOS z

<400> SEQUENCE: 81

Met Leu Leu Leu Val Thr Ser Leu Leu Leu Cys Glu Leu Pro His Pro
1               5                   10                  15

Ala Phe Leu Leu Ile Pro Glu Val Gln Leu Val Gln Ser Gly Ala Glu
            20                  25                  30

Val Lys Lys Pro Gly Ala Ser Val Lys Val Ser Cys Lys Ala Ser Gly
        35                  40                  45

```
Tyr Thr Phe Thr Ser Tyr Tyr Met His Trp Val Arg Gln Ala Pro Gly
    50                  55                  60

Gln Gly Leu Glu Trp Met Gly Leu Ile Asn Pro Ser Gly Gly Ser Thr
65                  70                  75                  80

Ser Tyr Ala Gln Lys Phe Gln Gly Arg Val Thr Met Thr Arg Asp Thr
                85                  90                  95

Ser Thr Ser Thr Val Tyr Met Glu Leu Ser Ser Leu Arg Ser Glu Asp
            100                 105                 110

Thr Ala Val Tyr Tyr Cys Ala Arg Ser Asp Arg Gly Ile Thr Ala Thr
        115                 120                 125

Asp Ala Phe Asp Ile Trp Gly Gln Gly Thr Met Val Thr Val Ser Ser
130                 135                 140

Gly Gly Gly Gly Ser Gly Gly Gly Ser Gly Gly Gly Gly Ser Gln
145                 150                 155                 160

Ser Val Leu Thr Gln Pro Pro Ser Val Ser Val Ala Pro Gly Arg Met
                165                 170                 175

Ala Lys Ile Thr Cys Gly Gly Ser Asp Ile Gly Asn Lys Asn Val His
            180                 185                 190

Trp Tyr Gln Gln Lys Pro Gly Gln Ala Pro Val Leu Val Val Tyr Asp
        195                 200                 205

Asp Tyr Asp Arg Pro Ser Gly Ile Pro Glu Arg Phe Ser Gly Ser Asn
210                 215                 220

Ser Gly Asp Ala Ala Thr Leu Thr Ile Ser Thr Val Glu Val Gly Asp
225                 230                 235                 240

Glu Ala Asp Tyr Phe Cys Gln Val Trp Asp Gly Ser Gly Asp Pro Tyr
                245                 250                 255

Trp Met Phe Gly Gly Gly Thr Gln Leu Thr Val Leu Gly Ala Ala Ala
            260                 265                 270

Thr Thr Thr Pro Ala Pro Arg Pro Pro Thr Pro Ala Pro Thr Ile Ala
        275                 280                 285

Ser Gln Pro Leu Ser Leu Arg Pro Glu Ala Cys Arg Pro Ala Ala Gly
290                 295                 300

Gly Ala Val His Thr Arg Gly Leu Asp Phe Ala Cys Asp Val Ala Ala
305                 310                 315                 320

Ile Leu Gly Leu Gly Leu Val Leu Gly Leu Leu Gly Pro Leu Ala Ile
                325                 330                 335

Leu Leu Ala Leu Tyr Leu Leu Arg Arg Asp Gln Arg Leu Pro Pro Asp
            340                 345                 350

Ala His Lys Pro Pro Gly Gly Gly Ser Phe Arg Thr Pro Ile Gln Glu
        355                 360                 365

Glu Gln Ala Asp Ala His Ser Thr Leu Ala Lys Ile Arg Val Lys Phe
370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
            420                 425                 430

Asn Pro Gln Glu Gly Leu Tyr Asn Glu Leu Gln Lys Asp Lys Met Ala
        435                 440                 445

Glu Ala Tyr Ser Glu Ile Gly Met Lys Gly Glu Arg Arg Arg Gly Lys
450                 455                 460

Gly His Asp Gly Leu Tyr Gln Gly Leu Ser Thr Ala Thr Lys Asp Thr
```

```
              465                 470                 475                 480
Tyr Asp Ala Leu His Met Gln Ala Leu Pro Pro Arg Ala Lys Arg
                    485                 490                 495
Gly Ser Gly Ala Thr Asn Phe Ser Leu Leu Lys Gln Ala Gly Asp Val
                500                 505                 510
Glu Glu Asn Pro Gly Pro Arg Ala Lys Arg Asn Ile Met Ala Leu Pro
                515                 520                 525
Val Thr Ala Leu Leu Leu Pro Leu Ala Leu Leu Leu His Ala Ala Arg
            530                 535                 540
Pro Gln Val Gln Leu Gln Gln Ser Gly Pro Gly Leu Val Lys Pro Ser
545                 550                 555                 560
Gln Thr Leu Ser Leu Thr Cys Ala Ile Ser Gly Asp Ser Val Ser Ser
                    565                 570                 575
Asn Ser Ala Ala Trp Asn Trp Ile Arg Gln Ser Pro Ser Arg Gly Leu
                580                 585                 590
Glu Trp Leu Gly Arg Thr Tyr Tyr Arg Ser Lys Trp Tyr Thr Asp Tyr
                595                 600                 605
Ala Val Ser Val Lys Asn Arg Ile Thr Ile Asn Pro Asp Thr Ser Lys
                610                 615                 620
Asn Gln Phe Ser Leu Gln Leu Asn Ser Val Thr Pro Glu Asp Thr Ala
625                 630                 635                 640
Val Tyr Tyr Cys Ala Gln Glu Val Glu Pro Gln Asp Ala Phe Asp Ile
                    645                 650                 655
Trp Gly Gln Gly Thr Met Val Thr Val Ser Ser Gly Gly Gly Gly Ser
                660                 665                 670
Gly Gly Gly Gly Ser Gly Gly Gly Ser Asp Ile Gln Met Thr Gln
            675                 680                 685
Ser Pro Ser Ser Val Ser Ala Ser Val Gly Asp Lys Val Thr Ile Thr
            690                 695                 700
Cys Arg Ala Ser Gln Asp Val Ser Gly Trp Leu Ala Trp Tyr Gln Gln
705                 710                 715                 720
Lys Pro Gly Leu Ala Pro Gln Leu Leu Ile Phe Gly Ala Ser Thr Leu
                725                 730                 735
Gln Gly Glu Val Pro Ser Arg Phe Ser Gly Ser Gly Ser Gly Thr Asp
                740                 745                 750
Phe Thr Leu Thr Ile Ser Ser Leu Gln Pro Glu Asp Phe Ala Thr Tyr
                755                 760                 765
Tyr Cys Gln Gln Ala Lys Tyr Phe Pro Tyr Thr Phe Gly Arg Gly Thr
770                 775                 780
Lys Leu Glu Ile Lys Ala Ser Ala Thr Thr Thr Pro Ala Pro Arg Pro
785                 790                 795                 800
Pro Thr Pro Ala Pro Thr Ile Ala Ser Gln Pro Leu Ser Leu Arg Pro
                805                 810                 815
Glu Ala Cys Arg Pro Ala Ala Gly Gly Ala Val His Thr Arg Gly Leu
                820                 825                 830
Asp Phe Ala Cys Asp Ile Tyr Ile Trp Ala Pro Leu Ala Gly Thr Cys
            835                 840                 845
Gly Val Leu Leu Leu Ser Leu Val Ile Thr Leu Tyr Cys Trp Leu Thr
            850                 855                 860
Lys Lys Lys Tyr Ser Ser Ser Val His Asp Pro Asn Gly Glu Tyr Met
865                 870                 875                 880
Phe Met Arg Ala Val Asn Thr Ala Lys Lys Ser Arg Leu Thr Asp Val
                    885                 890                 895
```

```
Thr Leu Arg Val Lys Phe Ser Arg Ser Ala Asp Ala Pro Ala Tyr Gln
            900                 905                 910

Gln Gly Gln Asn Gln Leu Tyr Asn Glu Leu Asn Leu Gly Arg Arg Glu
        915                 920                 925

Glu Tyr Asp Val Leu Asp Lys Arg Arg Gly Arg Asp Pro Glu Met Gly
    930                 935                 940

Gly Lys Pro Arg Arg Lys Asn Pro Gln Glu Gly Leu Tyr Asn Glu Leu
945                 950                 955                 960

Gln Lys Asp Lys Met Ala Glu Ala Tyr Ser Glu Ile Gly Met Lys Gly
                965                 970                 975

Glu Arg Arg Arg Gly Lys Gly His Asp Gly Leu Tyr Gln Gly Leu Ser
            980                 985                 990

Thr Ala Thr Lys Asp Thr Tyr Asp Ala Leu His Met Gln Ala Leu Pro
        995                 1000                1005

Pro Arg
    1010

<210> SEQ ID NO 82
<211> LENGTH: 2892
<212> TYPE: DNA
<213> ORGANISM: Artificial Sequence
<220> FEATURE:
<223> OTHER INFORMATION: CAR D0149 CD19 CD8H&TM CD27 z_CD22 CD8H&TM
      ICOS3 z

<400> SEQUENCE: 82
atgcactggg tgcgacaggc ccctggacaa gggcttgagt ggatgggatt aatcaaccct      60
agtggtggta gcacaagcta cgcacagaag ttccagggca gagtcaccat gaccagggac     120
acgtccacga gcacagtcta catggagctg agcagcctga gatctgagga cacggccgtg     180
tattactgtg cgagatcgga tcggggaatt accgccacgg acgcttttga tatctggggc     240
caagggacaa tggtcaccgt ctcttcaggc ggaggaggct ccggggggag aggttccggg     300
ggcgggggtt cccagtctgt gctgactcag ccaccctcgg tgtcagtggc cccagggcgg     360
atggccaaga ttacctgtgg gggaagtgac attggaaata aaaatgtcca ctggtatcag     420
cagaagccag gccaggcccc tgtcctggtt gtctatgatg attacgaccg ccctcaggg      480 atccctgagc gattctctgg ctccaactct gggacgcgg ccaccctgac gatcagcacg      540
gtcgaagtcg gggatgaggc cgactatttc tgtcaggtgt gggacggtag tggtgatcct     600
tattggatgt tcggcggagg gacccagctc accgttttag gtgcggccgc gactaccact     660
cctgcaccac ggccacctac cccagccccc accattgcaa gccagccact tcactgcgc      720 cccgaagcgt gtagaccagc tgctggagga gccgtgcata cccgagggct ggacttcgcc     780
tgtgacatct acatctgggc cccattggct ggaacttgcg gcgtgctgct cttgtctctg     840
gtcattaccc tgtactgcca acggcgcaaa taccgctcca ataaaggcga agtccggta      900 gaacccgcag aaccttgcca ctacagttgt cccagagaag aagagggttc tacaatacct     960
attcaagagg actataggaa accagagccc gcatgtagtc ccagagtgaa gttcagccgc    1020
tcagccgatg caccggccta ccagcaggga cagaaccagc tctacaacga gctcaacctg    1080
ggtcggcggg aagaatatga cgtgctggac aaacggcgcg gcagagatcc ggagatgggg    1140
ggaaagccga ggaggaagaa ccctcaagag ggcctgtaca cgaactgca aggacaag      1200 atggcggaag cctactccga gatcggcatg aaggagaac gccggagagg aagggtcat      1260 gacggactgt accagggcct gtcaactgcc actaaggaca cttacgatgc gctccatatg    1320
```

```
caagctttgc ccccgcggcg cgcgaaacgc ggcagcggcg cgaccaactt tagcctgctg    1380
aaacaggcgg gcgatgtgga agaaaacccg ggcccgcgag caaagaggaa tattatggct    1440
ctgcctgtta cggcactgct ccttccgctt gcattgttgt tgcacgcagc gcggccccaa    1500
gtgcagctgc agcagtccgg tcctggactg gtcaagccgt cccagactct gagcctgact    1560
tgcgcaatta gcggggactc agtctcgtcc aattcggcgg cctggaactg gatccggcag    1620
tcaccatcaa ggggcctgga atggctcggg cgcacttact accggtccaa atggtatacc    1680
gactacgccg tgtccgtgaa gaatcggatc accattaacc ccgacacctc gaagaaccag    1740
ttctcactcc aactgaacag cgtgaccccc gaggataccg cggtgtacta ctgcgcacaa    1800
gaagtggaac cgcaggacgc cttcgacatt tggggacagg gaacgatggt cacagtgtcg    1860
tccggtggag gaggttccgg aggcggtgga tctggaggcg gaggttcgga tatccagatg    1920
acccagagcc cctcctcggt gtccgcatcc gtgggcgata aggtcaccat tacctgtaga    1980
gcgtcccagg acgtgtccgg atggctggcc tggtaccagc agaagccagg cttggctcct    2040
caactgctga tcttcggcgc cagcactctt caggggaag tgccatcacg cttctccgga    2100
tccggttccg gcaccgactt caccctgacc atcagcagcc tccagcctga ggacttcgcc    2160
acttactact gccaacaggc caagtacttc ccctatacct tcggaagagg cactaagctg    2220
gaaatcaagg ctagcgcaac cactacgcct gctccgcggc ctccaacgcc cgcgcccacg    2280
atagctagtc agccgttgtc tctccgacca gaggcgtgta gaccggccgc tggcggagcc    2340
gtacatactc gcggactcga cttcgcttgc gacatctaca tttgggcacc cttggctggg    2400
acctgtgggg tgctgttgct gtccttggtt attacgttgt actgctggct gacaaaaaag    2460
aagtattcat ctagtgtaca tgatccgaac ggtgaataca tgttcatgcg cgcggtgaac    2520
acggccaaga agagcagact gaccgacgta acccttagag tcaaattttc caggtccgca    2580 gatgccccg cgtaccagca aggccagaac caactttaca cgaactgaa cctgggtcgc    2640 cgggaggaat atgatgtgct ggataaacga aggggaggg accctgagat gggagggaaa    2700
cctcgcagga aaaacccgca ggaaggtttg tacaacgagt tgcagaagga taagatggct    2760
gaggcttact ctgaaatagg gatgaaggga gagagacgga gaggaaaagg ccatgatggc    2820
ctttaccagg gcttgagcac agcaacaaag gatacttacg acgctcttca catgcaagct    2880
ctgccaccac gg                                                       2892
```

<210> SEQ ID NO 83
<211> LENGTH: 964
<212> TYPE: PRT
<213> ORGANISM: Artificial Sequence
<220> FEATURE:
<223> OTHER INFORMATION: CAR D0149 CD19 CD8H&TM ICOS z CD22 CD8H&TM
      ICOS z

<400> SEQUENCE: 83

Met His Trp Val Arg Gln Ala Pro Gly Gln Gly Leu Glu Trp Met Gly
1               5                   10                  15

Leu Ile Asn Pro Ser Gly Gly Ser Thr Ser Tyr Ala Gln Lys Phe Gln
            20                  25                  30

Gly Arg Val Thr Met Thr Arg Asp Thr Ser Thr Ser Thr Val Tyr Met
        35                  40                  45

Glu Leu Ser Ser Leu Arg Ser Glu Asp Thr Ala Val Tyr Tyr Cys Ala
    50                  55                  60

Arg Ser Asp Arg Gly Ile Thr Ala Thr Asp Ala Phe Asp Ile Trp Gly

```
                65                  70                  75                  80
Gln Gly Thr Met Val Thr Val Ser Ser Gly Gly Gly Ser Gly Gly
                    85                  90                  95
Gly Gly Ser Gly Gly Gly Ser Gln Ser Val Leu Thr Gln Pro Pro
                100                 105                 110
Ser Val Ser Val Ala Pro Gly Arg Met Ala Lys Ile Thr Cys Gly
            115                 120                 125
Ser Asp Ile Gly Asn Lys Asn Val His Trp Tyr Gln Gln Lys Pro Gly
130                 135                 140
Gln Ala Pro Val Leu Val Val Tyr Asp Asp Tyr Asp Arg Pro Ser Gly
145                 150                 155                 160
Ile Pro Glu Arg Phe Ser Gly Ser Asn Ser Gly Asp Ala Ala Thr Leu
                165                 170                 175
Thr Ile Ser Thr Val Glu Val Gly Asp Glu Ala Asp Tyr Phe Cys Gln
            180                 185                 190
Val Trp Asp Gly Ser Gly Asp Pro Tyr Trp Met Phe Gly Gly Gly Thr
        195                 200                 205
Gln Leu Thr Val Leu Gly Ala Ala Ala Thr Thr Thr Pro Ala Pro Arg
    210                 215                 220
Pro Pro Thr Pro Ala Pro Thr Ile Ala Ser Gln Pro Leu Ser Leu Arg
225                 230                 235                 240
Pro Glu Ala Cys Arg Pro Ala Ala Gly Gly Ala Val His Thr Arg Gly
                245                 250                 255
Leu Asp Phe Ala Cys Asp Ile Tyr Ile Trp Ala Pro Leu Ala Gly Thr
            260                 265                 270
Cys Gly Val Leu Leu Leu Ser Leu Val Ile Thr Leu Tyr Cys Gln Arg
        275                 280                 285
Arg Lys Tyr Arg Ser Asn Lys Gly Glu Ser Pro Val Glu Pro Ala Glu
    290                 295                 300
Pro Cys His Tyr Ser Cys Pro Arg Glu Glu Gly Ser Thr Ile Pro
305                 310                 315                 320
Ile Gln Glu Asp Tyr Arg Lys Pro Glu Pro Ala Cys Ser Pro Arg Val
                325                 330                 335
Lys Phe Ser Arg Ser Ala Asp Ala Pro Ala Tyr Gln Gln Gly Gln Asn
            340                 345                 350
Gln Leu Tyr Asn Glu Leu Asn Leu Gly Arg Arg Glu Glu Tyr Asp Val
        355                 360                 365
Leu Asp Lys Arg Arg Gly Arg Asp Pro Glu Met Gly Gly Lys Pro Arg
    370                 375                 380
Arg Lys Asn Pro Gln Glu Gly Leu Tyr Asn Glu Leu Gln Lys Asp Lys
385                 390                 395                 400
Met Ala Glu Ala Tyr Ser Glu Ile Gly Met Lys Gly Glu Arg Arg Arg
                405                 410                 415
Gly Lys Gly His Asp Gly Leu Tyr Gln Gly Leu Ser Thr Ala Thr Lys
            420                 425                 430
Asp Thr Tyr Asp Ala Leu His Met Gln Ala Leu Pro Pro Arg Arg Ala
        435                 440                 445
Lys Arg Gly Ser Gly Ala Thr Asn Phe Ser Leu Leu Lys Gln Ala Gly
    450                 455                 460
Asp Val Glu Glu Asn Pro Gly Pro Arg Ala Lys Arg Asn Ile Met Ala
465                 470                 475                 480
Leu Pro Val Thr Ala Leu Leu Leu Pro Leu Ala Leu Leu Leu His Ala
                485                 490                 495
```

```
Ala Arg Pro Gln Val Gln Leu Gln Gln Ser Gly Pro Gly Leu Val Lys
            500                 505                 510

Pro Ser Gln Thr Leu Ser Leu Thr Cys Ala Ile Ser Gly Asp Ser Val
        515                 520                 525

Ser Ser Asn Ser Ala Ala Trp Asn Trp Ile Arg Gln Ser Pro Ser Arg
530                 535                 540

Gly Leu Glu Trp Leu Gly Arg Thr Tyr Tyr Arg Ser Lys Trp Tyr Thr
545                 550                 555                 560

Asp Tyr Ala Val Ser Val Lys Asn Arg Ile Thr Ile Asn Pro Asp Thr
                565                 570                 575

Ser Lys Asn Gln Phe Ser Leu Gln Leu Asn Ser Val Thr Pro Glu Asp
            580                 585                 590

Thr Ala Val Tyr Tyr Cys Ala Gln Glu Val Glu Pro Gln Asp Ala Phe
        595                 600                 605

Asp Ile Trp Gly Gln Gly Thr Met Val Thr Val Ser Ser Gly Gly Gly
    610                 615                 620

Gly Ser Gly Gly Gly Gly Ser Gly Gly Gly Gly Ser Asp Ile Gln Met
625                 630                 635                 640

Thr Gln Ser Pro Ser Ser Val Ser Ala Ser Val Gly Asp Lys Val Thr
                645                 650                 655

Ile Thr Cys Arg Ala Ser Gln Asp Val Ser Gly Trp Leu Ala Trp Tyr
            660                 665                 670

Gln Gln Lys Pro Gly Leu Ala Pro Gln Leu Leu Ile Phe Gly Ala Ser
        675                 680                 685

Thr Leu Gln Gly Glu Val Pro Ser Arg Phe Ser Gly Ser Gly Ser Gly
    690                 695                 700

Thr Asp Phe Thr Leu Thr Ile Ser Ser Leu Gln Pro Glu Asp Phe Ala
705                 710                 715                 720

Thr Tyr Tyr Cys Gln Gln Ala Lys Tyr Phe Pro Tyr Thr Phe Gly Arg
                725                 730                 735

Gly Thr Lys Leu Glu Ile Lys Ala Ser Ala Thr Thr Thr Pro Ala Pro
            740                 745                 750

Arg Pro Pro Thr Pro Ala Pro Thr Ile Ala Ser Gln Pro Leu Ser Leu
        755                 760                 765

Arg Pro Glu Ala Cys Arg Pro Ala Ala Gly Gly Ala Val His Thr Arg
    770                 775                 780

Gly Leu Asp Phe Ala Cys Asp Ile Tyr Ile Trp Ala Pro Leu Ala Gly
785                 790                 795                 800

Thr Cys Gly Val Leu Leu Leu Ser Leu Val Ile Thr Leu Tyr Cys Trp
                805                 810                 815

Leu Thr Lys Lys Lys Tyr Ser Ser Ser Val His Asp Pro Asn Gly Glu
            820                 825                 830

Tyr Met Phe Met Arg Ala Val Asn Thr Ala Lys Lys Ser Arg Leu Thr
        835                 840                 845

Asp Val Thr Leu Arg Val Lys Phe Ser Arg Ser Ala Asp Ala Pro Ala
    850                 855                 860

Tyr Gln Gln Gly Gln Asn Gln Leu Tyr Asn Glu Leu Asn Leu Gly Arg
865                 870                 875                 880

Arg Glu Glu Tyr Asp Val Leu Asp Lys Arg Gly Arg Asp Pro Glu
                885                 890                 895

Met Gly Gly Lys Pro Arg Arg Lys Asn Pro Gln Glu Gly Leu Tyr Asn
            900                 905                 910
```

-continued

```
Glu Leu Gln Lys Asp Lys Met Ala Glu Ala Tyr Ser Glu Ile Gly Met
        915                 920                 925

Lys Gly Glu Arg Arg Gly Lys Gly His Asp Gly Leu Tyr Gln Gly
    930             935                 940

Leu Ser Thr Ala Thr Lys Asp Thr Tyr Asp Ala Leu His Met Gln Ala
945                 950                 955                 960

Leu Pro Pro Arg
```